(12) United States Patent
Allard et al.

(10) Patent No.: US 11,124,806 B2
(45) Date of Patent: Sep. 21, 2021

(54) METHODS FOR PRODUCING ISOBUTENE FROM 3-METHYLCROTONIC ACID

(71) Applicants: Global Bioenergies, Evry (FR); Scientist of Fortune, S.A., Luxembourg (LU)

(72) Inventors: Mathieu Allard, Saint-Vrain (FR); Maria Anissimova, Nozay (FR); Philippe Marlière, Tournai (BE)

(73) Assignees: Global Bioenergies, Evry (FR); Scientist of Fortune, SA, Luxembourg (LU)

( * ) Notice: Subject to any disclaimer, the term of this patent is extended or adjusted under 35 U.S.C. 154(b) by 436 days.

(21) Appl. No.: 15/776,495

(22) PCT Filed: Nov. 17, 2016

(86) PCT No.: PCT/EP2016/077956
§ 371 (c)(1),
(2) Date: May 16, 2018

(87) PCT Pub. No.: WO2017/085167
PCT Pub. Date: May 26, 2017

(65) Prior Publication Data
US 2018/0371503 A1    Dec. 27, 2018

(30) Foreign Application Priority Data

Nov. 17, 2015 (EP) .................................... 15194984

(51) Int. Cl.
| | |
|---|---|
| *C12P 5/02* | (2006.01) |
| *C12N 9/00* | (2006.01) |
| *C12N 15/52* | (2006.01) |
| *C12N 9/88* | (2006.01) |
| *C12N 9/10* | (2006.01) |
| *C12N 9/12* | (2006.01) |
| *C12P 7/40* | (2006.01) |
| *C12N 9/16* | (2006.01) |

(52) U.S. Cl.
CPC ............ *C12P 5/026* (2013.01); *C12N 9/1029* (2013.01); *C12N 9/1085* (2013.01); *C12N 9/1217* (2013.01); *C12N 9/13* (2013.01); *C12N 9/16* (2013.01); *C12N 9/88* (2013.01); *C12N 9/93* (2013.01); *C12N 15/52* (2013.01); *C12P 7/40* (2013.01); *C12Y 205/01* (2013.01); *C12Y 207/02007* (2013.01); *C12Y 207/02014* (2013.01); *C12Y 207/02015* (2013.01); *C12Y 208/03001* (2013.01); *C12Y 208/03008* (2013.01); *C12Y 301/02001* (2013.01); *C12Y 301/0202* (2013.01); *C12Y 301/02018* (2013.01); *C12Y 401/01006* (2013.01); *C12Y 401/01063* (2013.01); *C12Y 604/01004* (2013.01); *C12Y 604/01005* (2013.01)

(58) Field of Classification Search
CPC ....................................................... C12P 5/026
See application file for complete search history.

(56) References Cited

U.S. PATENT DOCUMENTS

2011/0053232 A1    3/2011    Wang et al.

FOREIGN PATENT DOCUMENTS

| JP | 2001199930 A | 7/2001 |
|---|---|---|
| WO | 2001053243 A1 | 7/2001 |
| WO | 2013186215 A1 | 12/2013 |
| WO | 2014080024 A2 | 5/2014 |
| WO | 2016034691 A1 | 3/2016 |
| WO | 2016042012 A1 | 3/2016 |

OTHER PUBLICATIONS

Dhar et al., J. Industrial Microbiology and Biotechnology, 28, 81-87, 2002.*
Fukuda et al., Agric. Biol. Chem., 49(5), 1541-1543, 1985.*
Aberhart et al., "Studies on the Substrate Stereochemistry of Enoyl-CoA Hydratase (Crotonase): Nonstereospecific Hydration of {β-Methylcrotonate in Biotin-Deficient Rats", Bioorganic Chemistry, vol. 10, No. 4, pp. 375-387, (1981).
European Search Report dated Aug. 26, 2016, received in EP 15 19 4984.9.
Gerbling et al., "Peroxisomal Degradation of 2-Oxoisocaproate. Evidence for Free Acid Intermediates", Botanica Acta, vol. 106, No. 5, pp. 380-387, (1993).
Partial European Search Report dated May 18, 2016, received in application 15194984.9.

(Continued)

*Primary Examiner* — Maryam Monshipouri
(74) *Attorney, Agent, or Firm* — Michele M. Wales; InHouse Patent Counsel, LLC

(57) ABSTRACT

Described are methods for the production of isobutene comprising the enzymatic conversion of 3-methylcrotonic acid into isobutene wherein said 3-methylcrotonic acid is obtained by the enzymatic conversion of 3-methylcrotonyl-CoA into 3-methylcrotonic acid or wherein said 3-methylcrotonic acid is obtained by the enzymatic conversion of 3-hydroxyisovalerate (HIV) into 3-methylcrotonic acid. It is described that the enzymatic conversion of 3-methylcrotonic acid into isobutene can, e.g., be achieved by making use of a 3-methylcrotonic acid decarboxylase, preferably an FMN-dependent decarboxylase associated with an FMN prenyl transferase, an aconitate decarboxylase (EC 4.1.1.6), a methylcrotonyl-CoA carboxylase (EC 6.4.1.4), or a geranoyl-CoA carboxylase (EC 6.4.1.5).

Figure 1:
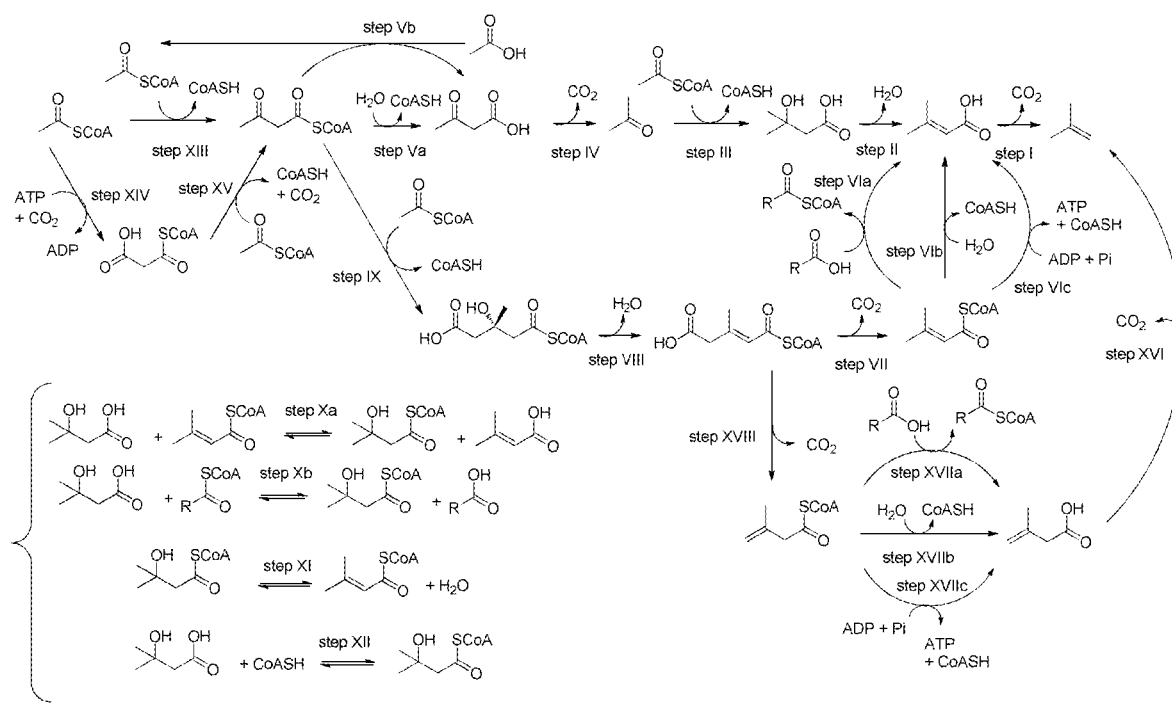

16 Claims, 20 Drawing Sheets
Specification includes a Sequence Listing.

(56) References Cited

OTHER PUBLICATIONS

Written Opinion and International Search Report dated May 15, 2017 in PCT/EP2016/077956.
International Preliminary Report on Patentability dated May 31, 2018 and received in PCT/EP2016/077956.
Dhar et al., "Purification and Characterization of a Galactornyces Reessii Hydratase that Converts 3-Methylcrotonic Acid to 3-Hydroxy-3-Methylbutyric Acid", J. Industrial Microbiology and Biotechnology, vol. 28, pp. 81-87 (2002).
Japanese Office Action and English Translation dated Aug. 18, 2020 received in corresponding JP Application 2018-525566.
Niu et al., "Benzene-Free Synthesis of Adipic Acid", Biotechnol Prog., vol. 18, No. 2, pp. 201-211 (2002).

* cited by examiner 3-hydroxyisovaleric acid   3-methylcrotonyl-CoA   3-hydroxyisovaleryl-CoA   3-methylcrotonic acid
                                        *aka* prenoyl-CoA                                         *aka* prenate 3-hydroxyisovaleric acid    acyl-CoA         3-hydroxyisovaleryl-CoA     acid 3-methyl-3-butenoic acid → isobutene + CO₂

3-methyl-3-butenoyl-CoA → 3-methyl-3-butenoic acid + CoASH 3-methyl-3-butenoyl-CoA + acid → 3-methyl-3-butenoic acid + acyl-CoA 3-methyl-3-butenoyl-CoA + H₂O → 3-methyl-3-butenoic acid + CoASH

SEQUENCE LISTING

<160> NUMBER OF SEQ ID NOS: 101

<210> SEQ ID NO 1
<211> LENGTH: 462

<212> TYPE: PRT
<213> ORGANISM: Caenorhabditis elegans

<400> SEQUENCE: 1

```
Met Ser Leu Gly Gln Leu Ser Tyr Thr Pro Val Thr Asp Val Gly Ile
1               5                   10                  15

Gly Ala Ile Glu Leu Tyr Phe Pro Gln Asn Phe Val Asp Gln Asn Asp
            20                  25                  30

Leu Glu Lys Phe Asn Asn Val Ser Ser Gly Lys Tyr Thr Ile Gly Leu
        35                  40                  45

Gly Gln Gln Gln Met Gly Phe Cys Ser Asp Asn Glu Asp Ile Val Ser
    50                  55                  60

Ile Ser Leu Thr Val Thr Arg Lys Leu Ile Glu Thr Tyr Lys Ile Ser
65                  70                  75                  80

Thr Asp Ser Ile Gly Cys Leu Val Val Gly Thr Glu Thr Met Ile Asp
                85                  90                  95

Lys Ser Lys Ser Val Lys Thr Ala Leu Met Asp Leu Phe Pro Gly Asn
            100                 105                 110

Ser Asp Ile Glu Gly Val Asp Ile Lys Asn Ala Cys Phe Gly Gly Ala
        115                 120                 125

Gln Ala Leu Leu His Ala Ile Asp Trp Val Thr Val Asn His Pro Leu
    130                 135                 140

Asp Lys Lys Asn Ala Ile Val Val Ala Asp Ile Ala Ile Tyr Glu
145                 150                 155                 160

Glu Gly Pro Ala Arg Cys Thr Gly Gly Ala Gly Ala Ile Ala Phe Leu
                165                 170                 175

Ile Cys Pro Asp Ala Ser Ile Pro Ile Asp Arg Gln Phe Ser Ala Cys
            180                 185                 190

His Met Lys Asn Thr Trp Asp Phe Phe Lys Pro Ile Thr Pro Ile Pro
        195                 200                 205

Ser Glu Tyr Pro Val Val Asp Gly Ser Leu Ser Leu Ser Ser Tyr Leu
    210                 215                 220

Glu Ala Val Arg Met Thr Tyr Thr Tyr Phe Ile Ser Lys Val Asn Arg
225                 230                 235                 240

His Thr Thr Gly Ile Asp Gly Leu Asn Ser Phe Asp Gly Val Phe Leu
                245                 250                 255

His Ser Pro Phe Thr Lys Met Val Gln Lys Gly Leu Ala Val Met Asn
            260                 265                 270

Tyr Thr Asp Ser Gln Leu Arg His Lys Gln Leu Asn Gly Asn Gly Val
        275                 280                 285

Asp His Lys Leu Asp Glu Asn Asp Arg Ala Gly Leu Ala Lys Met Ile
    290                 295                 300

Glu Leu Ser Ala Gln Val Trp Lys Glu Lys Thr Asp Pro Tyr Leu Val
305                 310                 315                 320

Phe Asn Arg Arg Ile Gly Asn Met Tyr Thr Pro Ser Leu Phe Ala Gln
                325                 330                 335

Leu Leu Ala Tyr Leu Ala Ala Asp Asp Cys Val Thr Gly Glu Lys Ser
            340                 345                 350

Ile Leu Phe Phe Ala Tyr Gly Ser Gly Leu Ala Ser Ile Phe Pro
        355                 360                 365

Gly Arg Val Arg Gln Thr Ser Asn Leu Asp Lys Ile Arg Gln Val Ala
    370                 375                 380

Ile Arg Ala Ile Lys Arg Leu Asp Asp Arg Ile Gln Phe Thr Pro Glu
385                 390                 395                 400
```

Glu Phe Thr Glu Thr Leu Gln Lys Arg Glu Val Phe Leu Arg Ser Lys
            405                 410                 415

Glu Ile Pro Lys Ser Pro Ser Glu Thr Ser Leu Phe Pro Asn Thr Tyr
            420                 425                 430

Phe Leu Asp Asn Met Asp Lys Leu Tyr Arg Arg Ser Tyr Thr Leu His
            435                 440                 445

Glu Glu Pro Asn Gly Val Gln Asn Gly Asn Gly Ile His His
            450                 455                 460

<210> SEQ ID NO 2
<211> LENGTH: 447
<212> TYPE: PRT
<213> ORGANISM: Schizosaccharomyces pombe

<400> SEQUENCE: 2

Met Ser Phe Asp Arg Lys Asp Ile Gly Ile Lys Gly Leu Val Leu Tyr
1               5                   10                  15

Thr Pro Asn Gln Tyr Val Glu Gln Ala Ala Leu Glu Ala His Asp Gly
            20                  25                  30

Val Ser Thr Gly Lys Tyr Thr Ile Gly Leu Gly Leu Thr Lys Met Ala
            35                  40                  45

Phe Val Asp Asp Arg Glu Asp Ile Tyr Ser Phe Gly Leu Thr Ala Leu
    50                  55                  60

Ser Gln Leu Ile Lys Arg Tyr Gln Ile Asp Ile Ser Lys Ile Gly Arg
65                  70                  75                  80

Leu Glu Val Gly Thr Glu Thr Ile Ile Asp Lys Ser Lys Ser Val Lys
            85                  90                  95

Ser Val Leu Met Gln Leu Phe Gly Asp Asn His Asn Val Glu Gly Ile
            100                 105                 110

Asp Cys Val Asn Ala Cys Tyr Gly Gly Val Asn Ala Leu Phe Asn Thr
            115                 120                 125

Ile Asp Trp Ile Glu Ser Ser Ala Trp Asp Gly Arg Asp Gly Ile Val
    130                 135                 140

Val Ala Gly Asp Ile Ala Leu Tyr Ala Lys Gly Asn Ala Arg Pro Thr
145                 150                 155                 160

Gly Gly Ala Gly Cys Val Ala Leu Leu Val Gly Pro Asn Ala Pro Ile
            165                 170                 175

Val Phe Glu Pro Gly Leu Arg Gly Thr Tyr Met Gln His Ala Tyr Asp
            180                 185                 190

Phe Tyr Lys Pro Asp Leu Thr Ser Glu Tyr Pro Tyr Val Asp Gly His
            195                 200                 205

Phe Ser Leu Glu Cys Tyr Val Lys Ala Leu Asp Gly Ala Tyr Ala Asn
    210                 215                 220

Tyr Asn Val Arg Asp Val Ala Lys Asn Gly Lys Ser Gln Gly Leu Gly
225                 230                 235                 240

Leu Asp Arg Phe Asp Tyr Cys Ile Phe His Ala Pro Thr Cys Lys Gln
            245                 250                 255

Val Gln Lys Ala Tyr Ala Arg Leu Leu Tyr Thr Asp Ser Ala Ala Glu
            260                 265                 270

Pro Ser Asn Pro Glu Leu Glu Gly Val Arg Glu Leu Leu Ser Thr Leu
            275                 280                 285

Asp Ala Lys Lys Ser Leu Thr Asp Lys Ala Leu Glu Lys Gly Leu Met
    290                 295                 300

Ala Ile Thr Lys Glu Arg Phe Asn Lys Arg Val Ser Pro Ser Val Tyr

```
                305                 310                 315                 320
Ala Pro Thr Asn Cys Gly Asn Met Tyr Thr Ala Ser Ile Phe Ser Cys
                    325                 330                 335

Leu Thr Ala Leu Leu Ser Arg Val Pro Ala Asp Glu Leu Lys Gly Lys
                340                 345                 350

Arg Val Gly Ala Tyr Ser Tyr Gly Ser Gly Leu Ala Ala Ser Phe Phe
                355                 360                 365

Ser Phe Val Val Lys Gly Asp Val Ser Glu Ile Ala Lys Lys Thr Asn
            370                 375                 380

Leu Val Asn Asp Leu Asp Asn Arg His Cys Leu Thr Pro Thr Gln Tyr
385                 390                 395                 400

Glu Glu Ala Ile Glu Leu Arg His Gln Ala His Leu Lys Lys Asn Phe
                405                 410                 415

Thr Pro Lys Gly Ser Ile Glu Arg Leu Arg Ser Gly Thr Tyr Tyr Leu
                420                 425                 430

Thr Gly Ile Asp Asp Met Phe Arg Arg Ser Tyr Ser Val Lys Pro
                435                 440                 445

<210> SEQ ID NO 3
<211> LENGTH: 491
<212> TYPE: PRT
<213> ORGANISM: Saccharomyces cerevisiae

<400> SEQUENCE: 3

Met Lys Leu Ser Thr Lys Leu Cys Trp Cys Gly Ile Lys Gly Arg Leu
1               5                   10                  15

Arg Pro Gln Lys Gln Gln Leu His Asn Thr Asn Leu Gln Met Thr
                20                  25                  30

Glu Leu Lys Lys Gln Lys Thr Ala Glu Gln Lys Thr Arg Pro Gln Asn
            35                  40                  45

Val Gly Ile Lys Gly Ile Gln Ile Tyr Ile Pro Thr Gln Cys Val Asn
        50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125

Leu Ile Asp Lys Ser Lys Ser Val Lys Ser Val Leu Met Gln Leu Phe
    130                 135                 140

Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190

Tyr Asp Lys Gly Ala Ala Arg Pro Thr Gly Gly Ala Gly Thr Val Ala
        195                 200                 205

Met Trp Ile Gly Pro Asp Ala Pro Ile Val Phe Asp Ser Val Arg Ala
    210                 215                 220

Ser Tyr Met Glu His Ala Tyr Asp Phe Tyr Lys Pro Asp Phe Thr Ser
225                 230                 235                 240
```

Glu Tyr Pro Tyr Val Asp Gly His Phe Ser Leu Thr Cys Tyr Val Lys
                245                 250                 255

Ala Leu Asp Gln Val Tyr Lys Ser Tyr Ser Lys Lys Ala Ile Ser Lys
            260                 265                 270

Gly Leu Val Ser Asp Pro Ala Gly Ser Asp Ala Leu Asn Val Leu Lys
        275                 280                 285

Tyr Phe Asp Tyr Asn Val Phe His Val Pro Thr Cys Lys Leu Val Thr
    290                 295                 300

Lys Ser Tyr Gly Arg Leu Leu Tyr Asn Asp Phe Arg Ala Asn Pro Gln
305                 310                 315                 320

Leu Phe Pro Glu Val Asp Ala Glu Leu Ala Thr Arg Asp Tyr Asp Glu
                325                 330                 335

Ser Leu Thr Asp Lys Asn Ile Glu Lys Thr Phe Val Asn Val Ala Lys
            340                 345                 350

Pro Phe His Lys Glu Arg Val Ala Gln Ser Leu Ile Val Pro Thr Asn
        355                 360                 365

Thr Gly Asn Met Tyr Thr Ala Ser Val Tyr Ala Ala Phe Ala Ser Leu
    370                 375                 380

Leu Asn Tyr Val Gly Ser Asp Asp Leu Gln Gly Lys Arg Val Gly Leu
385                 390                 395                 400

Phe Ser Tyr Gly Ser Gly Leu Ala Ala Ser Leu Tyr Ser Cys Lys Ile
                405                 410                 415

Val Gly Asp Val Gln His Ile Ile Lys Glu Leu Asp Ile Thr Asn Lys
            420                 425                 430

Leu Ala Lys Arg Ile Thr Glu Thr Pro Lys Asp Tyr Glu Ala Ala Ile
        435                 440                 445

Glu Leu Arg Glu Asn Ala His Leu Lys Lys Asn Phe Lys Pro Gln Gly
    450                 455                 460

Ser Ile Glu His Leu Gln Ser Gly Val Tyr Tyr Leu Thr Asn Ile Asp
465                 470                 475                 480

Asp Lys Phe Arg Arg Ser Tyr Asp Val Lys Lys
                485                 490

<210> SEQ ID NO 4
<211> LENGTH: 461
<212> TYPE: PRT
<213> ORGANISM: Arabidopsis thaliana

<400> SEQUENCE: 4

Met Ala Lys Asn Val Gly Ile Leu Ala Met Asp Ile Tyr Phe Pro Pro
1               5                   10                  15

Thr Cys Val Gln Gln Glu Ala Leu Glu Ala His Asp Gly Ala Ser Lys
            20                  25                  30

Gly Lys Tyr Thr Ile Gly Leu Gly Gln Asp Cys Leu Ala Phe Cys Thr
        35                  40                  45

Glu Leu Glu Asp Val Ile Ser Met Ser Phe Asn Ala Val Thr Ser Leu
    50                  55                  60

Phe Glu Lys Tyr Lys Ile Asp Pro Asn Gln Ile Gly Arg Leu Glu Val
65                  70                  75                  80

Gly Ser Glu Thr Val Ile Asp Lys Ser Lys Ser Ile Lys Thr Phe Leu
                85                  90                  95

Met Gln Leu Phe Glu Lys Cys Gly Asn Thr Asp Val Glu Gly Val Asp
            100                 105                 110

Ser Thr Asn Ala Cys Tyr Gly Gly Thr Ala Ala Leu Leu Asn Cys Val
        115                 120                 125

Asn Trp Val Glu Ser Asn Ser Trp Asp Gly Arg Tyr Gly Leu Val Ile
            130                 135                 140

Cys Thr Asp Ser Ala Val Tyr Ala Glu Gly Pro Ala Arg Pro Thr Gly
145                 150                 155                 160

Gly Ala Ala Ala Ile Ala Met Leu Ile Gly Pro Asp Ala Pro Ile Val
                165                 170                 175

Phe Glu Ser Lys Leu Arg Ala Ser His Met Ala His Val Tyr Asp Phe
            180                 185                 190

Tyr Lys Pro Asn Leu Ala Ser Glu Tyr Pro Val Val Asp Gly Lys Leu
        195                 200                 205

Ser Gln Thr Cys Tyr Leu Met Ala Leu Asp Ser Cys Tyr Lys His Leu
    210                 215                 220

Cys Asn Lys Phe Glu Lys Ile Glu Gly Lys Glu Phe Ser Ile Asn Asp
225                 230                 235                 240

Ala Asp Tyr Ile Val Phe His Ser Pro Tyr Asn Lys Leu Val Gln Lys
                245                 250                 255

Ser Phe Ala Arg Leu Leu Tyr Asn Asp Phe Leu Arg Asn Ala Ser Ser
            260                 265                 270

Ile Asp Glu Ala Ala Lys Glu Lys Phe Thr Pro Tyr Ser Ser Leu Thr
        275                 280                 285

Leu Asp Glu Ser Tyr Gln Ser Arg Asp Leu Glu Lys Val Ser Gln Gln
    290                 295                 300

Ile Ser Lys Pro Phe Tyr Asp Ala Lys Val Gln Pro Thr Thr Leu Ile
305                 310                 315                 320

Pro Lys Glu Val Gly Asn Met Tyr Thr Ala Ser Leu Tyr Ala Ala Phe
                325                 330                 335

Ala Ser Leu Ile His Asn Lys His Asn Asp Leu Ala Gly Lys Arg Val
            340                 345                 350

Val Met Phe Ser Tyr Gly Ser Gly Ser Thr Ala Thr Met Phe Ser Leu
        355                 360                 365

Arg Leu Asn Asp Asn Lys Pro Pro Phe Ser Ile Ser Asn Ile Ala Ser
    370                 375                 380

Val Met Asp Val Gly Gly Lys Leu Lys Ala Arg His Glu Tyr Ala Pro
385                 390                 395                 400

Glu Lys Phe Val Glu Thr Met Lys Leu Met Glu His Arg Tyr Gly Ala
                405                 410                 415

Lys Asp Phe Val Thr Thr Lys Glu Gly Ile Ile Asp Leu Leu Ala Pro
            420                 425                 430

Gly Thr Tyr Tyr Leu Lys Glu Val Asp Ser Leu Tyr Arg Arg Phe Tyr
        435                 440                 445

Gly Lys Lys Gly Glu Asp Gly Ser Val Ala Asn Gly His
    450                 455                 460

<210> SEQ ID NO 5
<211> LENGTH: 482
<212> TYPE: PRT
<213> ORGANISM: Dictyostelium discoideum

<400> SEQUENCE: 5

Met Thr Lys Pro Glu Asn Ile Gly Ile His Gly Ile Glu Val Tyr Phe
1               5                   10                  15

Pro Ser Thr Tyr Val Ala Gln Glu Asp Leu Glu Lys Phe Asp Gly Val
            20                  25                  30

Ser Gln Gly Lys Tyr Thr Leu Gly Leu Gly Gln Thr Asn Met Ala Phe

```
              35                  40                  45
Cys Gly Asp Arg Glu Asp Ile Tyr Ser Leu Ser Leu Asn Ala Val Asn
 50                  55                  60

Asn Leu Met Asp Lys Phe Asn Val Asp Pro Asn Ser Ile Gly Arg Leu
 65                  70                  75                  80

Glu Val Gly Thr Glu Thr Val Ile Asp Lys Ser Lys Ser Val Lys Thr
                 85                  90                  95

Val Leu Met Asp Leu Phe Ala Lys His Gly Asn Thr Ser Ile Asp Gly
                100                 105                 110

Ile Asp Thr Ile Asn Ala Cys Tyr Gly Gly Thr Ser Ala Leu His Asn
                115                 120                 125

Ala Leu Gln Trp Met Glu Ser Ser Tyr Trp Asp Gly Arg Asn Ala Ile
                130                 135                 140

Val Val Ala Gly Asp Ile Ala Val Tyr Glu Lys Gly Pro Ala Arg Pro
145                 150                 155                 160

Thr Gly Gly Ala Gly Val Val Ala Met Leu Ile Gly Pro Asn Ala Pro
                165                 170                 175

Ile Thr Phe Glu Ser Gly Leu Arg Gly Val His Met Glu Asn Val Tyr
                180                 185                 190

Asp Phe Tyr Lys Pro Asp Met Asp Ser Glu Tyr Pro Arg Val Asp Gly
                195                 200                 205

Lys Leu Ser Ile Ser Cys Tyr Phe Arg Ala Ile Asp Asn Cys Tyr Asn
210                 215                 220

Arg Tyr Ala Lys Ala Phe Glu Lys Lys Tyr Gly Lys Ser Phe Ser Leu
225                 230                 235                 240

Asp Gln Val Asp Phe Ala Leu Phe His Ser Pro Tyr Asn Lys Leu Val
                245                 250                 255

Gln Lys Ser Phe Gly Arg Met Leu Tyr Asn Asp Phe Leu Asn Asn Pro
                260                 265                 270

Asn Asp Ser Arg Tyr Ala Ser Leu Glu Ala Tyr Lys Asn Val Lys Pro
                275                 280                 285

Glu Asp Thr Tyr Phe Asp Ser Val Leu Glu Lys Ala Leu Ser Ala Ile
                290                 295                 300

Thr Lys Asn Asp Tyr Ala Thr Lys Val Ala Pro Thr Thr Leu Leu Ala
305                 310                 315                 320

Lys Gln Leu Gly Asn Thr Tyr Cys Gly Ser Thr Tyr Ser Gly Leu Leu
                325                 330                 335

Ser Leu Leu Asp Glu Lys Ser Asn Asp Leu Val Gly Lys Arg Val Leu
                340                 345                 350

Thr Phe Ser Tyr Gly Ser Gly Leu Ala Ala Ser Ala Phe Ser Phe Lys
                355                 360                 365

Val Glu Lys Pro Ile Asn His Ile Val Glu Lys Val Asp Leu Lys Asn
                370                 375                 380

Arg Leu Ala Lys Arg Val Arg Val Glu Pro Glu Ile Phe Thr Glu Lys
385                 390                 395                 400

Leu Ser Leu Arg Glu Thr Arg His Asn Leu Lys Asn Tyr Val Pro Ser
                405                 410                 415

Asp Glu Thr Thr Asn Met Phe Pro Gly Ser Tyr Leu Ser Ser Val
                420                 425                 430

Asp Asn Ala Gly Ile Arg Lys Tyr Asp Arg Tyr Ser Thr Ser Ala
                435                 440                 445

Val Leu Gly Ala Phe Gln Arg Arg Gln Gln Ile Ser Gln Ser Thr Ile
450                 455                 460
```

```
Lys Ser Leu Asn Leu Phe Arg Ala Thr Lys Ser Val Leu Ser Ile Leu
465                 470                 475                 480

Lys Lys

<210> SEQ ID NO 6
<211> LENGTH: 453
<212> TYPE: PRT
<213> ORGANISM: Blattella germanica

<400> SEQUENCE: 6

Met Trp Pro Ser Asp Val Gly Ile Val Ala Leu Glu Leu Ile Phe Pro
1               5                   10                  15

Ser Gln Tyr Val Asp Gln Val Asp Leu Glu Val Tyr Asp Asn Val Ser
            20                  25                  30

Ala Gly Lys Tyr Thr Val Gly Leu Gly Gln Ala Arg Met Gly Phe Cys
        35                  40                  45

Thr Asp Arg Glu Asp Ile Asn Ser Leu Cys Leu Thr Val Val Ser Arg
50                  55                  60

Leu Met Glu Arg Trp Ser Ile Pro Tyr Ser Gln Ile Gly Arg Leu Glu
65                  70                  75                  80

Val Gly Thr Glu Thr Leu Leu Asp Lys Ser Lys Ser Val Lys Thr Val
                85                  90                  95

Leu Met Gln Leu Phe Lys Asp Asn Thr Asp Ile Glu Gly Val Asp Thr
            100                 105                 110

Val Asn Ala Cys Tyr Gly Gly Thr Ser Ala Leu Phe Asn Ala Ile Ser
        115                 120                 125

Trp Val Glu Ser Ser Ser Trp Asp Gly Arg Tyr Ala Leu Val Val Ala
130                 135                 140

Gly Asp Ile Ala Val Tyr Ala Lys Gly Ser Ala Arg Pro Thr Gly Gly
145                 150                 155                 160

Ala Gly Ala Val Ala Met Leu Val Gly Ala Asn Ala Pro Leu Val Phe
                165                 170                 175

Asp Arg Gly Val Arg Ser Ser His Met Gln His Ala Tyr Asp Phe Tyr
            180                 185                 190

Lys Pro Asp Leu Ser Ser Leu Tyr Pro Thr Val Asp Gly Lys Leu Ser
        195                 200                 205

Ile Gln Cys Tyr Leu Ser Ala Leu Asp His Cys Tyr Gln Leu Tyr Cys
210                 215                 220

Ser Lys Ile Gln Lys Gln Leu Gly Glu Lys Phe Asp Ile Glu Arg Leu
225                 230                 235                 240

Asp Ala Val Leu Phe His Ala Pro Tyr Cys Lys Leu Val Gln Lys Ser
                245                 250                 255

Leu Ala Arg Leu Val Leu Asn Asp Phe Val Arg Ala Ser Glu Glu Glu
            260                 265                 270

Arg Thr Thr Lys Tyr Ser Ser Leu Glu Ala Leu Lys Gly Val Lys Leu
        275                 280                 285

Glu Asp Thr Tyr Phe Asp Arg Glu Val Glu Lys Ala Val Met Thr Tyr
290                 295                 300

Ser Lys Asn Met Phe Glu Glu Lys Thr Lys Pro Ser Leu Leu Leu Ala
305                 310                 315                 320

Asn Gln Val Gly Asn Met Tyr Thr Pro Ser Leu Tyr Gly Gly Leu Val
                325                 330                 335

Ser Leu Leu Val Ser Lys Ser Ala Gln Glu Leu Ala Gly Lys Arg Val
            340                 345                 350
```

-continued

```
Ala Leu Phe Ser Tyr Gly Ser Gly Leu Ala Ser Ser Met Phe Ser Leu
            355                 360                 365

Arg Ile Ser Ser Asp Ala Ser Ala Lys Ser Ser Leu Gln Arg Leu Val
            370                 375                 380

Ser Asn Leu Ser His Ile Lys Pro Gln Leu Asp Leu Arg His Lys Val
385                 390                 395                 400

Ser Pro Glu Glu Phe Ala Gln Thr Met Glu Thr Arg Glu His Asn His
                405                 410                 415

His Lys Ala Pro Tyr Thr Pro Glu Gly Ser Ile Asp Val Leu Phe Pro
            420                 425                 430

Gly Thr Trp Tyr Leu Glu Ser Val Asp Ser Leu Tyr Arg Arg Ser Tyr
            435                 440                 445

Lys Gln Val Pro Gly
        450

<210> SEQ ID NO 7
<211> LENGTH: 522
<212> TYPE: PRT
<213> ORGANISM: Gallus gallus

<400> SEQUENCE: 7

Met Pro Gly Ser Leu Pro Val Asn Thr Glu Ser Cys Trp Pro Lys Asp
1               5                   10                  15

Val Gly Ile Val Ala Leu Glu Ile Tyr Phe Pro Ser Gln Tyr Val Asp
                20                  25                  30

Gln Thr Glu Leu Glu Lys Tyr Asp Gly Val Asp Ala Gly Lys Tyr Thr
            35                  40                  45

Ile Gly Leu Gly Gln Ser Lys Met Gly Phe Cys Ser Asp Arg Glu Asp
        50                  55                  60

Ile Asn Ser Leu Cys Leu Thr Val Val Gln Lys Leu Met Glu Arg Asn
65                  70                  75                  80

Ser Leu Ser Tyr Asp Cys Ile Gly Arg Leu Glu Val Gly Thr Glu Thr
                85                  90                  95

Ile Ile Asp Lys Ser Lys Ser Val Lys Thr Val Leu Met Gln Leu Phe
            100                 105                 110

Glu Glu Ser Gly Asn Thr Asp Val Glu Gly Ile Asp Thr Thr Asn Ala
        115                 120                 125

Cys Tyr Gly Gly Thr Ala Ala Leu Phe Asn Ala Ile Asn Trp Ile Glu
    130                 135                 140

Ser Ser Ser Trp Asp Gly Arg Tyr Ala Leu Val Val Ala Gly Asp Ile
145                 150                 155                 160

Ala Val Tyr Ala Thr Gly Asn Ala Arg Pro Thr Gly Gly Ala Gly Ala
                165                 170                 175

Val Ala Met Leu Val Gly Ser Asn Ala Pro Leu Ile Phe Glu Arg Gly
            180                 185                 190

Leu Arg Gly Thr His Met Gln His Ala Tyr Asp Phe Tyr Lys Pro Asp
        195                 200                 205

Met Val Ser Glu Tyr Pro Val Val Asp Gly Lys Leu Ser Ile Gln Cys
    210                 215                 220

Tyr Leu Ser Ala Leu Asp Arg Cys Tyr Ser Val Tyr Arg Asn Lys Ile
225                 230                 235                 240

His Ala Gln Trp Gln Lys Glu Gly Thr Asp Arg Gly Phe Thr Leu Asn
                245                 250                 255

Asp Phe Gly Phe Met Ile Phe His Ser Pro Tyr Cys Lys Leu Val Gln
```

```
                    260                 265                 270
Lys Ser Val Ala Arg Leu Leu Asn Asp Phe Leu Ser Asp Gln Asn
        275                 280                 285
Ala Glu Thr Ala Asn Gly Val Phe Ser Gly Leu Glu Ala Phe Arg Asp
        290                 295                 300
Val Lys Leu Glu Asp Thr Tyr Phe Asp Arg Asp Val Glu Lys Ala Phe
305                 310                 315                 320
Met Lys Ala Ser Ala Glu Leu Phe Asn Gln Lys Thr Lys Ala Ser Leu
                325                 330                 335
Leu Val Ser Asn Gln Asn Gly Asn Met Tyr Thr Pro Ser Val Tyr Gly
        340                 345                 350
Cys Leu Ala Ser Leu Leu Ala Gln Tyr Ser Pro Glu His Leu Ala Gly
        355                 360                 365
Gln Arg Ile Ser Glu Phe Ser Tyr Gly Ser Gly Phe Ala Ala Thr Leu
        370                 375                 380
Tyr Ser Ile Arg Val Thr Gln Asp Ala Thr Pro Gly Ser Ala Leu Asp
385                 390                 395                 400
Lys Ile Thr Ala Ser Leu Ser Asp Leu Lys Ala Arg Leu Asp Ser Arg
                405                 410                 415
Lys Cys Ile Ala Pro Asp Val Phe Ala Glu Asn Met Lys Ile Arg Gln
                420                 425                 430
Glu Thr His His Leu Ala Asn Tyr Ile Pro Gln Cys Ser Val Glu Asp
                435                 440                 445
Leu Phe Glu Gly Thr Trp Tyr Leu Val Arg Val Asp Glu Lys His Arg
        450                 455                 460
Arg Thr Tyr Ala Arg Arg Pro Val Met Gly Asp Gly Pro Leu Glu Ala
465                 470                 475                 480
Gly Val Glu Val Val His Pro Gly Ile Val His Glu His Ile Pro Ser
                485                 490                 495
Pro Ala Lys Lys Val Pro Arg Ile Pro Ala Thr Thr Glu Ser Glu Gly
                500                 505                 510
Val Thr Val Ala Ile Ser Asn Gly Val His
        515                 520

<210> SEQ ID NO 8
<211> LENGTH: 520
<212> TYPE: PRT
<213> ORGANISM: Homo sapiens

<400> SEQUENCE: 8

Met Pro Gly Ser Leu Pro Leu Asn Ala Glu Ala Cys Trp Pro Lys Asp
1               5                   10                  15
Val Gly Ile Val Ala Leu Glu Ile Tyr Phe Pro Ser Gln Tyr Val Asp
                20                  25                  30
Gln Ala Glu Leu Glu Lys Tyr Asp Gly Val Asp Ala Gly Lys Tyr Thr
        35                  40                  45
Ile Gly Leu Gly Gln Ala Lys Met Gly Phe Cys Thr Asp Arg Glu Asp
    50                  55                  60
Ile Asn Ser Leu Cys Met Thr Val Val Gln Asn Leu Met Glu Arg Asn
65                  70                  75                  80
Asn Leu Ser Tyr Asp Cys Ile Gly Arg Leu Glu Val Gly Thr Glu Thr
                85                  90                  95
Ile Ile Asp Lys Ser Lys Ser Val Lys Thr Asn Leu Met Gln Leu Phe
                100                 105                 110
```

```
Glu Glu Ser Gly Asn Thr Asp Ile Glu Gly Ile Asp Thr Thr Asn Ala
            115                 120                 125
Cys Tyr Gly Gly Thr Ala Ala Val Phe Asn Ala Val Asn Trp Ile Glu
            130                 135                 140
Ser Ser Ser Trp Asp Gly Arg Tyr Ala Leu Val Val Ala Gly Asp Ile
145                 150                 155                 160
Ala Val Tyr Ala Thr Gly Asn Ala Arg Pro Thr Gly Val Gly Ala
                165                 170                 175
Val Ala Leu Leu Ile Gly Pro Asn Ala Pro Leu Ile Phe Glu Arg Gly
            180                 185                 190
Leu Arg Gly Thr His Met Gln His Ala Tyr Asp Phe Tyr Lys Pro Asp
            195                 200                 205
Met Leu Ser Glu Tyr Pro Ile Val Asp Gly Lys Leu Ser Ile Gln Cys
            210                 215                 220
Tyr Leu Ser Ala Leu Asp Arg Cys Tyr Ser Val Tyr Cys Lys Lys Ile
225                 230                 235                 240
His Ala Gln Trp Gln Lys Glu Gly Asn Asp Lys Asp Phe Thr Leu Asn
                245                 250                 255
Asp Phe Gly Phe Met Ile Phe His Ser Pro Tyr Cys Lys Leu Val Gln
            260                 265                 270
Lys Ser Leu Ala Arg Met Leu Leu Asn Asp Phe Leu Asn Asp Gln Asn
            275                 280                 285
Arg Asp Lys Asn Ser Ile Tyr Ser Gly Leu Glu Ala Phe Gly Asp Val
            290                 295                 300
Lys Leu Glu Asp Thr Tyr Phe Asp Arg Asp Val Glu Lys Ala Phe Met
305                 310                 315                 320
Lys Ala Ser Ser Glu Leu Phe Ser Gln Lys Thr Lys Ala Ser Leu Leu
                325                 330                 335
Val Ser Asn Gln Asn Gly Asn Met Tyr Thr Ser Ser Val Tyr Gly Ser
            340                 345                 350
Leu Ala Ser Val Leu Ala Gln Tyr Ser Pro Gln Gln Leu Ala Gly Lys
            355                 360                 365
Arg Ile Gly Val Phe Ser Tyr Gly Ser Gly Leu Ala Ala Thr Leu Tyr
            370                 375                 380
Ser Leu Lys Val Thr Gln Asp Ala Thr Pro Gly Ser Ala Leu Asp Lys
385                 390                 395                 400
Ile Thr Ala Ser Leu Cys Asp Leu Lys Ser Arg Leu Asp Ser Arg Thr
                405                 410                 415
Gly Val Ala Pro Asp Val Phe Ala Glu Asn Met Lys Leu Arg Glu Asp
            420                 425                 430
Thr His His Leu Val Asn Tyr Ile Pro Gln Gly Ser Ile Asp Ser Leu
            435                 440                 445
Phe Glu Gly Thr Trp Tyr Leu Val Arg Val Asp Glu Lys His Arg Arg
            450                 455                 460
Thr Tyr Ala Arg Arg Pro Thr Pro Asn Asp Asp Thr Leu Asp Glu Gly
465                 470                 475                 480
Val Gly Leu Val His Ser Asn Ile Ala Thr Glu His Ile Pro Ser Pro
                485                 490                 495
Ala Lys Lys Val Pro Arg Leu Pro Ala Thr Ala Ala Glu Pro Glu Ala
            500                 505                 510
Ala Val Ile Ser Asn Gly Val Trp
            515                 520
```

-continued

```
<210> SEQ ID NO 9
<211> LENGTH: 508
<212> TYPE: PRT
<213> ORGANISM: Homo sapiens

<400> SEQUENCE: 9

Met Gln Arg Leu Leu Thr Pro Val Lys Arg Ile Leu Gln Leu Thr Arg
1               5                   10                  15

Ala Val Gln Glu Thr Ser Leu Thr Pro Ala Arg Leu Leu Pro Val Ala
            20                  25                  30

His Gln Arg Phe Ser Thr Ala Ser Ala Val Pro Leu Ala Lys Thr Asp
        35                  40                  45

Thr Trp Pro Lys Asp Val Gly Ile Leu Ala Leu Glu Val Tyr Phe Pro
    50                  55                  60

Ala Gln Tyr Val Asp Gln Thr Asp Leu Glu Lys Tyr Asn Asn Val Glu
65                  70                  75                  80

Ala Gly Lys Tyr Thr Val Gly Leu Gly Gln Thr Arg Met Gly Phe Cys
                85                  90                  95

Ser Val Gln Glu Asp Ile Asn Ser Leu Cys Leu Thr Val Val Gln Arg
            100                 105                 110

Leu Met Glu Arg Ile Gln Leu Pro Trp Asp Ser Val Gly Arg Leu Glu
        115                 120                 125

Val Gly Thr Glu Thr Ile Ile Asp Lys Ser Lys Ala Val Lys Thr Val
    130                 135                 140

Leu Met Glu Leu Phe Gln Asp Ser Gly Asn Thr Asp Ile Glu Gly Ile
145                 150                 155                 160

Asp Thr Thr Asn Ala Cys Tyr Gly Gly Thr Ala Ser Leu Phe Asn Ala
                165                 170                 175

Ala Asn Trp Met Glu Ser Ser Ser Trp Asp Gly Arg Tyr Ala Met Val
            180                 185                 190

Val Cys Gly Asp Ile Ala Val Tyr Pro Ser Gly Asn Ala Arg Pro Thr
        195                 200                 205

Gly Gly Ala Gly Ala Val Ala Met Leu Ile Gly Pro Lys Ala Pro Leu
    210                 215                 220

Ala Leu Glu Arg Gly Leu Arg Gly Thr His Met Glu Asn Val Tyr Asp
225                 230                 235                 240

Phe Tyr Lys Pro Asn Leu Ala Ser Glu Tyr Pro Ile Val Asp Gly Lys
                245                 250                 255

Leu Ser Ile Gln Cys Tyr Leu Arg Ala Leu Asp Arg Cys Tyr Thr Ser
            260                 265                 270

Tyr Arg Lys Lys Ile Gln Asn Gln Trp Lys Gln Ala Gly Ser Asp Arg
        275                 280                 285

Pro Phe Thr Leu Asp Asp Leu Gln Tyr Met Ile Phe His Thr Pro Phe
    290                 295                 300

Cys Lys Met Val Gln Lys Ser Leu Ala Arg Leu Met Phe Asn Asp Phe
305                 310                 315                 320

Leu Ser Ala Ser Ser Asp Thr Gln Thr Ser Leu Tyr Lys Gly Leu Glu
                325                 330                 335

Ala Phe Gly Gly Leu Lys Leu Glu Asp Thr Tyr Thr Asn Lys Asp Leu
            340                 345                 350

Asp Lys Ala Leu Leu Lys Ala Ser Gln Asp Met Phe Asp Lys Lys Thr
        355                 360                 365

Lys Ala Ser Leu Tyr Leu Ser Thr His Asn Gly Asn Met Tyr Thr Ser
    370                 375                 380
```

```
Ser Leu Tyr Gly Cys Leu Ala Ser Leu Leu Ser His His Ser Ala Gln
385                 390                 395                 400

Glu Leu Ala Gly Ser Arg Ile Gly Ala Phe Ser Tyr Gly Ser Gly Leu
            405                 410                 415

Ala Ala Ser Phe Phe Ser Phe Arg Val Ser Gln Asp Ala Ala Pro Gly
            420                 425                 430

Ser Pro Leu Asp Lys Leu Val Ser Ser Thr Ser Asp Leu Pro Lys Arg
            435                 440                 445

Leu Ala Ser Arg Lys Cys Val Ser Pro Glu Glu Phe Thr Glu Ile Met
450                 455                 460

Asn Gln Arg Glu Gln Phe Tyr His Lys Val Asn Phe Ser Pro Pro Gly
465                 470                 475                 480

Asp Thr Asn Ser Leu Phe Pro Gly Thr Trp Tyr Leu Glu Arg Val Asp
            485                 490                 495

Glu Gln His Arg Arg Lys Tyr Ala Arg Arg Pro Val
            500                 505

<210> SEQ ID NO 10
<211> LENGTH: 468
<212> TYPE: PRT
<213> ORGANISM: Dictyostelium discoideum

<400> SEQUENCE: 10

Met Lys Lys Thr Lys Asp Ile Gly Ile Cys Ala Ile Asp Ile Tyr Phe
1               5                   10                  15

Pro Gln Thr Tyr Val Asn Gln Ser Glu Leu Lys Lys Tyr Asp Lys Val
            20                  25                  30

Ser Asn Gly Lys Tyr Thr Ile Gly Leu Gly Gln Thr Asn Met Ser Phe
        35                  40                  45

Val Gly Asp Arg Glu Asp Ile Val Ser Met Ala Met Thr Ser Val Lys
    50                  55                  60

Met Met Met Ser Lys Tyr Ser Ile Asp Tyr Gln Ser Ile Gly Arg Leu
65                  70                  75                  80

Glu Val Gly Thr Glu Thr Ile Ile Asp Lys Ser Lys Ser Val Lys Ser
                85                  90                  95

Ser Ile Met Ser Leu Phe Gln Glu Tyr Gly Asn Thr Ser Leu Glu Gly
            100                 105                 110

Val Asp Thr Leu Asn Ala Cys Tyr Gly Gly Thr Asn Ala Leu Phe Asn
        115                 120                 125

Ser Leu Gln Trp Ile Glu Ser Ser Tyr Trp Asp Gly Arg Tyr Ala Leu
    130                 135                 140

Val Val Thr Gly Asp Ile Ala Val Tyr Ser Lys Gly Ala Ala Arg Pro
145                 150                 155                 160

Thr Gly Gly Ala Gly Val Val Thr Met Leu Ile Gly Pro Asn Ala Thr
                165                 170                 175

Leu Ile Phe Asp Gln Ser Leu Arg Gly Thr His Met Glu Asn Val Asn
            180                 185                 190

Asp Phe Tyr Lys Pro Asp Leu Ser Ser Glu Tyr Pro Tyr Val Asp Gly
        195                 200                 205

Lys Leu Ser Ile Glu Cys Tyr Leu Arg Ala Leu Asp Lys Cys Tyr Leu
    210                 215                 220

Glu Tyr Lys Lys Lys Phe Glu Ser Ile Asn Asp Asp Asn Lys Phe Ser
225                 230                 235                 240

Met Asp Ser Phe Asp Tyr Val Cys Phe His Ser Pro Tyr Asn Arg Leu
                245                 250                 255
```

```
Val Gln Lys Ser Tyr Ala Arg Leu Ile Tyr Asn Asp Phe Leu Gln Asn
                260                 265                 270

Pro Asn Asn Pro Lys Tyr Gln Asp Leu Leu Pro Phe Lys Asp Leu Ser
                275                 280                 285

Thr Gly Lys Asp Ser Tyr Ile Asn Ser Lys Leu Asp Gln Ile Thr Leu
                290                 295                 300

Lys Leu Ser Leu Asp Asp Phe Lys Thr Lys Val Asn Pro Ser Thr Leu
305                 310                 315                 320

Leu Ser Lys Glu Cys Gly Asn Ser Tyr Cys Gly Ser Val Tyr Ser Gly
                325                 330                 335

Ile Leu Ser Leu Leu Ser Asn Val Asn Asp Leu Asn Asn Lys Lys Val
                340                 345                 350

Leu Val Phe Ser Tyr Gly Ser Gly Leu Ala Ala Ser Leu Phe Ser Phe
                355                 360                 365

Arg Ile Asn Asn Asn Lys Asn Arg Asn Asn Asn Asn Asn Asn Asn Asn
                370                 375                 380

Cys Phe Phe Lys Thr Thr Asn Asp Ile Gly Lys Ile Ser Asn Ile Lys
385                 390                 395                 400

Glu Arg Leu Ser Asn Arg Val Lys Val Ser Pro Glu Glu Phe Thr Arg
                405                 410                 415

Ile Leu Asp Ile Arg Glu Lys Ser His Gln Met Val Gly Ala Arg Thr
                420                 425                 430

Pro Ile Asp Thr Leu Asp Tyr Ile Ser Ala Gly Thr Phe Tyr Leu Glu
                435                 440                 445

Lys Ile Asp Glu Lys Leu Ile Arg His Tyr Lys Ser Lys Pro Ile Ile
                450                 455                 460

Ser Ser Lys Leu
465

<210> SEQ ID NO 11
<211> LENGTH: 388
<212> TYPE: PRT
<213> ORGANISM: Staphylococcus epidermidis

<400> SEQUENCE: 11

Met Asn Ile Gly Ile Asp Lys Ile Ser Phe Tyr Val Pro Lys Tyr Tyr
1               5                   10                  15

Val Asp Met Ala Lys Leu Ala Glu Ala Arg Gln Val Asp Pro Asn Lys
                20                  25                  30

Phe Leu Ile Gly Ile Gly Gln Thr Glu Met Thr Val Ser Pro Val Asn
                35                  40                  45

Gln Asp Ile Val Ser Met Gly Ala Asn Ala Ala Lys Asp Ile Ile Thr
                50                  55                  60

Glu Glu Asp Lys Lys Asn Ile Gly Met Val Ile Val Ala Thr Glu Ser
65                  70                  75                  80

Ala Ile Asp Asn Ala Lys Ala Ala Ala Val Gln Ile His His Leu Leu
                85                  90                  95

Gly Ile Gln Pro Phe Ala Arg Cys Phe Glu Met Lys Glu Ala Cys Tyr
                100                 105                 110

Ala Ala Thr Pro Ala Ile Gln Leu Ala Lys Asp Tyr Leu Ala Gln Arg
                115                 120                 125

Pro Asn Glu Lys Val Leu Val Ile Ala Ser Asp Thr Ala Arg Tyr Gly
                130                 135                 140

Ile His Ser Gly Gly Glu Pro Thr Gln Gly Ala Gly Ala Val Ala Met
```

```
                145                 150                 155                 160
        Met Ile Ser His Asp Pro Ser Ile Leu Lys Leu Asn Asp Ala Val
                        165                 170                 175

Ala Tyr Thr Glu Asp Val Tyr Asp Phe Trp Arg Pro Thr Gly His Gln
                        180                 185                 190

Tyr Pro Leu Val Ala Gly Ala Leu Ser Lys Asp Ala Tyr Ile Lys Ser
                        195                 200                 205

Phe Gln Glu Ser Trp Asn Glu Tyr Ala Arg Arg His Asn Lys Thr Leu
                210                 215                 220

Ala Asp Phe Ala Ser Leu Cys Phe His Val Pro Phe Thr Lys Met Gly
        225                 230                 235                 240

Gln Lys Ala Leu Asp Ser Ile Ile Asn His Ala Asp Glu Thr Thr Gln
                        245                 250                 255

Asp Arg Leu Asn Ser Ser Tyr Gln Asp Ala Val Asp Tyr Asn Arg Tyr
                        260                 265                 270

Val Gly Asn Ile Tyr Thr Gly Ser Leu Tyr Leu Ser Leu Ile Ser Leu
                        275                 280                 285

Leu Glu Thr Arg Asp Leu Lys Gly Gly Gln Thr Ile Gly Leu Phe Ser
                290                 295                 300

Tyr Gly Ser Gly Ser Val Gly Glu Phe Phe Ser Gly Thr Leu Val Asp
        305                 310                 315                 320

Gly Phe Lys Glu Gln Leu Asp Val Glu Arg His Lys Ser Leu Leu Asn
                        325                 330                 335

Asn Arg Ile Glu Val Ser Val Asp Glu Tyr Glu His Phe Phe Lys Arg
                        340                 345                 350

Phe Asp Gln Leu Glu Leu Asn His Glu Leu Glu Lys Ser Asn Ala Asp
                        355                 360                 365

Arg Asp Ile Phe Tyr Leu Lys Ser Ile Asp Asn Asn Ile Arg Glu Tyr
                        370                 375                 380

His Ile Ala Glu
        385

<210> SEQ ID NO 12
<211> LENGTH: 389
<212> TYPE: PRT
<213> ORGANISM: Lactobacillus fermentum

<400> SEQUENCE: 12

Met Lys Ile Gly Ile Asp Lys Leu Ala Phe Ala Thr Thr Pro Tyr Tyr
        1               5                   10                  15

Leu Ala Met Glu Asp Leu Ala Gln Gly Arg Asn Val Asp Pro Asn Lys
                        20                  25                  30

Tyr Leu Ile Gly Ile Gly Gln Ser Lys Gln Ala Val Val Pro Pro Thr
                        35                  40                  45

Gln Asp Val Val Thr Leu Ala Ala Ala Ala Asp Lys Leu Leu Asp
                50                  55                  60

Pro Val Glu Arg Asp Gln Val Ser Thr Val Ile Val Ala Thr Glu Ser
        65                  70                  75                  80

Gly Ile Asp Asn Ser Lys Ala Ala Ala Val Tyr Val Lys His Leu Leu
                        85                  90                  95

Lys Leu Ser Asp Phe Thr Arg Ala Val Glu Val Lys Glu Ala Cys Tyr
                        100                 105                 110

Ser Ala Thr Ala Ala Leu Gln Phe Ala Arg Gly Leu Val Ala Leu Asn
                        115                 120                 125
```

```
Pro Gln Glu Lys Ile Leu Val Ile Ala Ser Asp Ile Ala Arg Tyr Gly
        130                 135                 140

Leu Glu Thr Gly Gly Glu Val Thr Gln Gly Ala Gly Val Ala Met
145                 150                 155                 160

Leu Ile Thr Ala Asn Pro Arg Val Leu Ala Ile Glu Pro Thr Ser Val
                    165                 170                 175

Ala Tyr Thr Lys Asp Val Met Asp Phe Trp Arg Pro Leu Tyr Ala Glu
                180                 185                 190

Glu Ala Leu Val Asn Gly Lys Tyr Ser Thr Asn Val Tyr Ile Asp Phe
            195                 200                 205

Phe Lys Gln Cys Trp Thr Arg Tyr Gln Gln Leu Ala Gly Tyr Gly Leu
210                 215                 220

Glu Asp Phe Ala Ala Leu Ala Phe His Leu Pro Phe Thr Lys Met Gly
225                 230                 235                 240

Lys Lys Ala Leu Glu Ala Glu Leu Gly Asp Arg Asp Gln Val Ala
                245                 250                 255

Thr Arg Leu Arg Ala Asn Leu Thr Ala Gly Gln Glu Ala Cys Arg Gln
                260                 265                 270

Val Gly Asn Leu Tyr Thr Gly Ser Leu Tyr Leu Gly Leu Met Ser Leu
                275                 280                 285

Leu Thr Glu Gly Asp Val Lys Pro Gly Glu Arg Ile Gly Leu Phe Ser
290                 295                 300

Tyr Gly Ser Gly Ala Glu Gly Glu Phe Phe Ala Gly Ile Leu Gln Pro
305                 310                 315                 320

Gly Tyr Gln Glu Gly Leu Gly Asp Leu Asn Glu Gln Leu Ala Ala Arg
                325                 330                 335

Thr Gln Val Ser Leu Ala Glu Tyr Glu Asp Leu Phe Asn Gln Gln Leu
                340                 345                 350

Gly Leu Lys Glu Glu Asp Val Thr Phe Lys Thr Pro Ala Ala Gly Gln
            355                 360                 365

Arg Phe Val Leu Val Gly Gln Lys Asp His Gln Arg Gln Tyr Arg Asp
    370                 375                 380

Leu Ala Glu Arg Asp
385

<210> SEQ ID NO 13
<211> LENGTH: 351
<212> TYPE: PRT
<213> ORGANISM: Hyperthermus butylicus

<400> SEQUENCE: 13

Met Pro Arg Gly Ser Gly Ile Val Gly Trp Gly Gly Tyr Val Pro Arg
1               5                   10                  15

Tyr Arg Ile Lys Ala Ala Glu Ile Val Arg Val Trp Gly Trp Glu Pro
                20                  25                  30

Ser Val Pro Ala Gly Leu Gly Val Lys Glu Lys Ala Val Glu Asn Val
                35                  40                  45

Asp Glu Asp Ser Val Thr Met Gly Tyr Glu Ala Ala Arg Asn Ala Ile
50                  55                  60

Ala Arg Ala Asn Val Asp Pro Arg Glu Ile Lys Ala Val Phe Phe Gly
65                  70                  75                  80

Thr Glu Ser Lys Pro Tyr Ala Val Lys Pro Ser Ala Thr Ile Ile Ala
                85                  90                  95

Glu Ala Leu Gly Ile Thr Pro Glu Thr Met Ala Ser Asp Leu Glu Phe
                100                 105                 110
```

Ala Cys Arg Ala Ala Ser Glu Gly Leu Arg Ala Ser Leu Ala Leu Val
            115                 120                 125

Glu Ala Gly Tyr Met Lys Tyr Ala Leu Val Val Ala Ser Asp Thr Ala
    130                 135                 140

Gln Ala Asn Pro Gly Asp Val Leu Glu Phe Thr Ala Ala Ser Gly Ala
145                 150                 155                 160

Ala Ala Phe Val Val Gly Pro Ala Ser Glu Ser Val Ala Val Leu Glu
                165                 170                 175

Gly Val Tyr Thr Tyr Val Thr Asp Thr Pro Asp Phe Trp Arg Gly Gln
            180                 185                 190

His Ser Arg Tyr Pro Met His Gly Glu Ala Phe Thr Gly Glu Pro Ala
            195                 200                 205

Tyr Phe His His Ile Glu Ser Ala Val Lys Gly Leu Met Glu Lys Leu
            210                 215                 220

Gly Leu Lys Pro Glu Asp Phe Asp Tyr Ala Val Phe His Gln Pro Asn
225                 230                 235                 240

Gly Lys Phe Pro Leu Arg Val Gly Ala Arg Leu Gly Phe Pro Lys Glu
                245                 250                 255

Lys Ile Leu Pro Gly Leu Leu Thr Pro Ile Ile Gly Asn Thr Tyr Asn
            260                 265                 270

Ala Ser Ala Leu Leu Gly Phe Ala Arg Ile Leu Asp Gln Ala Lys Pro
            275                 280                 285

Gly Gln Arg Ile Leu Val Ala Pro Phe Gly Ser Gly Ala Gly Ser Asp
            290                 295                 300

Ala Tyr Ser Phe Ile Val Thr Asp Arg Ile Glu Ala Arg Asn Arg
305                 310                 315                 320

Ala Pro Lys Val Asp Asp Tyr Val Asn Trp Lys Arg Tyr Ile Asp Tyr
                325                 330                 335

Ala Met His Ala Arg Met Arg Lys Leu Tyr Asp Arg Arg Pro Val
            340                 345                 350

<210> SEQ ID NO 14
<211> LENGTH: 349
<212> TYPE: PRT
<213> ORGANISM: Chloroflexus aggregans

<400> SEQUENCE: 14

Met Met Lys Pro Asn Gln Pro Val Gly Ile Ile Gly Tyr Gly Val Tyr
1               5                   10                  15

Ile Pro Arg Tyr Arg Ile Ala Ala Arg Glu Ile Ala Arg Ile Trp Thr
            20                  25                  30

Asp Gly Gln Asn Gly Val Pro Val Glu Ala Lys Ser Val Pro Gly Pro
        35                  40                  45

Asp Glu Asp Thr Ile Thr Met Ala Ile Glu Ala Ala Arg Asn Ala Leu
    50                  55                  60

Val Arg Ala Asp Ile Pro Ala Ser Ala Leu Gly Ala Val Trp Ile Gly
65                  70                  75                  80

Ser Glu Ser His Pro Tyr Ser Val Lys Pro Ser Gly Thr Val Val Ala
                85                  90                  95

Asp Ala Leu Gly Ala Gly Pro Trp Val Ser Ala Ala Asp Trp Glu Phe
            100                 105                 110

Ala Cys Lys Ala Gly Ser Glu Ala Leu Thr Ala Ala Met Ala Leu Val
            115                 120                 125

Gly Ser Gly Met Gln Arg Tyr Ala Leu Ala Ile Gly Ala Asp Thr Ala

```
            130                 135                 140
Gln Gly Arg Pro Gly Asp Ala Leu Glu Tyr Thr Ala Ser Ala Gly Ala
145                 150                 155                 160

Ala Ala Leu Ile Val Gly Pro Ala Thr Glu Ala Leu Ala Thr Ile Asp
                165                 170                 175

Ala Thr Val Ser Tyr Val Thr Asp Thr Pro Asp Phe Tyr Arg Arg Ala
                180                 185                 190

Asp Arg Pro Tyr Pro Val His Gly Asn Arg Phe Thr Gly Glu Pro Ala
                195                 200                 205

Tyr Phe His Gln Ile Gln Ser Ala Ala Ser Glu Leu Leu Arg Gln Leu
                210                 215                 220

Asn Arg Thr Ala Ala Asp Phe Thr Tyr Ala Val Phe His Gln Pro Asn
225                 230                 235                 240

Ala Lys Phe Pro Gln Thr Val Ala Lys Arg Leu Gly Phe Thr Asp Ala
                245                 250                 255

Gln Ile Ala Pro Gly Leu Leu Ser Pro Gln Ile Gly Asn Thr Tyr Ser
                260                 265                 270

Gly Ala Ala Leu Leu Gly Leu Cys Ala Ile Leu Asp Val Ala Lys Pro
                275                 280                 285

Gly Asp Thr Ile Phe Val Thr Ser Tyr Gly Ser Gly Ala Gly Ser Asp
                290                 295                 300

Ala Tyr Ala Leu Thr Val Thr Glu Ala Ile Val Glu Arg Arg Glu Arg
305                 310                 315                 320

Ala Pro Leu Thr Ala Ala Tyr Leu Ala Arg Lys Val Met Ile Asp Tyr
                325                 330                 335

Ala Met Tyr Ala Lys Trp Arg Gly Lys Leu Val Met Gly
                340                 345

<210> SEQ ID NO 15
<211> LENGTH: 387
<212> TYPE: PRT
<213> ORGANISM: Lactobacillus delbrueckii

<400> SEQUENCE: 15

Met Asp Ile Gly Ile Asp Gln Ile Gly Phe Tyr Thr Pro Asn Lys Phe
1               5                   10                  15

Val Asp Met Val Asp Leu Ala Asn Ala Arg Asn Gln Asp Pro Asn Lys
                20                  25                  30

Phe Leu Ile Gly Ile Gly Gln Asp Arg Met Ala Val Ala Asp Lys Thr
                35                  40                  45

Gln Asp Ala Val Ser Met Gly Ile Asn Ala Thr Ala Glu Tyr Leu Asp
                50                  55                  60

Gln Val Asp Leu Glu Gln Leu Gly Leu Leu Ile Phe Ala Thr Glu Ser
65                  70                  75                  80

Gly Ile Asp Gln Ser Lys Ser Ala Ser Leu Phe Val Lys Glu Ala Leu
                85                  90                  95

Asn Leu Pro Ala Arg Ile Arg Thr Phe Glu Ile Lys Glu Ala Cys Phe
                100                 105                 110

Ala Leu Thr Ala Ser Leu Gln Val Ala Arg Asp Tyr Val Arg Ala His
                115                 120                 125

Pro His His Ser Ala Met Ile Ile Gly Ser Asp Ile Ala Arg Tyr Gly
                130                 135                 140

Leu Ala Thr Ala Gly Glu Val Thr Gln Gly Ala Gly Ala Ile Ser Met
145                 150                 155                 160
```

```
Leu Ile Lys Glu Asn Pro Ala Ile Ile Ala Leu Glu Asp Gly His Thr
            165                 170                 175

Ser His Ser Glu Asn Ile Asn Asp Phe Trp Pro Asn Asn Leu Ala
        180                 185                 190

Thr Ala Val Val Asp Gly His Tyr Ser Arg Asp Val Tyr Leu Asp Phe
            195                 200                 205

Phe Lys Ser Thr Phe Lys Pro Phe Leu Ala Glu Lys Gln Leu Gln Val
        210                 215                 220

Ser Asp Phe Ala Gly Ile Cys Tyr His Leu Pro Tyr Thr Lys Met Gly
225                 230                 235                 240

Tyr Lys Ala His Lys Ile Ala Ile Glu Gly Gln Asp Asp Glu Thr Val
                245                 250                 255

Lys Arg Leu Ser Asp Asn Phe Gln Leu Ser Ala Lys Tyr Ser Arg Gln
            260                 265                 270

Val Gly Asn Ile Tyr Thr Ala Ser Leu Tyr Met Ser Val Leu Ser Leu
        275                 280                 285

Leu Glu Asn Gly Asp Leu Glu Ala Gly Asp Arg Ile Gly Phe Phe Ser
        290                 295                 300

Tyr Gly Ser Gly Ala Met Ala Glu Phe Phe Ser Gly Lys Val Val Ala
305                 310                 315                 320

Gly Tyr Gln Lys Arg Leu Arg Pro Ala Leu His Ala Arg Met Leu Lys
                325                 330                 335

Glu Arg Ile Arg Leu Gly Val Gly Gln Tyr Glu Asp Ile Phe Thr Glu
            340                 345                 350

Gly Leu Glu Ala Leu Pro Glu Asn Val Glu Phe Thr Ser Asp Ala Asn
        355                 360                 365

His Gly Thr Trp Tyr Leu Ala Gly Gln Glu Gly Tyr Val Arg Gln Tyr
        370                 375                 380

Lys Gln Lys
385

<210> SEQ ID NO 16
<211> LENGTH: 388
<212> TYPE: PRT
<213> ORGANISM: Staphylococcus haemolyticus

<400> SEQUENCE: 16

Met Ser Ile Gly Ile Asp Lys Ile Asn Phe Tyr Val Pro Lys Tyr Tyr
1               5                   10                  15

Val Asp Met Ala Lys Leu Ala Glu Ala Arg Gln Val Asp Pro Asn Lys
            20                  25                  30

Phe Leu Ile Gly Ile Gly Gln Thr Gln Met Ala Val Ser Pro Val Ser
        35                  40                  45

Gln Asp Ile Val Ser Met Gly Ala Asn Ala Ala Lys Asp Ile Ile Thr
    50                  55                  60

Asp Asp Asp Lys Lys His Ile Gly Met Val Ile Val Ala Thr Glu Ser
65                  70                  75                  80

Ala Ile Asp Asn Ala Lys Ala Ala Val Gln Ile His Asn Leu Leu
                85                  90                  95

Gly Val Gln Pro Phe Ala Arg Cys Phe Glu Met Lys Glu Ala Cys Tyr
            100                 105                 110

Ala Ala Thr Pro Ala Ile Gln Leu Ala Lys Asp Tyr Ile Glu Lys Arg
        115                 120                 125

Pro Asn Glu Lys Val Leu Val Ile Ala Ser Asp Thr Ala Arg Tyr Gly
    130                 135                 140
```

Ile Gln Ser Gly Gly Glu Pro Thr Gln Gly Ala Gly Val Ala Met
145                 150                 155                 160

Leu Ile Ser Asn Asn Pro Ser Ile Leu Glu Leu Asn Asp Asp Ala Val
            165                 170                 175

Ala Tyr Thr Glu Asp Val Tyr Asp Phe Trp Arg Pro Thr Gly His Lys
        180                 185                 190

Tyr Pro Leu Val Ala Gly Ala Leu Ser Lys Asp Ala Tyr Ile Lys Ser
            195                 200                 205

Phe Gln Glu Ser Trp Asn Glu Tyr Ala Arg Arg Glu Asp Lys Thr Leu
210                 215                 220

Ser Asp Phe Glu Ser Leu Cys Phe His Val Pro Phe Thr Lys Met Gly
225                 230                 235                 240

Lys Lys Ala Leu Asp Ser Ile Ile Asn Asp Ala Asp Glu Thr Thr Gln
            245                 250                 255

Glu Arg Leu Thr Ser Gly Tyr Glu Asp Ala Val Tyr Tyr Asn Arg Tyr
        260                 265                 270

Val Gly Asn Ile Tyr Thr Gly Ser Leu Tyr Leu Ser Leu Ile Ser Leu
            275                 280                 285

Leu Glu Asn Arg Ser Leu Lys Gly Gly Gln Thr Ile Gly Leu Phe Ser
290                 295                 300

Tyr Gly Ser Gly Ser Val Gly Glu Phe Phe Ser Ala Thr Leu Val Glu
305                 310                 315                 320

Gly Tyr Glu Lys Gln Leu Asp Ile Glu Gly His Lys Ala Leu Leu Asn
            325                 330                 335

Glu Arg Gln Glu Val Ser Val Glu Asp Tyr Glu Ser Phe Phe Lys Arg
        340                 345                 350

Phe Asp Asp Leu Glu Phe Asp His Ala Thr Glu Gln Thr Asp Asp Asp
            355                 360                 365

Lys Ser Ile Tyr Tyr Leu Glu Asn Ile Gln Asp Asp Ile Arg Gln Tyr
        370                 375                 380

His Ile Pro Lys
385

<210> SEQ ID NO 17
<211> LENGTH: 420
<212> TYPE: PRT
<213> ORGANISM: Bacillus subtilis

<400> SEQUENCE: 17

Met Val Ser Ala Gly Ile Glu Ala Met Asn Val Phe Gly Gly Thr Ala
1               5                   10                  15

Tyr Leu Asp Val Met Glu Leu Ala Lys Tyr Arg His Leu Asp Thr Ala
            20                  25                  30

Arg Phe Glu Asn Leu Leu Met Lys Glu Lys Ala Val Ala Leu Pro Tyr
        35                  40                  45

Glu Asp Pro Val Thr Phe Gly Val Asn Ala Ala Lys Pro Ile Ile Asp
    50                  55                  60

Ala Leu Ser Glu Ala Glu Lys Asp Arg Ile Glu Leu Leu Ile Thr Cys
65                  70                  75                  80

Ser Glu Ser Gly Ile Asp Phe Gly Lys Ser Leu Ser Thr Tyr Ile His
                85                  90                  95

Glu Tyr Leu Gly Leu Asn Arg Asn Cys Arg Leu Phe Glu Val Lys Gln
            100                 105                 110

Ala Cys Tyr Ser Gly Thr Ala Gly Phe Gln Met Ala Val Asn Phe Ile

```
                115                 120                 125
Leu Ser Gln Thr Ser Pro Gly Ala Lys Ala Leu Val Ile Ala Ser Asp
    130                 135                 140

Ile Ser Arg Phe Leu Ile Ala Glu Gly Gly Asp Ala Leu Ser Glu Asp
145                 150                 155                 160

Trp Ser Tyr Ala Glu Pro Ser Ala Gly Ala Gly Ala Val Ala Val Leu
                165                 170                 175

Val Gly Glu Asn Pro Glu Val Phe Gln Ile Asp Pro Gly Ala Asn Gly
            180                 185                 190

Tyr Tyr Gly Tyr Glu Val Met Asp Thr Cys Arg Pro Ile Pro Asp Ser
        195                 200                 205

Glu Ala Gly Asp Ser Asp Leu Ser Leu Met Ser Tyr Leu Asp Cys Cys
    210                 215                 220

Gln Gln Thr Phe Leu Glu Tyr Gln Lys Arg Val Pro Gly Ala Asn Tyr
225                 230                 235                 240

Gln Asp Thr Phe Gln Tyr Leu Ala Tyr His Thr Pro Phe Gly Gly Met
                245                 250                 255

Val Lys Gly Ala His Arg Thr Met Met Arg Lys Val Ala Lys Val Lys
            260                 265                 270

Thr Ser Gly Ile Glu Thr Asp Phe Leu Thr Arg Val Lys Pro Gly Leu
        275                 280                 285

Asn Tyr Cys Gln Arg Val Gly Asn Ile Met Gly Ala Ala Leu Phe Leu
    290                 295                 300

Ala Leu Ala Ser Thr Ile Asp Gln Gly Arg Phe Asp Thr Pro Lys Arg
305                 310                 315                 320

Ile Gly Cys Phe Ser Tyr Gly Ser Gly Cys Cys Ser Glu Phe Tyr Ser
                325                 330                 335

Gly Ile Thr Thr Pro Gln Gly Gln Glu Arg Gln Arg Thr Phe Gly Ile
            340                 345                 350

Glu Lys His Leu Asp Arg Arg Tyr Gln Leu Ser Met Glu Glu Tyr Glu
        355                 360                 365

Leu Leu Phe Lys Gly Ser Gly Met Val Arg Phe Gly Thr Arg Asn Val
    370                 375                 380

Lys Leu Asp Phe Glu Met Ile Pro Gly Ile Met Gln Ser Thr Gln Glu
385                 390                 395                 400

Lys Pro Arg Leu Phe Leu Glu Glu Ile Ser Glu Phe His Arg Lys Tyr
                405                 410                 415

Arg Trp Ile Ser
            420

<210> SEQ ID NO 18
<211> LENGTH: 388
<212> TYPE: PRT
<213> ORGANISM: Mycobacterium marinum

<400> SEQUENCE: 18

Met Val Ser Ile Gly Ile His Asp Leu Ser Ile Ala Thr Ala His Tyr
1               5                   10                  15

Val Leu Asp His Ala Thr Leu Ala Glu His His Gly Val Asp Val Asn
            20                  25                  30

Lys Tyr Leu Ile Gly Leu Gly Gln Gln Gln Met Ser Ile Val Ala Pro
        35                  40                  45

Asp Glu Asp Ile Val Thr Leu Ala Ala Ala Ala Asp Pro Ile Ile
    50                  55                  60
```

```
Lys Arg His Gly Ser Gln Lys Ile Arg Thr Ile Val Ile Gly Thr Glu
 65                  70                  75                  80

Thr Gly Val Asp Gln Ser Lys Ser Ala Gly Ile Trp Val Ser Ser Leu
                 85                  90                  95

Leu Gly Leu Pro Ser Ser Ala Arg Val Leu Glu Val Lys Gln Ala Cys
            100                 105                 110

Tyr Gly Ala Thr Gly Ala Leu Gln Leu Ala Leu Ala Leu Val His Arg
        115                 120                 125

Asp Pro Thr Gln Gln Val Leu Val Ile Ala Ala Asp Val Ala Arg Tyr
    130                 135                 140

Asp Leu Asp Ser Pro Gly Glu Pro Thr Gln Gly Ala Ala Ala Ala Ala
145                 150                 155                 160

Met Leu Val Ser Ala Asp Pro Ala Leu Leu Arg Leu Glu Glu Pro Thr
                165                 170                 175

Gly Ile Tyr Thr Ala Asp Ile Met Asp Phe Trp Arg Pro Asn Tyr Arg
            180                 185                 190

Ser Thr Ala Leu Val Asp Gly Lys Ala Ser Val Thr Ala Tyr Met Glu
        195                 200                 205

Ala Ala Ser Gly Ala Trp Lys Asp Tyr Thr Glu Arg Gly Gly Arg Ala
    210                 215                 220

Phe Gly Glu Phe Ala Ala Phe Cys Tyr His Gln Pro Phe Thr Lys Met
225                 230                 235                 240

Ala Tyr Lys Ala His Lys Gln Leu Ala Ala Glu Ala Gly Glu Asp Ala
                245                 250                 255

Ser Gly Ala Ala Val Gln Ala Ala Val Gly Asn Thr Val Glu Tyr Asn
            260                 265                 270

Arg Arg Ile Gly Asn Ser Tyr Thr Ala Ser Leu Tyr Leu Ala Leu Ala
        275                 280                 285

Ala Leu Leu Asp Gln Ala Asp Asp Leu Ser Asp Gln Pro Ile Ala Met
    290                 295                 300

Leu Ser Tyr Gly Ser Gly Cys Val Ala Glu Leu Phe Ala Gly Thr Val
305                 310                 315                 320

Thr Pro Gly Tyr Gln Gln His Leu Arg Thr Asp Gln His Arg Ala Ala
                325                 330                 335

Leu Glu Thr Arg Ile Pro Leu Ser Tyr Glu His Tyr Arg Arg Leu His
            340                 345                 350

Asn Leu Thr Leu Pro Thr Asn Gly Asn His His Ser Leu Pro Val Glu
        355                 360                 365

Thr Ser Arg Pro Phe Arg Leu Thr Ala Ile Ser Glu His Lys Arg Met
    370                 375                 380

Tyr Gly Ala Val
385

<210> SEQ ID NO 19
<211> LENGTH: 435
<212> TYPE: PRT
<213> ORGANISM: Zea mays

<400> SEQUENCE: 19

Met Leu Ala Ala Ser Thr Lys Val Gly Ser Arg Leu Ala Ser Pro His
 1               5                  10                  15

Ala Ser Leu Ser Ala Gly Ala Ala Ala Ala Leu Ala Ser Ser Pro
            20                  25                  30

Val Leu Gly Ser Gly Met Leu Pro Gly Ala Gly Phe Gly Glu Thr Gly
        35                  40                  45
```

```
Asn His His Ala Ala Asp Ala Pro Pro Leu Pro Cys Ser Ser Ser
         50                  55                  60

Gly Asp Ser Arg Glu Tyr Tyr Gln Trp Lys Arg Leu Val Asn Gln Arg
 65                  70                  75                  80

Gln Ser Thr Leu His Val Gly Glu Val Pro Ala Leu Gly His His
                 85                  90                  95

Val Phe Gly Ala Gly Cys Ser Ser Arg Lys Gln His Ile Tyr Arg Tyr
                100                 105                 110

Phe Ser Ser Ser His Gln Gly Ser Ile Trp Ala Arg Ser Lys Ile
                115                 120                 125

Leu His Asp Leu Pro Gly Tyr Val Lys Ile Val Glu Val Gly Pro Arg
130                 135                 140

Asp Gly Leu Gln Asn Glu Lys Asp Ile Val Pro Thr Pro Val Lys Val
145                 150                 155                 160

Glu Leu Ile Arg Arg Leu Ala Thr Ser Gly Leu Pro Val Val Glu Ala
                165                 170                 175

Thr Ser Phe Val Ser Pro Lys Trp Val Pro Gln Leu Ala Asp Ala Lys
                180                 185                 190

Asp Val Met Glu Ala Val Arg Thr Ile Gly Gly Val Arg Phe Pro Val
                195                 200                 205

Leu Thr Pro Asn Leu Lys Gly Phe Glu Ala Ala Ile Ala Ala Gly Ala
210                 215                 220

Lys Glu Ile Ala Ile Phe Ala Ser Ala Ser Glu Gly Phe Ser Lys Ser
225                 230                 235                 240

Asn Ile Asn Cys Thr Ile Lys Glu Ser Ile Ala Arg Tyr Asn Asp Val
                245                 250                 255

Ala Leu Ala Ala Lys Glu Lys Glu Ile Pro Val Arg Gly Tyr Val Ser
                260                 265                 270

Cys Val Val Gly Cys Pro Val Asp Gly Pro Val Pro Pro Ser Asn Val
                275                 280                 285

Ala Tyr Val Ala Lys Glu Leu Tyr Asp Met Gly Cys Tyr Glu Val Ser
                290                 295                 300

Leu Gly Asp Thr Ile Gly Val Gly Thr Pro Gly Thr Val Val Pro Met
305                 310                 315                 320

Leu Glu Ala Ala Ile Ser Val Val Pro Val Glu Lys Leu Ala Val His
                325                 330                 335

Phe His Asp Thr Tyr Gly Gln Ser Leu Ser Asn Ile Leu Ile Ser Leu
                340                 345                 350

Gln Met Gly Val Ser Val Val Asp Ser Ser Val Ala Gly Leu Gly Gly
                355                 360                 365

Cys Pro Tyr Ala Lys Gly Ala Ser Gly Asn Val Ala Thr Glu Asp Val
                370                 375                 380

Val Tyr Met Leu Asn Gly Leu Gly Val Lys Thr Gly Val Asp Leu Gly
385                 390                 395                 400

Lys Val Met Ala Ala Gly Glu Phe Ile Cys Arg His Leu Gly Arg Gln
                405                 410                 415

Ser Gly Ser Lys Ala Ala Thr Ala Leu Ser Lys Val Thr Ala Asn Ala
                420                 425                 430

Ser Lys Leu
        435

<210> SEQ ID NO 20
<211> LENGTH: 335
```

```
<212> TYPE: PRT
<213> ORGANISM: Danio rerio
<220> FEATURE:
<223> OTHER INFORMATION: Danio rerio (Brachydanio rerio)

<400> SEQUENCE: 20
```

Met Gly Asn Val Ser Ser Ala Val Lys His Cys Leu Ser Tyr Glu Thr
1               5                   10                  15

Phe Leu Arg Asp Tyr Pro Trp Leu Pro Arg Leu Leu Trp Glu Glu Lys
            20                  25                  30

Cys Ser Glu Leu Pro Lys Leu Pro Val Tyr Val Lys Ile Val Glu Val
        35                  40                  45

Gly Pro Arg Asp Gly Leu Gln Asn Glu Lys Glu Ile Val Pro Thr Glu
    50                  55                  60

Val Lys Ile Gln Leu Ile Asp Leu Leu Ser Gln Thr Gly Leu Pro Val
65                  70                  75                  80

Ile Glu Ala Thr Ser Phe Val Ser Ser Lys Trp Val Ala Gln Met Ala
                85                  90                  95

Asp His Thr Ala Val Leu Lys Gly Ile Lys Arg Ser Pro Asp Val Arg
            100                 105                 110

Tyr Pro Val Leu Thr Pro Asn Ile Gln Gly Phe Gln Ala Ala Val Ala
        115                 120                 125

Ala Gly Ala Asn Glu Val Ala Val Phe Gly Ser Ala Ser Glu Thr Phe
    130                 135                 140

Ser Arg Lys Asn Ile Asn Cys Ser Ile Glu Glu Ser Leu Gln Arg Phe
145                 150                 155                 160

Glu Gln Val Val Ser Ala Ala Lys Gln Glu Gly Ile Pro Val Arg Gly
                165                 170                 175

Tyr Val Ser Cys Ala Leu Gly Cys Pro Tyr Glu Gly Gln Val Lys Pro
            180                 185                 190

Ser Gln Val Thr Lys Val Ala Lys Arg Leu Phe Glu Leu Gly Cys Tyr
        195                 200                 205

Glu Val Ser Leu Gly Asp Thr Ile Gly Val Gly Thr Ala Gly Ser Met
    210                 215                 220

Ala Glu Met Leu Ser Asp Val Leu Thr Glu Val Pro Ala Gly Ala Leu
225                 230                 235                 240

Ala Val His Cys His Asp Thr Tyr Gly Gln Ala Leu Pro Asn Ile Leu
                245                 250                 255

Ile Ala Leu Gln Met Gly Val Ser Val Val Asp Ala Ser Val Ala Gly
            260                 265                 270

Leu Gly Gly Cys Pro Phe Ala Lys Gly Ala Ser Gly Asn Val Ser Thr
        275                 280                 285

Glu Asp Leu Leu Tyr Met Leu His Gly Leu Gly Ile Glu Thr Gly Val
    290                 295                 300

Asp Leu Leu Lys Val Met Glu Ala Gly Asp Phe Ile Cys Lys Ala Leu
305                 310                 315                 320

Asn Arg Lys Thr Asn Ser Lys Val Ser Gln Ala Thr Arg Asn Asn
                325                 330                 335

```
<210> SEQ ID NO 21
<211> LENGTH: 325
<212> TYPE: PRT
<213> ORGANISM: Bos taurus

<400> SEQUENCE: 21
```

Met Ala Thr Val Lys Lys Val Leu Pro Arg Arg Leu Val Gly Leu Ala

```
  1               5                  10                 15
Thr Leu Arg Ala Val Ser Thr Ser Val Gly Thr Phe Pro Lys Gln
            20                  25                 30
Val Lys Ile Val Glu Val Gly Pro Arg Asp Gly Leu Gln Asn Glu Lys
            35                  40                 45
Asn Ile Val Pro Thr Pro Val Lys Ile Lys Leu Ile Asp Met Leu Ser
 50                  55                 60
Glu Ala Gly Leu Pro Val Val Glu Ala Thr Ser Phe Val Ser Pro Lys
 65                  70                 75                 80
Trp Val Pro Gln Met Ala Asp His Ala Glu Val Leu Lys Gly Ile Gln
                85                  90                 95
Lys Phe Pro Gly Val Asn Tyr Pro Val Leu Thr Pro Asn Phe Lys Gly
            100                 105                110
Phe Gln Ala Ala Val Ala Ala Gly Ala Lys Glu Val Ala Ile Phe Gly
            115                 120                125
Ala Ala Ser Glu Leu Phe Thr Lys Lys Asn Ile Asn Cys Ser Ile Asp
            130                 135                140
Glu Ser Leu Gln Arg Phe Asp Glu Ile Leu Lys Ala Ala Arg Ala Ala
145                 150                 155                160
Gly Ile Ser Val Arg Gly Tyr Val Ser Cys Val Leu Gly Cys Pro Tyr
                165                 170                175
Glu Gly Lys Ile Ser Pro Ala Lys Val Ala Glu Val Thr Lys Lys Leu
            180                 185                190
Tyr Ser Met Gly Cys Tyr Glu Ile Ser Leu Gly Asp Thr Ile Gly Val
                195                 200                205
Gly Thr Pro Gly Ala Met Lys Asp Met Leu Ser Ala Val Leu Gln Glu
            210                 215                220
Val Pro Val Thr Ala Leu Ala Val His Cys His Asp Thr Tyr Gly Gln
225                 230                 235                240
Ala Leu Ala Asn Thr Leu Thr Ala Leu Gln Met Gly Val Ser Val Met
                245                 250                255
Asp Ser Ser Val Ala Gly Leu Gly Gly Cys Pro Tyr Ala Gln Gly Ala
                260                 265                270
Ser Gly Asn Leu Ala Thr Glu Asp Leu Val Tyr Met Leu Ala Gly Leu
            275                 280                285
Gly Ile His Thr Gly Val Asn Leu Gln Lys Leu Leu Glu Ala Gly Ala
            290                 295                300
Phe Ile Cys Gln Ala Leu Asn Arg Arg Thr Asn Ser Lys Val Ala Gln
305                 310                 315                320
Ala Thr Cys Lys Leu
            325

<210> SEQ ID NO 22
<211> LENGTH: 325
<212> TYPE: PRT
<213> ORGANISM: Homo sapiens

<400> SEQUENCE: 22

Met Ala Ala Met Arg Lys Ala Leu Pro Arg Arg Leu Val Gly Leu Ala
 1               5                  10                 15
Ser Leu Arg Ala Val Ser Thr Ser Ser Met Gly Thr Leu Pro Lys Arg
            20                  25                 30
Val Lys Ile Val Glu Val Gly Pro Arg Asp Gly Leu Gln Asn Glu Lys
            35                  40                 45
```

```
Asn Ile Val Ser Thr Pro Val Lys Ile Lys Leu Ile Asp Met Leu Ser
 50                  55                  60

Glu Ala Gly Leu Ser Val Ile Glu Thr Thr Ser Phe Val Ser Pro Lys
 65                  70                  75                  80

Trp Val Pro Gln Met Gly Asp His Thr Glu Val Leu Lys Gly Ile Gln
                 85                  90                  95

Lys Phe Pro Gly Ile Asn Tyr Pro Val Leu Thr Pro Asn Leu Lys Gly
                100                 105                 110

Phe Glu Ala Ala Val Ala Ala Gly Ala Lys Val Val Ile Phe Gly
                115                 120                 125

Ala Ala Ser Glu Leu Phe Thr Lys Lys Asn Ile Asn Cys Ser Ile Glu
130                 135                 140

Glu Ser Phe Gln Arg Phe Asp Ala Ile Leu Lys Ala Ala Gln Ser Ala
145                 150                 155                 160

Asn Ile Ser Val Arg Gly Tyr Val Ser Cys Ala Leu Gly Cys Pro Tyr
                165                 170                 175

Glu Gly Lys Ile Ser Pro Ala Lys Val Ala Glu Val Thr Lys Lys Phe
                180                 185                 190

Tyr Ser Met Gly Cys Tyr Glu Ile Ser Leu Gly Asp Thr Ile Gly Val
                195                 200                 205

Gly Thr Pro Gly Ile Met Lys Asp Met Leu Ser Ala Val Met Gln Glu
210                 215                 220

Val Pro Leu Ala Ala Leu Ala Val His Cys His Asp Thr Tyr Gly Gln
225                 230                 235                 240

Ala Leu Thr Asn Thr Leu Met Ala Leu Gln Met Gly Val Ser Val Val
                245                 250                 255

Asp Ser Ser Val Ala Gly Leu Gly Gly Cys Pro Tyr Ala Gln Gly Ala
                260                 265                 270

Ser Gly Asn Leu Ala Thr Glu Asp Leu Val Tyr Met Leu Glu Gly Leu
                275                 280                 285

Gly Ile His Thr Gly Val Asn Leu Gln Lys Leu Leu Glu Ala Gly Asn
                290                 295                 300

Phe Ile Cys Gln Ala Leu Asn Arg Lys Thr Ser Ser Lys Val Ala Gln
305                 310                 315                 320

Ala Thr Cys Lys Leu
                325

<210> SEQ ID NO 23
<211> LENGTH: 299
<212> TYPE: PRT
<213> ORGANISM: Pseudomonas putida
<220> FEATURE:
<223> OTHER INFORMATION: Pseudomonas putida Q88H25

<400> SEQUENCE: 23

Met Ser Leu Pro Lys His Val Arg Leu Val Glu Val Gly Pro Arg Asp
1               5                   10                  15

Gly Leu Gln Asn Glu Ala Gln Pro Ile Ser Val Ala Asp Lys Val Arg
                20                  25                  30

Leu Val Asn Asp Leu Thr Glu Ala Gly Leu Ala Tyr Ile Glu Val Gly
                35                  40                  45

Ser Phe Val Ser Pro Lys Trp Val Pro Gln Met Ala Gly Ser Ala Glu
 50                  55                  60

Val Phe Ala Gly Ile Gln Gln Arg Pro Gly Val Thr Tyr Ala Ala Leu
 65                  70                  75                  80
```

```
Ala Pro Asn Leu Arg Gly Phe Glu Asp Ala Leu Ala Ala Gly Val Lys
                 85                  90                  95

Glu Val Ala Val Phe Ala Ala Ser Glu Ala Phe Ser Gln Arg Asn
            100                 105                 110

Ile Asn Cys Ser Ile Ser Glu Ser Leu Lys Arg Phe Glu Pro Ile Met
            115                 120                 125

Asp Ala Ala Arg Ser His Gly Met Arg Val Arg Gly Tyr Val Ser Cys
            130                 135                 140

Val Leu Gly Cys Pro Tyr Glu Gly Lys Val Ser Ala Glu Gln Val Ala
145                 150                 155                 160

Pro Val Ala Arg Ala Leu His Asp Met Gly Cys Tyr Glu Val Ser Leu
                165                 170                 175

Gly Asp Thr Ile Gly Thr Gly Thr Ala Gly Asp Thr Arg Arg Leu Phe
                180                 185                 190

Glu Val Val Ser Ala Gln Val Pro Arg Glu Gln Leu Ala Gly His Phe
            195                 200                 205

His Asp Thr Tyr Gly Gln Ala Leu Ala Asn Val Tyr Ala Ser Leu Leu
            210                 215                 220

Glu Gly Ile Ser Val Phe Asp Ser Ser Val Ala Gly Leu Gly Gly Cys
225                 230                 235                 240

Pro Tyr Ala Lys Gly Ala Thr Gly Asn Ile Ala Ser Glu Asp Val Val
                245                 250                 255

Tyr Leu Leu Gln Gly Leu Gly Ile Glu Thr Gly Ile Asp Leu Gly Leu
            260                 265                 270

Leu Ile Ala Ala Gly Gln Arg Ile Ser Gly Val Leu Gly Arg Asp Asn
            275                 280                 285

Gly Ser Arg Val Ala Arg Ala Cys Ser Ala Gln
    290                 295

<210> SEQ ID NO 24
<211> LENGTH: 312
<212> TYPE: PRT
<213> ORGANISM: Acinetobacter baumannii
<220> FEATURE:
<223> OTHER INFORMATION: Acinetobacter baumannii B7H4C6

<400> SEQUENCE: 24

Met Thr Ala Phe Ser Asp Leu Leu Val Val Gln Glu Val Ser Pro Arg
1               5                   10                  15

Asp Gly Leu Gln Ile Glu Pro Thr Trp Val Pro Thr Asp Lys Lys Ile
            20                  25                  30

Asp Leu Ile Asn Gln Leu Ser Thr Met Gly Phe Ser Arg Ile Glu Ala
        35                  40                  45

Gly Ser Phe Val Ser Pro Lys Ala Ile Pro Asn Leu Arg Asp Gly Glu
    50                  55                  60

Glu Val Phe Thr Gly Ile Thr Arg His Lys Asp Ile Ile Tyr Val Gly
65                  70                  75                  80

Leu Ile Pro Asn Leu Lys Gly Ala Leu Arg Ala Val Glu Ala Asn Ala
                85                  90                  95

Asn Glu Leu Asn Leu Val Leu Ser Ala Ser Gln Thr His Asn Leu Ala
            100                 105                 110

Asn Met Arg Met Thr Lys Ala Gln Ser Phe Ala Gly Phe Thr Glu Ile
            115                 120                 125

Val Glu Gln Leu Gln Gly Lys Thr Gln Phe Asn Gly Thr Val Ala Thr
            130                 135                 140
```

```
Thr Phe Gly Cys Pro Phe Glu Gly Lys Ile Ser Glu Arg Glu Val Phe
145                 150                 155                 160

Ser Leu Val Glu His Tyr Leu Lys Leu Gly Ile His Asn Ile Thr Leu
            165                 170                 175

Ala Asp Thr Thr Gly Met Ala Asn Pro Val Gln Val Lys Arg Ile Val
        180                 185                 190

Ser His Val Leu Ser Leu Ile Ser Pro Glu Gln Leu Thr Leu His Phe
    195                 200                 205

His Asn Thr Arg Gly Leu Gly Leu Thr Asn Val Leu Ala Ala Tyr Glu
210                 215                 220

Val Gly Ala Arg Arg Phe Asp Ala Ala Leu Gly Gly Leu Gly Gly Cys
225                 230                 235                 240

Pro Phe Ala Pro Gly Ala Ser Gly Asn Ile Cys Thr Glu Asp Leu Val
            245                 250                 255

Asn Met Cys Glu Glu Ile Gly Ile Pro Thr Thr Ile Asp Leu Asp Ala
        260                 265                 270

Leu Ile Gln Leu Ser Arg Thr Leu Pro Ala Leu Leu Gly His Asp Thr
    275                 280                 285

Pro Ser Gln Leu Ala Lys Ala Gly Arg Asn Thr Asp Leu His Pro Ile
290                 295                 300

Pro Asp Tyr Ile Lys Ser Leu Asn
305                 310

<210> SEQ ID NO 25
<211> LENGTH: 286
<212> TYPE: PRT
<213> ORGANISM: Thermus thermophilus
<220> FEATURE:
<223> OTHER INFORMATION: Thermus thermophilus Q72IH0

<400> SEQUENCE: 25

Met Lys Ala Ser Val Arg Trp Val Glu Cys Pro Arg Asp Ala Trp Gln
1               5                   10                  15

Gly Phe Ser Arg Phe Ile Pro Thr Glu Glu Lys Val Ala Phe Leu Asn
            20                  25                  30

Glu Leu Leu Glu Ala Gly Phe Ala His Leu Asp Leu Thr Ser Phe Val
        35                  40                  45

Ser Pro Lys Trp Val Pro Gln Met Gln Asp Ala Glu Glu Val Leu Lys
    50                  55                  60

Ala Leu Pro Pro Asn Gly Arg Thr Tyr Leu Ala Ile Val Ala Asn
65                  70                  75                  80

Glu Lys Gly Leu Glu Arg Ala Leu Ala Ala Pro Asn Leu Thr His Val
            85                  90                  95

Gly Tyr Pro Phe Ser Leu Ser Glu Thr Phe Gln Gln Arg Asn Thr Asn
            100                 105                 110

Arg Ser Ile Glu Ala Ser Trp Pro Leu Val Gly Ala Met Val Glu Arg
        115                 120                 125

Thr Glu Gly Arg Leu Gly Leu Val Val Tyr Leu Ser Met Ala Phe Gly
    130                 135                 140

Asn Pro Tyr Gly Asp Pro Trp Ser Val Glu Ala Val Leu Glu Ala Leu
145                 150                 155                 160

Ala Arg Leu Lys Glu Met Gly Val Arg Glu Ile Ala Leu Ala Asp Thr
            165                 170                 175

Tyr Gly Val Ala Glu Pro Glu Arg Ile His Glu Val Leu Lys Ala Ala
            180                 185                 190
```

```
Val Ala Arg Phe Gly Pro Glu Gly Leu Gly Ala His Leu His Ala Arg
            195                 200                 205

Pro Glu Gly Ala Leu Ala Lys Val Glu Ala Val Leu Ala Ala Gly Val
        210                 215                 220

Thr Trp Leu Glu Gly Ala Leu Ala Gly Val Gly Gly Cys Pro Phe Ala
225                 230                 235                 240

Gly Asp Glu Leu Val Gly Asn Leu Pro Thr Glu Val Val Leu Pro His
                245                 250                 255

Leu Glu Lys Arg Gly Leu Ala Thr Gly Val Asp Leu Ser Arg Leu Pro
            260                 265                 270

Leu Leu Ala Glu Glu Ala Ala Arg Leu Lys Ala Leu Tyr Ala
        275                 280                 285

<210> SEQ ID NO 26
<211> LENGTH: 301
<212> TYPE: PRT
<213> ORGANISM: Clostridium acetobutylicum
<220> FEATURE:
<223> OTHER INFORMATION: Phosphate butyryltransferase
<220> FEATURE:
<223> OTHER INFORMATION: Clostridium acetobutylicum ATCC 824

<400> SEQUENCE: 26

Met Ile Lys Ser Phe Asn Glu Ile Ile Met Lys Val Lys Ser Lys Glu
1               5                   10                  15

Met Lys Lys Val Ala Val Ala Val Ala Gln Asp Glu Pro Val Leu Glu
            20                  25                  30

Ala Val Arg Asp Ala Lys Lys Asn Gly Ile Ala Asp Ala Ile Leu Val
        35                  40                  45

Gly Asp His Asp Glu Ile Val Ser Ile Ala Leu Lys Ile Gly Met Asp
    50                  55                  60

Val Asn Asp Phe Glu Ile Val Asn Glu Pro Asn Val Lys Lys Ala Ala
65                  70                  75                  80

Leu Lys Ala Val Glu Leu Val Ser Thr Gly Lys Ala Asp Met Val Met
                85                  90                  95

Lys Gly Leu Val Asn Thr Ala Thr Phe Leu Arg Ser Val Leu Asn Lys
            100                 105                 110

Glu Val Gly Leu Arg Thr Gly Lys Thr Met Ser His Val Ala Val Phe
        115                 120                 125

Glu Thr Glu Lys Phe Asp Arg Leu Leu Phe Leu Thr Asp Val Ala Phe
    130                 135                 140

Asn Thr Tyr Pro Glu Leu Lys Glu Lys Ile Asp Ile Val Asn Asn Ser
145                 150                 155                 160

Val Lys Val Ala His Ala Ile Gly Ile Glu Asn Pro Lys Val Ala Pro
                165                 170                 175

Ile Cys Ala Val Glu Val Ile Asn Pro Lys Met Pro Ser Thr Leu Asp
            180                 185                 190

Ala Ala Met Leu Ser Lys Met Ser Asp Arg Gly Gln Ile Lys Gly Cys
        195                 200                 205

Val Val Asp Gly Pro Leu Ala Leu Asp Ile Ala Leu Ser Glu Glu Ala
    210                 215                 220

Ala His His Lys Gly Val Thr Gly Glu Val Ala Gly Lys Ala Asp Ile
225                 230                 235                 240

Phe Leu Met Pro Asn Ile Glu Thr Gly Asn Val Met Tyr Lys Thr Leu
                245                 250                 255

Thr Tyr Thr Thr Asp Ser Lys Asn Gly Gly Ile Leu Val Gly Thr Ser
```

260                 265                 270
Ala Pro Val Val Leu Thr Ser Arg Ala Asp Ser His Glu Thr Lys Met
            275                 280                 285

Asn Ser Ile Ala Leu Ala Ala Leu Val Ala Gly Asn Lys
            290                 295                 300

<210> SEQ ID NO 27
<211> LENGTH: 329
<212> TYPE: PRT
<213> ORGANISM: Corynebacterium glutamicum
<220> FEATURE:
<223> OTHER INFORMATION: Phosphate acetyltransferase
<220> FEATURE:
<223> OTHER INFORMATION: Corynebacterium glutamicum ATCC 13032

<400> SEQUENCE: 27

Met Ser Ala Glu Leu Phe Glu Asn Trp Leu Leu Lys Arg Ala Arg Ala
1               5                   10                  15

Glu His Ser His Ile Val Leu Pro Glu Gly Asp Asp Arg Ile Leu
            20                  25                  30

Met Ala Ala His Gln Leu Leu Asp Gln Asp Ile Cys Asp Ile Thr Ile
            35                  40                  45

Leu Gly Asp Pro Val Lys Ile Lys Glu Arg Ala Thr Glu Leu Gly Leu
    50                  55                  60

His Leu Asn Thr Ala Tyr Leu Val Asn Pro Leu Thr Asp Pro Arg Leu
65                  70                  75                  80

Glu Glu Phe Ala Glu Gln Phe Ala Glu Leu Arg Lys Ser Lys Ser Val
                85                  90                  95

Thr Ile Asp Glu Ala Arg Glu Ile Met Lys Asp Ile Ser Tyr Phe Gly
            100                 105                 110

Thr Met Met Val His Asn Gly Asp Ala Asp Gly Met Val Ser Gly Ala
            115                 120                 125

Ala Asn Thr Thr Ala His Thr Ile Lys Pro Ser Phe Gln Ile Ile Lys
    130                 135                 140

Thr Val Pro Glu Ala Ser Val Val Ser Ser Ile Phe Leu Met Val Leu
145                 150                 155                 160

Arg Gly Arg Leu Trp Ala Phe Gly Asp Cys Ala Val Asn Pro Asn Pro
                165                 170                 175

Thr Ala Glu Gln Leu Gly Glu Ile Ala Val Val Ser Ala Lys Thr Ala
            180                 185                 190

Ala Gln Phe Gly Ile Asp Pro Arg Val Ala Ile Leu Ser Tyr Ser Thr
            195                 200                 205

Gly Asn Ser Gly Gly Gly Ser Asp Val Asp Arg Ala Ile Asp Ala Leu
    210                 215                 220

Ala Glu Ala Arg Arg Leu Asn Pro Glu Leu Cys Val Asp Gly Pro Leu
225                 230                 235                 240

Gln Phe Asp Ala Ala Val Asp Pro Gly Val Ala Arg Lys Lys Met Pro
                245                 250                 255

Asp Ser Asp Val Ala Gly Gln Ala Asn Val Phe Ile Phe Pro Asp Leu
            260                 265                 270

Glu Ala Gly Asn Ile Gly Tyr Lys Thr Ala Gln Arg Thr Gly His Ala
            275                 280                 285

Leu Ala Val Gly Pro Ile Leu Gln Gly Leu Asn Lys Pro Val Asn Asp
    290                 295                 300

Leu Ser Arg Gly Ala Thr Val Pro Asp Ile Val Asn Thr Val Ala Ile
305                 310                 315                 320

```
Thr Ala Ile Gln Ala Gly Gly Arg Ser
            325

<210> SEQ ID NO 28
<211> LENGTH: 402
<212> TYPE: PRT
<213> ORGANISM: Salmonella enterica
<220> FEATURE:
<223> OTHER INFORMATION: Salty propionate kinase
<220> FEATURE:
<223> OTHER INFORMATION: subsp. enterica serovar Typhimurium str. LT2

<400> SEQUENCE: 28

Met Asn Glu Phe Pro Val Val Leu Val Ile Asn Cys Gly Ser Ser Ser
1               5                   10                  15

Ile Lys Phe Ser Val Leu Asp Val Ala Thr Cys Asp Val Leu Met Ala
            20                  25                  30

Gly Ile Ala Asp Gly Met Asn Thr Glu Asn Ala Phe Leu Ser Ile Asn
        35                  40                  45

Gly Asp Lys Pro Ile Asn Leu Ala His Ser Asn Tyr Glu Asp Ala Leu
    50                  55                  60

Lys Ala Ile Ala Phe Glu Leu Glu Lys Arg Asp Leu Thr Asp Ser Val
65                  70                  75                  80

Ala Leu Ile Gly His Arg Ile Ala His Gly Gly Glu Leu Phe Thr Gln
                85                  90                  95

Ser Val Ile Ile Thr Asp Glu Ile Ile Asp Asn Ile Arg Arg Val Ser
            100                 105                 110

Pro Leu Ala Pro Leu His Asn Tyr Ala Asn Leu Ser Gly Ile Asp Ala
        115                 120                 125

Ala Arg His Leu Phe Pro Ala Val Arg Gln Val Ala Val Phe Asp Thr
    130                 135                 140

Ser Phe His Gln Thr Leu Ala Pro Glu Ala Tyr Leu Tyr Gly Leu Pro
145                 150                 155                 160

Trp Glu Tyr Phe Ser Ser Leu Gly Val Arg Arg Tyr Gly Phe His Gly
                165                 170                 175

Thr Ser His Arg Tyr Val Ser Arg Arg Ala Tyr Glu Leu Leu Asp Leu
            180                 185                 190

Asp Glu Lys Asp Ser Gly Leu Ile Val Ala His Leu Gly Asn Gly Ala
        195                 200                 205

Ser Ile Cys Ala Val Arg Asn Gly Gln Ser Val Asp Thr Ser Met Gly
    210                 215                 220

Met Thr Pro Leu Glu Gly Leu Met Met Gly Thr Arg Ser Gly Asp Val
225                 230                 235                 240

Asp Phe Gly Ala Met Ala Trp Ile Ala Lys Glu Thr Gly Gln Thr Leu
                245                 250                 255

Ser Asp Leu Glu Arg Val Val Asn Lys Glu Ser Gly Leu Leu Gly Ile
            260                 265                 270

Ser Gly Leu Ser Ser Asp Leu Arg Val Leu Glu Lys Ala Trp His Glu
        275                 280                 285

Gly His Glu Arg Ala Arg Leu Ala Ile Lys Thr Phe Val His Arg Ile
    290                 295                 300

Ala Arg His Ile Ala Gly His Ala Ala Ser Leu His Arg Leu Asp Gly
305                 310                 315                 320

Ile Ile Phe Thr Gly Gly Ile Gly Glu Asn Ser Val Leu Ile Arg Gln
                325                 330                 335
```

```
Leu Val Ile Glu His Leu Gly Val Leu Gly Leu Thr Leu Asp Val Glu
            340                 345                 350

Met Asn Lys Gln Pro Asn Ser His Gly Glu Arg Ile Ile Ser Ala Asn
355                 360                 365

Pro Ser Gln Val Ile Cys Ala Val Ile Pro Thr Asn Glu Glu Lys Met
370                 375                 380

Ile Ala Leu Asp Ala Ile His Leu Gly Asn Val Lys Ala Pro Val Glu
385                 390                 395                 400

Phe Ala

<210> SEQ ID NO 29
<211> LENGTH: 402
<212> TYPE: PRT
<213> ORGANISM: Escherichia coli
<220> FEATURE:
<223> OTHER INFORMATION: Propionate kinase
<220> FEATURE:
<223> OTHER INFORMATION: Escherichia coli K-12

<400> SEQUENCE: 29

Met Asn Glu Phe Pro Val Val Leu Val Ile Asn Cys Gly Ser Ser Ser
1               5                   10                  15

Ile Lys Phe Ser Val Leu Asp Ala Ser Asp Cys Glu Val Leu Met Ser
                20                  25                  30

Gly Ile Ala Asp Gly Ile Asn Ser Glu Asn Ala Phe Leu Ser Val Asn
            35                  40                  45

Gly Gly Glu Pro Ala Pro Leu Ala His His Ser Tyr Glu Gly Ala Leu
        50                  55                  60

Lys Ala Ile Ala Phe Glu Leu Glu Lys Arg Asn Leu Asn Asp Ser Val
65                  70                  75                  80

Ala Leu Ile Gly His Arg Ile Ala His Gly Gly Ser Ile Phe Thr Glu
                85                  90                  95

Ser Ala Ile Ile Thr Asp Glu Val Ile Asp Asn Ile Arg Arg Val Ser
            100                 105                 110

Pro Leu Ala Pro Leu His Asn Tyr Ala Asn Leu Ser Gly Ile Glu Ser
        115                 120                 125

Ala Gln Gln Leu Phe Pro Gly Val Thr Gln Val Ala Val Phe Asp Thr
130                 135                 140

Ser Phe His Gln Thr Met Ala Pro Glu Ala Tyr Leu Tyr Gly Leu Pro
145                 150                 155                 160

Trp Lys Tyr Tyr Glu Glu Leu Gly Val Arg Arg Tyr Gly Phe His Gly
                165                 170                 175

Thr Ser His Arg Tyr Val Ser Gln Arg Ala His Ser Leu Leu Asn Leu
            180                 185                 190

Ala Glu Asp Asp Ser Gly Leu Val Val Ala His Leu Gly Asn Gly Ala
        195                 200                 205

Ser Ile Cys Ala Val Arg Asn Gly Gln Ser Val Asp Thr Ser Met Gly
210                 215                 220

Met Thr Pro Leu Glu Gly Leu Met Met Gly Thr Arg Ser Gly Asp Val
225                 230                 235                 240

Asp Phe Gly Ala Met Ser Trp Val Ala Ser Gln Thr Asn Gln Ser Leu
                245                 250                 255

Gly Asp Leu Glu Arg Val Val Asn Lys Glu Ser Gly Leu Leu Gly Ile
            260                 265                 270

Ser Gly Leu Ser Ser Asp Leu Arg Val Leu Glu Lys Ala Trp His Glu
        275                 280                 285
```

```
Gly His Glu Arg Ala Gln Leu Ala Ile Lys Thr Phe Val His Arg Ile
    290                 295                 300

Ala Arg His Ile Ala Gly His Ala Ala Ser Leu Arg Arg Leu Asp Gly
305                 310                 315                 320

Ile Ile Phe Thr Gly Gly Ile Gly Glu Asn Ser Ser Leu Ile Arg Arg
                325                 330                 335

Leu Val Met Glu His Leu Ala Val Leu Gly Leu Glu Ile Asp Thr Glu
            340                 345                 350

Met Asn Asn Arg Ser Asn Ser Cys Gly Glu Arg Ile Val Ser Ser Glu
        355                 360                 365

Asn Ala Arg Val Ile Cys Ala Val Ile Pro Thr Asn Glu Glu Lys Met
    370                 375                 380

Ile Ala Leu Asp Ala Ile His Leu Gly Lys Val Asn Ala Pro Ala Glu
385                 390                 395                 400

Phe Ala
```

```
<210> SEQ ID NO 30
<211> LENGTH: 154
<212> TYPE: PRT
<213> ORGANISM: Haemophilus influenzae
<220> FEATURE:
<223> OTHER INFORMATION: Acyl-CoA thioesterase YciA
<220> FEATURE:
<223> OTHER INFORMATION: Haemophilus influenzae R2866

<400> SEQUENCE: 30
```

```
Met Ser Ala Asn Phe Thr Asp Lys Asn Gly Arg Gln Ser Lys Gly Val
1               5                   10                  15

Leu Leu Leu Arg Thr Leu Ala Met Pro Ser Asp Thr Asn Ala Asn Gly
            20                  25                  30

Asp Ile Phe Gly Gly Trp Ile Met Ser Gln Met Asp Met Gly Gly Ala
        35                  40                  45

Ile Leu Ala Lys Glu Ile Ala His Gly Arg Val Val Thr Val Ala Val
    50                  55                  60

Glu Ser Met Asn Phe Ile Lys Pro Ile Ser Val Gly Asp Val Val Cys
65                  70                  75                  80

Cys Tyr Gly Glu Cys Leu Lys Val Gly Arg Ser Ser Ile Lys Ile Lys
                85                  90                  95

Val Glu Val Trp Val Lys Lys Val Ala Ser Glu Pro Ile Gly Glu Arg
            100                 105                 110

Tyr Cys Val Thr Asp Ala Val Phe Thr Phe Val Ala Val Asp Asn Asn
        115                 120                 125

Gly Arg Ser Arg Thr Ile Pro Arg Glu Asn Asn Gln Glu Leu Glu Lys
    130                 135                 140

Ala Leu Ala Leu Ile Ser Glu Gln Pro Leu
145                 150
```

```
<210> SEQ ID NO 31
<211> LENGTH: 140
<212> TYPE: PRT
<213> ORGANISM: Homo sapiens
<220> FEATURE:
<223> OTHER INFORMATION: Acyl-coenzyme A thioesterase

<400> SEQUENCE: 31
```

```
Met Thr Ser Met Thr Gln Ser Leu Arg Glu Val Ile Lys Ala Met Thr
1               5                   10                  15
```

```
Lys Ala Arg Asn Phe Glu Arg Val Leu Gly Lys Ile Thr Leu Val Ser
            20                  25                  30

Ala Ala Pro Gly Lys Val Ile Cys Glu Met Lys Val Glu Glu Glu His
        35                  40                  45

Thr Asn Ala Ile Gly Thr Leu His Gly Gly Leu Thr Ala Thr Leu Val
 50                  55                  60

Asp Asn Ile Ser Thr Met Ala Leu Leu Cys Thr Glu Arg Gly Ala Pro
 65                  70                  75                  80

Gly Val Ser Val Asp Met Asn Ile Thr Tyr Met Ser Pro Ala Lys Leu
                85                  90                  95

Gly Glu Asp Ile Val Ile Thr Ala His Val Leu Lys Gln Gly Lys Thr
            100                 105                 110

Leu Ala Phe Thr Ser Val Asp Leu Thr Asn Lys Ala Thr Gly Lys Leu
        115                 120                 125

Ile Ala Gln Gly Arg His Thr Lys His Leu Gly Asn
    130                 135                 140

<210> SEQ ID NO 32
<211> LENGTH: 132
<212> TYPE: PRT
<213> ORGANISM: Escherichia coli
<220> FEATURE:
<223> OTHER INFORMATION: Escherichia coli K-12

<400> SEQUENCE: 32

Met Ser Thr Thr His Asn Val Pro Gln Gly Asp Leu Val Leu Arg Thr
 1               5                  10                  15

Leu Ala Met Pro Ala Asp Thr Asn Ala Asn Gly Asp Ile Phe Gly Gly
            20                  25                  30

Trp Leu Met Ser Gln Met Asp Ile Gly Gly Ala Ile Leu Ala Lys Glu
        35                  40                  45

Ile Ala His Gly Arg Val Val Thr Val Arg Val Glu Gly Met Thr Phe
 50                  55                  60

Leu Arg Pro Val Ala Val Gly Asp Val Val Cys Cys Tyr Ala Arg Cys
 65                  70                  75                  80

Val Gln Lys Gly Thr Thr Ser Val Ser Ile Asn Ile Glu Val Trp Val
                85                  90                  95

Lys Lys Val Ala Ser Glu Pro Ile Gly Gln Arg Tyr Lys Ala Thr Glu
            100                 105                 110

Ala Leu Phe Lys Tyr Val Ala Val Asp Pro Glu Gly Lys Pro Arg Ala
        115                 120                 125

Leu Pro Val Glu
    130

<210> SEQ ID NO 33
<211> LENGTH: 286
<212> TYPE: PRT
<213> ORGANISM: Escherichia coli
<220> FEATURE:
<223> OTHER INFORMATION: Escherichia coli K-12

<400> SEQUENCE: 33

Met Ser Gln Ala Leu Lys Asn Leu Leu Thr Leu Leu Asn Leu Glu Lys
 1               5                  10                  15

Ile Glu Glu Gly Leu Phe Arg Gly Gln Ser Glu Asp Leu Gly Leu Arg
            20                  25                  30

Gln Val Phe Gly Gly Gln Val Val Gly Gln Ala Leu Tyr Ala Ala Lys
        35                  40                  45
```

```
Glu Thr Val Pro Glu Glu Arg Leu Val His Ser Phe His Ser Tyr Phe
            50                  55                  60

Leu Arg Pro Gly Asp Ser Lys Lys Pro Ile Ile Tyr Asp Val Glu Thr
 65                  70                  75                  80

Leu Arg Asp Gly Asn Ser Phe Ser Ala Arg Arg Val Ala Ala Ile Gln
                    85                  90                  95

Asn Gly Lys Pro Ile Phe Tyr Met Thr Ala Ser Phe Gln Ala Pro Glu
                100                 105                 110

Ala Gly Phe Glu His Gln Lys Thr Met Pro Ser Ala Pro Ala Pro Asp
            115                 120                 125

Gly Leu Pro Ser Glu Thr Gln Ile Ala Gln Ser Leu Ala His Leu Leu
            130                 135                 140

Pro Pro Val Leu Lys Asp Lys Phe Ile Cys Asp Arg Pro Leu Glu Val
145                 150                 155                 160

Arg Pro Val Glu Phe His Asn Pro Leu Lys Gly His Val Ala Glu Pro
                165                 170                 175

His Arg Gln Val Trp Ile Arg Ala Asn Gly Ser Val Pro Asp Asp Leu
                180                 185                 190

Arg Val His Gln Tyr Leu Leu Gly Tyr Ala Ser Asp Leu Asn Phe Leu
                195                 200                 205

Pro Val Ala Leu Gln Pro His Gly Ile Gly Phe Leu Glu Pro Gly Ile
            210                 215                 220

Gln Ile Ala Thr Ile Asp His Ser Met Trp Phe His Arg Pro Phe Asn
225                 230                 235                 240

Leu Asn Glu Trp Leu Leu Tyr Ser Val Glu Ser Thr Ser Ala Ser Ser
                245                 250                 255

Ala Arg Gly Phe Val Arg Gly Glu Phe Tyr Thr Gln Asp Gly Val Leu
                260                 265                 270

Val Ala Ser Thr Val Gln Glu Gly Val Met Arg Asn His Asn
            275                 280                 285

<210> SEQ ID NO 34
<211> LENGTH: 289
<212> TYPE: PRT
<213> ORGANISM: Pseudomonas putida

<400> SEQUENCE: 34

Met Ser His Val Leu Asp Asp Leu Val Asp Leu Leu Ser Leu Glu Ser
 1                   5                  10                  15

Ile Glu Glu Asn Leu Phe Arg Gly Arg Ser Gln Asp Leu Gly Phe Arg
                 20                  25                  30

Gln Leu Tyr Gly Gly Gln Val Leu Gly Gln Ser Leu Ser Ala Ala Ser
             35                  40                  45

Gln Thr Val Glu Asp Ala Arg His Val His Ser Leu His Gly Tyr Phe
 50                  55                  60

Leu Arg Pro Gly Asp Ala Ser Leu Pro Val Val Tyr Ser Val Asp Arg
 65                  70                  75                  80

Val Arg Asp Gly Gly Ser Phe Ser Thr Arg Arg Val Thr Ala Ile Gln
                 85                  90                  95

Lys Gly Gln Thr Ile Phe Thr Cys Ser Ala Ser Phe Gln Tyr Asp Glu
                100                 105                 110

Glu Gly Phe Glu His Gln Ala Gln Met Pro Asp Val Val Gly Pro Glu
            115                 120                 125

Asn Leu Pro Thr Glu Val Glu Leu Ala His Ala Met Ala Asp Gln Leu
```

```
                130                 135                 140
Pro Glu Arg Ile Arg Asp Lys Val Leu Cys Ala Lys Pro Ile Glu Ile
145                 150                 155                 160

Arg Pro Val Thr Glu Arg Asp Pro Phe Asn Pro Lys Pro Gly Asp Pro
                165                 170                 175

Val Lys Tyr Ala Trp Phe Arg Ala Asp Gly Asn Leu Pro Asp Val Pro
            180                 185                 190

Ala Leu His Lys Tyr Met Leu Ala Tyr Ala Ser Asp Phe Gly Leu Leu
            195                 200                 205

Thr Thr Ala Leu Leu Pro His Gly Lys Ser Val Trp Gln Arg Asp Met
        210                 215                 220

Gln Ile Ala Ser Leu Asp His Ser Leu Trp Phe His Gly Asn Leu Arg
225                 230                 235                 240

Ala Asp Gln Trp Leu Leu Tyr Ala Thr Asp Ser Pro Trp Ala Gly Asn
                245                 250                 255

Ser Arg Gly Phe Cys Arg Gly Ser Ile Phe Asn Gln Ala Gly Gln Leu
            260                 265                 270

Val Ala Ser Ser Ser Gln Glu Gly Leu Ile Arg His Arg Lys Asp Trp
        275                 280                 285

Ala

<210> SEQ ID NO 35
<211> LENGTH: 258
<212> TYPE: PRT
<213> ORGANISM: Unknown
<220> FEATURE:
<223> OTHER INFORMATION: Myxococcus species

<400> SEQUENCE: 35

Met Pro Glu Phe Lys Val Asp Ala Arg Gly Pro Ile Glu Ile Trp Thr
1               5                   10                  15

Ile Asp Gly Glu Ser Arg Arg Asn Ala Ile Ser Arg Ala Met Leu Gln
            20                  25                  30

Glu Leu Gly Glu Met Val Thr Arg Val Ser Ser Ser Arg Glu Val Arg
        35                  40                  45

Ala Val Val Ile Thr Gly Ala Gly Asp Lys Ala Phe Cys Ala Gly Ala
    50                  55                  60

Asp Leu Lys Glu Arg Ala Thr Met Ala Glu Asp Glu Val Arg Ala Phe
65                  70                  75                  80

Leu Asp Gly Leu Arg Arg Thr Phe Arg Ala Leu Glu Lys Ser Asp Cys
                85                  90                  95

Val Phe Ile Ala Ala Ile Asn Gly Ala Ala Phe Gly Gly Gly Thr Glu
            100                 105                 110

Leu Ala Leu Ala Cys Asp Leu Arg Val Ala Ala Pro Ala Ala Glu Leu
        115                 120                 125

Gly Leu Thr Glu Val Lys Leu Gly Ile Ile Pro Gly Gly Gly Gly Thr
    130                 135                 140

Gln Arg Leu Thr Arg Leu Val Gly Pro Gly Arg Ala Lys Asp Leu Ile
145                 150                 155                 160

Leu Thr Ala Arg Arg Ile Asn Ala Ala Glu Ala Phe Ser Val Gly Leu
                165                 170                 175

Val Asn Arg Leu Ala Pro Glu Gly His Leu Leu Ala Val Ala Tyr Gly
            180                 185                 190

Leu Ala Glu Ser Val Val Glu Asn Ala Pro Ile Ala Val Ala Thr Ala
        195                 200                 205
```

```
Lys His Ala Ile Asp Glu Gly Thr Gly Leu Glu Leu Asp Asp Ala Leu
    210                 215                 220

Ala Leu Glu Leu Arg Lys Tyr Glu Glu Ile Leu Lys Thr Glu Asp Arg
225                 230                 235                 240

Leu Glu Gly Leu Arg Ala Phe Ala Glu Lys Arg Ala Pro Val Tyr Lys
                245                 250                 255

Gly Arg

<210> SEQ ID NO 36
<211> LENGTH: 447
<212> TYPE: PRT
<213> ORGANISM: Schizosaccharomyces pombe
<220> FEATURE:
<223> OTHER INFORMATION: Schizosaccharomyces pombe (strain 972 / ATCC
      24843)

<400> SEQUENCE: 36

Met Ser Phe Asp Arg Lys Asp Ile Gly Ile Lys Gly Leu Val Leu Tyr
1               5                   10                  15

Thr Pro Asn Gln Tyr Val Glu Gln Ala Ala Leu Glu Ala His Asp Gly
                20                  25                  30

Val Ser Thr Gly Lys Tyr Thr Ile Gly Leu Gly Leu Thr Lys Met Ala
            35                  40                  45

Phe Val Asp Asp Arg Glu Asp Ile Tyr Ser Phe Gly Leu Thr Ala Leu
    50                  55                  60

Ser Gln Leu Ile Lys Arg Tyr Gln Ile Asp Ile Ser Lys Ile Gly Arg
65                  70                  75                  80

Leu Glu Val Gly Thr Glu Thr Ile Ile Asp Lys Ser Lys Ser Val Lys
                85                  90                  95

Ser Val Leu Met Gln Leu Phe Gly Asp Asn His Asn Val Glu Gly Ile
                100                 105                 110

Asp Cys Val Asn Ala Cys Tyr Gly Gly Val Asn Ala Leu Phe Asn Thr
            115                 120                 125

Ile Asp Trp Ile Glu Ser Ser Ala Trp Asp Gly Arg Asp Gly Ile Val
    130                 135                 140

Val Ala Gly Asp Ile Ala Leu Tyr Ala Lys Gly Asn Ala Arg Pro Thr
145                 150                 155                 160

Gly Gly Ala Gly Cys Val Ala Leu Leu Val Gly Pro Asn Ala Pro Ile
                165                 170                 175

Val Phe Glu Pro Gly Leu Arg Gly Thr Tyr Met Gln His Ala Tyr Asp
            180                 185                 190

Phe Tyr Lys Pro Asp Leu Thr Ser Glu Tyr Pro Tyr Val Asp Gly His
    195                 200                 205

Phe Ser Leu Glu Cys Tyr Val Lys Ala Leu Asp Gly Ala Tyr Ala Asn
    210                 215                 220

Tyr Asn Val Arg Asp Val Ala Lys Asn Gly Lys Ser Gln Gly Leu Gly
225                 230                 235                 240

Leu Asp Arg Phe Asp Tyr Cys Ile Phe His Ala Pro Thr Cys Lys Gln
                245                 250                 255

Val Gln Lys Ala Tyr Ala Arg Leu Leu Tyr Thr Asp Ser Ala Ala Glu
            260                 265                 270

Pro Ser Asn Pro Glu Leu Glu Gly Val Arg Glu Leu Leu Ser Thr Leu
    275                 280                 285

Asp Ala Lys Lys Ser Leu Thr Asp Lys Ala Leu Glu Lys Gly Leu Met
290                 295                 300
```

```
Ala Ile Thr Lys Glu Arg Phe Asn Lys Arg Val Ser Pro Ser Val Tyr
305                 310                 315                 320

Ala Pro Thr Asn Cys Gly Asn Met Tyr Thr Ala Ser Ile Phe Ser Cys
            325                 330                 335

Leu Thr Ala Leu Leu Ser Arg Val Pro Ala Asp Glu Leu Lys Gly Lys
        340                 345                 350

Arg Val Gly Ala Tyr Ser Tyr Gly Ser Gly Leu Ala Ala Ser Phe Phe
    355                 360                 365

Ser Phe Val Val Lys Gly Asp Val Ser Glu Ile Ala Lys Lys Thr Asn
370                 375                 380

Leu Val Asn Asp Leu Asp Asn Arg His Cys Leu Thr Pro Thr Gln Tyr
385                 390                 395                 400

Glu Glu Ala Ile Glu Leu Arg His Gln Ala His Leu Lys Lys Asn Phe
                405                 410                 415

Thr Pro Lys Gly Ser Ile Glu Arg Leu Arg Ser Gly Thr Tyr Tyr Leu
            420                 425                 430

Thr Gly Ile Asp Asp Met Phe Arg Arg Ser Tyr Ser Val Lys Pro
        435                 440                 445

<210> SEQ ID NO 37
<211> LENGTH: 392
<212> TYPE: PRT
<213> ORGANISM: Clostridium acetobutylicum
<220> FEATURE:
<223> OTHER INFORMATION: Clostridium acetobutylicum ATCC 824

<400> SEQUENCE: 37

Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220
```

-continued

```
Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390

<210> SEQ ID NO 38
<211> LENGTH: 258
<212> TYPE: PRT
<213> ORGANISM: Bacillus subtilis
<220> FEATURE:
<223> OTHER INFORMATION: subsp. subtilis str. RO-NN-1

<400> SEQUENCE: 38

Met Asn Ala Ile Ser Leu Ala Val Asp Gln Phe Val Ala Val Leu Thr
1               5                   10                  15

Ile His Asn Pro Pro Ala Asn Ala Leu Ser Ser Arg Ile Leu Glu Glu
            20                  25                  30

Leu Ser Ser Cys Leu Asp Gln Cys Glu Thr Asp Ala Gly Val Arg Ser
        35                  40                  45

Ile Ile Ile His Gly Glu Gly Arg Phe Phe Ser Ala Gly Ala Asp Ile
    50                  55                  60

Lys Glu Phe Thr Ser Leu Lys Gly Asn Glu Asp Phe Ser Leu Leu Ala
65                  70                  75                  80

Glu Arg Gly Gln Gln Leu Met Glu Arg Ile Glu Ser Phe Pro Lys Pro
                85                  90                  95

Ile Ile Ala Ala Ile His Gly Ala Leu Gly Gly Gly Leu Glu Leu
            100                 105                 110

Ala Met Ala Cys His Ile Arg Ile Ala Ala Asp Asp Ala Lys Leu Gly
        115                 120                 125

Leu Pro Glu Leu Asn Leu Gly Ile Ile Pro Gly Phe Ala Gly Thr Gln
    130                 135                 140

Arg Leu Pro Arg Tyr Val Gly Thr Ala Lys Ala Leu Glu Leu Ile Gly
145                 150                 155                 160

Ser Gly Glu Pro Ile Ser Gly Lys Glu Ala Leu Asp Leu Gly Leu Val
                165                 170                 175

Ser Ile Gly Ala Lys Asp Glu Ala Glu Val Ile Glu Lys Ala Lys Ala
            180                 185                 190
```

```
Leu Ala Ala Lys Phe Ala Glu Lys Ser Pro Gln Thr Leu Ala Ser Leu
        195                 200                 205

Leu Glu Leu Leu Tyr Ser Asn Lys Val Tyr Ser Tyr Glu Gly Ser Leu
    210                 215                 220

Lys Leu Glu Ala Lys Arg Phe Gly Glu Ala Phe Glu Ser Glu Asp Ala
225                 230                 235                 240

Lys Glu Gly Ile Gln Ala Phe Leu Glu Lys Arg Lys Pro Gln Phe Lys
                245                 250                 255

Gly Glu

<210> SEQ ID NO 39
<211> LENGTH: 263
<212> TYPE: PRT
<213> ORGANISM: Bacillus anthracis

<400> SEQUENCE: 39

Met Lys Asn Glu Arg Leu Val Ile Cys Ser Lys Gly Ser Ser Ala
1               5                   10                  15

Val Ile Thr Ile Gln Asn Pro Pro Val Asn Ala Leu Ser Leu Glu Val
            20                  25                  30

Val Gln Gln Leu Ile Asn Val Leu Glu Glu Ile Glu Met Asp Asp Asp
        35                  40                  45

Ile Ala Val Val Ile Ile Thr Gly Ile Gly Gly Lys Ala Phe Val Ala
    50                  55                  60

Gly Gly Asp Ile Lys Glu Phe Pro Gly Trp Ile Gly Lys Gly Glu Lys
65                  70                  75                  80

Tyr Ala Glu Met Lys Ser Ile Glu Leu Gln Arg Pro Leu Asn Gln Leu
                85                  90                  95

Glu Asn Leu Ser Lys Pro Thr Ile Ala Ala Ile Asn Gly Leu Ala Leu
            100                 105                 110

Gly Gly Gly Cys Glu Leu Ala Leu Ala Cys Asp Leu Arg Val Ile Glu
        115                 120                 125

Glu Gln Ala Leu Ile Gly Leu Pro Glu Ile Thr Leu Gly Leu Phe Pro
130                 135                 140

Gly Ala Gly Gly Thr Gln Arg Leu Pro Arg Leu Ile Gly Glu Gly Lys
145                 150                 155                 160

Ala Lys Glu Met Met Phe Thr Gly Lys Pro Ile Thr Ala Lys Glu Ala
                165                 170                 175

Lys Glu Ile Asn Leu Val Asn Tyr Ile Thr Ser Arg Gly Glu Ala Leu
            180                 185                 190

Asn Lys Ala Lys Glu Ile Ala Lys Asp Ile Ser Glu Phe Ser Leu Pro
        195                 200                 205

Ala Leu Ser Tyr Met Lys Leu Ala Ile Arg Glu Gly Leu Ala Val Pro
    210                 215                 220

Leu Gln Glu Gly Leu Gln Ile Glu Ala Arg Tyr Phe Gly Lys Val Phe
225                 230                 235                 240

Gln Thr Glu Asp Val Lys Glu Gly Val Lys Ala Phe Ile Glu Lys Arg
                245                 250                 255

Val Pro Arg Phe Thr Asn Lys
            260

<210> SEQ ID NO 40
<211> LENGTH: 229
<212> TYPE: PRT
<213> ORGANISM: Candida albicans
```

<220> FEATURE:
<223> OTHER INFORMATION: Candida albicans (strain SC5314 / ATCC MYA-2876)

<400> SEQUENCE: 40

Met Ile Ala Arg Val Cys Leu Arg Arg Ser Asn Val Leu Pro Ile Phe
1               5                   10                  15

Gln Ile Pro Ser Arg Lys Tyr Ser Ile Asn Tyr Glu Lys Val Asn Asn
            20                  25                  30

Ser Ile Tyr Asn Asn Val Ile Lys Pro Lys Arg Ile Val Leu Ala Ile
        35                  40                  45

Thr Gly Ala Thr Gly Thr Gln Ile Gly Val Arg Leu Leu Glu Ile Leu
50                  55                  60

Lys Glu Leu Gly Val Glu Thr His Leu Val Met Ser Lys Trp Gly Ile
65                  70                  75                  80

Ala Thr Leu Lys Tyr Glu Thr Asp Tyr Gln Val Asp Tyr Val Thr Ser
                85                  90                  95

Leu Ala Thr Lys Thr Tyr Ser Ala Arg Asp Val Thr Ala Pro Ile Ser
            100                 105                 110

Ser Gly Ser Phe Val His Asp Gly Met Ile Val Ala Pro Cys Ser Met
        115                 120                 125

Lys Ser Leu Ser Ala Ile Arg Thr Gly Phe Thr Glu Asp Leu Ile Val
130                 135                 140

Arg Ala Ala Asp Val Ser Leu Lys Glu Arg Lys Leu Leu Leu Val
145                 150                 155                 160

Ala Arg Glu Thr Pro Leu Ser Asp Ile His Leu Asp Asn Met Leu Tyr
                165                 170                 175

Leu Ser Arg Met Gly Val Thr Ile Phe Pro Pro Val Pro Ala Phe Tyr
            180                 185                 190

Thr Lys Pro Lys Thr Ile Asp Asp Ile Val Glu Gln Thr Cys Gly Arg
        195                 200                 205

Ile Leu Asp Asn Phe Gly Ile Asn Ile Asp Thr Phe Glu Arg Trp Asp
    210                 215                 220

Gly Ile Asn His Arg
225

<210> SEQ ID NO 41
<211> LENGTH: 227
<212> TYPE: PRT
<213> ORGANISM: Aspergillus niger

<400> SEQUENCE: 41

Met Phe Asn Ser Leu Leu Ser Gly Thr Thr Thr Pro Asn Ser Gly Arg
1               5                   10                  15

Ala Ser Pro Pro Ala Ser Glu Met Pro Ile Asp Asn Asp His Val Ala
            20                  25                  30

Val Ala Arg Pro Ala Pro Arg Arg Arg Ile Val Val Ala Met Thr
        35                  40                  45

Gly Ala Thr Gly Ala Met Leu Gly Ile Lys Val Leu Ile Ala Leu Arg
50                  55                  60

Arg Leu Asn Val Glu Thr His Leu Val Met Ser Lys Trp Ala Glu Ala
65                  70                  75                  80

Thr Ile Lys Tyr Glu Thr Asp Tyr His Pro Ser Asn Val Arg Ala Leu
                85                  90                  95

Ala Asp Tyr Val His Asn Ile Asn Asp Met Ala Ala Pro Val Ser Ser
            100                 105                 110

```
Gly Ser Phe Arg Ala Asp Gly Met Ile Val Val Pro Cys Ser Met Lys
            115                 120                 125

Thr Leu Ala Ala Ile His Ser Gly Phe Cys Asp Asp Leu Ile Ser Arg
            130                 135                 140

Thr Ala Asp Val Met Leu Lys Glu Arg Arg Leu Val Leu Val Ala
145                 150                 155                 160

Arg Glu Thr Pro Leu Ser Glu Ile His Leu Arg Asn Met Leu Glu Val
            165                 170                 175

Thr Arg Ala Gly Ala Val Ile Phe Pro Pro Val Pro Ala Phe Tyr Ile
            180                 185                 190

Lys Ala Gly Ser Ile Glu Asp Leu Ile Asp Gln Ser Val Gly Arg Met
            195                 200                 205

Leu Asp Leu Phe Asp Leu Asp Thr Gly Asp Phe Glu Arg Trp Asn Gly
            210                 215                 220

Trp Glu Lys
225

<210> SEQ ID NO 42
<211> LENGTH: 242
<212> TYPE: PRT
<213> ORGANISM: Saccharomyces cerevisiae
<220> FEATURE:
<223> OTHER INFORMATION: Saccharomyces cerevisiae S288c

<400> SEQUENCE: 42

Met Leu Leu Phe Pro Arg Arg Thr Asn Ile Ala Phe Phe Lys Thr Thr
1               5                   10                  15

Gly Ile Phe Ala Asn Phe Pro Leu Leu Gly Arg Thr Ile Thr Thr Ser
            20                  25                  30

Pro Ser Phe Leu Thr His Lys Leu Ser Lys Glu Val Thr Arg Ala Ser
            35                  40                  45

Thr Ser Pro Pro Arg Pro Lys Arg Ile Val Val Ala Ile Thr Gly Ala
            50                  55                  60

Thr Gly Val Ala Leu Gly Ile Arg Leu Leu Gln Val Leu Lys Glu Leu
65                  70                  75                  80

Ser Val Glu Thr His Leu Val Ile Ser Lys Trp Gly Ala Ala Thr Met
            85                  90                  95

Lys Tyr Glu Thr Asp Trp Glu Pro His Asp Val Ala Ala Leu Ala Thr
            100                 105                 110

Lys Thr Tyr Ser Val Arg Asp Val Ser Ala Cys Ile Ser Ser Gly Ser
            115                 120                 125

Phe Gln His Asp Gly Met Ile Val Val Pro Cys Ser Met Lys Ser Leu
            130                 135                 140

Ala Ala Ile Arg Ile Gly Phe Thr Glu Asp Leu Ile Thr Arg Ala Ala
145                 150                 155                 160

Asp Val Ser Ile Lys Glu Asn Arg Lys Leu Leu Leu Val Thr Arg Glu
            165                 170                 175

Thr Pro Leu Ser Ser Ile His Leu Glu Asn Met Leu Ser Leu Cys Arg
            180                 185                 190

Ala Gly Val Ile Ile Phe Pro Pro Val Pro Ala Phe Tyr Thr Arg Pro
            195                 200                 205

Lys Ser Leu His Asp Leu Leu Glu Gln Ser Val Gly Arg Ile Leu Asp
            210                 215                 220

Cys Phe Gly Ile His Ala Asp Thr Phe Pro Arg Trp Glu Gly Ile Lys
225                 230                 235                 240
```

Ser Lys

<210> SEQ ID NO 43
<211> LENGTH: 180
<212> TYPE: PRT
<213> ORGANISM: Cryptococcus gattii
<220> FEATURE:
<223> OTHER INFORMATION: serotype B
<220> FEATURE:
<223> OTHER INFORMATION: Cryptococcus gattii WM276

<400> SEQUENCE: 43

```
Met Arg Arg Lys Arg Tyr Val Val Ala Val Thr Gly Ala Thr Gly Ala
1               5                   10                  15

Thr Leu Ala Ile Arg Leu Leu Gln Ala Leu Arg Ala Leu Asp Ile Glu
            20                  25                  30

Thr His Leu Ile Ile Ser Lys Trp Ala Val Lys Thr Leu Lys Tyr Glu
        35                  40                  45

Thr Asp Met Ile Glu Arg Glu Leu Lys Asp Leu Ala Asp Tyr Ser Tyr
    50                  55                  60

Ser Asn Ser Asp Leu Ala Ala Pro Pro Ser Ser Gly Ser Phe Ile His
65                  70                  75                  80

Asp Gly Met Phe Ile Ile Pro Cys Ser Met Lys Thr Leu Ala Ala Val
                85                  90                  95

Arg Ile Gly Leu Gly Asp Glu Leu Ile Ser Arg Ser Ala Asp Val Cys
            100                 105                 110

Leu Lys Glu Gly Arg Lys Leu Met Leu Val Val Arg Glu Thr Pro Leu
        115                 120                 125

Asn Asp Ile His Leu Glu Asn Met Leu Phe Leu Arg Arg Ala Gly Ala
    130                 135                 140

Ile Ile Phe Pro Pro Val Pro Ala Tyr Tyr Ile Arg Pro Gln Thr Ile
145                 150                 155                 160

Asp Asp Leu Thr Asn Gln Thr Val Gly Arg Ile Leu Asp Ser Ser Lys
                165                 170                 175

Cys Ser Gln Lys
            180
```

<210> SEQ ID NO 44
<211> LENGTH: 189
<212> TYPE: PRT
<213> ORGANISM: Escherichia coli
<220> FEATURE:
<223> OTHER INFORMATION: Escherichia coli K-12

<400> SEQUENCE: 44

```
Met Lys Arg Leu Ile Val Gly Ile Ser Gly Ala Ser Gly Ala Ile Tyr
1               5                   10                  15

Gly Val Arg Leu Leu Gln Val Leu Arg Asp Val Thr Asp Ile Glu Thr
            20                  25                  30

His Leu Val Met Ser Gln Ala Ala Arg Gln Thr Leu Ser Leu Glu Thr
        35                  40                  45

Asp Phe Ser Leu Arg Glu Val Gln Ala Leu Ala Asp Val Thr His Asp
    50                  55                  60

Ala Arg Asp Ile Ala Ala Ser Ile Ser Ser Gly Ser Phe Gln Thr Leu
65                  70                  75                  80

Gly Met Val Ile Leu Pro Cys Ser Ile Lys Thr Leu Ser Gly Ile Val
                85                  90                  95
```

```
His Ser Tyr Thr Asp Gly Leu Leu Thr Arg Ala Ala Asp Val Val Leu
            100                 105                 110

Lys Glu Arg Arg Pro Leu Val Leu Cys Val Arg Glu Thr Pro Leu His
        115                 120                 125

Leu Gly His Leu Arg Leu Met Thr Gln Ala Ala Glu Ile Gly Ala Val
    130                 135                 140

Ile Met Pro Pro Val Pro Ala Phe Tyr His Arg Pro Gln Ser Leu Asp
145                 150                 155                 160

Asp Val Ile Asn Gln Thr Val Asn Arg Val Leu Asp Gln Phe Ala Ile
                165                 170                 175

Thr Leu Pro Glu Asp Leu Phe Ala Arg Trp Gln Gly Ala
            180                 185

<210> SEQ ID NO 45
<211> LENGTH: 192
<212> TYPE: PRT
<213> ORGANISM: Bacillus subtilis

<400> SEQUENCE: 45

Met Lys Leu Val Ile Gly Met Thr Gly Ala Thr Gly Ala Ile Phe Gly
1               5                   10                  15

Ile Arg Leu Leu Glu Tyr Leu Lys Ala Ala Glu Ile Glu Thr His Leu
            20                  25                  30

Val Val Ser Pro Trp Ala Asn Val Thr Ile Thr His Gly Thr Asp Tyr
        35                  40                  45

Thr Leu Lys Asp Val Glu Lys Leu Ala Ser Tyr Thr Tyr Ser His Lys
    50                  55                  60

Asp Gln Ala Ala Ala Ile Ser Ser Gly Ser Phe Glu Thr Asp Gly Met
65                  70                  75                  80

Ile Ile Ala Pro Cys Ser Met Lys Ser Leu Ala Ser Ile Arg Thr Gly
                85                  90                  95

Met Ala Asp Asn Leu Leu Thr Arg Ala Ala Asp Val Ile Leu Lys Glu
            100                 105                 110

Arg Lys Lys Leu Val Leu Leu Thr Arg Glu Thr Pro Leu Ser Gln Ile
        115                 120                 125

His Leu Glu Asn Met Leu Ala Leu Thr Lys Met Gly Ser Val Ile Leu
    130                 135                 140

Pro Pro Met Pro Ala Phe Tyr Asn Lys Pro Ala Asp Met Asp Glu Leu
145                 150                 155                 160

Ile Asp His Ile Val Phe Arg Thr Leu Asp Gln Phe Gly Ile Arg Leu
                165                 170                 175

Pro Glu Ala Lys Arg Trp Tyr Gly Ile Glu Lys Gln Lys Gly Gly Ile
            180                 185                 190

<210> SEQ ID NO 46
<211> LENGTH: 209
<212> TYPE: PRT
<213> ORGANISM: Pseudomonas aeruginosa

<400> SEQUENCE: 46

Met Ser Gly Pro Glu Arg Ile Thr Leu Ala Met Thr Gly Ala Ser Gly
1               5                   10                  15

Ala Gln Tyr Gly Leu Arg Leu Leu Asp Cys Leu Val Gln Glu Glu Arg
            20                  25                  30

Glu Val His Phe Leu Ile Ser Lys Ala Ala Gln Leu Val Met Ala Thr
        35                  40                  45
```

```
Glu Thr Asp Val Ala Leu Pro Ala Lys Pro Gln Ala Met Gln Ala Phe
 50                  55                  60

Leu Thr Glu Tyr Cys Gly Ala Ala Gly Gln Ile Arg Val Phe Gly
 65                  70                  75                  80

Gln Asn Asp Trp Met Ala Pro Pro Ala Ser Gly Ser Ser Ala Pro Asn
                 85                  90                  95

Ala Met Val Ile Cys Pro Cys Ser Thr Gly Thr Leu Ser Ala Val Ala
                100                 105                 110

Thr Gly Ala Cys Asn Asn Leu Ile Glu Arg Ala Ala Asp Val Ala Leu
                115                 120                 125

Lys Glu Arg Arg Pro Leu Val Leu Val Pro Arg Glu Ala Pro Phe Ser
130                 135                 140

Ser Ile His Leu Glu Asn Met Leu Lys Leu Ser Asn Leu Gly Ala Val
145                 150                 155                 160

Ile Leu Pro Ala Ala Pro Gly Phe Tyr His Gln Pro Gln Ser Val Glu
                165                 170                 175

Asp Leu Val Asp Phe Val Val Ala Arg Ile Leu Asn Thr Leu Gly Ile
                180                 185                 190

Pro Gln Asp Met Leu Pro Arg Trp Gly Glu Gln His Leu Val Ser Asp
                195                 200                 205

Glu

<210> SEQ ID NO 47
<211> LENGTH: 219
<212> TYPE: PRT
<213> ORGANISM: Unknown
<220> FEATURE:
<223> OTHER INFORMATION: Enterobacter species DC4

<400> SEQUENCE: 47

Met Leu Arg Gln Val Arg Ala Asn Ala Leu Thr Cys Asn Ser Pro Gln
  1               5                  10                  15

Asn Pro Ala Gln Ser Ala Leu Lys Ser Val Arg Ala Lys Ile Met Lys
                 20                  25                  30

Arg Leu Ile Val Gly Leu Ser Gly Ala Ser Gly Ala Ile Tyr Gly Val
                 35                  40                  45

Arg Leu Leu Gln Val Leu Arg Asn Val Ala Glu Val Glu Thr His Leu
 50                  55                  60

Val Met Ser Gln Ala Ala Arg Gln Thr Leu Ser Leu Glu Thr Asp Leu
 65                  70                  75                  80

Ser Leu Arg Asp Val Gln Ala Leu Ala Asp Val Val His Asp Ala Arg
                 85                  90                  95

Asp Ile Ala Ala Ser Ile Ser Ser Gly Ser Phe Lys Thr Ala Gly Met
                100                 105                 110

Val Ile Leu Pro Cys Ser Ile Lys Thr Leu Ser Gly Ile Val Asn Ser
                115                 120                 125

Tyr Thr Asp Thr Leu Val Thr Arg Ala Ala Asp Val Val Leu Lys Glu
130                 135                 140

Arg Arg Pro Leu Val Leu Cys Val Arg Glu Thr Pro Leu His Leu Gly
145                 150                 155                 160

His Leu Arg Leu Met Thr Gln Ala Ala Glu Leu Gly Ala Ile Ile Met
                165                 170                 175

Pro Pro Val Pro Ala Phe Tyr His Arg Pro Thr Ser Leu Asp Asp Val
                180                 185                 190

Ile Asn Gln Thr Val Asn Arg Val Leu Asp Gln Phe Asp Ile Asp Leu
```

-continued

```
              195                 200                 205
Pro Glu Asp Leu Phe Thr Arg Trp Gln Gly Ala
    210                 215
```

<210> SEQ ID NO 48
<211> LENGTH: 503
<212> TYPE: PRT
<213> ORGANISM: Saccharomyces cerevisiae
<220> FEATURE:
<223> OTHER INFORMATION: Saccharomyces cerevisiae S288c

<400> SEQUENCE: 48

```
Met Arg Lys Leu Asn Pro Ala Leu Glu Phe Arg Asp Phe Ile Gln Val
1               5                  10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
```

```
                340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500

<210> SEQ ID NO 49
<211> LENGTH: 168
<212> TYPE: PRT
<213> ORGANISM: Unknown
<220> FEATURE:
<223> OTHER INFORMATION: Enterobacter species MGH 24

<400> SEQUENCE: 49

Met Ser Thr Phe Asp Lys His Asp Leu Ser Gly Phe Val Gly Lys His
1               5                   10                  15

Leu Val Tyr Thr Tyr Asp Asn Gly Trp Asn Tyr Glu Ile Tyr Val Lys
            20                  25                  30

Asn Glu Thr Thr Leu Asp Tyr Arg Ile His Ser Gly Leu Val Ala Asn
        35                  40                  45

Arg Trp Val Lys Asp Gln Gln Ala Tyr Ile Val Arg Val Gly Glu Ser
    50                  55                  60

Ile Tyr Lys Ile Ser Trp Thr Glu Pro Thr Gly Thr Asp Val Ser Leu
65                  70                  75                  80

Ile Val Asn Leu Gly Asp Lys Leu Phe His Gly Thr Ile Phe Phe Pro
                85                  90                  95

Arg Trp Val Met Asn Asn Pro Glu Lys Thr Val Cys Phe Gln Asn Asp
            100                 105                 110

His Ile Pro Leu Met Asn Ser Tyr Arg Asp Ala Gly Pro Ala Tyr Pro
        115                 120                 125

Thr Glu Val Ile Asp Glu Phe Ala Thr Ile Thr Phe Val Arg Asp Cys
    130                 135                 140

Gly Ala Asn Asn Glu Ser Val Ile Ala Cys Ala Ala Ser Glu Leu Pro
145                 150                 155                 160

Asn Asp Phe Pro Ala Asn Leu Asn
                165

<210> SEQ ID NO 50
<211> LENGTH: 161
<212> TYPE: PRT
```

<213> ORGANISM: Bacillus pumilus

<400> SEQUENCE: 50

Met Asp Gln Phe Val Gly Leu His Met Ile Tyr Thr Tyr Glu Asn Gly
1               5                   10                  15

Trp Glu Tyr Glu Ile Tyr Ile Lys Asn Asp His Thr Ile Asp Tyr Arg
            20                  25                  30

Ile His Ser Gly Met Val Gly Gly Arg Trp Val Arg Asp Gln Glu Val
        35                  40                  45

Asn Ile Val Lys Leu Thr Lys Gly Val Tyr Lys Val Ser Trp Thr Glu
    50                  55                  60

Pro Thr Gly Thr Asp Val Ser Leu Asn Phe Met Pro Glu Glu Lys Arg
65                  70                  75                  80

Met His Gly Val Ile Phe Phe Pro Lys Trp Val His Glu Arg Pro Asp
                85                  90                  95

Ile Thr Val Cys Tyr Gln Asn Asp Tyr Ile Asp Leu Met Lys Glu Ser
            100                 105                 110

Arg Glu Lys Tyr Glu Thr Tyr Pro Lys Tyr Val Val Pro Glu Phe Ala
        115                 120                 125

Asp Ile Thr Tyr Ile His His Ala Gly Val Asn Asp Glu Thr Ile Ile
    130                 135                 140

Ala Glu Ala Pro Tyr Glu Gly Met Thr Asp Glu Ile Arg Ala Gly Arg
145                 150                 155                 160

Lys

<210> SEQ ID NO 51
<211> LENGTH: 534
<212> TYPE: PRT
<213> ORGANISM: Aspergillus niger
<220> FEATURE:
<223> OTHER INFORMATION: Aspergillus niger CBS 513.88

<400> SEQUENCE: 51

Met Leu Arg Met Leu Arg Pro Gly Arg Arg Ile Pro Thr His Pro Ser
1               5                   10                  15

Arg Ser Phe Ser Thr Thr Pro His Arg Ser Asn Asp Ser Pro Ala Leu
            20                  25                  30

Asn Phe Arg Ser Leu Leu Ser Ala Leu Arg Ala Gln Asp Asp Leu Val
        35                  40                  45

Asp Ile Thr Gln Pro Ala Ser Pro Asp Leu Glu Ile Ala Ala Leu Thr
    50                  55                  60

Arg Arg Val Tyr Glu Ser His Ser Pro Ala Pro Leu Phe His Asn Val
65                  70                  75                  80

Thr Asp Thr Asp Pro Glu Thr Gly Leu Phe Lys Ile Leu Gly Ala Pro
                85                  90                  95

Val Gly Leu Arg Ala Asp Pro Ala Thr Arg Phe Gly Arg Leu Ala Ile
            100                 105                 110

Gln Leu Gly Leu Pro Gln Asn Ala Thr Pro Leu Asp Ile Leu Glu Lys
        115                 120                 125

Leu Ile Ala Ala Lys His Ser Thr Pro Leu Pro Pro Thr Pro Val Pro
    130                 135                 140

Ala Ser Ser Ala Pro Cys Lys Glu Asn Ile Leu His Gly Ser Gln Ile
145                 150                 155                 160

Asp Met Thr Lys Trp Pro Ile Pro Arg Leu His Pro Leu Asp Gly Gly
                165                 170                 175

Asn Tyr Leu Ala Thr Tyr Gly Phe His Ile Leu Gln Ser Pro Asp Lys
                180                 185                 190

Ala Trp Thr Ser Trp Ser Ile Ser Arg Thr Met His Val Ala Asn Thr
            195                 200                 205

Pro Arg Thr Ile Val Ala Pro Ile Met Pro Gly Gln His Ile Ala Gln
210                 215                 220

Val His Gln Met Trp Ala Asp Gln Gly Ala Lys Asp Thr Pro Trp Ala
225                 230                 235                 240

Leu Val Leu Gly Gly Pro Ala Ala Phe Val Gly Gly Met Pro
                245                 250                 255

Leu Pro Ala Phe Val Ser Glu Asp Gly Tyr Ile Gly Ala Leu Cys Gly
            260                 265                 270

Glu Ala Met Asp Val Val Lys Cys Glu Thr Asn Asp Leu Tyr Val Pro
            275                 280                 285

Ala Asn Ala Glu Ile Val Leu Glu Gly Arg Ile Ser Thr Thr Glu Lys
            290                 295                 300

Val Gly Glu Gly Pro Met Gly Glu Tyr His Gly Tyr Met Phe Gln Asp
305                 310                 315                 320

Lys Ala Val Pro Glu Pro Arg Ile Glu Val Asp Cys Val Thr Tyr Arg
                325                 330                 335

Arg Asp Pro Val Val Pro Ile Cys Val Ala Gly Leu Ala Pro Asp Glu
            340                 345                 350

Thr His Thr Val Trp Gly Ala Ile Ser Ala Glu Ile Leu Asp Ala
            355                 360                 365

Leu Arg Gly Ala Glu Leu Pro Val Lys Met Ala Trp Met Pro Tyr Glu
370                 375                 380

Ala Gln Cys Cys Trp Val Val Ser Val Asp Val Glu Arg Leu Gly
385                 390                 395                 400

Arg Met Gly Ile Lys Lys Glu Glu Leu Ser Arg Arg Val Gly Glu Val
                405                 410                 415

Val Phe Gly Thr His Ala Gly Trp Glu Ala Pro Lys Val Phe Val Val
            420                 425                 430

Gly Asp Asp Val Asp Val Thr Asp Ile Gly Gln Phe Val Trp Ala Leu
            435                 440                 445

Ala Thr Arg Tyr Arg Pro Gly Ala Asp Glu Leu Val Phe Glu Glu Ala
450                 455                 460

Asp Gly Leu Pro Met Ile Pro Tyr Met Thr Arg Ala Ser Arg Arg Glu
465                 470                 475                 480

Val Pro Asn Pro Gly Lys Gly Lys Ser Val Val Asn Leu Leu Leu
                485                 490                 495

Pro Ser Glu Phe Glu Gly Lys Arg Pro Trp Val Pro Gly Ser Phe Glu
            500                 505                 510

Gly Leu Tyr Ser Glu Glu Leu Lys Gln Lys Val Leu Gly Arg Trp Gly
            515                 520                 525

Glu Leu Phe Glu Lys Lys
    530

<210> SEQ ID NO 52
<211> LENGTH: 513
<212> TYPE: PRT
<213> ORGANISM: Candida dubliniensis
<220> FEATURE:
<223> OTHER INFORMATION: Candida dubliniensis CD36

<400> SEQUENCE: 52

```
Met Ser Leu Asn Pro Ala Leu Lys Phe Arg Asp Phe Ile Gln Val Leu
 1               5                  10                  15

Lys Asn Glu Gly Asp Leu Ile Glu Ile Asp Thr Glu Val Asp Pro Asn
             20                  25                  30

Leu Glu Val Gly Ala Ile Thr Arg Lys Ala Tyr Glu Asn Lys Leu Ala
             35                  40                  45

Ala Pro Leu Phe Asn Asn Leu Lys Gln Asp Pro Glu Asn Ile Asp Pro
 50                  55                  60

Lys Asn Leu Phe Arg Ile Leu Gly Cys Pro Gly Gly Leu Arg Gly Phe
 65                  70                  75                  80

Gly Asn Asp His Ala Arg Ile Ala Leu His Leu Gly Leu Asp Ser Gln
                 85                  90                  95

Thr Pro Met Lys Glu Ile Ile Asp Phe Leu Val Ala Asn Arg Asn Pro
                100                 105                 110

Lys Lys Tyr Ile Pro Pro Val Leu Val Pro Asn Asp Gln Ser Pro His
                115                 120                 125

Lys Lys His His Leu Thr Lys Glu Gln Ile Asp Leu Thr Lys Leu Pro
 130                 135                 140

Val Pro Leu Leu His His Gly Asp Gly Lys Phe Ile Gln Thr Tyr
 145                 150                 155                 160

Gly Met Trp Val Leu Gln Thr Pro Asp Lys Ser Trp Thr Asn Trp Ser
                165                 170                 175

Ile Ala Arg Gly Met Val His Asp Ser Lys Ser Ile Thr Gly Leu Val
                180                 185                 190

Ile Asn Pro Gln His Val Lys Gln Val Ser Asp Ala Trp Val Ala Ala
                195                 200                 205

Gly Lys Gly Asp Lys Ile Pro Phe Ala Leu Cys Phe Gly Val Pro Pro
 210                 215                 220

Ala Ala Ile Leu Val Ser Ser Met Pro Ile Pro Asp Gly Ala Thr Glu
 225                 230                 235                 240

Ala Glu Tyr Ile Gly Gly Leu Cys Asn Gln Ala Val Pro Val Val Lys
                245                 250                 255

Cys Glu Thr Asn Asp Leu Glu Val Pro Ala Asp Cys Glu Met Val Phe
                260                 265                 270

Glu Gly Tyr Leu Asp Arg Asp Thr Leu Val Arg Glu Gly Pro Phe Gly
                275                 280                 285

Glu Met His Gly Tyr Cys Phe Pro Lys Asp His His Thr Gln Pro Leu
                290                 295                 300

Tyr Arg Val Asn His Ile Ser Tyr Arg Asp Gln Ala Ile Met Pro Ile
 305                 310                 315                 320

Ser Asn Pro Gly Leu Cys Thr Asp Glu Thr His Thr Leu Ile Gly Gly
                325                 330                 335

Leu Val Ser Ala Glu Thr Lys Tyr Leu Ile Ser Gln His Pro Val Leu
                340                 345                 350

Ser Lys Ile Val Glu Asp Val Phe Thr Pro Tyr Glu Ala Gln Ala Leu
                355                 360                 365

Trp Leu Ala Val Lys Ile Asn Thr His Glu Leu Val Lys Leu Lys Thr
 370                 375                 380

Asn Ala Lys Glu Leu Ser Asn Leu Val Gly Asp Phe Leu Phe Arg Ser
 385                 390                 395                 400

Lys Glu Cys Tyr Lys Val Cys Ser Ile Leu His Glu Ile Ile Leu Val
                405                 410                 415

Gly Asp Asp Ile Asp Ile Phe Asp Phe Lys Gln Leu Ile Trp Ala Tyr
```

```
                420              425              430
Thr Thr Arg His Thr Pro Val Gln Asp Gln Leu Tyr Phe Asp Val
        435              440              445

Lys Pro Phe Ala Leu Ala Pro Phe Ala Ser Gln Gly Pro Leu Ile Lys
    450              455              460

Thr Arg Gln Gly Gly Lys Cys Val Thr Thr Cys Ile Phe Pro Lys Gln
465              470              475              480

Phe Thr Asp Pro Asp Phe Glu Phe Val Thr Cys Asn Phe Asn Gly Tyr
                485              490              495

Pro Glu Glu Val Lys Asn Lys Ile Ser Gln Asn Trp Asp Lys Tyr Tyr
            500              505              510

Lys

<210> SEQ ID NO 53
<211> LENGTH: 497
<212> TYPE: PRT
<213> ORGANISM: Escherichia coli
<220> FEATURE:
<223> OTHER INFORMATION: Escherichia coli K-12

<400> SEQUENCE: 53

Met Asp Ala Met Lys Tyr Asn Asp Leu Arg Asp Phe Leu Thr Leu Leu
1               5                   10                  15

Glu Gln Gln Gly Glu Leu Lys Arg Ile Thr Leu Pro Val Asp Pro His
            20                  25                  30

Leu Glu Ile Thr Glu Ile Ala Asp Arg Thr Leu Arg Ala Gly Gly Pro
        35                  40                  45

Ala Leu Leu Phe Glu Asn Pro Lys Gly Tyr Ser Met Pro Val Leu Cys
    50                  55                  60

Asn Leu Phe Gly Thr Pro Lys Arg Val Ala Met Gly Met Gly Gln Glu
65                  70                  75                  80

Asp Val Ser Ala Leu Arg Glu Val Gly Lys Leu Leu Ala Phe Leu Lys
                85                  90                  95

Glu Pro Glu Pro Pro Lys Gly Phe Arg Asp Leu Phe Asp Lys Leu Pro
            100                 105                 110

Gln Phe Lys Gln Val Leu Asn Met Pro Thr Lys Arg Leu Arg Gly Ala
        115                 120                 125

Pro Cys Gln Gln Lys Ile Val Ser Gly Asp Asp Val Asp Leu Asn Arg
    130                 135                 140

Ile Pro Ile Met Thr Cys Trp Pro Glu Asp Ala Ala Pro Leu Ile Thr
145                 150                 155                 160

Trp Gly Leu Thr Val Thr Arg Gly Pro His Lys Glu Arg Gln Asn Leu
                165                 170                 175

Gly Ile Tyr Arg Gln Gln Leu Ile Gly Lys Asn Lys Leu Ile Met Arg
            180                 185                 190

Trp Leu Ser His Arg Gly Gly Ala Leu Asp Tyr Gln Glu Trp Cys Ala
        195                 200                 205

Ala His Pro Gly Glu Arg Phe Pro Val Ser Val Ala Leu Gly Ala Asp
    210                 215                 220

Pro Ala Thr Ile Leu Gly Ala Val Thr Pro Val Pro Asp Thr Leu Ser
225                 230                 235                 240

Glu Tyr Ala Phe Ala Gly Leu Leu Arg Gly Thr Lys Thr Glu Val Val
                245                 250                 255

Lys Cys Ile Ser Asn Asp Leu Glu Val Pro Ala Ser Ala Glu Ile Val
            260                 265                 270
```

```
Leu Glu Gly Tyr Ile Glu Gln Gly Glu Thr Ala Pro Glu Gly Pro Tyr
            275                 280                 285

Gly Asp His Thr Gly Tyr Tyr Asn Glu Val Asp Ser Phe Pro Val Phe
        290                 295                 300

Thr Val Thr His Ile Thr Gln Arg Glu Asp Ala Ile Tyr His Ser Thr
305                 310                 315                 320

Tyr Thr Gly Arg Pro Pro Asp Glu Pro Ala Val Leu Gly Val Ala Leu
                325                 330                 335

Asn Glu Val Phe Val Pro Ile Leu Gln Lys Gln Phe Pro Glu Ile Val
                340                 345                 350

Asp Phe Tyr Leu Pro Pro Glu Gly Cys Ser Tyr Arg Leu Ala Val Val
                355                 360                 365

Thr Ile Lys Lys Gln Tyr Ala Gly His Ala Lys Arg Val Met Met Gly
            370                 375                 380

Val Trp Ser Phe Leu Arg Gln Phe Met Tyr Thr Lys Phe Val Ile Val
385                 390                 395                 400

Cys Asp Asp Asp Val Asn Ala Arg Asp Trp Asn Asp Val Ile Trp Ala
                405                 410                 415

Ile Thr Thr Arg Met Asp Pro Ala Arg Asp Thr Val Leu Val Glu Asn
                420                 425                 430

Thr Pro Ile Asp Tyr Leu Asp Phe Ala Ser Pro Val Ser Gly Leu Gly
                435                 440                 445

Ser Lys Met Gly Leu Asp Ala Thr Asn Lys Trp Pro Gly Glu Thr Gln
            450                 455                 460

Arg Glu Trp Gly Arg Pro Ile Lys Lys Asp Pro Asp Val Val Ala His
465                 470                 475                 480

Ile Asp Ala Ile Trp Asp Glu Leu Ala Ile Phe Asn Asn Gly Lys Ser
                485                 490                 495

Ala

<210> SEQ ID NO 54
<211> LENGTH: 473
<212> TYPE: PRT
<213> ORGANISM: Bacillus megaterium
<220> FEATURE:
<223> OTHER INFORMATION: Bacillus megaterium QM B1551

<400> SEQUENCE: 54

Met Ala Tyr Lys Asp Phe Arg Asp Phe Leu Asn Thr Leu His Lys Glu
1               5                   10                  15

Gly Gln Leu Leu Thr Val Thr Asp Glu Val Gln Pro Asp Pro Asp Leu
                20                  25                  30

Gly Ser Ala Gly Gln Ala Ile Ser Asn Leu Gly Asp Gln Thr Pro Gly
            35                  40                  45

Leu Leu Phe Thr Asn Ile Tyr Gly Tyr Asn Asn Ala Lys Val Ala Leu
        50                  55                  60

Asn Val Met Gly Ser Trp Ser Asn His Ala Leu Met Met Gly Leu Pro
65                  70                  75                  80

Lys Ser Thr Pro Val Lys Glu Gln Phe Glu Phe Ala Arg Arg Tyr
                85                  90                  95

Glu Lys Phe Pro Val Lys Val Lys Arg Glu Glu Thr Ala Pro Phe His
                100                 105                 110

Glu Cys Glu Ile Lys Asp Asp Ile Asn Leu Phe Asp Leu Leu Pro Leu
            115                 120                 125
```

```
Phe Arg Leu Asn Gln Gly Asp Gly Gly Tyr Tyr Leu Asp Lys Ala Cys
        130                 135                 140

Val Ile Ser Arg Asp Gln His Asp Lys Glu Asn Phe Gly Lys Gln Asn
145                 150                 155                 160

Val Gly Ile Tyr Arg Met Gln Val Lys Gly Lys Asp Arg Leu Gly Ile
                165                 170                 175

Gln Pro Val Pro Gln His Asp Ile Ala Ile His Leu Lys Gln Ala Glu
            180                 185                 190

Glu Lys Gly Glu Asn Leu Pro Val Ser Ile Ala Leu Gly Cys Glu Pro
        195                 200                 205

Ala Ile Val Thr Ala Ala Thr Pro Leu His Tyr Asp Gln Ser Glu
210                 215                 220

Tyr Glu Met Ala Gly Ala Ile Gln Gly Glu Pro Tyr Arg Ile Val Lys
225                 230                 235                 240

Ser Gln Leu Ser Asp Leu Asp Val Pro Trp Gly Ala Glu Val Ile Leu
                245                 250                 255

Glu Gly Glu Ile Leu Ala Gly Glu Arg Glu Tyr Glu Gly Pro Phe Gly
            260                 265                 270

Glu Phe Thr Gly His Tyr Ser Gly Gly Arg Ser Met Pro Val Ile Lys
        275                 280                 285

Ile Asn Arg Val Tyr His Arg Lys Asp Pro Ile Phe Glu Ser Leu Tyr
290                 295                 300

Ile Gly Met Pro Trp Thr Glu Thr Asp Tyr Leu Ile Gly Ile Asn Thr
305                 310                 315                 320

Ser Val Pro Leu Tyr Gln Gln Leu Lys Glu Ala Tyr Pro Glu Glu Ile
                325                 330                 335

Glu Ala Val Asn Ala Met Tyr Thr His Gly Leu Val Ala Ile Val Ser
            340                 345                 350

Thr Lys Ser Arg Tyr Gly Gly Phe Ala Lys Ala Val Gly Met Arg Ala
        355                 360                 365

Leu Thr Thr Pro His Gly Leu Gly Tyr Cys Lys Leu Val Ile Leu Val
370                 375                 380

Asp Glu Asp Val Asp Pro Phe Asn Leu Pro Gln Val Met Trp Ala Leu
385                 390                 395                 400

Ser Thr Lys Met His Pro Lys His Asp Val Ile Thr Val Pro Asn Leu
                405                 410                 415

Ser Val Leu Pro Leu Asp Pro Gly Ser Glu Pro Ala Gly Ile Thr Asp
            420                 425                 430

Lys Met Ile Leu Asp Ala Thr Thr Pro Val Ala Pro Glu Thr Arg Gly
        435                 440                 445

His Tyr Ser Gln Pro Leu Asp Thr Pro Leu Glu Thr Glu Lys Trp Glu
450                 455                 460

Lys Ile Leu Thr Asn Met Met Gln Lys
465                 470

<210> SEQ ID NO 55
<211> LENGTH: 423
<212> TYPE: PRT
<213> ORGANISM: Unknown
<220> FEATURE:
<223> OTHER INFORMATION: Methanothermobacter sp. CaT2

<400> SEQUENCE: 55

Met Arg Asn Phe Leu Asp Lys Ile Gly Glu Glu Ala Leu Val Val Glu
1               5                   10                  15
```

```
Asp Glu Val Ser Thr Ser Phe Glu Ala Ala Ser Ile Leu Arg Glu His
             20                  25                  30

Pro Arg Asp Leu Val Ile Leu Lys Asn Leu Lys Glu Ser Asp Ile Pro
         35                  40                  45

Val Ile Ser Gly Leu Cys Asn Thr Arg Glu Lys Ile Ala Leu Ser Leu
     50                  55                  60

Asn Cys Arg Val His Glu Ile Thr His Arg Ile Val Glu Ala Met Glu
 65                  70                  75                  80

Asn Pro Thr Pro Ile Ser Ser Val Gly Gly Leu Asp Gly Tyr Arg Ser
                 85                  90                  95

Gly Arg Ala Asp Leu Ser Glu Leu Pro Ile Leu Arg His Tyr Arg Arg
            100                 105                 110

Asp Gly Gly Pro Tyr Ile Thr Ala Gly Val Ile Phe Ala Arg Asp Pro
        115                 120                 125

Asp Thr Gly Val Arg Asn Ala Ser Ile His Arg Met Met Val Ile Gly
        130                 135                 140

Asp Asp Arg Leu Ala Val Arg Ile Val Pro Arg His Leu Tyr Thr Tyr
145                 150                 155                 160

Leu Gln Lys Ala Glu Glu Arg Gly Glu Asp Leu Glu Ile Ala Ile Ala
                165                 170                 175

Ile Gly Met Asp Pro Ala Thr Leu Leu Ala Thr Thr Ser Ile Pro
            180                 185                 190

Ile Asp Ala Asp Glu Met Glu Val Ala Asn Thr Phe His Glu Gly Glu
        195                 200                 205

Leu Glu Leu Val Arg Cys Glu Gly Val Asp Met Glu Val Pro Pro Ala
210                 215                 220

Glu Ile Ile Leu Glu Gly Arg Ile Leu Cys Gly Val Arg Glu Arg Glu
225                 230                 235                 240

Gly Pro Phe Val Asp Leu Thr Asp Thr Tyr Asp Val Val Arg Asp Glu
            245                 250                 255

Pro Val Ile Ser Leu Glu Arg Met His Ile Arg Lys Asp Ala Met Tyr
        260                 265                 270

His Ala Ile Leu Pro Ala Gly Phe Glu His Arg Leu Leu Gln Gly Leu
    275                 280                 285

Pro Gln Glu Pro Arg Ile Tyr Arg Ala Val Lys Asn Thr Val Pro Thr
290                 295                 300

Val Arg Asn Val Val Leu Thr Glu Gly Gly Cys Cys Trp Leu His Ala
305                 310                 315                 320

Ala Val Ser Ile Lys Lys Gln Thr Glu Gly Asp Gly Lys Asn Val Ile
                325                 330                 335

Met Ala Ala Leu Ala Ala His Pro Ser Leu Lys His Val Val Val Val
            340                 345                 350

Asp Glu Asp Ile Asp Val Leu Asp Pro Glu Glu Ile Glu Tyr Ala Ile
        355                 360                 365

Ala Thr Arg Val Lys Gly Asp Asp Asp Ile Leu Ile Val Pro Gly Ala
    370                 375                 380

Arg Gly Ser Ser Leu Asp Pro Ala Ala Leu Pro Asp Gly Thr Thr Thr
385                 390                 395                 400

Lys Val Gly Val Asp Ala Thr Ala Pro Leu Ala Ser Ala Glu Lys Phe
                405                 410                 415

Gln Arg Val Ser Arg Ser Glu
            420
```

<210> SEQ ID NO 56
<211> LENGTH: 494
<212> TYPE: PRT
<213> ORGANISM: Mycobacterium chelonae
<220> FEATURE:
<223> OTHER INFORMATION: Mycobacterium chelonae 1518

<400> SEQUENCE: 56

```
Met Ala Phe Asn Asp Leu Arg Arg Tyr Leu Ala Asp Leu Glu Ala His
1               5                   10                  15

Gly Glu Leu Arg Thr Ile Lys Thr Pro Val Ser Thr Glu Ile Gln Leu
            20                  25                  30

Gly Ala Ile Ala Arg Leu Ala Cys Glu Thr Tyr Gly Pro Ala Ala Leu
        35                  40                  45

Phe Glu Asn Leu Val Gly Tyr Pro Thr Phe Arg Gly Leu Ala Ala Phe
    50                  55                  60

Glu Thr Tyr Ser Gly Asn Pro Asp Asn Arg Ala Trp Arg Leu Ala Arg
65                  70                  75                  80

Ala Leu Gly Leu Ser Asp Asp Thr Gly Asp Gln Ile Val Asp Phe
                85                  90                  95

Leu Ala Gly Phe Arg Asp Thr Ala Gly Val Ala Pro Val Leu Val Glu
            100                 105                 110

Thr Gly Pro Val His Glu Asn Ile Val Arg Asp Arg Gly Glu Leu Leu
        115                 120                 125

Asp Tyr Leu Pro Ile Pro His Leu His Pro Gly Asp Gly Gly Pro Tyr
    130                 135                 140

Val Asn Thr Ile Gly Phe Phe Val Leu Glu Ser Pro Asp Arg Ser Trp
145                 150                 155                 160

Val Asn Trp Ala Val Ala Arg Cys Met Lys Leu Asp Gly Asp Arg Met
                165                 170                 175

Val Gly Met Thr Ala Val Met Gln His Ile Gly Met Leu Arg Arg Glu
            180                 185                 190

Trp Asp Lys Ile Gly Thr Ser Val Pro Phe Ala Leu Val Leu Gly Ala
        195                 200                 205

Asp Pro Ile Thr Thr Leu Ile Ser Gly Gly Pro Leu Ala Lys Phe Gly
    210                 215                 220

Ala Ser Glu Gly Asp Ile Ile Gly Ala Ile Arg Gly Glu Pro Leu Glu
225                 230                 235                 240

Val Val Glu Cys Val Thr Ser Ser Leu Arg Val Pro Ala His Ala Glu
                245                 250                 255

Ile Val Ile Glu Gly Tyr Ile Asp Leu Thr Glu Ser Ala Asp Glu Gly
            260                 265                 270

Pro Met Ala Glu Tyr His Gly Tyr Ile Asp Lys Ala Lys Asn Thr Thr
        275                 280                 285

Gly Ala Pro Asp Phe Gly Val Tyr His Ile Thr Ala Val Thr His Arg
    290                 295                 300

Asn Asp Ala Ile Tyr Pro Ser Thr Cys Ala Gly Lys Pro Val Asp Glu
305                 310                 315                 320

Asp His Thr Ile Thr Gly Pro Gly Val Ala Ala Ser Leu Asn Ala
                325                 330                 335

Leu Arg Ala Ala Ser Leu Pro Val Glu Lys Ala Trp Met Val Pro Glu
            340                 345                 350

Ser Ala Ser His Val Leu Ala Val Thr Val Ser Asp Gly Trp Ser Gly
        355                 360                 365

Glu Phe Pro Asp Ala Asn Glu Leu Cys Arg Lys Ile Gly Asn Ala Val
```

```
                370             375             380
Lys Thr Met Asp His Ser Ala Tyr Trp Val Gln Arg Ile Leu Val Thr
385                 390             395                 400

Asp Asn Asp Ile Asp Pro Thr Ser Pro Ser Asp Leu Trp Trp Ala Tyr
                405             410                 415

Ala Thr Arg Cys Arg Pro Gly Asp Asp Ser Ile Ile Leu Glu Asp Val
                420             425             430

Pro Ile Met Ala Leu Ser Pro Ile Val Asn Thr Arg Glu Glu Arg Thr
            435             440             445

Lys Thr Arg Gly Arg Val Glu Val Leu Asn Cys Leu Ile Pro Pro Tyr
450             455             460

Ala Asp Asp Leu Ser Val Thr Ser Ala Ala Leu Arg Gln Ala Tyr Pro
465             470             475                 480

His Asp Ala Ile Ala Phe Ala Glu Arg Thr Tyr Leu Gly Glu
                485             490
```

<210> SEQ ID NO 57
<211> LENGTH: 512
<212> TYPE: PRT
<213> ORGANISM: Hypocrea atroviridis
<220> FEATURE:
<223> OTHER INFORMATION: Hypocrea atroviridis (strain ATCC 20476)

<400> SEQUENCE: 57

```
Met Ser Ser Thr Thr Tyr Lys Ser Glu Ala Phe Asp Pro Glu Pro Pro
1               5                   10                  15

His Leu Ser Phe Arg Ser Phe Val Glu Ala Leu Arg Gln Asp Asn Asp
            20                  25                  30

Leu Val Asp Ile Asn Glu Pro Val Asp Pro Asp Leu Glu Ala Ala Ala
        35                  40                  45

Ile Thr Arg Leu Val Cys Glu Thr Asp Asp Lys Ala Pro Leu Phe Asn
    50                  55                  60

Asn Val Ile Gly Ala Lys Asp Gly Leu Trp Arg Ile Leu Gly Ala Pro
65                  70                  75                  80

Ala Ser Leu Arg Ser Ser Pro Lys Glu Arg Phe Gly Arg Leu Ala Arg
                85                  90                  95

His Leu Ala Leu Pro Pro Thr Ala Ser Ala Lys Asp Ile Leu Asp Lys
            100                 105                 110

Met Leu Ser Ala Asn Ser Ile Pro Pro Ile Glu Pro Val Ile Val Pro
        115                 120                 125

Thr Gly Pro Val Lys Glu Asn Ser Ile Glu Gly Glu Asn Ile Asp Leu
    130                 135                 140

Glu Ala Leu Pro Ala Pro Met Val His Gln Ser Asp Gly Gly Lys Tyr
145                 150                 155                 160

Ile Gln Thr Tyr Gly Met His Val Ile Gln Ser Pro Asp Gly Cys Trp
                165                 170                 175

Thr Asn Trp Ser Ile Ala Arg Ala Met Val Ser Gly Lys Arg Thr Leu
            180                 185                 190

Ala Gly Leu Val Ile Ser Pro Gln His Ile Arg Lys Ile Gln Asp Gln
        195                 200                 205

Trp Arg Ala Ile Gly Gln Glu Ile Pro Trp Ala Leu Ala Phe Gly
    210                 215                 220

Val Pro Pro Thr Ala Ile Met Ala Ser Ser Met Pro Ile Pro Asp Gly
225                 230                 235                 240

Val Ser Glu Ala Gly Tyr Val Gly Ala Ile Ala Gly Glu Pro Ile Lys
```

```
            245                 250                 255
Leu Val Lys Cys Asp Thr Asn Asn Leu Tyr Val Pro Ala Asn Ser Glu
            260                 265                 270

Ile Val Leu Glu Gly Thr Leu Ser Thr Thr Lys Met Ala Pro Glu Gly
            275                 280                 285

Pro Phe Gly Glu Met His Gly Tyr Val Tyr Pro Gly Glu Ser His Pro
            290                 295                 300

Gly Pro Val Tyr Thr Val Asn Lys Ile Thr Tyr Arg Asn Asn Ala Ile
305                 310                 315                 320

Leu Pro Met Ser Ala Cys Gly Arg Leu Thr Asp Glu Thr Gln Thr Met
            325                 330                 335

Ile Gly Thr Leu Ala Ala Ala Glu Ile Arg Gln Leu Cys Gln Asp Ala
            340                 345                 350

Gly Leu Pro Ile Thr Asp Ala Phe Ala Pro Phe Val Gly Gln Ala Thr
            355                 360                 365

Trp Val Ala Leu Lys Val Asp Thr Lys Arg Leu Arg Ala Met Lys Thr
370                 375                 380

Asn Gly Lys Ala Phe Ala Lys Arg Val Gly Asp Val Phe Thr Gln
385                 390                 395                 400

Lys Pro Gly Phe Thr Ile His Arg Leu Ile Leu Val Gly Asp Asp Ile
            405                 410                 415

Asp Val Tyr Asp Asp Lys Asp Val Met Trp Ala Phe Thr Arg Cys
            420                 425                 430

Arg Pro Gly Thr Asp Glu Val Phe Phe Asp Asp Val Val Gly Phe Gln
            435                 440                 445

Leu Ile Pro Tyr Met Ser His Gly Asn Ala Glu Ala Ile Lys Gly Gly
            450                 455                 460

Lys Val Val Ser Asp Ala Leu Leu Thr Ala Glu Tyr Thr Thr Gly Lys
465                 470                 475                 480

Asp Trp Glu Ser Ala Asp Phe Lys Asn Ser Tyr Pro Lys Ser Ile Gln
            485                 490                 495

Asp Lys Val Leu Asn Ser Trp Glu Arg Leu Gly Phe Lys Lys Leu Asp
            500                 505                 510

<210> SEQ ID NO 58
<211> LENGTH: 508
<212> TYPE: PRT
<213> ORGANISM: Sphaerulina musiva
<220> FEATURE:
<223> OTHER INFORMATION: Sphaerulina musiva (strain SO2202)

<400> SEQUENCE: 58

Met Ser Ser Ser Lys Gln Gln His Leu Ser His Ala Asn Gln Glu Leu
1               5                   10                  15

Pro His Leu Asn Phe Arg Ser Phe Val Gln Ala Leu Lys Asp Asp Gly
            20                  25                  30

Asp Leu Ile Glu Ile Asp Asp Glu Ile Asp Pro His Leu Glu Ala Gly
            35                  40                  45

Ala Ile Ile Arg Arg Ala Cys Glu Thr Asp Gly Lys Ala Pro Leu Leu
50                  55                  60

Asn Asn Leu Lys Gly Ala Lys Asp Gly Leu Trp Arg Ile Leu Gly Ala
65                  70                  75                  80

Pro Ala Ser Leu Arg Ser Asp Pro Ser Gln Lys Tyr Gly Arg Val Ala
            85                  90                  95

Arg His Leu Ala Leu Pro Pro Thr Ala Thr Met Lys Asp Ile Leu Asp
```

```
                  100                 105                 110
Lys Met Leu Ser Ala Ala His Ala Glu Pro Ile Pro Pro Asn Ile Val
            115                 120                 125
Glu Ser Gly Pro Val Lys Glu Asn Lys Leu Val Asp Gly Glu Phe Asp
            130                 135                 140
Leu Ser Thr Leu Pro Ala Pro Trp Leu His Gln Ala Asp Gly Gly Lys
145                 150                 155                 160
Tyr Ile Gln Thr Tyr Gly Met His Ile Val Gln Ser Pro Asp Gly Lys
            165                 170                 175
Trp Thr Asn Trp Ser Ile Ala Arg Ala Met Val His Asp Lys Asn His
            180                 185                 190
Leu Thr Gly Leu Val Ile Glu Pro Gln His Ile Trp Gln Ile His Gln
            195                 200                 205
Gln Trp Lys Lys Val Gly Lys Asp Val Pro Trp Ala Leu Ala Phe Gly
            210                 215                 220
Val Pro Pro Ala Ala Ile Met Ala Ala Ser Met Pro Ile Pro Asp Gly
225                 230                 235                 240
Val Thr Glu Ala Gly Tyr Ile Gly Ala Met Thr Gly Ser Ala Leu Asp
            245                 250                 255
Val Val Lys Cys Glu Thr Asn Gly Met Tyr Val Pro Ala Asn Ala Glu
            260                 265                 270
Ile Val Leu Glu Gly Thr Leu Ser Ile Thr Glu Thr Ala Pro Glu Gly
            275                 280                 285
Pro Phe Gly Glu Met His Gly Tyr Val Phe Pro Gly Asp Thr His Pro
            290                 295                 300
Trp Pro Lys Tyr Lys Val Asp Ala Ile Thr Tyr Arg Asn Gly Ala Ile
305                 310                 315                 320
Leu Pro Val Ser Asn Cys Gly Arg Ile Thr Asp Glu Thr His Thr Leu
            325                 330                 335
Ile Gly Pro Leu Ala Ala Ala Gln Ile Arg Gln Leu Cys Gln Asp Ala
            340                 345                 350
Gly Leu Pro Ile Thr Asp Ala Phe Ala Pro Phe His Thr Gln Val Thr
            355                 360                 365
Trp Val Ala Leu Lys Val Asp Ile Glu Lys Leu Gly Lys Met Asn Thr
            370                 375                 380
Thr Pro Glu Ala Phe Arg Lys Gln Val Gly Asp Leu Val Phe Asn His
385                 390                 395                 400
Lys Ala Gly Tyr Thr Ile His Arg Leu Val Leu Cys Gly Ser Asp Ile
            405                 410                 415
Asp Val Tyr Glu Trp Asp Asp Ile Ala Phe Ala Phe Ser Thr Arg Cys
            420                 425                 430
Arg Pro Asn Lys Asp Glu Thr Phe Tyr Glu Asp Cys Gln Gly Phe Pro
            435                 440                 445
Leu Ile Pro Tyr Met Ser His Gly Thr Gly Ser Pro Ile Lys Gly Gly
            450                 455                 460
Lys Val Ile Ser Asp Ala Leu Met Pro Ser Glu Tyr Arg Gly Gln Gln
465                 470                 475                 480
Asp Trp Gln Gln Ala Ser Phe Lys His Ser Tyr Pro Glu Ser Leu Gln
            485                 490                 495
Lys Ser Val Ile Glu Arg Trp Ala Ser Trp Gly Phe
            500                 505

<210> SEQ ID NO 59
```

<211> LENGTH: 498
<212> TYPE: PRT
<213> ORGANISM: Penicillium roqueforti

<400> SEQUENCE: 59

| | | | | | | | | | | | | | | |
|---|---|---|---|---|---|---|---|---|---|---|---|---|---|---|
| Met | Ala | Asn | Ile | Glu | Pro | His | Leu | Cys | Phe | Arg | Ser | Phe | Val | Glu | Ala |
| 1 | | | | 5 | | | | | 10 | | | | | 15 | |
| Leu | Lys | Ala | Asp | Asn | Asp | Leu | Val | Glu | Ile | Asp | Thr | Pro | Ile | Asp | Pro |
| | | | 20 | | | | | 25 | | | | | 30 | | |
| Asn | Leu | Glu | Ala | Ala | Ala | Ile | Thr | Arg | Leu | Val | Cys | Glu | Thr | Asn | Asp |
| | | 35 | | | | | 40 | | | | | 45 | | | |
| Lys | Ala | Pro | Leu | Phe | Asn | Asn | Ile | Ile | Gly | Thr | Glu | Lys | Gly | Leu | Phe |
| 50 | | | | | 55 | | | | | 60 | | | | | |
| Arg | Ile | Leu | Gly | Ala | Pro | Ala | Ser | Leu | Arg | Asn | Ser | Ser | Lys | Asp | Arg |
| 65 | | | | 70 | | | | | 75 | | | | | 80 | |
| Tyr | Gly | Arg | Leu | Ala | Arg | His | Leu | Ala | Leu | Pro | Pro | Thr | Ala | Ser | Met |
| | | | | 85 | | | | | 90 | | | | | 95 | |
| Arg | Asp | Ile | Leu | Asp | Lys | Met | Leu | Ser | Ala | Gly | Thr | Pro | Ile | Pro | Pro |
| | | | 100 | | | | | 105 | | | | | 110 | | |
| Asn | Ile | Val | Ser | Thr | Gly | Pro | Cys | Lys | Glu | Asn | Phe | Leu | Glu | Glu | Ser |
| | | 115 | | | | | 120 | | | | | 125 | | | |
| Gln | Ile | Asp | Leu | Thr | Lys | Leu | Pro | Ala | Pro | Leu | Ile | His | Gln | Ala | Asp |
| | 130 | | | | | 135 | | | | | 140 | | | | |
| Gly | Gly | Lys | Tyr | Ile | Gln | Thr | Tyr | Gly | Met | His | Ile | Val | Gln | Ser | Pro |
| 145 | | | | | 150 | | | | | 155 | | | | | 160 |
| Asp | Gly | Ser | Trp | Thr | Asn | Trp | Ser | Ile | Ala | Arg | Ala | Met | Val | Ser | Asp |
| | | | | 165 | | | | | 170 | | | | | 175 | |
| Asp | Lys | His | Leu | Thr | Gly | Leu | Val | Ile | Glu | Pro | Gln | His | Leu | Trp | Gln |
| | | | 180 | | | | | 185 | | | | | 190 | | |
| Ile | His | Gln | Met | Trp | Lys | Lys | Glu | Gly | Arg | Asp | Ala | Pro | Trp | Ala | Leu |
| | | 195 | | | | | 200 | | | | | 205 | | | |
| Ala | Phe | Gly | Val | Pro | Pro | Ala | Ala | Ile | Met | Ala | Ser | Ser | Met | Pro | Ile |
| | 210 | | | | | 215 | | | | | 220 | | | | |
| Pro | Asp | Gly | Val | Ser | Glu | Ala | Gly | Tyr | Val | Gly | Ser | Met | Thr | Gly | Ser |
| 225 | | | | | 230 | | | | | 235 | | | | | 240 |
| Ala | Leu | Asp | Leu | Val | Lys | Cys | Asp | Thr | Asn | Asp | Leu | Tyr | Val | Pro | Ala |
| | | | 245 | | | | | 250 | | | | | 255 | | |
| Thr | Ser | Glu | Ile | Val | Phe | Glu | Gly | Thr | Leu | Ser | Ile | Thr | Glu | Lys | Gly |
| | | | 260 | | | | | 265 | | | | | 270 | | |
| Pro | Glu | Gly | Pro | Phe | Gly | Glu | Met | His | Gly | Tyr | Val | Phe | Pro | Gly | Asp |
| | | 275 | | | | | 280 | | | | | 285 | | | |
| Val | His | Leu | Cys | Pro | Lys | Tyr | Lys | Val | Asn | Arg | Ile | Thr | Tyr | Arg | Asn |
| | 290 | | | | | 295 | | | | | 300 | | | | |
| Asp | Pro | Ile | Met | Pro | Met | Ser | Ser | Cys | Gly | Arg | Leu | Thr | Asp | Glu | Thr |
| 305 | | | | | 310 | | | | | 315 | | | | | 320 |
| His | Thr | Met | Ile | Gly | Ser | Leu | Ala | Ala | Val | Ile | Arg | Lys | Ile | Cys |
| | | | | 325 | | | | | 330 | | | | | 335 | |
| Gln | Gln | Ala | Gly | Leu | Pro | Val | Asn | Asp | Ala | Phe | Ala | Pro | Phe | Glu | Ser |
| | | | 340 | | | | | 345 | | | | | 350 | | |
| Gln | Val | Thr | Trp | Val | Ala | Leu | Arg | Ile | Asp | Thr | Ala | Lys | Leu | Arg | Glu |
| | | | | 355 | | | | | 360 | | | | | 365 | |
| Met | Lys | Thr | Thr | Pro | Lys | Glu | Phe | Ser | Lys | Val | Gly | Glu | Leu | Ile |
| | 370 | | | | | 375 | | | | | 380 | | | | |
| Phe | Asn | Ser | Lys | Ala | Gly | Tyr | Thr | Ile | His | Arg | Leu | Val | Leu | Cys | Gly |

```
                385                 390                 395                 400
Asp Asp Ile Asp Val Tyr Asn Gly Lys Asp Val Met Trp Ala Phe Ser
                    405                 410                 415

Thr Arg Cys Arg Pro Asn Leu Asp Glu Ile Phe Phe Glu Asp Val Pro
                    420                 425                 430

Gly Phe Pro Leu Ile Pro Tyr Met Ser His Gly Asn Gly Ser Pro Val
                    435                 440                 445

Lys Gly Gly Lys Val Val Ser Asp Ala Leu Leu Pro Cys Glu Tyr Thr
                    450                 455                 460

Thr Gly Lys Asn Trp Glu Ala Ala Asp Phe Glu Ser Ser Tyr Pro Glu
465                 470                 475                 480

Ala Val Lys Gln Lys Val Leu Ala Asn Trp Thr Lys Met Gly Phe Arg
                    485                 490                 495

Glu Glu

<210> SEQ ID NO 60
<211> LENGTH: 503
<212> TYPE: PRT
<213> ORGANISM: Fusarium oxysporum
<220> FEATURE:
<223> OTHER INFORMATION: Fusarium oxysporum f. sp. lycopersici

<400> SEQUENCE: 60

Met Pro Ser Lys Thr Leu Pro His Met Asp Phe Arg Ser Tyr Val Glu
1               5                   10                  15

Ala Leu Glu Ala Asp Gly Asp Leu Val Ser Ile Thr Glu Glu Cys Asp
                20                  25                  30

Pro His Leu Glu Val Gly Ala Ile Ile Arg Lys Val Val Glu Asn Asn
                35                  40                  45

Asp Lys Ala Pro Leu Phe Asn Lys Leu Lys Gly Gln Asp Glu Asn Gly
            50                  55                  60

Phe Trp Arg Ile Leu Gly Ala Pro Asn Ser Leu Arg Ser Asp Pro Lys
65              70                  75                  80

Gln Arg Tyr Gly Arg Leu Ala Arg His Leu Gly Leu Pro Thr Asp Ser
                85                  90                  95

Ser Met Lys Val Ile Leu Asp Lys Met Ile Ala Ala Lys Thr Thr Pro
                100                 105                 110

Pro Ile Pro Thr Val Val Glu Thr Gly Pro Cys Lys Glu His Ile
                115                 120                 125

Leu Thr Pro Asp Gln Phe Asp Leu Thr Lys Leu Pro Ala Pro Leu Leu
            130                 135                 140

His Gln Ser Asp Gly Gly Lys Tyr Ile Gln Thr Tyr Gly Met His Ile
145                 150                 155                 160

Val Gln Ser Pro Asp Gly Lys Trp Thr Asn Trp Ser Ile Ala Arg Ala
                165                 170                 175

Met Val Tyr Asp Arg Asn His Leu Ala Gly Leu Val Ile Lys Pro Gln
                180                 185                 190

His Leu Tyr Gln Ile His Glu Met Trp Lys Lys Glu Gly Arg Asp Met
                195                 200                 205

Pro Trp Ala Leu Ala Phe Gly Val Pro Pro Ala Ala Ile Met Ala Ser
            210                 215                 220

Ser Met Pro Leu Pro Asp Gly Leu Ser Glu Ala Glu Tyr Ile Gly Ser
225                 230                 235                 240

Leu Val Gly Ser Ser Leu Asp Val Ile Lys Cys Glu Thr Asn Gly Leu
                245                 250                 255
```

Tyr Val Pro Ala Asn Ser Glu Ile Val Phe Glu Gly Thr Cys Ser Ile
                260                 265                 270

Thr Glu Thr Ala Pro Glu Gly Pro Phe Gly Glu Met His Gly Tyr Val
            275                 280                 285

Phe Pro Gly Asp Ala His Pro Trp Pro Lys Tyr Thr Val Asp Leu Ile
290                 295                 300

Thr His Arg Lys Asp Ala Ile Leu Pro Val Ser Asn Cys Gly Arg Leu
305                 310                 315                 320

Thr Asp Glu Thr His Thr Met Ile Gly Pro Leu Ala Ala Ala Glu Ile
                325                 330                 335

Gly Phe Leu Leu Lys Ser Lys Gly Leu Pro Ile Lys Glu Ala Phe Ser
            340                 345                 350

Pro Phe Glu Ser Gln Val Thr Trp Val Ala Leu Gln Val Asp Thr Gln
            355                 360                 365

Lys Leu Arg Glu Met Lys Thr Thr Ser Glu Lys Phe Cys Arg Glu Ile
            370                 375                 380

Gly Asp Ile Ile Phe Asn His Lys Val Gly Tyr Thr Ile His Arg Leu
385                 390                 395                 400

Val Ile Val Gly Asp Asp Ile Asn Val Tyr Asp Phe Lys Asp Val Ile
                405                 410                 415

Trp Ala Phe Cys Thr Arg Cys Arg Pro Gly Thr Asp Glu Tyr Phe Phe
            420                 425                 430

Glu Asp Val Ala Gly Phe Pro Leu Ile Pro Tyr Met Ser His Gly Asn
            435                 440                 445

Gly Ala Pro Asn Arg Gly Gly Lys Val Val Ser Asp Ser Leu Leu Pro
450                 455                 460

Val Glu Tyr Thr Thr Gly Lys Asn Trp Glu Ala Ala Asp Phe Glu Asn
465                 470                 475                 480

Ser Phe Pro Glu Glu Ile Lys Asp Arg Val Cys Ser Arg Trp Gln Thr
                485                 490                 495

Leu Gly Phe Ser Ser Ala Lys
                500

<210> SEQ ID NO 61
<211> LENGTH: 503
<212> TYPE: PRT
<213> ORGANISM: Saccharomyces kudriavzevii
<220> FEATURE:
<223> OTHER INFORMATION: Saccharomyces kudriavzevii (strain ATCC
      MYA-4449)

<400> SEQUENCE: 61

Met Ser Ala Leu Asn Pro Ala Leu Gln Phe Arg Asp Phe Ile Gln Val
1               5                   10                  15

Leu Lys Asp Glu Asp Leu Ile Glu Ile Thr Lys Glu Val Asp Pro
            20                  25                  30

Asn Leu Glu Val Gly Ala Ile Met Arg Lys Ala Tyr Glu Ser Lys Leu
            35                  40                  45

Pro Ala Pro Phe Phe Lys Asn Ile Lys Gly Ala Ser Lys Asp Leu Phe
        50                  55                  60

Asn Ile Leu Gly Cys Pro Ala Gly Leu Arg Asn Lys Lys Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Asn Lys Lys Pro Leu

```
                    100                 105                 110
Pro Pro Ser Ser Ile Ser Ala Ser Ala Pro Cys Lys Ala His Val
            115                 120                 125

Leu Ser Glu Glu Ile His Leu Glu Ser Leu Pro Thr Pro Tyr Leu
            130                 135                 140

His Thr Ser Asp Gly Gly Asn Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
                180                 185                 190

His Ile Arg Gln Ile Ala Asp Ala Trp Gly Ala Ile Gly Lys Gly Asn
            195                 200                 205

Lys Ile Pro Phe Ala Leu Cys Phe Gly Val Pro Ala Ala Ile Leu
            210                 215                 220

Val Ser Ser Met Pro Ile Pro Glu Gly Val Ser Glu Ser Asp Tyr Val
225                 230                 235                 240

Gly Ala Ile Leu Gly Lys Pro Val Pro Val Lys Cys Glu Thr Asn
                245                 250                 255

Asp Leu Met Val Pro Ala Thr Ser Glu Ile Val Phe Glu Gly Thr Leu
                260                 265                 270

Ser Leu Thr Asp Thr His Ala Glu Gly Pro Phe Gly Glu Met His Gly
                275                 280                 285

Tyr Val Phe Gly Gly Gln Gly His Pro Cys Pro Leu Tyr Thr Val Lys
                290                 295                 300

Ala Met Thr His Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Lys Ser Gly Leu Pro Val Leu Asp Ala
                340                 345                 350

Phe Thr Pro Tyr Glu Ala Gln Ala Leu Trp Leu Val Leu Lys Val Asp
                355                 360                 365

Leu Lys Arg Leu Gln Ala Leu Lys Thr Thr Pro Glu Glu Phe Ser Lys
                370                 375                 380

Lys Val Gly Asp Ile Tyr Phe Arg Thr Lys Val Gly Phe Ile Ile His
385                 390                 395                 400

Glu Ile Val Leu Val Ala Asp Asp Ile Asp Ile Phe Asn Phe Lys Glu
                405                 410                 415

Val Phe Trp Ala Tyr Val Thr Arg His Thr Pro Val Ala Asp Gln Thr
                420                 425                 430

Ala Phe Asp Asp Val Thr Ser Phe Pro Leu Ala Pro Phe Val Ser Gln
                435                 440                 445

Ser Pro Arg Ser Lys Thr Met Lys Gly Gly Lys Cys Val Thr Asn Cys
                450                 455                 460

Ile Phe Arg Gln Gln Tyr Glu Arg Asp Phe Asp Tyr Val Thr Cys Ser
465                 470                 475                 480

Phe Glu Lys Gly Tyr Ser Lys Glu Leu Val Asp Arg Ile Asn Glu Asn
                485                 490                 495

Trp Arg Glu Tyr Gly Tyr Lys
                500

<210> SEQ ID NO 62
```

```
<211> LENGTH: 503
<212> TYPE: PRT
<213> ORGANISM: Saccharomyces cerevisiae
<220> FEATURE:
<223> OTHER INFORMATION: Saccharomyces cerevisiae S288c

<400> SEQUENCE: 62
```

Met Arg Lys Leu Asn Pro Ala Leu Glu Phe Arg Asp Phe Ile Gln Val
1               5                   10                  15

Leu Lys Asp Glu Asp Leu Ile Glu Ile Thr Glu Glu Ile Asp Pro
            20                  25                  30

Asn Leu Glu Val Gly Ala Ile Met Arg Lys Ala Tyr Glu Ser His Leu
            35                  40                  45

Pro Ala Pro Leu Phe Lys Asn Leu Lys Gly Ala Ser Lys Asp Leu Phe
        50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ala Pro Cys Lys Thr His Ile
        115                 120                 125

Leu Ser Glu Glu Lys Ile His Leu Gln Ser Leu Pro Thr Pro Tyr Leu
130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
370                 375                 380

```
Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500

<210> SEQ ID NO 63
<211> LENGTH: 503
<212> TYPE: PRT
<213> ORGANISM: Aspergillus parasiticus

<400> SEQUENCE: 63

Met Ala Ala Ile Ser Glu Val Asp His Ser Phe Arg Ala Phe Val Glu
1               5                   10                  15

Ala Leu Lys Ala Asp Asp Asp Leu Val Glu Ile Asn Thr Glu Ile Asp
                20                  25                  30

Ser Asn Leu Glu Ala Ala Ala Ile Thr Arg Leu Val Cys Glu Thr Asp
            35                  40                  45

Asp Lys Ala Pro Leu Phe Asn Asn Leu Lys Gly Met Gly Lys Asn Gly
        50                  55                  60

Leu Phe Arg Ile Leu Gly Ala Pro Gly Ser Leu Arg Lys Ser Lys Arg
65                  70                  75                  80

Asp Arg Tyr Gly Arg Leu Ala Arg His Leu Ala Leu Pro Pro Thr Ala
                85                  90                  95

Ser Met Lys Glu Ile Leu Asp Lys Met Leu Ser Ala Ser Gln Leu Pro
                100                 105                 110

Pro Ile Asp Pro Lys Ile Val Glu Thr Gly Pro Val Lys Glu Asn Ser
            115                 120                 125

Leu Glu Gly Asp Glu Ile Asp Leu Thr Ala Leu Pro Val Pro Met Val
        130                 135                 140

His Lys Ser Asp Gly Gly Lys Tyr Leu Gln Thr Tyr Gly Met His Ile
145                 150                 155                 160

Val Gln Ser Pro Asp Gly Lys Trp Thr Asn Trp Ser Ile Ala Arg Ala
                165                 170                 175

Met Val Lys Asp Lys Asn His Leu Thr Gly Leu Val Ile Glu Pro Gln
                180                 185                 190

His Ile Trp Gln Ile His Gln Met Trp Lys Glu Gly Lys Asp Val
            195                 200                 205

Pro Trp Ala Leu Cys Phe Gly Val Pro Ala Ala Ile Met Ala Ser
            210                 215                 220

Ser Met Pro Ile Pro Asp Gly Val Thr Glu Ala Gly Tyr Val Gly Ala
225                 230                 235                 240

Met Thr Gly Arg Ala Leu Glu Leu Val Lys Cys Asp Thr Asn His Leu
```

245                 250                 255

Tyr Val Pro Ala Asn Ala Glu Ile Val Leu Glu Gly Thr Leu Ser Ile
            260                 265                 270

Thr Glu Thr Ala Asp Glu Gly Pro Phe Gly Glu Met His Gly Tyr Val
        275                 280                 285

Phe Pro Gly Asp Ser His Lys Cys Pro Val Tyr Lys Val Asn Lys Ile
    290                 295                 300

Thr Tyr Arg Thr Asp Ala Ile Leu Pro Met Ser Ala Cys Gly Arg Leu
305                 310                 315                 320

Thr Asp Glu Thr His Thr Met Ile Gly Ser Leu Ala Ala Ala Glu Ile
                325                 330                 335

Arg Lys Ile Cys Gln Leu Ala Gly Leu Pro Ile Thr Asp Thr Phe Ser
            340                 345                 350

Pro Phe Glu Ala Gln Val Thr Trp Val Ala Leu Lys Val Asp Thr Ala
        355                 360                 365

Lys Leu Arg Gln Met Asn Leu Thr Pro Lys Glu Leu Gln Lys Trp Val
    370                 375                 380

Gly Asp Val Val Phe Asn His Lys Ala Gly Tyr Thr Ile His Arg Leu
385                 390                 395                 400

Val Leu Val Gly Asp Asp Ile Asp Pro Tyr Glu Trp Lys Asp Val Met
                405                 410                 415

Trp Ala Phe Ala Thr Arg Cys Arg Pro Asn Ala Asp Glu Met Phe Phe
            420                 425                 430

Glu Asp Val Arg Gly Phe Pro Leu Ile Pro Tyr Met Gly His Gly Thr
        435                 440                 445

Gly Ser Pro Thr Lys Gly Gly Lys Val Val Ser Asp Ala Leu Met Pro
    450                 455                 460

Thr Glu Tyr Thr Thr Gly Ala Asp Trp Glu Ala Ala Asp Phe Glu His
465                 470                 475                 480

Ser Tyr Pro Glu Glu Ile Lys Ala Lys Val Arg Ala Gln Trp Gln Ala
                485                 490                 495

Leu Gly Phe Arg Lys Gln Glu
            500

<210> SEQ ID NO 64
<211> LENGTH: 513
<212> TYPE: PRT
<213> ORGANISM: Candida albicans

<400> SEQUENCE: 64

Met Ser Leu Asn Pro Ala Leu Lys Phe Arg Asp Phe Ile Gln Val Leu
1               5                   10                  15

Lys Asn Glu Gly Asp Leu Val Glu Ile Asp Thr Glu Val Asp Pro Asn
            20                  25                  30

Leu Glu Val Gly Ala Ile Thr Arg Lys Ala Tyr Glu Asn Lys Leu Ala
        35                  40                  45

Ala Pro Leu Phe Asn Asn Leu Lys Gln Asp Pro Gly Asn Val Asp Pro
    50                  55                  60

Lys Asn Leu Phe Arg Ile Leu Gly Cys Pro Gly Gly Leu Arg Gly Phe
65                  70                  75                  80

Gly Asn Asp His Ala Arg Ile Ala Leu His Leu Gly Leu Asp Ser Gln
                85                  90                  95

Thr Pro Met Lys Glu Ile Val Asp Phe Leu Val Ala Asn Arg Asn Pro
            100                 105                 110

```
Lys Lys Phe Ile Pro Pro Val Leu Val Pro Asn Glu Lys Ser Pro His
            115                 120                 125
Lys Lys His His Leu Thr His Glu Gln Ile Asp Leu Thr Lys Leu Pro
130                 135                 140
Val Pro Leu Leu His His Gly Asp Gly Gly Lys Phe Ile Gln Thr Tyr
145                 150                 155                 160
Gly Met Trp Val Leu Gln Thr Pro Asp Lys Ser Trp Thr Asn Trp Ser
                165                 170                 175
Ile Ala Arg Gly Met Val His Asp Ser Lys Ser Ile Thr Gly Leu Val
            180                 185                 190
Ile Asn Pro Gln His Val Lys Gln Val Ser Asp Ala Trp Val Ala Ala
            195                 200                 205
Gly Lys Gly Asp Lys Ile Pro Phe Ala Leu Cys Phe Gly Val Pro Pro
210                 215                 220
Ala Ala Ile Leu Val Ser Ser Met Pro Ile Pro Asp Gly Ala Thr Glu
225                 230                 235                 240
Ala Glu Tyr Ile Gly Gly Leu Cys Asn Gln Ala Val Pro Val Val Lys
                245                 250                 255
Cys Glu Thr Asn Asp Leu Glu Val Pro Ala Asp Cys Glu Met Val Phe
                260                 265                 270
Glu Gly Tyr Leu Asp Arg Asp Thr Leu Val Thr Glu Gly Pro Phe Gly
            275                 280                 285
Glu Met His Gly Tyr Cys Phe Pro Gln Asp His His Thr Gln Pro Leu
            290                 295                 300
Tyr Arg Val Asn His Ile Ser Tyr Arg Asp Glu Ala Ile Met Pro Ile
305                 310                 315                 320
Ser Asn Pro Gly Leu Cys Thr Asp Glu Thr His Thr Leu Ile Gly Gly
                325                 330                 335
Leu Val Ser Ala Glu Thr Lys Tyr Leu Ile Ser Gln His Leu Val Leu
            340                 345                 350
Ser Lys Ile Val Glu Asp Val Phe Thr Pro Tyr Glu Ala Gln Ala Leu
            355                 360                 365
Trp Leu Ala Val Lys Ile Asn Ile Gln Glu Leu Ile Lys Leu Lys Thr
370                 375                 380
Asn Ala Lys Glu Leu Ser Asn Leu Val Gly Asp Phe Leu Phe Lys Ser
385                 390                 395                 400
Lys Glu Cys Tyr Lys Val Cys Ser Ile Leu His Glu Val Ile Leu Val
                405                 410                 415
Gly Asp Asp Ile Asp Ile Phe Asp Phe Lys Gln Leu Ile Trp Ala Tyr
            420                 425                 430
Thr Thr Arg His Thr Pro Val Gln Asp Gln Val Tyr Phe Asp Asp Val
            435                 440                 445
Lys Pro Phe Pro Leu Ala Pro Phe Ile Ser Gln Gly Ser Leu Ile Lys
            450                 455                 460
Thr Arg Gln Gly Gly Lys Cys Val Thr Ser Cys Ile Phe Pro Lys Gln
465                 470                 475                 480
Phe Thr Asp Pro Asp Phe Lys Phe Val Thr Cys Asn Phe Asp Gly Tyr
                485                 490                 495
Pro Glu Glu Val Lys Asn Lys Val Ser Gln Asn Trp Glu Lys Tyr Tyr
                500                 505                 510

Lys

<210> SEQ ID NO 65
```

```
<211> LENGTH: 500
<212> TYPE: PRT
<213> ORGANISM: Grosmannia clavigera
<220> FEATURE:
<223> OTHER INFORMATION: Grosmannia clavigera kw1407

<400> SEQUENCE: 65

Met Ala Ser Ser Gln Asp Leu Pro His Met Ser Phe Arg Ala Phe Val
1               5                   10                  15

Asp Glu Leu Arg Ala Asp Gly Asp Ile Val Glu Ile Asn Asp Glu Cys
            20                  25                  30

Asp Ala Asp Leu Glu Val Gly Ala Ile Ile Arg Leu Ala Cys Glu Thr
        35                  40                  45

Asp Ala Lys Ala Pro Leu Phe Asn Lys Leu Lys Gly Met Asp Gly Asn
    50                  55                  60

Gly Leu Trp Arg Ile Leu Gly Ala Pro Asn Ser Leu Arg Ala Asp Pro
65                  70                  75                  80

Ala Gln Arg Phe Gly Arg Leu Ala Arg His Ile Asn Leu Pro Pro Thr
                85                  90                  95

Ala Ser Met Lys Glu Ile Leu Asp Lys Met Gly Ala Ala Lys Ser Thr
            100                 105                 110

Pro Pro Ile Pro Pro Lys Thr Val Pro Thr Gly Ser Cys Lys Glu Val
        115                 120                 125

Lys Leu Thr Pro Asp Gln Phe Asp Leu Thr Thr Leu Pro Ser Pro Gln
    130                 135                 140

Leu His Lys Ser Asp Gly Gly Lys Tyr Val Gln Thr Tyr Gly Met His
145                 150                 155                 160

Ile Val Gln Thr Pro Asp Gly Lys Trp Thr Asn Trp Ser Ile Ala Arg
                165                 170                 175

Ala Met Val His Asp Arg Asn His Leu Val Gly Leu Val Ile Pro Pro
            180                 185                 190

Gln His Ile Trp Lys Val Gln Gln Glu Trp Lys Lys Ile Gly Lys Asp
        195                 200                 205

Met Pro Trp Ala Leu Val Phe Gly Val Pro Ala Ala Ile Met Ala
    210                 215                 220

Ala Ser Met Pro Leu Pro Asp Gly Leu Ser Glu Ala Glu Tyr Ile Gly
225                 230                 235                 240

Ser Leu Val Gly Thr Ala Leu Glu Val Thr Lys Cys Asp Thr Asn Asp
                245                 250                 255

Leu Leu Val Pro Ala Asn Ser Glu Ile Val Phe Glu Gly Phe Met Ser
            260                 265                 270

Ser Thr Glu Thr Ala Pro Glu Gly Pro Phe Gly Glu Met His Gly Tyr
        275                 280                 285

Val Phe Pro Gly Asp Ala His Pro Gln Pro Leu Tyr Thr Val Asn Met
    290                 295                 300

Ile Thr His Arg Lys Asp Ala Ile Leu Pro Val Ser Asn Cys Gly Arg
305                 310                 315                 320

Leu Thr Asp Glu Thr His Thr Met Ile Gly Pro Leu Val Ala Val Glu
                325                 330                 335

Ile Asn Val Met Leu Lys Ala Ala Gly Leu Pro Ile Thr Asp Ala Tyr
            340                 345                 350

Thr Pro Phe Glu Ser Gln Val Thr Trp Cys Ala Val Lys Val Asp Thr
        355                 360                 365

Ala Lys Leu Arg Glu Leu Lys Thr Thr Pro Lys Glu Phe Cys Arg Lys
    370                 375                 380
```

```
Ile Gly Asp Leu Ile Phe Asn Thr Lys Val Gly Ser Thr Ile His Arg
385                 390                 395                 400

Ile Ala Val Val Gly Asp Ile Asp Ile Phe Asn Phe Lys Asp Val
            405                 410                 415

Ile Trp Ala Phe Cys Thr Arg Cys Arg Pro Gly Met Asp Glu Tyr Leu
            420                 425                 430

Phe Glu Asp Val Pro Gly Phe Pro Leu Ile Pro Tyr Met Ser His Gly
            435                 440                 445

Asn Gly Pro Ala Asn Arg Gly Gly Lys Val Val Ser Asp Cys Leu Leu
            450                 455                 460

Pro Lys Glu Tyr Thr Thr Gly Lys Asn Trp Glu Ala Ala Ser Phe Lys
465                 470                 475                 480

Glu Ser Ile Pro Glu Ser Val Gln Ala Lys Val Leu Gly Asn Trp Lys
            485                 490                 495

Ala Trp Gly Phe
            500

<210> SEQ ID NO 66
<211> LENGTH: 490
<212> TYPE: PRT
<213> ORGANISM: Aspergillus terreus

<400> SEQUENCE: 66

Met Thr Lys Gln Ser Ala Asp Ser Asn Ala Lys Ser Gly Val Thr Ser
1               5                   10                  15

Glu Ile Cys His Trp Ala Ser Asn Leu Ala Thr Asp Asp Ile Pro Ser
            20                  25                  30

Asp Val Leu Glu Arg Ala Lys Tyr Leu Ile Leu Asp Gly Ile Ala Cys
            35                  40                  45

Ala Trp Val Gly Ala Arg Val Pro Trp Ser Glu Lys Tyr Val Gln Ala
50                  55                  60

Thr Met Ser Phe Glu Pro Pro Gly Ala Cys Arg Val Ile Gly Tyr Gly
65                  70                  75                  80

Gln Lys Leu Gly Pro Val Ala Ala Ala Met Thr Asn Ser Ala Phe Ile
            85                  90                  95

Gln Ala Thr Glu Leu Asp Asp Tyr His Ser Glu Ala Pro Leu His Ser
            100                 105                 110

Ala Ser Ile Val Leu Pro Ala Val Phe Ala Ala Ser Glu Val Leu Ala
            115                 120                 125

Glu Gln Gly Lys Thr Ile Ser Gly Ile Asp Val Ile Leu Ala Ala Ile
            130                 135                 140

Val Gly Phe Glu Ser Gly Pro Arg Ile Gly Lys Ala Ile Tyr Gly Ser
145                 150                 155                 160

Asp Leu Leu Asn Asn Gly Trp His Cys Gly Ala Val Tyr Gly Ala Pro
            165                 170                 175

Ala Gly Ala Leu Ala Thr Gly Lys Leu Leu Gly Leu Thr Pro Asp Ser
            180                 185                 190

Met Glu Asp Ala Leu Gly Ile Ala Cys Thr Gln Ala Cys Gly Leu Met
            195                 200                 205

Ser Ala Gln Tyr Gly Gly Met Val Lys Val Gln His Gly Phe Ala
            210                 215                 220

Ala Arg Asn Gly Leu Leu Gly Leu Leu Ala His Gly Gly Tyr Glu
225                 230                 235                 240

Ala Met Lys Gly Val Leu Glu Arg Ser Tyr Gly Gly Phe Leu Lys Met
```

245                 250                 255
Phe Thr Lys Gly Asn Gly Arg Glu Pro Pro Tyr Lys Glu Glu Val
            260                 265                 270

Val Ala Gly Leu Gly Ser Phe Trp His Thr Phe Thr Ile Arg Ile Lys
            275                 280                 285

Leu Tyr Ala Cys Cys Gly Leu Val His Gly Pro Val Glu Ala Ile Glu
            290                 295                 300

Asn Leu Gln Gly Arg Tyr Pro Glu Leu Leu Asn Arg Ala Asn Leu Ser
305                 310                 315                 320

Asn Ile Arg His Val His Val Gln Leu Ser Thr Ala Ser Asn Ser His
                325                 330                 335

Cys Gly Trp Ile Pro Glu Glu Arg Pro Ile Ser Ser Ile Ala Gly Gln
                340                 345                 350

Met Ser Val Ala Tyr Ile Leu Ala Val Gln Leu Val Asp Gln Cys
            355                 360                 365

Leu Leu Ser Gln Phe Ser Glu Phe Asp Asp Asn Leu Glu Arg Pro Glu
            370                 375                 380

Val Trp Asp Leu Ala Arg Lys Val Thr Ser Ser Gln Ser Glu Glu Phe
385                 390                 395                 400

Asp Gln Asp Gly Asn Cys Leu Ser Ala Gly Arg Val Arg Ile Glu Phe
                405                 410                 415

Asn Asp Gly Ser Ser Ile Thr Glu Ser Val Glu Lys Pro Leu Gly Val
            420                 425                 430

Lys Glu Pro Met Pro Asn Glu Arg Ile Leu His Lys Tyr Arg Thr Leu
            435                 440                 445

Ala Gly Ser Val Thr Asp Glu Ser Arg Val Lys Glu Ile Glu Asp Leu
            450                 455                 460

Val Leu Gly Leu Asp Arg Leu Thr Asp Ile Ser Pro Leu Leu Glu Leu
465                 470                 475                 480

Leu Asn Cys Pro Val Lys Ser Pro Leu Val
                485                 490

<210> SEQ ID NO 67
<211> LENGTH: 649
<212> TYPE: PRT
<213> ORGANISM: Pseudomonas amygdali
<220> FEATURE:
<223> OTHER INFORMATION: Pseudomonas amygdali pv. tabaci str. ATCC 11528

<400> SEQUENCE: 67

Met Ser Thr Pro Glu Leu Thr Thr Leu Leu Ile Ala Asn Arg Gly Glu
1               5                   10                  15

Ile Ala Cys Arg Ile Met Arg Thr Ala Lys Thr Met Gly Leu Thr Thr
            20                  25                  30

Val Ala Val His Ser Ala Ile Asp Arg Asp Ala Arg His Ser Arg Glu
        35                  40                  45

Ala Asp Ile Arg Val Asp Leu Gly Gly Ser Lys Ala Ala Glu Ser Tyr
    50                  55                  60

Leu Ala Ile Asp Lys Leu Ile Asp Ala Ala Arg Ala Ser Gly Ala Gln
65                  70                  75                  80

Ala Ile His Pro Gly Tyr Gly Phe Leu Ser Glu Asn Ala Asp Phe Ala
                85                  90                  95

Arg Ala Ile Glu Glu Ala Gly Leu Ile Phe Leu Gly Pro Pro Ala Ser
            100                 105                 110

Ala Ile Asp Ala Met Gly Ser Lys Ser Ala Ala Lys Ser Leu Met Glu

```
            115                 120                 125
Gln Ala Gly Val Pro Leu Val Pro Gly Tyr His Gly Asp Ala Gln Asp
        130                 135                 140

Ile Glu Thr Phe Arg Ser Ala Ala Glu Arg Ile Gly Tyr Pro Val Leu
145                 150                 155                 160

Leu Lys Ala Thr Ala Gly Gly Gly Lys Gly Met Lys Val Val Glu
                165                 170                 175

His Ser Gly Glu Leu Ala Glu Ala Leu Ala Ser Ala Gln Arg Glu Ala
            180                 185                 190

Leu Ser Ser Phe Gly Asp Ala Arg Met Leu Val Glu Lys Tyr Val Leu
        195                 200                 205

Thr Pro Arg His Val Glu Ile Gln Val Phe Ala Asp Arg His Gly His
    210                 215                 220

Cys Leu Tyr Leu Asn Glu Arg Asp Cys Ser Ile Gln Arg Arg His Gln
225                 230                 235                 240

Lys Val Val Glu Glu Ala Pro Ala Pro Gly Leu Thr Pro Glu Leu Arg
                245                 250                 255

Lys Ala Met Gly Glu Ala Ala Val Lys Ala Ala Gln Ala Ile Gly Tyr
            260                 265                 270

Val Gly Ala Gly Thr Val Glu Phe Leu Leu Asp Ala Arg Gly Glu Phe
        275                 280                 285

Phe Phe Met Glu Met Asn Thr Arg Leu Gln Val Glu His Pro Val Thr
    290                 295                 300

Glu Tyr Ile Thr Gly Leu Asp Leu Val Glu Trp Gln Ile Arg Val Ala
305                 310                 315                 320

Arg Gly Glu Pro Leu Pro Ile Thr Gln Glu Gln Val Pro Leu Ile Gly
                325                 330                 335

His Ala Ile Glu Val Arg Leu Tyr Ala Glu Asp Pro Ala Asn Asp Phe
            340                 345                 350

Leu Pro Ala Thr Gly Thr Leu Glu Leu Tyr Arg Glu Ser Ala Ser Gly
        355                 360                 365

Pro Gly Lys Arg Val Asp Ser Gly Val Ser Glu Gly Asp Asn Ile Ser
    370                 375                 380

Pro Phe Tyr Asp Pro Met Leu Gly Lys Leu Ile Ala Trp Gly Glu Asn
385                 390                 395                 400

Arg Glu Gln Ala Arg Leu Arg Leu Leu Ala Met Leu Asp Glu Phe Ala
                405                 410                 415

Val Gly Gly Val Arg Thr Asn Leu Ala Phe Leu Arg Arg Ile Ile Ala
            420                 425                 430

His Pro Ala Phe Ala Ala Glu Leu Asp Thr Gly Phe Ile Pro Arg
        435                 440                 445

Tyr Gln Asp Lys Leu Leu Pro Gln Thr Gly Glu Leu Cys Glu Glu Leu
    450                 455                 460

Trp Gln Ala Ala Glu Ala Phe Ser Gln Ser Glu Pro Ala Arg Val
465                 470                 475                 480

Asp Gln Ala Asp Leu His Ser Pro Trp Ala Val Thr Ala Gly Phe Arg
                485                 490                 495

Ala Gly Leu Pro Ala Glu Arg Asp Leu Arg Leu Ser Cys Asn Gly Gln
            500                 505                 510

Thr Arg Thr Val Tyr Leu Arg Asn Ser Ser Asp Ser Pro Phe Lys Leu
        515                 520                 525

Ser Asn Glu His Leu Thr Val Glu His Asn Gly Val Arg Ser His
    530                 535                 540
```

```
Leu Ala Ile Arg Arg Gly Gly Thr Leu Tyr Leu Lys Trp Gln Gly Asp
545                 550                 555                 560

Leu His Thr Ile Thr Arg Leu Asp Pro Ile Ala Gln Ala Asp Val Ser
                565                 570                 575

Asp Ser Gln His Gly Gly Leu Thr Ala Pro Met Asn Gly Ser Ile Val
            580                 585                 590

Arg Val Leu Val Glu Val Gly Gln Ala Val Glu Ser Gly Ala Gln Leu
        595                 600                 605

Met Val Leu Glu Ala Met Lys Met Glu His Ser Ile Arg Ala Ala Ser
610                 615                 620

Ala Gly Val Val Thr Ala Leu Tyr Cys His Gly Glu Met Val Asn
625                 630                 635                 640

Glu Gly Ala Val Leu Val Glu Leu Thr
                645
```

<210> SEQ ID NO 68
<211> LENGTH: 325
<212> TYPE: PRT
<213> ORGANISM: Aspergillus clavatus

<400> SEQUENCE: 68

```
Met Ala Lys Ile Asp Val His His Phe Tyr Pro Gln Ala Met Arg
1               5                   10                  15

Glu Ala Leu Glu Arg Ala Gly Gly Asp Pro Ser Gly Trp Tyr Ile Pro
                20                  25                  30

Pro Trp Thr Leu Asp Leu Asp Lys Glu Ile Ser Arg Val Leu Lys Val
            35                  40                  45

Gln Thr Thr Ile Leu Ser Val Thr Ala Pro Gly Pro Gly Ile Glu Thr
50                  55                  60

Asp Pro Gly Lys Ala Ala Leu Ala Arg Leu Cys Asn Glu Glu Ala
65                  70                  75                  80

Ala Ala Ile Arg Asp Ala His Pro Leu Gln Tyr Gly Phe Phe Ala Ser
                85                  90                  95

Val Pro Ser Leu Phe Asp Thr Ala Ala Val Leu Ala Glu Ile Glu His
            100                 105                 110

Ala Phe Thr Asn Leu His Ala Asp Gly Val Thr Leu Tyr Thr Arg Tyr
        115                 120                 125

Gly Ala Gly His Ser Tyr Leu Gly Asp Glu Arg Phe Arg Pro Val Trp
130                 135                 140

Ala Glu Leu Ser Lys Arg Arg Ala Val Val Phe Ile His Pro Thr His
145                 150                 155                 160

Ala Val Asp Thr Gln Leu Ile Asn Ser Trp Met Pro Gln Pro Met Phe
                165                 170                 175

Asp Tyr Pro His Glu Thr Gly Arg Thr Ala Met Asp Leu Leu Thr Arg
            180                 185                 190

Gly Val Ile Arg Asp Tyr Pro Gly Cys Lys Ile Ile Leu Ser His Ala
        195                 200                 205

Gly Gly Thr Leu Pro Tyr Leu Ile His Arg Ala Ala Thr Met Leu Pro
210                 215                 220

Phe Met Pro Arg Asn Leu Gly Met Ser Arg Glu Ile Val Glu Ala
225                 230                 235                 240

Ala Arg Thr Leu Tyr Phe Asp Thr Ala Ile Ser Ala Asn Pro Val Thr
                245                 250                 255

Leu Lys Ala Leu Leu Glu Phe Ala Lys Pro Gly His Val Leu Phe Gly
```

```
                260                 265                 270
Ser Asp Phe Pro Asn Ala Pro Arg Gly Ala Ile Thr His Phe Thr Ser
            275                 280                 285

Phe Leu Glu Gly Tyr Asp Asn Met Ser Glu Glu Thr Arg Arg Leu Val
            290                 295                 300

Glu Arg Glu Ala Ala Leu Glu Leu Phe Pro Arg Leu Arg Gly Gln Ser
305                 310                 315                 320

Thr Arg Ala Cys Leu
                325

<210> SEQ ID NO 69
<211> LENGTH: 267
<212> TYPE: PRT
<213> ORGANISM: Geobacillus stearothermophilus

<400> SEQUENCE: 69

Met Ala Leu Thr Val Lys Val Ser Leu Tyr Arg Lys Phe Ala Glu Leu
1               5                   10                  15

Leu Asn Glu Ala Glu Arg Glu Lys Arg Glu Val Ala Arg Ile Thr Glu
            20                  25                  30

Glu Val Pro Asp Leu Ser Ala Glu Glu Ala Tyr Lys Ile Gln Glu Glu
        35                  40                  45

Leu Ile Lys Ile Lys Thr Asn Ser Gly His Arg Ile Ile Gly Pro Lys
    50                  55                  60

Met Gly Leu Thr Ser Gln Ala Lys Met Ala Gln Met Lys Val Lys Glu
65                  70                  75                  80

Pro Ile Tyr Gly Tyr Leu Phe Asp Tyr Met Phe Val Pro Ser Gly Gly
                85                  90                  95

Ala Ile His Met Ser Glu Leu Ile His Pro Lys Val Glu Val Glu Ile
            100                 105                 110

Ala Phe Ile Leu Gly Glu Asp Leu Glu Gly Pro His Val Thr Ser Thr
        115                 120                 125

Gln Val Leu Ser Ala Thr Lys Tyr Val Ala Pro Ala Leu Glu Ile Ile
    130                 135                 140

Asp Ser Arg Tyr Gln Asp Phe Thr Phe Thr Leu Pro Asp Val Ile Ala
145                 150                 155                 160

Asp Asn Ala Ser Ser Arg Val Val Ile Gly Asn Thr Met Thr Pro
                165                 170                 175

Ile His Ser Leu Lys Thr Asp Leu Asp Leu Ile Gly Ala Ala Leu Tyr
            180                 185                 190

Ile Asn Gly Glu Leu Lys Ala Cys Gly Ala Gly Ala Ala Val Phe Asn
        195                 200                 205

His Pro Ala Asn Ser Val Ala Val Leu Ala Asn Met Leu Ala Arg Lys
    210                 215                 220

Gly Glu Arg Leu Lys Ala Gly Asp Ile Ile Leu Thr Gly Gly Ile Thr
225                 230                 235                 240

Glu Ala Ile Gln Leu Ser Ala Gly Asp Thr Val Ile Gly Gln Leu Asp
                245                 250                 255

Gln Leu Gly Asp Val Ser Leu Ser Val Lys Glu
            260                 265

<210> SEQ ID NO 70
<211> LENGTH: 429
<212> TYPE: PRT
<213> ORGANISM: Salmonella enterica
<220> FEATURE:
```

<223> OTHER INFORMATION: Salmonella enterica subsp. enterica serovar Dublin

<400> SEQUENCE: 70

```
Met Lys Gly Thr Val Phe Ala Val Ala Leu Asn His Arg Ser Gln Leu
1               5                   10                  15

Asp Ala Trp Gln Glu Ala Phe Ser Gln Pro Pro Tyr Asn Ala Pro Pro
            20                  25                  30

Lys Thr Ala Val Trp Phe Ile Lys Pro Arg Asn Thr Val Ile Arg His
        35                  40                  45

Gly Glu Pro Ile Leu Tyr Pro Gln Gly Glu Lys Val Leu Ser Gly Ala
    50                  55                  60

Thr Val Ala Leu Ile Val Gly Lys Thr Ala Ser Arg Lys Arg Ser Glu
65                  70                  75                  80

Ala Ala Ala Glu Tyr Ile Ala Gly Tyr Ala Leu Ala Asn Glu Val Ser
                85                  90                  95

Leu Pro Glu Glu Ser Phe Tyr Arg Pro Ala Ile Lys Ala Lys Cys Arg
            100                 105                 110

Asp Gly Phe Cys Pro Leu Gly Glu Met Ala Pro Leu Ser Asp Val Asp
        115                 120                 125

Asn Leu Thr Ile Ile Thr Glu Ile Asn Gly Arg Glu Ala Asp His Trp
130                 135                 140

Asn Thr Ala Asp Leu Gln Arg Ser Ala Ala Gln Leu Leu Ser Ala Leu
145                 150                 155                 160

Ser Glu Phe Ala Thr Leu Asn Pro Gly Asp Ala Ile Leu Leu Gly Thr
                165                 170                 175

Pro Gln Asn Arg Val Ala Leu Arg Pro Gly Asp Arg Val Arg Ile Leu
            180                 185                 190

Ala Lys Gly Leu Pro Ala Leu Glu Asn Pro Val Val Ala Glu Asp Glu
        195                 200                 205

Phe Ala Arg Asn Gln Thr Phe Thr Trp Pro Leu Ser Ala Thr Gly Thr
    210                 215                 220

Leu Phe Ala Leu Gly Leu Asn Tyr Ala Asp His Ala Ser Glu Leu Ala
225                 230                 235                 240

Phe Thr Pro Pro Lys Glu Pro Leu Val Phe Ile Lys Ala Pro Asn Thr
                245                 250                 255

Phe Thr Glu His His Gln Thr Ser Val Arg Pro Asn Asn Val Glu Tyr
            260                 265                 270

Met His Tyr Glu Ala Glu Leu Val Val Ile Gly Lys Thr Ala Arg
        275                 280                 285

Lys Val Ser Glu Ala Glu Ala Met Glu Tyr Val Ala Gly Tyr Thr Val
    290                 295                 300

Cys Asn Asp Tyr Ala Ile Arg Asp Tyr Leu Glu Asn Tyr Tyr Arg Pro
305                 310                 315                 320

Asn Leu Arg Val Lys Ser Arg Asp Gly Leu Thr Pro Ile Gly Pro Trp
                325                 330                 335

Ile Val Asp Lys Glu Ala Val Ser Asp Pro His Asn Leu Thr Leu Arg
            340                 345                 350

Thr Phe Val Asn Gly Glu Leu Arg Gln Glu Gly Thr Thr Ala Asp Leu
        355                 360                 365

Ile Phe Ser Ile Pro Phe Leu Ile Ser Tyr Leu Ser Glu Phe Met Thr
    370                 375                 380

Leu Gln Pro Gly Asp Met Ile Ala Thr Gly Thr Pro Lys Gly Leu Ser
385                 390                 395                 400
```

```
Asp Val Val Pro Gly Asp Glu Val Val Leu Glu Ile Lys Gly Val Gly
                405                 410                 415

Arg Leu Val Asn Gln Ile Val Cys Glu Glu Ser Ala Asn
            420                 425

<210> SEQ ID NO 71
<211> LENGTH: 891
<212> TYPE: PRT
<213> ORGANISM: Escherichia coli
<220> FEATURE:
<223> OTHER INFORMATION: Escherichia coli K-12

<400> SEQUENCE: 71

Met Ser Ser Thr Leu Arg Glu Ala Ser Lys Asp Thr Leu Gln Ala Lys
1               5                   10                  15

Asp Lys Thr Tyr His Tyr Tyr Ser Leu Pro Leu Ala Ala Lys Ser Leu
            20                  25                  30

Gly Asp Ile Thr Arg Leu Pro Lys Ser Leu Lys Val Leu Leu Glu Asn
        35                  40                  45

Leu Leu Arg Trp Gln Asp Gly Asn Ser Val Thr Glu Glu Asp Ile His
    50                  55                  60

Ala Leu Ala Gly Trp Leu Lys Asn Ala His Ala Asp Arg Glu Ile Ala
65                  70                  75                  80

Tyr Arg Pro Ala Arg Val Leu Met Gln Asp Phe Thr Gly Val Pro Ala
                85                  90                  95

Val Val Asp Leu Ala Ala Met Arg Glu Ala Val Lys Arg Leu Gly Gly
            100                 105                 110

Asp Thr Ala Lys Val Asn Pro Leu Ser Pro Val Asp Leu Val Ile Asp
        115                 120                 125

His Ser Val Thr Val Asp Arg Phe Gly Asp Asp Glu Ala Phe Glu Glu
    130                 135                 140

Asn Val Arg Leu Glu Met Glu Arg Asn His Glu Arg Tyr Val Phe Leu
145                 150                 155                 160

Lys Trp Gly Lys Gln Ala Phe Ser Arg Phe Ser Val Val Pro Pro Gly
                165                 170                 175

Thr Gly Ile Cys His Gln Val Asn Leu Glu Tyr Leu Gly Lys Ala Val
            180                 185                 190

Trp Ser Glu Leu Gln Asp Gly Glu Trp Ile Ala Tyr Pro Asp Thr Leu
        195                 200                 205

Val Gly Thr Asp Ser His Thr Thr Met Ile Asn Gly Leu Gly Val Leu
    210                 215                 220

Gly Trp Gly Val Gly Gly Ile Glu Ala Glu Ala Ala Met Leu Gly Gln
225                 230                 235                 240

Pro Val Ser Met Leu Ile Pro Asp Val Val Gly Phe Lys Leu Thr Gly
                245                 250                 255

Lys Leu Arg Glu Gly Ile Thr Ala Thr Asp Leu Val Leu Thr Val Thr
            260                 265                 270

Gln Met Leu Arg Lys His Gly Val Val Gly Lys Phe Val Glu Phe Tyr
        275                 280                 285

Gly Asp Gly Leu Asp Ser Leu Pro Leu Ala Asp Arg Ala Thr Ile Ala
    290                 295                 300

Asn Met Ser Pro Glu Tyr Gly Ala Thr Cys Gly Phe Phe Pro Ile Asp
305                 310                 315                 320

Ala Val Thr Leu Asp Tyr Met Arg Leu Ser Gly Arg Ser Glu Asp Gln
                325                 330                 335
```

```
Val Glu Leu Val Glu Lys Tyr Ala Lys Ala Gln Gly Met Trp Arg Asn
            340                 345                 350

Pro Gly Asp Glu Pro Ile Phe Thr Ser Thr Leu Glu Leu Asp Met Asn
            355                 360                 365

Asp Val Glu Ala Ser Leu Ala Gly Pro Lys Arg Pro Gln Asp Arg Val
370                 375                 380

Ala Leu Pro Asp Val Pro Lys Ala Phe Ala Ala Ser Asn Glu Leu Glu
385                 390                 395                 400

Val Asn Ala Thr His Lys Asp Arg Gln Pro Val Asp Tyr Val Met Asn
            405                 410                 415

Gly His Gln Tyr Gln Leu Pro Asp Gly Ala Val Ile Ala Ala Ile
            420                 425                 430

Thr Ser Cys Thr Asn Thr Ser Asn Pro Ser Val Leu Met Ala Ala Gly
            435                 440                 445

Leu Leu Ala Lys Lys Ala Val Thr Leu Gly Leu Lys Arg Gln Pro Trp
450                 455                 460

Val Lys Ala Ser Leu Ala Pro Gly Ser Lys Val Val Ser Asp Tyr Leu
465                 470                 475                 480

Ala Lys Ala Lys Leu Thr Pro Tyr Leu Asp Glu Leu Gly Phe Asn Leu
            485                 490                 495

Val Gly Tyr Gly Cys Thr Thr Cys Ile Gly Asn Ser Gly Pro Leu Pro
            500                 505                 510

Asp Pro Ile Glu Thr Ala Ile Lys Lys Ser Asp Leu Thr Val Gly Ala
            515                 520                 525

Val Leu Ser Gly Asn Arg Asn Phe Glu Gly Arg Ile His Pro Leu Val
            530                 535                 540

Lys Thr Asn Trp Leu Ala Ser Pro Pro Leu Val Val Ala Tyr Ala Leu
545                 550                 555                 560

Ala Gly Asn Met Asn Ile Asn Leu Ala Ser Glu Pro Ile Gly His Asp
            565                 570                 575

Arg Lys Gly Asp Pro Val Tyr Leu Lys Asp Ile Trp Pro Ser Ala Gln
            580                 585                 590

Glu Ile Ala Arg Ala Val Glu Gln Val Ser Thr Glu Met Phe Arg Lys
            595                 600                 605

Glu Tyr Ala Glu Val Phe Glu Gly Thr Ala Glu Trp Lys Gly Ile Asn
            610                 615                 620

Val Thr Arg Ser Asp Thr Tyr Gly Trp Gln Glu Asp Ser Thr Tyr Ile
625                 630                 635                 640

Arg Leu Ser Pro Phe Phe Asp Glu Met Gln Ala Thr Pro Ala Pro Val
            645                 650                 655

Glu Asp Ile His Gly Ala Arg Ile Leu Ala Met Leu Gly Asp Ser Val
            660                 665                 670

Thr Thr Asp His Ile Ser Pro Ala Gly Ser Ile Lys Pro Asp Ser Pro
            675                 680                 685

Ala Gly Arg Tyr Leu Gln Gly Arg Gly Val Glu Arg Lys Asp Phe Asn
            690                 695                 700

Ser Tyr Gly Ser Arg Arg Gly Asn His Glu Val Met Met Arg Gly Thr
705                 710                 715                 720

Phe Ala Asn Ile Arg Ile Arg Asn Glu Met Val Pro Gly Val Glu Gly
            725                 730                 735

Gly Met Thr Arg His Leu Pro Asp Ser Asp Val Val Ser Ile Tyr Asp
            740                 745                 750
```

Ala Ala Met Arg Tyr Lys Gln Glu Gln Thr Pro Leu Ala Val Ile Ala
            755                 760                 765

Gly Lys Glu Tyr Gly Ser Gly Ser Ser Arg Asp Trp Ala Ala Lys Gly
    770                 775                 780

Pro Arg Leu Leu Gly Ile Arg Val Val Ile Ala Glu Ser Phe Glu Arg
785                 790                 795                 800

Ile His Arg Ser Asn Leu Ile Gly Met Gly Ile Leu Pro Leu Glu Phe
                805                 810                 815

Pro Gln Gly Val Thr Arg Lys Thr Leu Gly Leu Thr Gly Glu Lys
                820                 825                 830

Ile Asp Ile Gly Asp Leu Gln Asn Leu Gln Pro Gly Ala Thr Val Pro
        835                 840                 845

Val Thr Leu Thr Arg Ala Asp Gly Ser Gln Glu Val Val Pro Cys Arg
850                 855                 860

Cys Arg Ile Asp Thr Ala Thr Glu Leu Thr Tyr Tyr Gln Asn Asp Gly
865                 870                 875                 880

Ile Leu His Tyr Val Ile Arg Asn Met Leu Lys
                885                 890

<210> SEQ ID NO 72
<211> LENGTH: 467
<212> TYPE: PRT
<213> ORGANISM: Escherichia coli
<220> FEATURE:
<223> OTHER INFORMATION: Escherichia coli K-12

<400> SEQUENCE: 72

Met Asn Thr Val Arg Ser Glu Lys Asp Ser Met Gly Ala Ile Asp Val
1               5                   10                  15

Pro Ala Asp Lys Leu Trp Gly Ala Gln Thr Gln Arg Ser Leu Glu His
            20                  25                  30

Phe Arg Ile Ser Thr Glu Lys Met Pro Thr Ser Leu Ile His Ala Leu
        35                  40                  45

Ala Leu Thr Lys Arg Ala Ala Ala Lys Val Asn Glu Asp Leu Gly Leu
    50                  55                  60

Leu Ser Glu Glu Lys Ala Ser Ala Ile Arg Gln Ala Ala Asp Glu Val
65                  70                  75                  80

Leu Ala Gly Gln His Asp Asp Glu Phe Pro Leu Ala Ile Trp Gln Thr
                85                  90                  95

Gly Ser Gly Thr Gln Ser Asn Met Asn Met Asn Glu Val Leu Ala Asn
            100                 105                 110

Arg Ala Ser Glu Leu Leu Gly Gly Val Arg Gly Met Glu Arg Lys Val
        115                 120                 125

His Pro Asn Asp Asp Val Asn Lys Ser Gln Ser Ser Asn Asp Val Phe
    130                 135                 140

Pro Thr Ala Met His Val Ala Ala Leu Leu Ala Leu Arg Lys Gln Leu
145                 150                 155                 160

Ile Pro Gln Leu Lys Thr Leu Thr Gln Thr Leu Asn Glu Lys Ser Arg
                165                 170                 175

Ala Phe Ala Asp Ile Val Lys Ile Gly Arg Thr His Leu Gln Asp Ala
            180                 185                 190

Thr Pro Leu Thr Leu Gly Gln Glu Ile Ser Gly Trp Val Ala Met Leu
        195                 200                 205

Glu His Asn Leu Lys His Ile Glu Tyr Ser Leu Pro His Val Ala Glu
    210                 215                 220

```
Leu Ala Leu Gly Gly Thr Ala Val Gly Thr Gly Leu Asn Thr His Pro
225                 230                 235                 240

Glu Tyr Ala Arg Arg Val Ala Asp Glu Leu Ala Val Ile Thr Cys Ala
                245                 250                 255

Pro Phe Val Thr Ala Pro Asn Lys Phe Glu Ala Leu Ala Thr Cys Asp
            260                 265                 270

Ala Leu Val Gln Ala His Gly Ala Leu Lys Gly Leu Ala Ala Ser Leu
        275                 280                 285

Met Lys Ile Ala Asn Asp Val Arg Trp Leu Ala Ser Gly Pro Arg Cys
290                 295                 300

Gly Ile Gly Glu Ile Ser Ile Pro Glu Asn Glu Pro Gly Ser Ser Ile
305                 310                 315                 320

Met Pro Gly Lys Val Asn Pro Thr Gln Cys Glu Ala Leu Thr Met Leu
                325                 330                 335

Cys Cys Gln Val Met Gly Asn Asp Val Ala Ile Asn Met Gly Gly Ala
            340                 345                 350

Ser Gly Asn Phe Glu Leu Asn Val Phe Arg Pro Met Val Ile His Asn
        355                 360                 365

Phe Leu Gln Ser Val Arg Leu Leu Ala Asp Gly Met Glu Ser Phe Asn
370                 375                 380

Lys His Cys Ala Val Gly Ile Glu Pro Asn Arg Glu Arg Ile Asn Gln
385                 390                 395                 400

Leu Leu Asn Glu Ser Leu Met Leu Val Thr Ala Leu Asn Thr His Ile
                405                 410                 415

Gly Tyr Asp Lys Ala Ala Glu Ile Ala Lys Lys Ala His Lys Glu Gly
            420                 425                 430

Leu Thr Leu Lys Ala Ala Leu Ala Leu Gly Tyr Leu Ser Glu Ala
        435                 440                 445

Glu Phe Asp Ser Trp Val Arg Pro Glu Gln Met Val Gly Ser Met Lys
450                 455                 460

Ala Gly Arg
465

<210> SEQ ID NO 73
<211> LENGTH: 299
<212> TYPE: PRT
<213> ORGANISM: Bacillus subtilis
<220> FEATURE:
<223> OTHER INFORMATION: Bacillus subtilis subsp. subtilis str. 168

<400> SEQUENCE: 73

Met Lys Leu Lys Asp Leu Ile Gly Lys Ala Ser Ile His Lys Asn Lys
1               5                   10                  15

Thr Ile Ala Val Ala His Ala Glu Asp Glu Val Ile Arg Ala Val
            20                  25                  30

Lys Leu Ala Ala Glu His Leu Ser Ala Arg Phe Leu Leu Thr Gly Asp
        35                  40                  45

Ser Lys Lys Leu Asn Glu Leu Thr Ser Ser Met Gln Gly His Gln Val
    50                  55                  60

Glu Ile Val His Ala Asn Thr Pro Glu Glu Ser Ala Lys Leu Ala Val
65                  70                  75                  80

Arg Ala Val His His Lys Thr Ala Asp Val Leu Met Lys Gly Asn Val
                85                  90                  95

Pro Thr Ser Val Leu Leu Lys Ala Val Leu Asn Arg Gln Glu Gly Leu
            100                 105                 110
```

```
Arg Ser Ala Ser Val Leu Ser His Val Ala Val Phe Asp Ile Pro Asp
            115                 120                 125

Phe Asp Arg Leu Met Phe Val Thr Asp Ser Ala Met Asn Ile Ala Pro
        130                 135                 140

Ser Leu Glu Glu Leu Arg Gln Ile Leu Gln Asn Ala Val His Val Ala
145                 150                 155                 160

His Ala Val Gly Asn Asn Met Pro Lys Ala Ala Leu Ala Ala Val
                165                 170                 175

Glu Thr Val Asn Pro Lys Met Glu Ala Thr Val Asn Ala Ala Ala Leu
            180                 185                 190

Ala Gln Met Tyr Lys Arg Gly Gln Ile Lys Gly Cys Ile Val Asp Gly
        195                 200                 205

Pro Leu Ala Leu Asp Asn Ala Val Ser Gln Ile Ala Ala Ala Gln Lys
210                 215                 220

Lys Ile Ser Gly Asp Val Ala Gly Asn Ala Asp Ile Leu Leu Val Pro
225                 230                 235                 240

Thr Ile Glu Ala Gly Asn Ile Leu Tyr Lys Ser Leu Ile Tyr Phe Ala
            245                 250                 255

Lys Ala Ser Val Ala Ala Val Ile Thr Gly Ala Lys Ala Pro Ile Ala
        260                 265                 270

Leu Thr Ser Arg Ala Asp Ser Ala Glu Asn Lys Leu Tyr Ser Ile Ala
        275                 280                 285

Leu Ala Ile Cys Ala Ser Glu Glu Tyr Thr His
        290                 295

<210> SEQ ID NO 74
<211> LENGTH: 273
<212> TYPE: PRT
<213> ORGANISM: Enterococcus faecalis

<400> SEQUENCE: 74

Met Ile Thr Val Ser Ile Ala Gly Gly Ser Gln Pro Glu Ile Leu Gln
1               5                   10                  15

Leu Val Lys Lys Ala Leu Lys Glu Ala Glu Gln Pro Leu Gln Phe Ile
            20                  25                  30

Val Phe Asp Thr Asn Glu Asn Leu Asp Thr Glu Asn Leu Trp Lys Tyr
        35                  40                  45

Val His Cys Ser Asp Glu Ala Thr Val Ala Gln Glu Ala Val Ser Leu
    50                  55                  60

Val Ala Thr Gly Gln Ala Gln Ile Leu Leu Lys Gly Ile Ile Gln Thr
65                  70                  75                  80

His Thr Leu Leu Lys Glu Met Leu Lys Ser Glu His Gln Leu Lys Asn
                85                  90                  95

Lys Pro Ile Leu Ser His Val Ala Met Val Glu Leu Pro Ala Gly Lys
            100                 105                 110

Thr Phe Leu Leu Thr Asp Cys Ala Met Asn Ile Ala Pro Thr Gln Ala
        115                 120                 125

Thr Leu Ile Glu Ile Val Glu Asn Ala Lys Glu Val Ala Gln Lys Leu
    130                 135                 140

Gly Leu His His Pro Lys Ile Ala Leu Leu Ser Ala Ala Glu Asn Phe
145                 150                 155                 160

Asn Pro Lys Met Pro Ser Ser Val Leu Ala Lys Glu Val Thr Ala His
                165                 170                 175

Phe Asn Gly Gln Gln Glu Ala Thr Val Phe Gly Pro Leu Ser Leu Asp
            180                 185                 190
```

```
Leu Ala Thr Ser Glu Glu Ala Val Ala His Lys Arg Tyr Ser Gly Pro
        195                 200                 205

Ile Met Gly Asp Ala Asp Ile Leu Val Val Pro Thr Ile Asp Val Gly
    210                 215                 220

Asn Cys Leu Tyr Lys Ser Leu Thr Leu Phe Gly His Ala Lys Val Gly
225                 230                 235                 240

Gly Thr Ile Val Gly Thr Lys Val Pro Val Val Leu Thr Ser Arg Ser
                245                 250                 255

Asp Ser Thr Glu Ser Lys Phe His Ser Leu Arg Phe Ala Met Arg Gln
            260                 265                 270

Val

<210> SEQ ID NO 75
<211> LENGTH: 384
<212> TYPE: PRT
<213> ORGANISM: Lactobacillus casei
<220> FEATURE:
<223> OTHER INFORMATION: Lactobacillus casei W56

<400> SEQUENCE: 75

Met Arg Asp Cys Thr Thr Glu Arg Arg Cys Leu Met Thr Met His Pro
1               5                   10                  15

Lys Arg Asp Val Val Ile Val Ile Asn Pro Gly Ser Thr Ser Ser Lys
            20                  25                  30

Ile Ala Leu Phe Lys Ala Gly Lys Met Val Ala Glu Arg Thr Leu Asn
        35                  40                  45

His Ser Leu Ala Glu Leu Ser Gln Phe Asp Ser Val Ile Ala Gln Lys
    50                  55                  60

Asp Phe Arg Met Gln Ala Ile Gln Glu Phe Leu Ala Asp Gln Asp Phe
65                  70                  75                  80

Ser Ala Ser Glu Val Leu Ala Val Ala Gly Arg Gly Gly Leu Leu Lys
                85                  90                  95

Pro Ile Pro Gly Gly Thr Tyr Ala Val Asn Glu Ala Met Leu Asp Asp
            100                 105                 110

Leu Thr Ala Ala Lys Arg Asn Glu His Ala Ser Asn Leu Gly Ala Gly
        115                 120                 125

Leu Ala Gln Gln Val Ala Asp Gln Tyr Gly Val Lys Ala Tyr Val Val
    130                 135                 140

Asp Pro Pro Val Val Asp Glu Leu Gln Pro Leu Ala Arg Ile Ser Gly
145                 150                 155                 160

Leu Lys Gly Ile Glu Arg His Ser Ala Ala His Val Leu Asn Gln Lys
                165                 170                 175

Ala Met Ala Arg Gln Val Leu Ala Thr Met Gly Lys Thr Tyr Ala Thr
            180                 185                 190

Ser Arg Val Ile Val Ala His Ile Gly Gly Gly Leu Ser Ile His Ala
        195                 200                 205

His Glu Asn Gly Arg Met Ile Asp Gly Asn Asn Gly Ile Asp Gly Glu
    210                 215                 220

Gly Pro Tyr Ser Pro Glu Arg Ala Gly Ser Leu Pro Leu Val Asp Phe
225                 230                 235                 240

Val Ala Lys Val Leu Ala Glu Arg Leu Thr Leu Asp Gln Val Lys Lys
                245                 250                 255

Leu Leu Ala Ser Gln Ser Gly Leu Arg Ser Tyr Leu Asn Asp Ile Ser
            260                 265                 270
```

```
Ile Lys Asn Ile Val Thr Arg Ile Ala Glu Gly Asp Glu Thr Ala Lys
            275                 280                 285

Phe Tyr Leu Asp Gly Met Ile Tyr Gln Ile Lys Lys Gln Ile Ala Glu
        290                 295                 300

Met Ala Gly Val Leu Asn Gly Gln Val Asp Val Ile Ile Leu Thr Gly
305                 310                 315                 320

Gly Ala Ala Tyr Ala Thr Ala Val Thr Val Pro Leu Gln His Asp Leu
                325                 330                 335

Ala Trp Ile Ala Pro Val Val Arg Pro Gly Glu Met Glu Met Gln
                340                 345                 350

Ala Leu Tyr Glu Gly Val Met Arg Val Leu Asn His Glu Glu Pro Val
            355                 360                 365

Arg Val Tyr Gln Ser Asp Ala Ser Thr Ile Lys Gly Thr Gly Arg
        370                 375                 380

<210> SEQ ID NO 76
<211> LENGTH: 370
<212> TYPE: PRT
<213> ORGANISM: Unknown
<220> FEATURE:
<223> OTHER INFORMATION: Geobacillus sp. GHH01

<400> SEQUENCE: 76

Met Glu Glu Gln Lys Phe Arg Ile Leu Thr Ile Asn Pro Gly Ser Thr
1               5                   10                  15

Ser Thr Lys Ile Gly Val Phe Glu Asn Glu Arg Pro Leu Leu Glu Lys
            20                  25                  30

Thr Ile Arg His Glu Ala Asp Val Leu Arg Gln Tyr Lys Thr Ile Ala
        35                  40                  45

Asp Gln Tyr Glu Phe Arg Lys Gln Thr Ile Leu Gln Ala Leu Asp Glu
    50                  55                  60

Glu Gly Ile Asn Leu Ser Lys Leu Ser Ala Val Cys Gly Arg Gly Gly
65                  70                  75                  80

Leu Leu Arg Pro Ile Glu Gly Gly Thr Tyr Arg Val Asn Glu Ala Met
                85                  90                  95

Leu Glu Asp Leu Arg Arg Gly Tyr Ser Gly Gln His Ala Ser Asn Leu
            100                 105                 110

Gly Gly Ile Leu Ala His Glu Ile Ala Ser Ala Leu Asn Ile Pro Ala
        115                 120                 125

Phe Ile Val Asp Pro Val Val Asp Glu Leu Asp Pro Ile Ala Arg
    130                 135                 140

Ile Ser Gly Phe Pro Leu Ile Glu Arg Arg Ser Ile Phe His Ala Leu
145                 150                 155                 160

Asn Gln Lys Ala Val Ala Arg Arg Val Ala Lys Gln Leu Gly Lys Arg
                165                 170                 175

Tyr Asp Glu Leu Asn Leu Ile Val Ala His Met Gly Gly Gly Ile Thr
            180                 185                 190

Val Gly Ala His Lys Gln Gly Arg Val Val Asp Val Asn Asn Gly Leu
        195                 200                 205

Asp Gly Glu Gly Pro Phe Ser Pro Glu Arg Ala Gly Thr Val Pro Ala
    210                 215                 220

Gly Asp Leu Val Ala Leu Cys Phe Ser Gly Glu Tyr Tyr Arg Glu Glu
225                 230                 235                 240

Ile Met Asn Met Leu Val Gly Gly Gly Leu Val Gly Tyr Leu Gly
                245                 250                 255
```

```
Thr Asn Asp Ala Val Lys Val Glu Asn Met Ile Glu Ala Gly Asp Glu
                260                 265                 270

Lys Ala Lys Leu Val Tyr Glu Ala Met Ala Tyr Gln Val Ala Lys Glu
                275                 280                 285

Ile Gly Ala Ala Ser Ala Val Leu Ser Gly Lys Val Asp Ala Ile Ile
                290                 295                 300

Leu Thr Gly Gly Leu Ala Tyr Gly Lys Ser Phe Val Glu Gln Ile Thr
305                 310                 315                 320

Arg Arg Val Gln Trp Ile Ala Asp Val Ile Val His Pro Gly Glu Asn
                325                 330                 335

Glu Leu Gln Ala Leu Ala Glu Gly Ala Leu Arg Val Leu Arg Gly Glu
                340                 345                 350

Glu Glu Glu Lys Val Tyr Pro Gly Glu Ala Val Ser Pro Ile Pro Ala
                355                 360                 365

Arg Arg
    370
```

<210> SEQ ID NO 77
<211> LENGTH: 556
<212> TYPE: PRT
<213> ORGANISM: Methanobacterium formicicum
<220> FEATURE:
<223> OTHER INFORMATION: Methanobacterium formicicum DSM 3637

<400> SEQUENCE: 77

```
Met Ser Ser Leu Leu Glu Lys Phe Val Ser Gln Val Asn Phe Glu Ser
1               5                   10                  15

Tyr Pro Asp Phe Lys Asp Asn Phe Arg Ile Lys Ile Pro Glu Asn Phe
                20                  25                  30

Asn Phe Ala Tyr Asp Val Val Asp Glu Tyr Ala Arg Leu Tyr Pro Glu
                35                  40                  45

Lys Val Ala Met Val Trp Cys Asn Asp Asp Thr Asp Arg Ile Phe Thr
                50                  55                  60

Phe Lys Thr Leu Lys Glu Tyr Ser Asp Arg Ala Ala Asn Phe Phe Ala
65                  70                  75                  80

Gln Gln Gly Ile Lys Lys Gly Asp Arg Val Met Leu Thr Leu Lys Ser
                85                  90                  95

Arg Tyr Glu Phe Trp Phe Cys Ile Leu Ala Leu His Lys Leu Gly Ala
                100                 105                 110

Ile Thr Ile Pro Ala Thr His Met Leu Lys Thr Arg Asp Ile Val Tyr
                115                 120                 125

Arg Ile Lys Asn Ala Gly Ile Lys Met Val Val Cys Ile Ala Glu Asp
                130                 135                 140

Gly Val Pro Gly Tyr Phe Asp Glu Ala His Leu Gln Leu Asp Asp Ala
145                 150                 155                 160

Pro Phe Val Lys Ala Leu Val Gly Asp Glu Asp Arg Glu Gly Trp Phe
                165                 170                 175

Asn Phe Arg Lys Glu Leu Glu Asn Ala Ser Pro Glu Leu Gln Arg Pro
                180                 185                 190

Ser Gly Glu Glu Gly Thr Gln Asn Asp Asp Val Ala Leu Ile Tyr Phe
                195                 200                 205

Ser Ser Gly Thr Thr Gly Leu Pro Lys Met Ile Met His Asp Tyr Thr
                210                 215                 220

Tyr Pro Leu Gly His Ile Ile Thr Ala Lys Tyr Trp Gln Asn Val Val
225                 230                 235                 240
```

```
Glu Asp Gly Leu His Tyr Thr Val Ala Asp Thr Gly Trp Ala Lys Ala
                245                 250                 255

Met Trp Gly Gln Ile Tyr Gly Gln Trp Ile Ser Gly Thr Ala Ile Phe
            260                 265                 270

Val Tyr Asp Tyr Glu Arg Phe Asp Ala Ala Lys Met Leu Asp Lys Ala
            275                 280                 285

Ser His His Gly Val Thr Thr Phe Cys Ala Pro Thr Ile Tyr Arg
            290                 295                 300

Phe Leu Ile Lys Glu Asp Leu Ser Gln Tyr Asp Phe Ser Thr Leu Lys
305                 310                 315                 320

Tyr Ala Val Thr Ala Gly Glu Pro Leu Asn Pro Glu Val Tyr Asn Lys
                325                 330                 335

Phe Tyr Glu Phe Thr Gly Leu Arg Leu Arg Glu Gly Phe Gly Gln Thr
            340                 345                 350

Glu Cys Val Val Cys Ile Ala Asn Phe Pro Trp Ile Glu Pro Arg Pro
            355                 360                 365

Gly Ser Met Gly Lys Ser Ala Pro Glu Tyr Asp Ile Gln Ile Met Asp
            370                 375                 380

Lys Glu Gly Lys Gln Cys Asp Val Gly Glu Glu Gly Glu Ile Val Ile
385                 390                 395                 400

Lys Thr Ala Asp Gly Lys Pro Pro Gly Leu Phe Cys Gly Tyr Tyr Lys
                405                 410                 415

Glu Asp Asn Lys Thr Glu Ala Ala Trp Phe Asp Gly Tyr His Thr
            420                 425                 430

Gly Asp Thr Ala Trp Lys Asp Glu Asp Gly Tyr Leu Trp Phe Val Gly
            435                 440                 445

Arg Asn Asp Asp Met Ile Lys Ser Ser Gly Tyr Arg Ile Gly Pro Phe
450                 455                 460

Glu Val Glu Ser Ala Val Ile Ser His Gln Ala Val Leu Glu Cys Ala
465                 470                 475                 480

Ile Thr Gly Val Pro His Pro Val Arg Gly Gln Val Ile Lys Ala Thr
                485                 490                 495

Ile Val Leu Thr Gly Asp Tyr Glu Pro Ser Pro Glu Leu Ala Lys Glu
            500                 505                 510

Ile Gln Asn His Val Lys Gln Val Thr Ala Pro Tyr Lys Tyr Pro Arg
            515                 520                 525

Val Val Glu Phe Val Asp Glu Leu Pro Lys Thr Ile Ser Gly Lys Ile
            530                 535                 540

Arg Arg Val Glu Ile Arg Glu Lys Asp Glu Lys Glu
545                 550                 555

<210> SEQ ID NO 78
<211> LENGTH: 502
<212> TYPE: PRT
<213> ORGANISM: Klebsiella pneumoniae

<400> SEQUENCE: 78

Met Thr Ala Pro Ile Gln Asp Leu Arg Asp Ala Ile Ala Leu Leu Gln
1               5                  10                  15

Gln His Asp Asn Gln Tyr Leu Glu Thr Asp His Pro Val Asp Pro Asn
            20                  25                  30

Ala Glu Leu Ala Gly Val Tyr Arg His Ile Gly Ala Gly Gly Thr Val
            35                  40                  45

Lys Arg Pro Thr Arg Ile Gly Pro Ala Met Met Phe Asn Asn Ile Lys
50                  55                  60
```

```
Gly Tyr Pro His Ser Arg Ile Leu Val Gly Met His Ala Ser Arg Gln
 65                  70                  75                  80

Arg Ala Ala Leu Leu Leu Gly Cys Glu Ala Ser Gln Leu Ala Leu Glu
                 85                  90                  95

Val Gly Lys Ala Val Lys Lys Pro Val Ala Pro Val Val Pro Ala
            100                 105                 110

Ser Ser Ala Pro Cys Gln Glu Gln Ile Phe Leu Ala Asp Asp Pro Asp
            115                 120                 125

Phe Asp Leu Arg Thr Leu Leu Pro Ala Pro Thr Asn Thr Pro Ile Asp
130                 135                 140

Ala Gly Pro Phe Phe Cys Leu Gly Leu Ala Leu Ala Ser Asp Pro Val
145                 150                 155                 160

Asp Ala Ser Leu Thr Asp Val Thr Ile His Arg Leu Cys Val Gln Gly
                165                 170                 175

Arg Asp Glu Leu Ser Met Phe Leu Ala Ala Gly Arg His Ile Glu Val
                180                 185                 190

Phe Arg Gln Lys Ala Glu Ala Ala Gly Lys Pro Leu Pro Ile Thr Ile
            195                 200                 205

Asn Met Gly Leu Asp Pro Ala Ile Tyr Ile Gly Ala Cys Phe Glu Ala
210                 215                 220

Pro Thr Thr Pro Phe Gly Tyr Asn Glu Leu Gly Val Ala Gly Ala Leu
225                 230                 235                 240

Arg Gln Arg Pro Val Glu Leu Val Gln Gly Val Ser Val Pro Glu Lys
                245                 250                 255

Ala Ile Ala Arg Ala Glu Ile Val Ile Glu Gly Glu Leu Leu Pro Gly
                260                 265                 270

Val Arg Val Arg Glu Asp Gln His Thr Asn Ser Gly His Ala Met Pro
                275                 280                 285

Glu Phe Pro Gly Tyr Cys Gly Gly Ala Asn Pro Ser Leu Pro Val Ile
290                 295                 300

Lys Val Lys Ala Val Thr Met Arg Asn Asn Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Trp Asn Ala Val Glu Ala Ala Ile Pro Gly Phe Leu Gln
                340                 345                 350

Asn Val Tyr Ala His Thr Ala Gly Gly Gly Lys Phe Leu Gly Ile Leu
                355                 360                 365

Gln Val Lys Lys Arg Gln Pro Ala Asp Glu Gly Arg Gln Gly Gln Ala
            370                 375                 380

Ala Leu Leu Ala Leu Ala Thr Tyr Ser Glu Leu Lys Asn Ile Ile Leu
385                 390                 395                 400

Val Asp Glu Asp Val Asp Ile Phe Asp Ser Asp Ile Leu Trp Ala
                405                 410                 415

Met Thr Thr Arg Met Gln Gly Asp Val Ser Ile Thr Ile Pro Gly
                420                 425                 430

Ile Arg Gly His Gln Leu Asp Pro Ser Gln Thr Pro Glu Tyr Ser Pro
            435                 440                 445

Ser Ile Arg Gly Asn Gly Ile Ser Cys Lys Thr Ile Phe Asp Cys Thr
            450                 455                 460

Val Pro Trp Ala Leu Lys Ser His Phe Glu Arg Ala Pro Phe Ala Asp
465                 470                 475                 480
```

```
Val Asp Pro Arg Pro Phe Ala Pro Glu Tyr Phe Ala Arg Leu Glu Lys
                485                 490                 495

Asn Gln Gly Ser Ala Lys
                500

<210> SEQ ID NO 79
<211> LENGTH: 496
<212> TYPE: PRT
<213> ORGANISM: Enterobacter cloacae

<400> SEQUENCE: 79

Met Glu Asn Gln Ile Asn Asp Leu Arg Ser Ile Ala Leu Leu Gln
1               5                   10                  15

Arg His Glu Gly Gln Tyr Ile Glu Thr Asp Arg Pro Val Asp Pro Asn
                20                  25                  30

Ala Glu Leu Ala Gly Val Tyr Arg His Ile Gly Ala Gly Gly Thr Val
            35                  40                  45

Lys Arg Pro Thr Arg Thr Gly Pro Ala Met Met Phe Asn Ser Ile Lys
50                  55                  60

Gly Tyr Pro His Ser Arg Ile Leu Val Gly Met His Ala Ser Arg Glu
65                  70                  75                  80

Arg Ala Ala Leu Leu Leu Gly Cys Glu Pro Ser Glu Leu Ala Lys His
                85                  90                  95

Val Gly Gln Ala Val Lys Lys Pro Val Ala Pro Val Val Pro Ala
            100                 105                 110

Ser Gln Ala Pro Cys Gln Glu Gln Val Phe Tyr Ala Asp Asp Pro Asp
        115                 120                 125

Phe Asp Leu Arg Lys Leu Leu Pro Ala Pro Thr Asn Thr Pro Ile Asp
130                 135                 140

Ala Gly Pro Phe Phe Cys Leu Gly Leu Val Leu Ala Ser Asp Pro Glu
145                 150                 155                 160

Asp Ser Ser Leu Thr Asp Val Thr Ile His Arg Leu Cys Val Gln Glu
                165                 170                 175

Arg Asp Glu Leu Ser Met Phe Leu Ala Ala Gly Arg His Ile Glu Val
            180                 185                 190

Phe Arg Lys Lys Ala Glu Asp Ala Gly Lys Pro Leu Pro Val Thr Ile
        195                 200                 205

Asn Met Gly Leu Asp Pro Ala Ile Tyr Ile Gly Ala Cys Phe Glu Ala
210                 215                 220

Pro Thr Thr Pro Phe Gly Tyr Asn Glu Leu Gly Val Ala Gly Ala Leu
225                 230                 235                 240

Arg Gln Gln Pro Val Glu Leu Val Gln Val Ala Val Lys Glu Lys
                245                 250                 255

Ala Ile Ala Arg Ala Glu Ile Ile Glu Gly Glu Leu Leu Pro Gly
            260                 265                 270

Val Arg Val Arg Glu Asp Gln His Thr Asn Thr Gly His Ala Met Pro
        275                 280                 285

Glu Phe Pro Gly Tyr Cys Gly Glu Ala Asn Pro Ser Leu Pro Val Ile
290                 295                 300

Lys Val Lys Ala Val Thr Met Arg Asn His Ala Ile Leu Gln Thr Leu
305                 310                 315                 320

Val Gly Pro Gly Glu Glu His Thr Thr Leu Ala Gly Leu Pro Thr Glu
                325                 330                 335

Ala Ser Ile Arg Asn Ala Val Glu Glu Ala Ile Pro Gly Phe Leu Gln
            340                 345                 350
```

```
Asn Val Tyr Ala His Thr Ala Gly Gly Gly Lys Phe Leu Gly Ile Leu
        355                 360                 365

Gln Val Lys Lys Arg Gln Pro Ser Asp Glu Gly Arg Gln Gly Gln Ala
370                 375                 380

Ala Leu Ile Ala Leu Ala Thr Tyr Ser Glu Leu Lys Asn Ile Ile Leu
385                 390                 395                 400

Val Asp Glu Asp Val Asp Ile Phe Asp Ser Asp Asp Ile Leu Trp Ala
                405                 410                 415

Met Thr Thr Arg Met Gln Gly Asp Val Ser Ile Thr Asn Ile Pro Gly
            420                 425                 430

Ile Arg Gly His Gln Leu Asp Pro Ser Gln Ser Pro Asp Tyr Ser Thr
                435                 440                 445

Ser Ile Arg Gly Asn Gly Ile Ser Cys Lys Thr Ile Phe Asp Cys Thr
            450                 455                 460

Val Pro Trp Ala Leu Lys Asp Arg Phe Glu Arg Ala Pro Phe Met Glu
465                 470                 475                 480

Val Asp Pro Arg Pro Trp Ala Pro Glu Leu Phe Ala Asp Asn Thr Lys
                485                 490                 495

<210> SEQ ID NO 80
<211> LENGTH: 510
<212> TYPE: PRT
<213> ORGANISM: Unknown
<220> FEATURE:
<223> OTHER INFORMATION: Leptolyngbya species

<400> SEQUENCE: 80

Met Leu Ile Asp Gln Glu Gln Ala Lys Thr Asp His Pro Leu Gly Trp
1               5                   10                  15

Asn Val Pro Asp Ile Asn Asp Leu Arg Ala Ala Ile Ala His Leu Lys
                20                  25                  30

Lys Phe Lys Gly Gln Tyr Ile Glu Thr Asp His Pro Val Asp Pro Ile
            35                  40                  45

Ala Glu Leu Ala Gly Val Tyr Arg Tyr Ile Gly Ala Gly Gly Thr Val
50                  55                  60

Met Arg Pro Thr Arg Ile Gly Pro Ala Met Thr Phe Asn Asn Val Lys
65                  70                  75                  80

Gly Tyr Pro Asn Ser Arg Val Leu Val Gly Met Met Ala Ser Arg Glu
                85                  90                  95

Arg Val Ser Ile Leu Leu Gly Ala Pro Thr Arg Glu Leu Gly Met Gln
            100                 105                 110

Met Gly Lys Ala Val Lys Thr Ile Val Pro Pro Ala Thr Ile Asp Ala
        115                 120                 125

Lys Asp Ala Pro Cys Gln Glu Ile Tyr Arg Ala Asp Asp Pro Thr
            130                 135                 140

Phe Asp Leu Arg Lys Leu Leu Pro Ala Pro Thr Asn Thr Glu Glu Asp
145                 150                 155                 160

Ala Gly Pro Tyr Phe Cys Met Gly Leu Val Leu Gly Ser Asp Pro Asp
                165                 170                 175

Asp Glu Thr Asn Thr Asp Val Thr Ile His Arg Leu Cys Val Gln Ser
            180                 185                 190

Arg Asp Glu Met Ser Ile Phe Phe Ala Pro Gly Arg His Ile Asp Ala
        195                 200                 205

Tyr Arg Gln Lys Ala Glu Ala Ala Gly Lys Pro Leu Pro Ile Ser Val
    210                 215                 220
```

```
Asn Met Gly Leu Asp Pro Ala Ile His Ile Gly Ala Cys Phe Glu Ala
225                 230                 235                 240

Pro Thr Thr Pro Phe Gly Phe Asp Glu Leu Cys Val Ala Gly Gly Leu
                245                 250                 255

Arg Gly Lys Pro Val Glu Leu Val Asn Cys Val Thr Val Gln Gln Lys
            260                 265                 270

Ala Ile Ala Arg Ala Glu Ile Val Ile Glu Gly Glu Val Leu Pro Asn
        275                 280                 285

Val Arg Val Ala Glu Asp Gln Asn Thr His Thr Gly Tyr Ala Met Pro
    290                 295                 300

Glu Phe Pro Gly Tyr Thr Gly Pro Ala Asn Pro Ser Leu Pro Val Ile
305                 310                 315                 320

Lys Val Thr Ala Val Thr Met Arg His Asn Ala Ile Leu Gln Thr Leu
                325                 330                 335

Val Gly Pro Gly Glu Glu His Val Asn Leu Ala Gly Ile Pro Thr Glu
            340                 345                 350

Ala Ser Ile Tyr Asn Ala Val Glu Leu Ala Leu Pro Gly Leu Leu Gln
        355                 360                 365

Asn Val Tyr Ser His Ser Ser Gly Gly Gly Lys Phe Leu Ala Ile Leu
    370                 375                 380

Gln Ile Lys Lys Arg Val Ala Gly Asp Gly Ser Ala Arg Gln Ala
385                 390                 395                 400

Ala Leu Ile Ala Leu Ala Val Tyr Arg Glu Val Lys Asn Ile Ile Leu
                405                 410                 415

Val Asp Glu Asp Val Asp Leu Phe Asp Ser Asp Val Leu Trp Ala
            420                 425                 430

Met Gln Thr Arg Tyr Gln Gly Asp Thr Gly Thr Ile Val Val Pro Gly
        435                 440                 445

Ile Thr Gly His Val Leu Asp Pro Ser Gln Ile Pro Glu Tyr Ser Pro
450                 455                 460

Ser Ile His Thr Lys Gly Ser Thr Cys Lys Thr Ile Phe Asp Cys Thr
465                 470                 475                 480

Val Pro Phe Ala Leu Lys Glu His Phe Lys Arg Ala Gln Phe Arg Glu
                485                 490                 495

Leu Asp Pro Arg Pro Phe Ala Pro Glu Leu Phe Asn Glu Pro
            500                 505                 510

<210> SEQ ID NO 81
<211> LENGTH: 492
<212> TYPE: PRT
<213> ORGANISM: Unknown
<220> FEATURE:
<223> OTHER INFORMATION: Phascolarctobacterium species

<400> SEQUENCE: 81

Met Thr Thr Lys Ile Asn Asp Leu Arg Ser Ala Leu Asp Tyr Leu Arg
1               5                   10                  15

Thr Ile Pro Gly Gln Leu Val Glu Thr Asn Val Glu Ala Asp Pro Arg
                20                  25                  30

Ala Glu Ile Ser Gly Ile Tyr Arg Tyr Val Gly Ala Lys Gly Thr Val
            35                  40                  45

Lys Arg Pro Thr Arg Leu Gly Pro Ala Met Ile Phe Asn Asn Val Lys
        50                  55                  60

Gly His Pro Gly Ala Lys Val Ala Ile Gly Val Leu Ser Ser Arg Ala
65                  70                  75                  80
```

-continued

Arg Val Gly Tyr Leu Leu Gly Cys Glu Pro Glu Lys Leu Gly Phe Leu
                85                  90                  95
Leu Lys Asp Ser Val Ser Thr Pro Ile Ala Pro Val Val Ser Ala
            100                 105                 110
Asp Gln Ala Pro Cys Gln Glu Val Val His Leu Ala Thr Glu Glu Gly
            115                 120                 125
Phe Asp Ile Arg Lys Leu Ile Pro Ala Pro Thr Asn Thr Glu Glu Asp
130                 135                 140
Ala Gly Pro Tyr Val Thr Met Gly Leu Cys Tyr Gly Thr Asp Pro Glu
145                 150                 155                 160
Thr Gly Asp Thr Asp Ile Thr Ile His Arg Leu Cys Leu Gln Gly Lys
                165                 170                 175
Asp Glu Ile Ser Met Tyr Phe Val Pro Gly Arg His Leu Asp Val Phe
            180                 185                 190
Arg Gln Lys Tyr Glu Lys Ala Gly Lys Pro Met Pro Ile Ser Ile Ser
            195                 200                 205
Ile Gly Val Asp Pro Ala Ile Glu Ile Ala Ala Cys Phe Glu Pro Pro
210                 215                 220
Thr Thr Pro Leu Gly Phe Asn Glu Leu Ser Ile Ala Gly Ser Ile Arg
225                 230                 235                 240
Gly Glu Gly Val Gln Met Val Gln Cys Lys Thr Ile Asn Glu Lys Ala
                245                 250                 255
Ile Ala Arg Ala Glu Tyr Val Ile Glu Gly Glu Leu Leu Pro Asp Val
            260                 265                 270
Arg Val Arg Glu Asp Gln Asn Ser Asn Thr Gly Lys Ala Met Pro Glu
            275                 280                 285
Phe Pro Gly Tyr Thr Gly Ala Met Lys Pro Ala Ile Pro Leu Ile Lys
290                 295                 300
Val Lys Ala Val Thr His Arg Arg Asp Pro Ile Met Gln Ser Cys Ile
305                 310                 315                 320
Gly Pro Ser Glu Glu His Val Asn Met Ala Gly Ile Pro Thr Glu Ala
                325                 330                 335
Ser Ile Leu Gly Met Thr Glu Lys Ala Leu Pro Gly Asn Val Lys Asn
            340                 345                 350
Val Tyr Ala His Cys Ser Gly Gly Lys Tyr Met Ala Val Ile Gln
            355                 360                 365
Phe Val Lys Lys Ala Pro Pro Asp Glu Gly Arg Gln Arg Gln Ala Ala
370                 375                 380
Leu Leu Ala Phe Ser Ala Phe Ser Glu Leu Lys His Val Ile Leu Val
385                 390                 395                 400
Asp Asp Asp Val Asp Leu Phe Asp Thr Asp Asp Val Leu Trp Ala Leu
                405                 410                 415
Asn Thr Arg Phe Gln Gly Asp Val Asp Val Ile Thr Ile Pro Gly Val
            420                 425                 430
Arg Cys His Pro Leu Asp Pro Ser Gln Ser Pro Glu Phe Ser Pro Ser
            435                 440                 445
Ile Arg Asp Val Gly Ile Ser Cys Lys Thr Ile Phe Asp Cys Thr Val
450                 455                 460
Pro Phe Gly Leu Lys Glu His Phe Gln Arg Ser Lys Phe Lys Glu Val
465                 470                 475                 480
Asn Pro Ala Lys Trp Val Pro Glu Leu Phe Lys Lys
                485                 490

```
<210> SEQ ID NO 82
<211> LENGTH: 136
<212> TYPE: PRT
<213> ORGANISM: Escherichia coli
<220> FEATURE:
<223> OTHER INFORMATION: Escherichia coli K-12

<400> SEQUENCE: 82

Met Ile Trp Lys Arg Lys Ile Thr Leu Glu Ala Leu Asn Ala Met Gly
1               5                   10                  15

Glu Gly Asn Met Val Gly Phe Leu Asp Ile Arg Phe Glu His Ile Gly
            20                  25                  30

Asp Asp Thr Leu Glu Ala Thr Met Pro Val Asp Ser Arg Thr Lys Gln
        35                  40                  45

Pro Phe Gly Leu Leu His Gly Gly Ala Ser Val Val Leu Ala Glu Ser
    50                  55                  60

Ile Gly Ser Val Ala Gly Tyr Leu Cys Thr Glu Gly Glu Gln Lys Val
65                  70                  75                  80

Val Gly Leu Glu Ile Asn Ala Asn His Val Arg Ser Ala Arg Glu Gly
                85                  90                  95

Arg Val Arg Gly Val Cys Lys Pro Leu His Leu Gly Ser Arg His Gln
            100                 105                 110

Val Trp Gln Ile Glu Ile Phe Asp Glu Lys Gly Arg Leu Cys Cys Ser
        115                 120                 125

Ser Arg Leu Thr Thr Ala Ile Leu
    130                 135

<210> SEQ ID NO 83
<211> LENGTH: 136
<212> TYPE: PRT
<213> ORGANISM: Salmonella enterica

<400> SEQUENCE: 83

Met Ile Trp Lys Arg Glu Val Thr Leu Asp Ala Leu Asn Ala Met Gly
1               5                   10                  15

Glu Gly Asn Met Val Gly Leu Leu Asp Ile Arg Phe Glu Arg Ile Gly
            20                  25                  30

Asp Asp Thr Leu Glu Ala Thr Met Pro Val Asp His Arg Thr Lys Gln
        35                  40                  45

Pro Phe Gly Leu Leu His Gly Gly Ala Ser Val Val Leu Ala Glu Ser
    50                  55                  60

Ile Gly Ser Val Ala Gly Tyr Leu Cys Thr Gln Gly Glu Gln Lys Val
65                  70                  75                  80

Val Gly Leu Glu Val Asn Ala Asn His Val Arg Ser Ala Arg Gln Gly
                85                  90                  95

Arg Val Arg Gly Val Cys Lys Ala Leu His Thr Gly Ala Arg His Gln
            100                 105                 110

Val Trp Gln Ile Glu Ile Phe Asp Glu Gln Gly Arg Leu Cys Cys Ser
        115                 120                 125

Ser Arg Leu Thr Thr Ala Ile Val
    130                 135

<210> SEQ ID NO 84
<211> LENGTH: 517
<212> TYPE: PRT
<213> ORGANISM: Megasphaera sp.

<400> SEQUENCE: 84
```

```
Met Arg Lys Val Glu Ile Ile Thr Ala Glu Gln Ala Ala Gln Leu Val
1               5                   10                  15
Lys Asp Asn Asp Thr Ile Thr Ser Ile Gly Phe Val Ser Ser Ala His
            20                  25                  30
Pro Glu Ala Leu Thr Lys Ala Leu Glu Lys Arg Phe Leu Asp Thr Asn
                35                  40                  45
Thr Pro Gln Asn Leu Thr Tyr Ile Tyr Ala Gly Ser Gln Gly Lys Arg
    50                  55                  60
Asp Gly Arg Ala Ala Glu His Leu Ala His Thr Gly Leu Leu Lys Arg
65                  70                  75                  80
Ala Ile Ile Gly His Trp Gln Thr Val Pro Ala Ile Gly Lys Leu Ala
                85                  90                  95
Val Glu Asn Lys Ile Glu Ala Tyr Asn Phe Ser Gln Gly Thr Leu Val
            100                 105                 110
His Trp Phe Arg Ala Leu Ala Gly His Lys Leu Gly Val Phe Thr Asp
        115                 120                 125
Ile Gly Leu Glu Thr Phe Leu Asp Pro Arg Gln Leu Gly Gly Lys Leu
    130                 135                 140
Asn Asp Val Thr Lys Glu Asp Leu Val Lys Leu Ile Glu Val Asp Gly
145                 150                 155                 160
His Glu Gln Leu Phe Tyr Pro Thr Phe Pro Val Asn Val Ala Phe Leu
                165                 170                 175
Arg Gly Thr Tyr Ala Asp Glu Ser Gly Asn Ile Thr Met Asp Glu Glu
            180                 185                 190
Ile Gly Pro Phe Glu Ser Thr Ser Val Ala Gln Ala Val His Asn Cys
        195                 200                 205
Gly Gly Lys Val Val Gln Val Lys Asp Val Ala His Gly Ser
    210                 215                 220
Leu Asp Pro Arg Met Val Lys Ile Pro Gly Ile Tyr Val Asp Tyr Val
225                 230                 235                 240
Val Val Ala Ala Pro Glu Asp His Gln Gln Thr Tyr Asp Cys Glu Tyr
                245                 250                 255
Asp Pro Ser Leu Ser Gly Glu His Arg Ala Pro Glu Gly Ala Ala Asp
            260                 265                 270
Ala Ala Leu Pro Met Ser Ala Lys Lys Ile Ile Gly Arg Arg Gly Ala
        275                 280                 285
Leu Glu Leu Thr Glu Asn Ala Val Val Asn Leu Gly Val Gly Ala Pro
    290                 295                 300
Glu Tyr Val Ala Ser Val Ala Gly Glu Gly Ile Ala Asp Thr Ile
305                 310                 315                 320
Thr Leu Thr Val Glu Gly Gly Ala Ile Gly Gly Val Pro Gln Gly Gly
                325                 330                 335
Ala Arg Phe Gly Ser Ser Arg Asn Ala Asp Ala Ile Ile Asp His Thr
            340                 345                 350
Tyr Gln Phe Asp Phe Tyr Asp Gly Gly Leu Asp Ile Ala Tyr Leu
        355                 360                 365
Gly Leu Ala Gln Cys Asp Gly Ser Gly Asn Ile Asn Val Ser Lys Phe
    370                 375                 380
Gly Thr Asn Val Ala Gly Cys Gly Gly Phe Pro Asn Ile Ser Gln Gln
385                 390                 395                 400
Thr Pro Asn Val Tyr Phe Cys Gly Thr Phe Thr Ala Gly Gly Leu Lys
                405                 410                 415
```

```
Ile Ala Val Glu Asp Gly Lys Val Lys Ile Leu Gln Glu Gly Lys Ala
            420                 425                 430

Lys Lys Phe Ile Lys Ala Val Asp Gln Ile Thr Phe Asn Gly Ser Tyr
        435                 440                 445

Ala Ala Arg Asn Gly Lys His Val Leu Tyr Ile Thr Glu Arg Cys Val
450                 455                 460

Phe Glu Leu Thr Lys Glu Gly Leu Lys Leu Ile Glu Val Ala Pro Gly
465                 470                 475                 480

Ile Asp Ile Glu Lys Asp Ile Leu Ala His Met Asp Phe Lys Pro Ile
                485                 490                 495

Ile Asp Asn Pro Lys Leu Met Asp Ala Arg Leu Phe Gln Asp Gly Pro
            500                 505                 510

Met Gly Leu Lys Lys
        515

<210> SEQ ID NO 85
<211> LENGTH: 265
<212> TYPE: PRT
<213> ORGANISM: Unknown
<220> FEATURE:
<223> OTHER INFORMATION: Pseudomonas species

<400> SEQUENCE: 85

Met Asn Asn Leu Pro Val Cys Gln Thr Leu Leu Glu Leu His Asn
1               5                   10                  15

Gly Val Leu His Val Thr Leu Asn Arg Pro Glu Cys Arg Asn Ala Met
            20                  25                  30

Ser Ser Gln Met Val Ala Glu Leu Arg Ser Val Leu Ala Val Arg
        35                  40                  45

Asp Lys Pro Gly Val Arg Ala Leu Val Ile Gly Gly Val Gly Gly His
50                  55                  60

Phe Cys Ala Gly Gly Asp Ile Lys Asp Met Ala Asn Ala Arg Ala Gln
65                  70                  75                  80

Gly Pro Thr Ala His Arg Asp Leu Asn Arg Val Phe Gly Ala Leu Leu
                85                  90                  95

Gln Glu Val Gln His Ala Pro Gln Val Val Ile Thr Val Leu Gln Gly
            100                 105                 110

Ala Val Leu Gly Gly Gly Leu Gly Leu Ala Cys Val Ser Asp Ile Ala
        115                 120                 125

Leu Ala Asp His Gln Ala Gln Phe Gly Leu Pro Glu Thr Ser Leu Gly
130                 135                 140

Leu Leu Pro Ala Gln Ile Ala Pro Phe Val Val Gln Arg Ile Gly Leu
145                 150                 155                 160

Thr Glu Ala Arg Arg Leu Ala Leu Thr Ala Ala Arg Phe Asp Gly His
                165                 170                 175

Gln Ala Arg Arg Met Gly Leu Val His Phe Val Glu His Asp Pro Gln
            180                 185                 190

Ala Leu Ala Glu Arg Leu Asp Glu Val Leu Ala His Val Leu Cys Cys
        195                 200                 205

Ala Pro Gly Ala Asn Ala Ala Thr Lys Lys Leu Leu Leu Ala Ser Ala
210                 215                 220

Gly Gln Pro Ser Asp Glu Leu Leu Asp Gln Ala Ala Glu Trp Phe Ser
225                 230                 235                 240

Glu Ala Val Thr Gly Ala Glu Gly Val Glu Gly Thr Met Ala Phe Val
                245                 250                 255
```

```
Gln Lys Arg Lys Pro Gly Trp Ala Ser
        260                 265

<210> SEQ ID NO 86
<211> LENGTH: 277
<212> TYPE: PRT
<213> ORGANISM: Acinetobacter baumannii

<400> SEQUENCE: 86

Met Thr Leu Ser Ala Ser Leu His Ile Asp Ile Asp Ser Ile Gln
 1               5                  10                  15

Leu Glu Gln Asp Gly Ser Ile Leu Tyr Leu Trp Leu Asn Arg Pro Glu
                20                  25                  30

Ser Arg Asn Ala Met Asn Leu Asn Met Val Asn Ala Ile Gln Gln Val
                35                  40                  45

Phe Thr Ala Ile Arg Asp Asp Leu Ser Ile Arg Ala Val Ile Ile Arg
    50                  55                  60

Gly Glu Gly Gly Thr Phe Cys Ala Gly Gly Asp Ile Lys Asp Met Ala
65                  70                  75                  80

Ala Leu Arg Val Glu Ala Thr Asn Val Gly Ser Leu Gln Pro Tyr Thr
                85                  90                  95

Asn Phe Asn Arg Arg Phe Gly Ala Met Leu Glu Gln Val Glu Ala Ala
                100                 105                 110

Pro Gln Thr Val Val Ile Leu Glu Ser Ala Val Leu Gly Gly Gly
                115                 120                 125

Phe Gly Leu Ala Cys Val Ser Asp Val Ala Ile Ser Arg Asp Asn Ala
            130                 135                 140

Gln Phe Gly Leu Pro Glu Thr Gly Leu Gly Val Ile Pro Ala Gln Ile
145                 150                 155                 160

Ala Pro Phe Val Val Lys Arg Ile Gly Leu Thr Gln Ala Arg Arg Leu
                165                 170                 175

Ala Leu Leu Gly Met Arg Phe Glu Gly His Thr Ala Leu Ser Val Gly
                180                 185                 190

Val Val His Gln Ile Ala His Asn Glu Ile Glu Leu Glu Gln Ala Leu
                195                 200                 205

Gln Glu Thr Ile Gln Gln Ile Lys Arg Ala Ala Pro Gln Ala Ser Arg
            210                 215                 220

Val Thr Lys Ala Leu Leu His Arg Thr Leu Asn Glu Pro Leu Asn Gln
225                 230                 235                 240

Leu Leu Asp Asp Ala Ala Gln Gln Phe Ala Gln Ala Val Gly Ser Ala
                245                 250                 255

Glu Gly Gln Glu Gly Thr Met Ala Phe Ile Gln Lys Arg Leu Pro Asn
                260                 265                 270

Trp Ala Asp Glu Thr
            275

<210> SEQ ID NO 87
<211> LENGTH: 264
<212> TYPE: PRT
<213> ORGANISM: Pseudomonas aeruginosa

<400> SEQUENCE: 87

Met Ser Leu Pro His Cys Glu Thr Leu Leu Glu Pro Ile Glu Gly
 1               5                  10                  15

Val Leu Arg Ile Thr Leu Asn Arg Pro Gln Ser Arg Asn Ala Met Ser
                20                  25                  30
```

```
Leu Ala Met Val Gly Glu Leu Arg Ala Val Leu Ala Ala Val Arg Asp
         35                  40                  45

Asp Arg Ser Val Arg Ala Leu Val Leu Arg Gly Ala Asp Gly His Phe
 50                  55                  60

Cys Ala Gly Gly Asp Ile Lys Asp Met Ala Gly Ala Arg Ala Ala Gly
 65                  70                  75                  80

Ala Glu Ala Tyr Arg Thr Leu Asn Arg Ala Phe Gly Ser Leu Leu Glu
                 85                  90                  95

Glu Ala Gln Ala Ala Pro Gln Leu Leu Val Ala Leu Val Glu Gly Ala
             100                 105                 110

Val Leu Gly Gly Gly Phe Gly Leu Ala Cys Val Ser Asp Val Ala Ile
             115                 120                 125

Ala Ala Ala Asp Ala Gln Phe Gly Leu Pro Glu Thr Ser Leu Gly Ile
130                 135                 140

Leu Pro Ala Gln Ile Ala Pro Phe Val Val Arg Ile Gly Leu Thr
145                 150                 155                 160

Gln Ala Arg Arg Leu Ala Leu Thr Ala Ala Arg Phe Asp Gly Arg Glu
                 165                 170                 175

Ala Leu Arg Leu Gly Leu Val His Phe Cys Glu Ala Asp Ala Asp Ala
             180                 185                 190

Leu Glu Gln Arg Leu Glu Glu Thr Leu Glu Gln Leu Arg Arg Cys Ala
             195                 200                 205

Pro Asn Ala Asn Ala Ala Thr Lys Ala Leu Leu Leu Ala Ser Glu Ser
210                 215                 220

Gly Glu Leu Gly Ala Leu Leu Asp Asp Ala Ala Arg Gln Phe Ala Glu
225                 230                 235                 240

Ala Val Gly Gly Ala Glu Gly Ser Glu Gly Thr Leu Ala Phe Val Gln
                 245                 250                 255

Lys Arg Lys Pro Val Trp Ala Gln
             260

<210> SEQ ID NO 88
<211> LENGTH: 273
<212> TYPE: PRT
<213> ORGANISM: Marinobacter santoriniensis

<400> SEQUENCE: 88

Met Glu Gln Leu Pro His Cys Glu Thr Leu Leu Leu Glu Lys His Gly
 1               5                  10                  15

Pro Ala Leu Phe Leu Thr Ile Asn Arg Pro Asp Val Arg Asn Ala Met
                 20                  25                  30

Ser Leu Gln Met Val Ala Glu Leu Ser Thr Ile Phe Asn Gln Ile Glu
             35                  40                  45

Gln Asp Asn Thr Ile Arg Ala Val Val Ile Arg Gly Lys Asp Gly His
 50                  55                  60

Phe Cys Ala Gly Gly Asp Ile Lys Asp Met Ala Gly Ala Arg Gly Gln
 65                  70                  75                  80

Lys Ala Asp Glu Gly Gln His Asp Pro Phe Tyr Lys Leu Asn Arg Ala
                 85                  90                  95

Phe Gly His Met Ile Gln Gln Val Asn Glu Ser Ser Lys Val Val Ile
             100                 105                 110

Ala Val Thr Glu Gly Ala Val Met Gly Gly Gly Phe Gly Leu Ala Cys
             115                 120                 125

Val Ser Asp Val Ala Ile Ala Gly Pro Thr Ala Arg Phe Gly Met Pro
130                 135                 140
```

Glu Thr Ser Leu Gly Val Ile Pro Ala Gln Ile Ala Pro Phe Val Val
145                 150                 155                 160

Glu Arg Ile Gly Leu Thr Gln Ala Arg Arg Leu Ala Leu Leu Gly Leu
                165                 170                 175

Arg Ile Asp Ala Arg Glu Ala Cys Ala Leu Gly Ile Val His Gln Ala
            180                 185                 190

Ala Asp Ser Glu Thr Gln Leu Glu Glu Leu Leu Gln Ala Thr Leu Glu
            195                 200                 205

Arg Val Arg Leu Cys Ala Pro Asn Ala Thr Ala Glu Thr Lys Ala Leu
210                 215                 220

Leu His Arg Val Gly His Glu Pro Met Asn Lys Leu Leu Asp Ser Ala
225                 230                 235                 240

Ala Glu Thr Phe Ala Glu Ala Ile Arg Gly Pro Glu Gly Ala Glu Gly
            245                 250                 255

Thr Met Ala Phe Met Gln Lys Arg Glu Pro Lys Trp Ala Asp Asp Ser
            260                 265                 270

Asn

<210> SEQ ID NO 89
<211> LENGTH: 265
<212> TYPE: PRT
<213> ORGANISM: Pseudomonas knackmussii

<400> SEQUENCE: 89

Met Ser Glu Leu Pro Asn Cys Glu Thr Leu Leu Glu Arg Asp Gly
1               5                   10                  15

Gly Val Leu His Val Thr Leu Asn Arg Pro Asp Ser Arg Asn Ala Met
                20                  25                  30

Ser Leu Ala Met Val Gly Glu Leu Arg Ala Val Leu Ala Ala Val Arg
            35                  40                  45

Asp Asp Arg Ala Val Arg Ala Ile Val Leu Arg Gly Ala Gly Gly His
        50                  55                  60

Phe Cys Ala Gly Gly Asp Ile Lys Asp Met Ala Gly Ala Arg Ala Ala
65                  70                  75                  80

Gly Thr Asp Ala Tyr Ala Lys Leu Asn Arg Ala Phe Gly Ser Leu Leu
                85                  90                  95

Glu Glu Ala Gln Ala Gln Pro Gln Val Leu Val Ala Val Leu Glu Gly
            100                 105                 110

Ala Val Leu Gly Gly Gly Phe Gly Leu Ala Cys Val Ser Asp Ile Ala
        115                 120                 125

Ile Ala Ala Asp Gly Ala Gln Phe Gly Leu Pro Glu Thr Thr Leu Gly
130                 135                 140

Ile Leu Pro Ala Gln Ile Ala Pro Phe Val Ala Lys Arg Val Gly Leu
145                 150                 155                 160

Thr Gln Ala Arg Arg Leu Ala Leu Thr Ala Ala Arg Phe Asp Gly Arg
                165                 170                 175

Glu Ala Leu Arg Leu Gly Leu Val His Phe Ser Glu Ala Asp Ala Asp
            180                 185                 190

Ala Leu Gly Gln Arg Leu Ala Asp Cys Leu Glu Gln Val Arg Arg Cys
        195                 200                 205

Ala Pro Gly Ala Asn Ala Ala Thr Lys Ala Leu Leu Leu Ala Thr Glu
    210                 215                 220

Arg Glu Glu Leu Gly Ser Leu Leu Asp Gly Ala Ala Arg Gln Phe Ala
225                 230                 235                 240

```
Glu Ala Val Thr Gly Ser Gly Ala Glu Gly Thr Met Ala Phe Val
            245                 250                 255

Gln Lys Arg Lys Pro Asn Trp Ala Gln
            260                 265

<210> SEQ ID NO 90
<211> LENGTH: 264
<212> TYPE: PRT
<213> ORGANISM: Pseudomonas pseudoalcaligenes

<400> SEQUENCE: 90

Met Glu Leu Pro Lys Thr Glu Thr Leu Leu Glu His Ala Asp Gly
1               5                   10                  15

Leu Leu Arg Ile Thr Leu Asn Arg Pro Glu Ser Arg Asn Ala Met Ser
            20                  25                  30

Leu Ala Met Val Glu Glu Leu Arg Ala Val Leu Ala Ala Ala Arg Arg
        35                  40                  45

Ala Pro Glu Val Arg Val Leu Ala Leu Arg Gly Ala Gly Gly His Phe
    50                  55                  60

Cys Ala Gly Gly Asp Ile Lys Asp Met Ala Ser Ala Arg Ala Thr Gly
65                  70                  75                  80

Gly Glu Ala Tyr Gln Arg Leu Asn Arg Ala Phe Gly Arg Leu Leu Glu
                85                  90                  95

Glu Ala Gln Ala Gln Pro Gln Val Val Ile Ala Val Leu Glu Gly Ala
            100                 105                 110

Val Leu Gly Gly Gly Phe Gly Leu Ala Cys Val Ser Asp Ile Ala Leu
        115                 120                 125

Ala Ala Glu Ser Ala Gln Phe Gly Leu Pro Glu Thr Ser Leu Gly Ile
    130                 135                 140

Leu Pro Ala Gln Ile Ala Pro Phe Val Val Lys Arg Val Gly Leu Thr
145                 150                 155                 160

Gln Ala Arg Arg Leu Ala Leu Thr Ala Ala Arg Phe Asp Gly Thr Glu
                165                 170                 175

Ala Leu Arg Leu Gly Leu Val His Phe Thr Glu Ala Asp Asp Ala Ala
            180                 185                 190

Leu Asp Ala Arg Leu Ala Ala Thr Leu Asp Gln Val Arg Arg Cys Ala
        195                 200                 205

Pro Gly Ala Asn Ala Arg Thr Lys Ala Leu Leu Ala Thr Glu Glu
    210                 215                 220

Arg Glu Leu Gly Pro Leu Leu Asp Asp Ala Ala Ala Trp Phe Ala Glu
225                 230                 235                 240

Ala Val Thr Ser Ala Glu Gly Thr Glu Gly Thr Leu Ala Phe Val Gln
                245                 250                 255

Lys Arg Lys Pro Thr Trp Ala Gln
            260

<210> SEQ ID NO 91
<211> LENGTH: 264
<212> TYPE: PRT
<213> ORGANISM: Pseudomonas flexibilis

<400> SEQUENCE: 91

Met Ala Asp Leu Pro His Cys Asp Thr Leu Leu Leu Asn Leu Asp Ala
1               5                   10                  15

Gly Val Leu His Ile Thr Leu Asn Arg Pro Asp Ser Arg Asn Ala Met
            20                  25                  30
```

Ser Leu Ala Met Val His Glu Leu Arg Ala Val Leu Glu Ser Val Arg
        35                  40                  45

Asn Asp Pro Ala Val Arg Ala Leu Val Leu Arg Gly Ala Gly Gly His
 50                  55                  60

Phe Cys Ala Gly Gly Asp Ile Lys Asp Met Ala Gly Ala Arg Ala Lys
 65                  70                  75                  80

Gly His Asp Ala Tyr Arg Asp Leu Asn Arg Ala Phe Gly Ala Leu Leu
                85                  90                  95

Glu Glu Ala Gln Ala Ala Pro Gln Val Val Ala Val Leu Glu Gly
            100                 105                 110

Ala Val Leu Gly Gly Phe Gly Leu Ala Cys Val Ser Asp Ile Ala
            115                 120                 125

Ile Ala Ala Glu Gly Cys Lys Phe Gly Leu Pro Glu Thr Thr Leu Gly
145                 150                 155                 160

Ile Leu Pro Ala Gln Ile Ala Pro Phe Val Val Lys Arg Val Gly Leu
145                 150                 155                 160

Thr Gln Ala Arg Arg Leu Ala Leu Thr Ala Ala Arg Phe Asp Gly Ala
                165                 170                 175

Glu Ala Leu Arg Leu Gly Leu Val His Tyr Cys Glu Ala Ala Asp Arg
            180                 185                 190

Leu Asp Ser Arg Leu Ala Glu Val Ile Gln Val Arg Gln Cys Ala
            195                 200                 205

Pro Gln Ala Asn Ala Gln Thr Lys Ala Leu Leu Ala Ser Glu Thr
210                 215                 220

Glu Ala Met Asn Ser Leu Leu Asp Arg Ala Ala Glu Gln Phe Ala Ala
225                 230                 235                 240

Ala Val Thr Gly Ala Glu Gly Val Glu Gly Thr Met Ala Phe Val Gln
                245                 250                 255

Lys Arg Ala Pro Lys Trp Ala Gln
                260

<210> SEQ ID NO 92
<211> LENGTH: 271
<212> TYPE: PRT
<213> ORGANISM: Alcanivorax dieselolei

<400> SEQUENCE: 92

Met Thr Leu Pro Glu Thr Glu Thr Ile Thr Leu His Arg Asp Gly Thr
 1               5                  10                  15

Thr Leu Ser Val Thr Leu Asn Arg Pro Gln Ser Arg Asn Ala Met Ser
                20                  25                  30

Leu Ile Met Val Asp Glu Leu Met Ala Val Phe Asp Trp Val Glu Ala
            35                  40                  45

Asn Pro Asp Val Arg Ala Val Val Leu Arg Gly Ala Gly Gly His Phe
 50                  55                  60

Cys Ala Gly Gly Asp Ile Lys Asp Met Ala Gly Ala Arg Gln Gln Ala
 65                  70                  75                  80

Ala Ala Gly Asp Asp Gln Ala Phe Phe Thr Leu Asn Arg Arg Phe Gly
                85                  90                  95

Ala Met Val Ser Arg Ala Glu Arg Leu Pro Ala Val Leu Val Cys Val
            100                 105                 110

Leu Glu Gly Ala Val Leu Gly Gly Gly Phe Gly Leu Ala Cys Val Ser
            115                 120                 125

Asp Val Ala Leu Ala Ala Gly Asp Ala Arg Phe Gly Leu Pro Glu Thr

```
            130                 135                 140
Gly Leu Gly Val Ile Pro Ala Gln Ile Ala Pro Phe Val Arg Arg
145                 150                 155                 160

Ile Gly Leu Thr Gln Ala Arg Arg Leu Ala Leu Thr Gly Gly Arg Phe
                165                 170                 175

Asp Gly His Gly Ala Gln Ala Leu Gly Val Val His Glu Val Ala Asp
                180                 185                 190

Ser Thr Glu Glu Leu Glu Gln Arg Leu Arg Gln Val Leu Glu Gln Ile
                195                 200                 205

Arg Arg Cys Ala Pro His Ala Asn Arg Val Thr Lys Gln Leu Val Leu
            210                 215                 220

Ser Val Asp Glu Gln Pro Leu Asp Ala Val Leu Asp Gln Ala Ala Arg
225                 230                 235                 240

Asp Phe Ala Asn Ala Val Thr Ser Glu Glu Gly Gln Glu Gly Thr Leu
                245                 250                 255

Ala Phe Val Gln Lys Arg Ala Pro Ser Trp Ser Thr Asp Lys Glu
                260                 265                 270

<210> SEQ ID NO 93
<211> LENGTH: 3343
<212> TYPE: DNA
<213> ORGANISM: Artificial Sequence
<220> FEATURE:
<223> OTHER INFORMATION: Plasmid name pGB 5796

<400> SEQUENCE: 93
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttgcggcc gcggggttaa     420
ttaatttctc ctcttttaata aagcaaataa atttttatg atttgtttaa acctaggcat     480
gcctctagat tattatgcgc cctgccagcg ggcaaagaga tcttcaggaa gggttatcgc     540
aaactggtca agaacacgat taaccgtctg atttatcaca tcatcaaggg attgcgggcg     600
atgataaaac gccggaacgg gaggcataat caccgcaccg atttctgccg cctgagtcat     660
taaacgcaga tggcctaagt gcaatggtgt tcacgcacg cagagcacca acgggcgacg     720
ctctttcagc accacatctg ccgcacgggt cagtaagcca tcagtatagc tatggacaat     780
gccggaaagg gttttgattg aacagggtaa aatcaccatc cccagcgtct ggaaagaacc     840
ggaagagatg ctggcggcaa tatcgcgcgc atcgtgcgtg acatcggcta atgcctgcac     900
ttcgcgcaga gaaaaatccg tttcgaggga taaggtctgg cgcgctgcct ggctcatcac     960
cagatgcgtt tcgatatctg tgacatcgcg cagaacctgt aataagcgca cgccataaat    1020
cgcgccgctg gcaccgctga tgcctacaat gagtcgtttc ataaaaaaaa tgtatatctc    1080
cttcggtacc gagctcgaac ctgcaggaat tcgtaatcat ggtcatagct gtttcctgtg    1140
tgaaattgtt atccgctcac aattccacac aacatacgag ccggaagcat aaagtgtaaa    1200
gcctggggt cctaatgagt gagctaactc acattaattg cgttgcgctc actgcccgct    1260
ttccagtcgg gaaacctgtc gtgccagctg cattaatgaa tcggccaacg cgcggggaga    1320
```

-continued

```
ggcggtttgc gtattgggcg ctcttccgct tcctcgctca ctgactcgct gcgctcggtc    1380
gttcggctgc ggcgagcggt atcagctcac tcaaaggcgg taatacggtt atccacagaa    1440 tcagggqata acgcaggaaa gaacatgtga gcaaaaggcc agcaaaaggc caggaaccgt    1500
aaaaaggccg cgttgctggc gttttttccat aggctccgcc cccctgacga gcatcacaaa    1560
aatcgacgct caagtcagag gtggcgaaac ccgacaggac tataaagata ccaggcgttt    1620
ccccctggaa gctccctcgt gcgctctcct gttccgaccc tgccgcttac cggatacctg    1680
tccgcctttc tcccttcggg aagcgtggcg ctttctcata gctcacgctg taggtatctc    1740
agttcggtgt aggtcgttcg ctccaagctg ggctgtgtgc acgaaccccc cgttcagccc    1800
gaccgctgcg ccttatccgg taactatcgt cttgagtcca acccggtaag acgacttta    1860 tcgccactgg cagcagccac tggtaacagg attagcagag cgaggtatgt aggcggtgct    1920
acagagttct tgaagtggtg gcctaactac ggctacacta aaggacagt atttggtatc    1980 tgcgctctgc tgaagccagt taccttcgga aaaagagttg gtagctcttg atccggcaaa    2040
caaaccaccg ctggtagcgg tggttttttt gtttgcaagc agcagattac gcgcagaaaa    2100
aaaggatctc aagaagatcc tttgatcttt tctacggggt ctgacgctca gtggaacgaa    2160
aactcacgtt aagggatttt ggtcatgaga ttatcaaaaa ggatcttcac ctagatcctt    2220
ttaaattaaa aatgaagttt taaatcaatc taaagtatat atgagtaaac ttggtctgac    2280
agttaccaat gcttaatcag tgaggcacct atctcagcga tctgtctatt tcgttcatcc    2340
atagttgcct gactccccgt cgtgtagata actacgatac gggagggctt accatctggc    2400
cccagtgctg caatgatacc gcgagaccca cgctcaccgg ctccagattt atcagcaata    2460
aaccagccag ccggaagggc cgagcgcaga agtggtcctg caactttatc cgcctccatc    2520
cagtctatta attgttgccg ggaagctaga gtaagtagtt cgccagttaa tagtttgcgc    2580
aacgttgttg ccattgctac aggcatcgtg gtgtcacgct cgtcgtttgg tatggcttca    2640
ttcagctccg gttcccaacg atcaaggcga gttacatgat cccccatgtt gtgcaaaaaa    2700
gcggttagct ccttcggtcc tccgatcgtt gtcagaagta agttggccgc agtgttatca    2760
ctcatggtta tggcagcact gcataattct cttactgtca tgccatccgt aagatgcttt    2820
tctgtgactg gtgagtactc aaccaagtca ttctgagaat agtgtatgcg gcgaccgagt    2880
tgctcttgcc cggcgtcaat acgggataat accgcgccac atagcagaac tttaaaagtg    2940
ctcatcattg gaaaacgttc ttcggggcga aaactctcaa ggatcttacc gctgttgaga    3000
tccagttcga tgtaacccac tcgtgcaccc aactgatctt cagcatcttt tactttcacc    3060
agcgtttctg ggtgagcaaa aacaggaagg caaaatgccg caaaaaaggg aataagggcg    3120
acacggaaat gttgaatact catactcttc ctttttcaat attattgaag catttatcag    3180
ggttattgtc tcatgagcgg atacatattt gaatgtattt agaaaaataa acaaataggg    3240
gttccgcgca catttccccg aaaagtgcca cctgacgtct aagaaaccat tattatcatg    3300
acattaacct ataaaaatag gcgtatcacg aggccctttc gtc                      3343
```

<210> SEQ ID NO 94
<211> LENGTH: 12214
<212> TYPE: DNA
<213> ORGANISM: Artificial Sequence
<220> FEATURE:
<223> OTHER INFORMATION: Plasmid name pGB 5771

<400> SEQUENCE: 94

```
ctcactactt tagtcagttc cgcagtatta caaaaggatg tcgcaaacgc tgtttgctcc      60
tctacaaaac agaccttaaa accctaaagg cttaagtagc accctcgcaa gctcgggcaa     120
atcgctgaat attccttttg tctccgacca tcaggcacct gagtcgctgt cttttcgtg      180
acattcagtt cgctgcgctc acggctctgg cagtgaatgg gggtaaatgg cactacaggc     240
gccttttatg gattcatgca aggaaactac ccataataca agaaaagccc gtcacgcttc     300
tcagggcgtt ttatggcggg tctgctatgt ggtgctatct gacttttgc tgttcagcag      360
ttcctgccct ctgattttcc agtctgaccc tagtcaaggc cttaagtgag tcgtattacg     420
gactggccgt cgttttacaa cgtcgtgact gggaaaaccc tggcgttacc caacttaatc     480
gccttgcagc acatccccct tcgccagct ggcgtaatag cgaagaggcc cgcaccgatc      540
gcccttccca acagttgcgc agcctgaatg gcgaatggcg cctgatgcgg tattttctcc     600
ttacgcatct gtgcggtatt tcacaccgcc cggggaacta gtttaaac ttttcaatga      660
attcatttaa gcggccgcat caattctaga atttaaatag tcaaaagcct ccgaccggag     720
gcttttgact gacctattga caattaaagg ctaaaatgct ataattccac taatagaaat     780
aattttgttt aacttaggt ctctatcgta agaaggagat atatgaaaga agtggtgatt      840
gccagcgcag ttcgtaccgc aattggtagc tatggtaaaa gcctgaaaga tgttccggca     900
gttgatctgg gtgcaaccgc aattaaagaa gcagttaaaa aagccggtat aaaccggaa      960
gatgtgaacg aagttattct gggtaatgtt ctgcaagcag gtctgggtca gaatccggca    1020
cgtcaggcct cgtttaaagc aggtctgccg gttgaaattc cggcaatgac cattaacaaa    1080
gtttgtggta gcggtctgcg taccgttagc ctggcagcac agattatcaa gccggtgat    1140
gcagatgtta ttattgccgg tggtatggaa aatatgagcc gtgcaccgta tctggcaaat    1200
aatgcacgtt ggggttatcg tatgggtaat gccaaatttg tggatgagat gattaccgat    1260
ggtctgtggg atgccttta tgattatcac atgggtatta ccgcagagaa tattgcagaa    1320
cgttggaata ttagccgtga agaacaggat gaatttgcac tggcaagcca gaaaaagca    1380
gaagaagcaa ttaaaagcgg tcagttcaaa gatgaaattg tgccggttgt tatcaaaggt    1440
cgtaaaggtg aaaccgttgt tgataccgat gaacatccgc gttttggtag caccattgaa    1500
ggtctggcaa aactgaaacc ggcattcaaa aaagatggca ccgttaccgc aggtaatgca    1560
agcggtctga atgattgtgc agcagttctg gttattatga cgcagaaaaa agcaaaagaa    1620
ctgggtgtta accgctggc aaaaattgtg agctatggta gtgccggtgt tgatccggca    1680
attatgggtt atggtccgtt ttatgcaacc aaagcagcaa ttgaaaaagc aggttggacc    1740
gttgatgaac tggatctgat tgaaagcaat gaagcatttg cagcacagag cctggcagtt    1800
gcaaaagacc tgaaattcga tatgaataaa gtgaatgtga atggcggtgc aattgccctg    1860
ggtcatccga ttggtgcaag cggtgcacgt attctggtta ccctggttca tgcaatgcag    1920
aaacgtgatg caaaaaaagg tctggccacc ctgtgtattg tggtggtcaa gggcaccgca    1980
attctgctgg aaaaatgcta ataagcttga aggagatata atgaccattg gtattgataa    2040
aatcagcttt ttcgtgcctc cgtactatat tgatatgacc gcactggccg aagcacgtaa    2100
tgttgatccg ggtaaatttc atattggtat tggtcaggat cagatggccg ttaatccgat    2160
tagccaggat attgttacct tgcagcaaa tgcagcagaa gcaattctga ccaaagaaga    2220
taaagaggcc attgatatgg ttattgttgg caccgaaagc agcattgatg aaagcaaagc    2280
agcagcagtt gttctgcatc gtctgatggg tattcagccg tttgcacgta gctttgaaat    2340
taaagaagca tgttacggag caaccgcagg tctgcaactg gcaaaaaatc atgttgcact    2400
```

```
gcatccggat aaaaaagttc tggttgttgc agcagatatt gccaaatatg gtctgaatag   2460
cggtggtgaa ccgacccagg gtgccggtgc agttgcaatg ctggttgcaa gcgaaccgcg   2520
tattctggca ctgaaagaag ataatgttat gctgacccag gatatttatg attttttggcg  2580 tccgaccggt catccgtatc cgatggttga tggtccgctg agcaatgaaa cctatattca   2640
gagctttgca caggtgtggg atgaacataa aaaacgtacc ggtctggatt cgcagatta    2700 tgatgcactg gcatttcata tcccgtatac caaaatgggt aaaaaagcac tgctggccaa   2760
aattagcgat cagaccgaag ccgaacaaga acgcattctg gcacgttatg aagaaagcat   2820
tgtttatagc cgtcgtgtgg gtaatctgta taccggtagc ctgtatctgg gtctgattag   2880
cctgctggaa aatgcaacca ccctgaccgc aggtaatcag attggtctgt ttagctatgg   2940
tagcggtgcc gttgcagaat ttttcacagg tgaactggtt gcaggttatc agaatcatct   3000
gcaaaaagaa acccatctgg cactgctgga taatcgtacc gaactgagca ttgcagaata   3060
tgaagcaatg tttgcagaaa ccctggatac cgatattgat cagaccctgg aagatgaact   3120
gaaatatagc attagcgcca ttaataacac cgtgcgtagc tatcgtaact aataaggtag   3180
aaggagatat acatatgagt caggcgctaa aaaatttact gacattgtta aatctggaaa   3240
aaattgagga aggactcttt cgcggccaga gtgaagattt aggtttacgc caggtgtttg   3300
gcggccaggt cgtgggtcag gccttgtatg ctgcaaaaga gacggtccct gaagaacggc   3360
tggtacattc gtttcacagc tactttcttc gccctggcga tagtaagaag ccgattattt   3420
atgatgtcga aacgctgcgt gacggtaaca gcttcagcgc ccgccgggtt gctgctattc   3480
aaaacggcaa accgattttt tatatgactg cctctttcca ggcaccagaa gcgggtttcg   3540
aacatcaaaa aacaatgccg tccgcgccag cgcctgatgg cctcccttcg gaaacgcaaa   3600
tcgcccaatc gctggcgcac ctgctgccgc cagtgctgaa agataaattc atctgcgatc   3660
gtccgctgga gtccgtccg gtggagtttc ataaccccact gaaaggtcac gtcgcagaac   3720
cacatcgtca ggtgtggatt cgcgcaaatg gtagcgtgcc ggatgacctg cgcgttcatc   3780
agtatctgct cggttacgct tctgatctta cttcctgcc ggtagctcta cagccgcacg   3840
gcatcggttt tctcgaaccg gggattcaga ttgccaccat tgaccattcc atgtggttcc   3900
atcgcccgtt taatttgaat gaatggctgc tgtatagcgt ggagagcacc tcggcgtcca   3960
gcgcacgtgg ctttgtgcgc ggtgagtttt atacccaaga cggcgtactg gttgcctcga   4020
ccgttcagga agggggtgatg cgtaatcaca attaataaga acgaaggaga tataatgaaa   4080
accgcacgtt ggtgtagcct ggaagaagca gttgcaagca ttccggatgg tgcaagcctg   4140
gcaaccggtg gttttatgct gggtcgtgca ccgatggcac tggttatgga actgattgca   4200
cagggtaaac gtgatctggg tctgattagc ctgccgaatc cgctgccagc agaatttctg   4260
gttgccggtg gttgtctggc tcgtctggaa attgcatttg gtgcactgag tctgcaaggt   4320
cgtgttcgtc cgatgccgtg tctgaaacgt gcaatggaac agggcaccct ggcatggcgt   4380
gaacatgatg gttatcgtgt tgttcagcgt ctgcgtgcag caagcatggg tctgccgttt   4440
attccggcac cggatgcaga tgttagcggt ctggcacgta ccgaaccgcc tccgaccgtt   4500
gaagatccgt ttaccggtct gcgtgttgca gttgaaccgg catttatcc ggatgttgca   4560 ctgctgcacg cacgtgcagc cgatgaacgt ggtaatctgt atatggaaga tccgaccacc   4620
gatctgctgg ttgcgggtgc agcaaaaacg ttattgcaa ccgttgaaga acgtgttgca   4680
aaactgcctc gtgcaacccct gcctggtttt caggttgatc gtattgttct ggcaccgggt   4740
```

```
ggtgcactgc cgaccggttg tgcaggtctg tatccgcatg atgatgaaat gctggcacgt    4800
tatctgagcc tggcagaaac cggtcgtgaa gccgaatttc tggaaaccct gctgacccgt    4860
cgtgcagcat aatgaggatc cgaaggagat atacatatga gcgcaaccct ggatattaca    4920
ccggcagaaa ccgttgttag cctgctggca cgtcagattg atgatggtgg tgttgttgca    4980
accggtgttg caagtccgct ggcaattctg gccattgcag ttgcacgtgc cacccatgca    5040
ccggatctga cctatctggc atgtgttggt agcctggacc cggaaattcc gaccctgctg    5100
ccgagcagcg aagacctggg ttatctggat ggtcgtagcg cagaaattac cattccggac    5160
ctgtttgatc atgcacgtcg tggtcgtgtt gataccgttt tttttggtgc agccgaagtt    5220
gatgccgaag gtcgtaccaa tatgaccgca agcggtagtc tggataaacc gcgtaccaaa    5280
tttccgggtg ttgccggtgc agccaccctg cgtcagtggg ttcgtcgtcc ggttctgctg    5340
gttccgcgtc agagccgtcg taatctggtt ccggaagttc aggttgcaac cacccgtgat    5400
ccgcgtcgtc cggtgaccct gattagcgat ctgggtgttt ttgaactggg tgcaagcggt    5460
gcacgtctgc tggcacgcca tccgtgggca agcgaagaac atattgcaga acgtaccggt    5520
tttgcatttc aggttagcga agcactgagc gttaccagcc tgccggatgc acgtaccgtt    5580
gcagcaattc gtgcaattga tccgcatggc tatcgtgatg cactggttgg tgcataatta    5640
gtcagaagga gatatacata tgagcctgcc gcattgtgaa accctgctgc tggaaccgat    5700
tgaaggtgtt ctgcgtatta ccctgaatcg tccgcagagc cgtaatgcaa tgagcctggc    5760
aatggttggt gaactgcgtg cagttctggc agcagttcgt gatgatcgta gcgttcgtgc    5820
actggttctg cgtggtgcag atggtcattt ttgtgccggt ggtgatatta agatatggc     5880 aggcgcacgt gcagccggtg cagaagcata tcgtacactg aatcgtgcat tggtagccct    5940
gctggaagaa gcacaggcag caccgcagct gctggttgca ctggttgaag gtgccgttct    6000
gggtggtggt tttggtctgg catgtgttag tgatgttgca attgcagcag cagatgcaca    6060
gtttggtctg ccggaaacca gcctgggtat tctgcctgca cagattgcac gtttgttgt     6120 tcgtcgtatt ggtctgaccc aggcacgtcg tctggcactg accgcagcac gttttgatgg    6180
tcgtgaagca ctgcgtctgg gtctggttca tttttgtgaa gcagatgcag atgcactgga    6240
acagcgtctg gaagaaaccc tggaacagct gcgtcgttgt gcaccgaatg caaatgcagc    6300
aaccaaagca ctgctgctgg caagcgaaag cggtgaactg ggtgcactgc tggatgatgc    6360
agcacgtcag tttgccgaag cagttggtgg tgcagaaggt agcgaaggca ccctggcatt    6420
tgttcagaaa cgtaaaccgg tttgggcaca gtaataatga aagagaccag cctgatacag    6480
attaaatcag aacgcagaag cggtctgata aaacagaatt tgcctggcgg cagtagcgcg    6540
gtggtcccac ctgaccccat gccgaactca gaagtgaaac gccgtagcgc cgatggtagt    6600
gtggggtcac cccatgcgag agtagggaac tgccaggcat caaataaaac gaaaggctca    6660
gtcgaaagac tgggcctttc gttttatctg ttgtttgtcg gtgaactact agaatttaaa    6720
tagtcaaaag cctccgaccg gaggcttttg actgacctat tgacaattaa aggctaaaat    6780
gctataattc cactaataga ataattttg tttaacttta ggtctctatc gaccataatt     6840
aattaacttt aagaaggaga tatacatatg agcagcacca cctataaaag cgaagcattt    6900
gatccggaac cgcctcatct gagctttcgt agctttgttg aagcactgcg tcaggataat    6960
gatctggtgg atattaatga accggttgat ccggatctgg aagcagcagc aattacccgt    7020
ctggtttgtg aaaccgatga taagcaccg ctgtttaata cgtgattgg tgcaaaagat      7080 ggtctgtggc gtattctggg tgcaccggca agcctgcgta gcagcccgaa agaacgtttt    7140
```

```
ggtcgtctgg cacgtcatct ggcactgcct ccgaccgcaa gcgcaaaaga tattctggat   7200
aaaatgctga gcgccaatag cattccgcct attgaaccgg ttattgttcc gaccggtccg   7260
gttaaagaaa atagcattga aggcgaaaac attgatctgg aagccctgcc tgcaccgatg   7320
gttcatcaga gtgatggtgg caagtatatc cagacctatg gtatgcatgt tatccagagt   7380
ccggatggtt gttggaccaa ttggagcatt gcccgtgcaa tggttagcgg taaacgtacc   7440
ctggcaggtc tggttattag tccgcagcat attcgtaaaa ttcaggatca gtggcgtgca   7500
attggtcaag aagaaattcc ttgggcactg gcatttggtg ttccgcctac cgcaattatg   7560
gcaagcagta tgccgattcc ggatggtgtt agcgaagcag gttatgttgg tgcaattgcc   7620
ggtgaaccga ttaaactggt taaatgcgat accaacaatc tgtatgttcc ggcaaatagc   7680
gaaattgttc tggaaggcac cctgagcacc accaaaatgg caccggaagg tccgtttggt   7740
gaaatgcatg gttatgttta tccgggtgaa agccatccgg gtccggttta taccgttaac   7800
aaaattacct atcgcaacaa tgcaattctg ccgatgagcg catgtggtcg tctgaccgat   7860
gaaacccaga ccatgattgg caccctggca gcagcagaaa ttcgtcagct gtgtcaggat   7920
gcaggtctgc cgattaccga tgcatttgca ccgtttgttg gtcaggcaac ctgggttgca   7980
ctgaaagttg ataccaaacg tctgcgtgca atgaaaacca atggtaaagc atttgcaaaa   8040
cgtgttggtg atgttgtgtt tacccagaaa ccgggtttta ccattcatcg tctgattctg   8100
gttggtgatg atattgatgt gtatgacgat aaagatgtga tgtgggcatt taccacccgt   8160
tgtcgtccgg gtacagatga agttttttttt gatgatgttg tgggcttttca gctgatcccg   8220 tatatgagtc atggtaatgc cgaagcaatt aaaggtggta agttgttag tgatgcactg   8280 ctgaccgcag aatataccac cggtaaagat tgggaaagcg cagatttcaa aaacagctat   8340
ccgaaaagca tccaggataa agttctgaat agctgggaac gcctgggttt caaaaaactg   8400
gattaataac catggttata agagagacca gcctgactcc tgttgataga tccagtaatg   8460
acctcagaac tccatctgga tttgttcaga acgctcggtt gccgccgggc gttttttatt   8520
ggtgagaata actactagtt ggcgggcggc cgcttagctc tgcagatgag aaattcttga   8580
agacgaaagg gcctcgtgat acgcctattt ttataggtta atgtcatgat aataatggtt   8640
taagcttctt agaatagctc ttctatgagg tggcactttt cggggaaaga tatccgcata   8700
tatggtgcac tctcagtaca atctgctctg atgccgcata gttaagccag tatacactcc   8760
gctatcgcta cgtgactggg tcatggctgc gccccgacac ccgccaacac ccgctgacgc   8820
gccctgacgg gcttgtctgc tcccggcatc cgcttacaga caagctgtga ccgtctccgg   8880
gagctgcatg tgtcagaggt tttcaccgtc atcaccgaaa cgcgcgaggc agctgcggta   8940
aagctcatca gcgtggtcgt gaagcgattc acagatgtct gcctgttcat cggtacccttt   9000 catgatatat ctcccaattt gtgtagggct tattatgcac gcttaaaaat aataaaagca   9060
gacttgacct gatagtttgg ctgtgagcaa ttatgtgctt agtgcatcta acgcttgagt   9120
taagccgcgc cgcgaagcgg cgtcggcttg aacgaattgt tagacattat ttgccgacta   9180
ccttggtgat ctcgcctttc acgtagtgga caaattcttc caactgatct gcgcgcgagg   9240
ccaagcgatc ttcttcttgt ccaagataag cctgtctagc ttcaagtatg acgggctgat   9300
actgggccgg caggcgctcc attgcccagt cggcagcgac atccttcggc gcgattttgc   9360
cggttactgc gctgtaccaa atgcgggaca acgtaagcac tacatttcgc tcatcgccag   9420
cccagtcggg cggcgagttc catagcgtta aggtttcatt tagcgcctca aatagatcct   9480
```

```
gttcaggaac cggatcaaag agttcctccg ccgctggacc taccaaggca acgctatgtt   9540
ctcttgcttt tgtcagcaag atagccagat caatgtcgat cgtggctggc tcgaagatac   9600
ctgcaagaat gtcattgcgc tgccattctc caaattgcag ttcgcgctta gctggataac   9660
gccacggaat gatgtcgtcg tgcacaacaa tggtgacttc tacagcgcgg agaatctcgc   9720
tctctccagg ggaagccgaa gtttccaaaa ggtcgttgat caaagctcgc cgcgttgttt   9780
catcaagcct tacggtcacc gtaaccagca aatcaatatc actgtgtggc ttcaggccgc   9840
catccactgc ggagccgtac aaatgtacgg ccagcaacgt cggttcgaga tggcgctcga   9900
tgacgccaac tacctctgat agttgagtcg atacttcggc gatcaccgct tccctcatga   9960
tgtttaactt tgttttaggg cgactgccct gctgcgtaac atcgttgctg ctccataaca  10020
tcaaacatcg acccacggcg taacgcgctt gctgcttgga tgcccgaggc atagactgta  10080
ccccaaaaaa acagtcataa caagccatga aaaccgccac gagctcctgt cagaccaagt  10140
ttacgagctc gcttggactc ctgttgatag atccagtaat gacctcagaa ctccatctgg  10200
atttgttcag aacgctcggt tgccgccggg cgttttttat tggtgagaat ccaagcacta  10260
gggacagtaa gacgggtaag cctgttgatg ataccgctgc cttactgggt gcattagcca  10320
gtctgaatga cctgtcacgg gataatccga agtggtcaga ctggaaaatc agagggcagg  10380
aactgctgaa cagcaaaaag tcagatagca ccacatagca gacccgccat aaaacgccct  10440
gagaagcccg tgacgggctt ttcttgtatt atgggtagtt ccttgcatg aatccataaa  10500
aggcgcctgt agtgccattt accccattc actgccagag ccgtgagcgc agcgaactga  10560
atgtcacgaa aaagacagcg actcaggtgc ctgatggtcg agagacaaaag gaatattcag  10620
cgatttgccc gagcttgcga gggtgctact taagccttta gggttttaag gtctgttttg  10680
tagaggagca acagcgtttt gcgacatcct tttgtaatac tgcggaactg actaaagtag  10740
tgagttatac acagggctgg gatctattct tttatctttt ttttattctt tctttattct  10800
ataaattata accacttgaa tataaacaaa aaaaacacac aaaggtctag cggaatttac  10860
agagggtcta gcagaattta caagtttttcc agcaaaggtc tagcagaatt tacagatacc  10920
cacaactcaa aggaaaagga catgtaatta tcattgacta gcccatctca attggtatag  10980
tgattaaaat cacctagacc aattgagatg tatgtctgaa ttagttgttt tcaaagcaaa  11040
tgaactagcg attagtcgct atgacttaac ggagcatgaa accaagctaa ttttatgctg  11100
tgtggcacta ctcaaccccca cgattgaaaa ccctacaagg aaagaacgga cggtatcgtt  11160
cacttataac caatacgctc agatgatgaa catcagtagg gaaatgctt atggtgtatt  11220
agctaaagca accagagagc tgatgacgag aactgtggaa atcaggaatc ctttggttaa  11280
aggctttgag attttccagt ggacaaacta tgccaagttc tcaagcgaaa aattagaatt  11340
agttttttagt gaagagatat tgccttatct tttccagtta aaaaaattca taaaatataa  11400
tctggaacat gttaagtctt ttgaaaacaa atactctatg aggatttatg agtggttatt  11460
aaaagaacta acacaaaaga aaactcacaa ggcaaatata gagattagcc ttgatgaatt  11520
taagttcatg ttaatgcttg aaaataacta ccatgagttt aaaaggctta accaatgggt  11580
tttgaaacca ataagtaaag atttaaacac ttacagcaat atgaaattgg tggttgataa  11640
gcgaggccgc ccgactgata cgttgatttt ccaagttgaa ctagatagac aaatggatct  11700
cgtaaccgaa cttgagaaca accagataaa aatgaatggt gacaaaatac caacaaccat  11760
tacatcgat tcctacctac gtaacggact aagaaaaaca ctacacgatg ctttaactgc  11820
aaaaattcag ctcaccagtt ttgaggcaaa atttttgagt gacatgcaaa gtaagcatga  11880
```

```
tctcaatggt tcgttctcat ggctcacgca aaaacaacga accacactag agaacatact   11940
ggctaaatac ggaaggatct gaggttctta tggctcttgt atctatcagt gaagcatcaa   12000
gactaacaaa caaagtaga acaactgttc accgttagat atcaaaggga aaactgtcca    12060
taagcacaga tgaaacggt gtaaaaaga tagatacatc agagcttta cgagtttttg      12120 gtgcatttaa agctgttcac catgaacaga tcgacaatgt aacgcatgca ccgagcgcag   12180
cgagtcagtg agcgaggaag cggaacagcg cctg                               12214
```

<210> SEQ ID NO 95
<211> LENGTH: 274
<212> TYPE: PRT
<213> ORGANISM: Ustilago maydis

<400> SEQUENCE: 95

```
Met Thr Ala Ser Ala Leu Ala Tyr Leu Glu Pro Asp Ser Ser Ala Glu
1               5                   10                  15

Leu Thr Gly Val Tyr His Leu Val Leu Asp Arg Pro Glu Ala Arg Asn
            20                  25                  30

Ala Ile Ser Arg Ser Leu Leu Gln Asp Val Leu Gln Cys Leu Gln Val
        35                  40                  45

Leu Val Cys Lys Ile Thr Gln Pro Lys Gln Asp Glu Pro Leu Pro Arg
    50                  55                  60

Val Leu Ile Leu Arg Ala Asn Gly Pro Cys Phe Cys Ala Gly Ala Asp
65                  70                  75                  80

Leu Lys Glu Arg Arg Glu Met Ser Glu Ala Glu Val Ile Glu Phe Leu
                85                  90                  95

Gln Asp Leu Arg His Met Leu Glu Gln Val Glu Lys Leu Pro Ile Pro
            100                 105                 110

Thr Leu Ala Ala Ile Asp Gly Pro Ala Leu Gly Gly Gly Leu Glu Leu
        115                 120                 125

Ala Leu Ala Cys Asp Phe Arg Ile Ala Ala Glu Thr Val Ser Lys Ile
    130                 135                 140

Gly Phe Pro Glu Val Lys Leu Gly Ile Ile Pro Gly Ala Gly Gly Thr
145                 150                 155                 160

Gln Arg Ala Pro Arg Ile Ile Gly Met Gln Arg Ala Lys Glu Leu Ile
                165                 170                 175

Tyr Thr Gly Thr Gln Leu Asn Ala Thr Gln Ala Lys Asp Leu Gly Leu
            180                 185                 190

Ile Asp His Val Ala Pro Gly Ser Thr Cys Leu Lys Leu Cys Gln Glu
        195                 200                 205

Leu Ala Gln Gln Met Met Pro Ser Ala Pro Leu Ala Leu Arg Ala Ala
    210                 215                 220

Lys Met Ala Ile Ser Met Gly Ala Asn Val Glu Leu Ala Arg Gly Leu
225                 230                 235                 240

Asp Leu Glu Trp Ala Cys Tyr Glu Pro Leu Leu Glu Ser Lys Asp Arg
                245                 250                 255

Arg Glu Ala Leu Asp Ala Phe Gln Gln Lys Arg Lys Pro Ile Phe Thr
            260                 265                 270

Gly Lys
```

<210> SEQ ID NO 96
<211> LENGTH: 262
<212> TYPE: PRT
<213> ORGANISM: Unknown

<220> FEATURE:
<223> OTHER INFORMATION: Bacillus sp. GeD10

<400> SEQUENCE: 96

```
Met Leu Gln Leu Gln Asn Ile Ser Val Asp Tyr Val Thr Pro His Val
1               5                   10                  15

Val Lys Ile Ser Leu Tyr Arg Glu Arg Gln Ala Asn Ser Leu Ser Leu
            20                  25                  30

Ala Leu Leu Glu Glu Leu Gln Asn Ile Leu Thr Gln Ile Ser Glu Glu
        35                  40                  45

Ser Asn Thr Arg Val Val Ile Leu Thr Gly Ala Gly Glu Lys Ala Phe
    50                  55                  60

Cys Ala Gly Ala Asp Leu Lys Glu Arg Ala Gly Met Asn Glu Glu Gln
65                  70                  75                  80

Val Arg His Ala Val Ser Met Ile Arg Thr Thr Met Glu Met Val Glu
                85                  90                  95

Gln Leu Pro Gln Pro Val Ile Ala Ala Ile Asn Gly Ile Ala Leu Gly
            100                 105                 110

Gly Gly Thr Glu Leu Ser Leu Ala Cys Asp Phe Arg Ile Ala Ala Glu
        115                 120                 125

Ser Ala Ser Leu Gly Leu Thr Glu Thr Thr Leu Ala Ile Ile Pro Gly
    130                 135                 140

Ala Gly Gly Thr Gln Arg Leu Pro Arg Leu Ile Gly Val Gly Arg Ala
145                 150                 155                 160

Lys Glu Leu Ile Tyr Thr Gly Arg Arg Ile Ser Ala Gln Glu Ala Lys
                165                 170                 175

Glu Tyr Gly Leu Val Glu Phe Val Val Pro Ala Asn Leu Leu Glu Glu
            180                 185                 190

Lys Ala Ile Glu Ile Ala Glu Lys Ile Ala Ser Asn Gly Pro Ile Ala
        195                 200                 205

Val Arg Leu Ala Lys Glu Ala Ile Ser Asn Gly Ile Gln Val Asp Leu
    210                 215                 220

His Thr Gly Leu Gln Met Glu Lys Gln Ala Tyr Glu Gly Val Ile His
225                 230                 235                 240

Thr Lys Asp Arg Leu Glu Gly Leu Gln Ala Phe Lys Glu Lys Arg Thr
                245                 250                 255

Pro Thr Tyr Lys Gly Glu
            260
```

<210> SEQ ID NO 97
<211> LENGTH: 263
<212> TYPE: PRT
<213> ORGANISM: Labilithrix luteola

<400> SEQUENCE: 97

```
Met Ala Asp Glu Ser Phe Pro Val Glu Val Glu Gln Arg Gly Asn Val
1               5                   10                  15

Val Ile Trp Thr Ile Asp Arg Glu Ser Arg Met Asn Ser Leu Ser Arg
            20                  25                  30

Ala Thr Leu Phe Ala Leu Gly Lys Leu Thr Arg Glu Ala Val Ser Asn
        35                  40                  45

Pro Ser Val Arg Ala Ile Val Ile Thr Gly Arg Gly Glu Lys Ala Phe
    50                  55                  60

Cys Ala Gly Ala Asp Leu Lys Glu Arg Gln Gly Met Thr Glu Asn Asp
65                  70                  75                  80
```

Ile Arg Val Gln Val Glu Leu Tyr Arg Ser Glu Leu Gly Pro Leu Asp
            85                  90                  95

Arg Ser Pro Lys Pro Val Ile Ala Ala Leu Asn Gly Val Ala Phe Gly
            100                 105                 110

Gly Gly Leu Glu Leu Ala Leu Val Cys Asp Met Arg Val Ala Ala Ser
            115                 120                 125

His Ala Leu Ile Gly Leu Pro Glu Thr Thr Leu Gly Ile Ile Pro Gly
            130                 135                 140

Ala Gly Gly Thr Gln Arg Leu Pro Arg Ile Val Gly Glu Ala Arg Ala
145                 150                 155                 160

Lys Glu Met Ile Leu Leu Gly Arg Lys Leu Ser Ala Thr Glu Ala His
                165                 170                 175

Ala Trp Gly Leu Val Asn Arg Val Thr Pro Glu Gly Ala Asn Val Val
            180                 185                 190

Glu Asp Thr Leu Ala Phe Ile Asp Pro Ile Ala Asn Gly Ala Pro Ile
            195                 200                 205

Ala Gln Ala Ala Ala Leu Glu Ala Ile Asp Arg Ser Phe Asp Thr Thr
            210                 215                 220

Leu Glu Leu Gly Leu Glu Leu Glu Lys Val Ser Tyr Asp Lys Val Leu
225                 230                 235                 240

Val Ser Glu Asp Arg Arg Glu Ala Leu Ala Ala Phe Ala Glu Lys Arg
                245                 250                 255

Lys Pro Gln Phe Lys Gly Arg
            260

<210> SEQ ID NO 98
<211> LENGTH: 258
<212> TYPE: PRT
<213> ORGANISM: Myxococcus xanthus

<400> SEQUENCE: 98

Met Pro Glu Phe Lys Val Asp Ala Arg Gly Pro Ile Glu Ile Trp Thr
1               5                   10                  15

Ile Asp Gly Glu Ser Arg Arg Asn Ala Ile Ser Arg Ala Met Leu Lys
            20                  25                  30

Glu Leu Gly Glu Leu Val Thr Arg Val Ser Ser Ser Arg Asp Val Arg
            35                  40                  45

Ala Val Val Ile Thr Gly Ala Gly Asp Lys Ala Phe Cys Ala Gly Ala
            50                  55                  60

Asp Leu Lys Glu Arg Ala Thr Met Ala Glu Asp Glu Val Arg Ala Phe
65                  70                  75                  80

Leu Asp Gly Leu Arg Arg Thr Phe Arg Ala Ile Glu Lys Ser Asp Cys
                85                  90                  95

Val Phe Ile Ala Ala Ile Asn Gly Ala Ala Leu Gly Gly Gly Thr Glu
            100                 105                 110

Leu Ala Leu Ala Cys Asp Leu Arg Val Ala Ala Pro Ala Ala Glu Leu
            115                 120                 125

Gly Leu Thr Glu Val Lys Leu Gly Ile Ile Pro Gly Gly Gly Gly Thr
            130                 135                 140

Gln Arg Leu Ala Arg Leu Val Gly Pro Gly Arg Ala Lys Asp Leu Ile
145                 150                 155                 160

Leu Thr Ala Arg Arg Ile Asn Ala Ala Glu Ala Phe Ser Val Gly Leu
                165                 170                 175

Ala Asn Arg Leu Ala Pro Glu Gly His Leu Leu Ala Val Ala Tyr Gly
            180                 185                 190

```
Leu Ala Glu Ser Val Val Glu Asn Ala Pro Ile Ala Val Ala Thr Ala
        195                 200                 205

Lys His Ala Ile Asp Glu Gly Thr Gly Leu Glu Leu Asp Asp Ala Leu
    210                 215                 220

Ala Leu Glu Leu Arg Lys Tyr Glu Glu Ile Leu Lys Thr Glu Asp Arg
225                 230                 235                 240

Leu Glu Gly Leu Arg Ala Phe Ala Glu Lys Arg Ala Pro Val Tyr Lys
                245                 250                 255

Gly Arg

<210> SEQ ID NO 99
<211> LENGTH: 383
<212> TYPE: PRT
<213> ORGANISM: Enterococcus faecalis

<400> SEQUENCE: 99

Met Thr Ile Gly Ile Asp Lys Ile Ser Phe Phe Val Pro Pro Tyr Tyr
1               5                   10                  15

Ile Asp Met Thr Ala Leu Ala Glu Ala Arg Asn Val Asp Pro Gly Lys
            20                  25                  30

Phe His Ile Gly Ile Gly Gln Asp Gln Met Ala Val Asn Pro Ile Ser
        35                  40                  45

Gln Asp Ile Val Thr Phe Ala Ala Asn Ala Ala Glu Ala Ile Leu Thr
    50                  55                  60

Lys Glu Asp Lys Glu Ala Ile Asp Met Val Ile Val Gly Thr Glu Ser
65                  70                  75                  80

Ser Ile Asp Glu Ser Lys Ala Ala Ala Val Val Leu His Arg Leu Met
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Leu Ala Lys Asn His Val Ala Leu His
        115                 120                 125

Pro Asp Lys Lys Val Leu Val Val Ala Ala Asp Ile Ala Lys Tyr Gly
    130                 135                 140

Leu Asn Ser Gly Gly Glu Pro Thr Gln Gly Ala Gly Ala Val Ala Met
145                 150                 155                 160

Leu Val Ala Ser Glu Pro Arg Ile Leu Ala Leu Lys Glu Asp Asn Val
                165                 170                 175

Met Leu Thr Gln Asp Ile Tyr Asp Phe Trp Arg Pro Thr Gly His Pro
            180                 185                 190

Tyr Pro Met Val Asp Gly Pro Leu Ser Asn Glu Thr Tyr Ile Gln Ser
        195                 200                 205

Phe Ala Gln Val Trp Asp Glu His Lys Lys Arg Thr Gly Leu Asp Phe
    210                 215                 220

Ala Asp Tyr Asp Ala Leu Ala Phe His Ile Pro Tyr Thr Lys Met Gly
225                 230                 235                 240

Lys Lys Ala Leu Leu Ala Lys Ile Ser Asp Gln Thr Glu Ala Glu Gln
                245                 250                 255

Glu Arg Ile Leu Ala Arg Tyr Glu Glu Ser Ile Ile Tyr Ser Arg Arg
            260                 265                 270

Val Gly Asn Leu Tyr Thr Gly Ser Leu Tyr Leu Gly Leu Ile Ser Leu
        275                 280                 285

Leu Glu Asn Ala Thr Thr Leu Thr Ala Gly Asn Gln Ile Gly Leu Phe
    290                 295                 300
```

```
Ser Tyr Gly Ser Gly Ala Val Ala Glu Phe Phe Thr Gly Glu Leu Val
305                 310                 315                 320

Ala Gly Tyr Gln Asn His Leu Gln Lys Glu Thr His Leu Ala Leu Leu
            325                 330                 335

Asp Asn Arg Thr Glu Leu Ser Ile Ala Glu Tyr Glu Ala Met Phe Ala
        340                 345                 350

Glu Thr Leu Asp Thr Asp Ile Asp Gln Thr Leu Glu Asp Glu Leu Lys
            355                 360                 365

Tyr Ser Ile Ser Ala Ile Asn Asn Thr Val Arg Ser Tyr Arg Asn
370                 375                 380
```

<210> SEQ ID NO 100
<211> LENGTH: 265
<212> TYPE: PRT
<213> ORGANISM: Myxococcus xanthus

<400> SEQUENCE: 100

```
Met Lys Thr Ala Arg Trp Cys Ser Leu Glu Glu Ala Val Ala Ser Ile
1               5                   10                  15

Pro Asp Gly Ala Ser Leu Ala Thr Gly Gly Phe Met Leu Gly Arg Ala
            20                  25                  30

Pro Met Ala Leu Val Met Glu Leu Ile Ala Gln Gly Lys Arg Asp Leu
        35                  40                  45

Gly Leu Ile Ser Leu Pro Asn Pro Leu Pro Ala Glu Phe Leu Val Ala
    50                  55                  60

Gly Gly Cys Leu Ala Arg Leu Glu Ile Ala Phe Gly Ala Leu Ser Leu
65                  70                  75                  80

Gln Gly Arg Val Arg Pro Met Pro Cys Leu Lys Arg Ala Met Glu Gln
                85                  90                  95

Gly Thr Leu Ala Trp Arg Glu His Asp Gly Tyr Arg Val Val Gln Arg
            100                 105                 110

Leu Arg Ala Ala Ser Met Gly Leu Pro Phe Ile Pro Ala Pro Asp Ala
        115                 120                 125

Asp Val Ser Gly Leu Ala Arg Thr Glu Pro Pro Thr Val Glu Asp
130                 135                 140

Pro Phe Thr Gly Leu Arg Val Ala Val Glu Pro Ala Phe Tyr Pro Asp
145                 150                 155                 160

Val Ala Leu Leu His Ala Arg Ala Ala Asp Glu Arg Gly Asn Leu Tyr
                165                 170                 175

Met Glu Asp Pro Thr Thr Asp Leu Leu Val Ala Gly Ala Ala Lys Arg
            180                 185                 190

Val Ile Ala Thr Val Glu Glu Arg Val Ala Lys Leu Pro Arg Ala Thr
        195                 200                 205

Leu Pro Gly Phe Gln Val Asp Arg Ile Val Leu Ala Pro Gly Gly Ala
    210                 215                 220

Leu Pro Thr Gly Cys Ala Gly Leu Tyr Pro His Asp Asp Glu Met Leu
225                 230                 235                 240

Ala Arg Tyr Leu Ser Leu Ala Glu Thr Gly Arg Glu Ala Glu Phe Leu
                245                 250                 255

Glu Thr Leu Leu Thr Arg Arg Ala Ala
            260                 265
```

<210> SEQ ID NO 101
<211> LENGTH: 246
<212> TYPE: PRT

<213> ORGANISM: Myxococcus xanthus

<400> SEQUENCE: 101

```
Met Ser Ala Thr Leu Asp Ile Thr Pro Ala Glu Thr Val Val Ser Leu
1               5                   10                  15
Leu Ala Arg Gln Ile Asp Gly Gly Val Val Ala Thr Gly Val Ala
            20                  25                  30
Ser Pro Leu Ala Ile Leu Ala Ile Ala Val Ala Arg Ala Thr His Ala
        35                  40                  45
Pro Asp Leu Thr Tyr Leu Ala Cys Val Gly Ser Leu Asp Pro Glu Ile
    50                  55                  60
Pro Thr Leu Leu Pro Ser Ser Glu Asp Leu Gly Tyr Leu Asp Gly Arg
65                  70                  75                  80
Ser Ala Glu Ile Thr Ile Pro Asp Leu Phe Asp His Ala Arg Arg Gly
            85                  90                  95
Arg Val Asp Thr Val Phe Phe Gly Ala Ala Glu Val Asp Ala Glu Gly
            100                 105                 110
Arg Thr Asn Met Thr Ala Ser Gly Ser Leu Asp Lys Pro Arg Thr Lys
            115                 120                 125
Phe Pro Gly Val Ala Gly Ala Ala Thr Leu Arg Gln Trp Val Arg Arg
    130                 135                 140
Pro Val Leu Leu Val Pro Arg Gln Ser Arg Arg Asn Leu Val Pro Glu
145                 150                 155                 160
Val Gln Val Ala Thr Thr Arg Asp Pro Arg Arg Pro Val Thr Leu Ile
            165                 170                 175
Ser Asp Leu Gly Val Phe Glu Leu Gly Ala Ser Gly Ala Arg Leu Leu
            180                 185                 190
Ala Arg His Pro Trp Ala Ser Glu Glu His Ile Ala Glu Arg Thr Gly
            195                 200                 205
Phe Ala Phe Gln Val Ser Glu Ala Leu Ser Val Thr Ser Leu Pro Asp
    210                 215                 220
Ala Arg Thr Val Ala Ala Ile Arg Ala Ile Asp Pro His Gly Tyr Arg
225                 230                 235                 240
Asp Ala Leu Val Gly Ala
            245
```

METHODS FOR PRODUCING ISOBUTENE FROM 3-METHYLCROTONIC ACID

CROSS-REFERENCE TO RELATED APPLICATIONS

This application is a § 371 National Stage Application of PCT/EP2016/077956 filed on Nov. 17, 2016, which claims priority to EP 15194984.9 filed on Nov. 17, 2015, both of which are hereby incorporated by reference in their entirety.

The present invention relates to methods for the production of isobutene comprising the enzymatic conversion of 3-methylcrotonic acid into isobutene wherein said 3-methylcrotonic acid is obtained by the enzymatic conversion of 3-methylcrotonyl-CoA into 3-methylcrotonic acid or wherein said 3-methylcrotonic acid is obtained by the enzymatic conversion of 3-hydroxyisovalerate (HIV) into 3-methylcrotonic acid. The enzymatic conversion of 3-methylcrotonic acid into isobutene can, e.g., be achieved by making use of a 3-methylcrotonic acid decarboxylase, preferably an FMN-dependent decarboxylase associated with an FMN prenyl transferase, an aconitate decarboxylase (EC 4.1.1.6), a methylcrotonyl-CoA carboxylase (EC 6.4.1.4), or a geranoyl-CoA carboxylase (EC 6.4.1.5). Further, said 3-methylcrotonyl-CoA can be obtained by the enzymatic conversion of 3-methylglutaconyl-CoA into 3-methylcrotonyl-CoA.

A large number of chemical compounds are currently derived from petrochemicals. Alkenes (such as ethylene, propylene, the different butenes, or else the pentenes, for example) are used in the plastics industry, for example for producing polypropylene or polyethylene, and in other areas of the chemical industry and that of fuels.

Butylene exists in four forms, one of which, isobutene (also referred to as isobutylene), enters into the composition of methyl-tert-butyl-ether (MTBE), an anti-knock additive for automobile fuel. Isobutene can also be used to produce isooctene, which in turn can be reduced to isooctane (2,2,4-trimethylpentane); the very high octane rating of isooctane makes it the best fuel for so-called "gasoline" engines. Alkenes such as isobutene are currently produced by catalytic cracking of petroleum products (or by a derivative of the Fischer-Tropsch process in the case of hexene, from coal or gas). The production costs are therefore tightly linked to the price of oil. Moreover, catalytic cracking is sometimes associated with considerable technical difficulties which increase process complexity and production costs.

The production by a biological pathway of alkenes such as isobutene is called for in the context of a sustainable industrial operation in harmony with geochemical cycles. The first generation of biofuels consisted in the fermentative production of ethanol, as fermentation and distillation processes already existed in the food processing industry. The production of second generation biofuels is in an exploratory phase, encompassing in particular the production of long chain alcohols (butanol and pentanol), terpenes, linear alkanes and fatty acids. Two recent reviews provide a general overview of research in this field: Ladygina et al. (Process Biochemistry 41 (2006), 1001) and Wackett (Current Opinions in Chemical Biology 21 (2008), 187). The conversion of isovalerate to isobutene by the yeast *Rhodotorula minuta* has been described (Fujii et al. (Appl. Environ. Microbiol. 54 (1988), 583)), but the efficiency of this reaction, less than 1 millionth per minute, or about 1 for 1000 per day, is far from permitting an industrial application. The reaction mechanism was elucidated by Fukuda et al. (BBRC 201 (1994), 516) and involves a cytochrome P450 enzyme which decarboxylates isovalerate by reduction of an oxoferryl group $Fe^V=O$. Large-scale biosynthesis of isobutene by this pathway seems highly unfavourable, since it would require the synthesis and degradation of one molecule of leucine to form one molecule of isobutene. Also, the enzyme catalyzing the reaction uses heme as cofactor, poorly lending itself to recombinant expression in bacteria and to improvement of enzyme parameters. For all these reasons, it appears very unlikely that this pathway can serve as a basis for industrial exploitation. Other microorganisms have been described as being marginally capable of naturally producing isobutene from isovalerate; the yields obtained are even lower than those obtained with *Rhodotorula minuta* (Fukuda et al. (Agric. Biol. Chem. 48 (1984), 1679)).

Gogerty et al. (Appl. Environm. Microbiol. 76 (2010), 8004-8010) and van Leeuwen et al. (Appl. Microbiol. Biotechnol. 93 (2012), 1377-1387) describe the production of isobutene from acetoacetyl-CoA by enzymatic conversions wherein the last step of the proposed pathway is the conversion of 3-hydroxy-3-methylbutyric acid (also referred to as 3-hydroxyisovalerate (HIV)) by making use of a mevalonate diphosphate decarboxylase. This reaction for the production of isobutene from 3-hydroxy-3-methylbutyric acid is also described in WO2010/001078. In Gogerty et al. (loc. cit.) and in van Leeuwen et al. (loc. cit.) the production of 3-hydroxy-3-methylbutyric acid is proposed to be achieved by the conversion of 3-methylcrotonyl-CoA via 3-hydroxy-3-methylbutyryl-CoA. In order to further improve the efficiency and variability of methods for producing isobutene from renewable resources, there is a need for alternative routes for the provision of isobutene and its precursors.

The present invention meets this demand by providing a method for the production of isobutene comprising the enzymatic conversion of 3-methylcrotonic acid (also termed 3-methyl-2-butenoic acid) into isobutene.

The enzymatic conversion of 3-methylcrotonic acid into isobutene is a decarboxylation reaction. A decarboxylation is a chemical reaction that removes a carboxyl group and releases carbon dioxide ($CO_2$).

The decarboxylation of 3-methylcrotonic acid has already been suggested in US-A1-2009/0092975 while there is no experimental evidence for this conversion. In US-A1-2009/0092975, a nucleic acid sequence called PAD1 derived from *Saccharomyces cerevisiae* is described and is disclosed to encode a decarboxylation enzyme. This enzyme is suggested to be useful as a selectable marker in a recombinant organism while it is described that a "weak acid" may be used as the selecting agent. 3-methylcrotonic acid is mentioned, among many others, as a potential "weak acid". However, it was only later found that the above PAD1, in reality, does not provide for the decarboxylase activity.

In fact, the bacterial ubiD and ubiX or the homologous eukaryotic fdc1 and pad1 genes have been implicated in the non-oxidative reversible decarboxylation. The combined action of phenylacrylic acid decarboxylase (PAD) and ferulic acid decarboxylase (FDC) is considered to be essential for the decarboxylation of phenylacrylic acid in *Saccharomyces cerevisiae* (J. Biosci. Bioeng. 109, (2010), 564-569; AMB Express, 5:12 (2015) 1-5; ACS Chem. Biol. 10 (2015), 1137-1144). Recently, the above enzyme family described as phenylacrylic acid decarboxylase (PAD) was characterized as an FMN prenyl-transferase and no longer as a decarboxylase. It has been shown that Fdc1 (but not PAD) is solely responsible for the reversible decarboxylase activity and that it requires a new type of cofactor, namely a prenylated flavin synthesized by the associated UbiX (or Pad1) protein. Thus, the real enzymatic activity of this PAD enzyme has been identified as the transformation of a flavin mononucleotide (FMN) cofactor with a prenyl moiety (from di-methyl-allyl-phosphate or pyrophosphate called DMAP or DMAPP).

Accordingly, in contrast to the prior art's belief, the real decarboxylase is the ferulic acid decarboxylase (FDC) in association with the modified FMN (prenylated-FMN). This mechanism of the ferulic acid decarboxylase (FDC) in association with the modified FMN (prenylated-FMN) (the latter provided by the PAD enzyme) was recently described and involves a surprising enzymatic mechanism, i.e., an α,β-unsaturated acid decarboxylation via a 1,3-dipolar cyclo-addition. Moreover, the structure of this FDC decarboxylase has recently been elucidated (Nature 522 (2015), 497-501; Nature, 522 (2015), 502-505; Appl. Environ. Microbiol. 81 (2015), 4216-4223).

The use of the above family of enzymes has previously been described for the conversion of α-β unsaturated carboxylic acid into terminal alkenes in US-A1-2009/0092975 as mentioned above while WO2012/018624 is directed to microorganisms and methods for the biosynthesis of aromatics, 2,4-pentadienoate and 1,3-butadiene and WO2013/028519 is directed to microorganisms and methods for producing 2,4-pentadienoate, butadiene, propylene, 1,3-butanediol and related alcohols.

Moreover, WO2013/186215 describes a method for preparing a mono-unsaturated alkene comprising contacting an aliphatic mono-unsaturated carboxylic acid with an Fdc1 polypeptide and a Pad1 polypeptide. However, in WO2013/186215, both, the Fdc1 polypeptide and the Pad1 polypeptide are classified as enzymes having a decarboxylase activity.

In contrast, in the present invention, the above enzymes are artificially implemented in a pathway which ultimately leads to the production of isobutene. Thus, in a main aspect, the present invention relates to a method for the production of isobutene comprising the enzymatic conversion of 3-methylcrotonic acid into isobutene (step I as shown in FIG. 1), wherein said method further comprises
(a) providing the 3-methylcrotonic acid by the enzymatic conversion of 3-methylcrotonyl-CoA into 3-methylcrotonic acid (steps VIa, VIb or VIc as shown in FIG. 1), or
(b) providing the 3-methylcrotonic acid by the enzymatic conversion of 3-hydroxyisovalerate (HIV) into 3-methylcrotonic acid (step II as shown in FIG. 1).

Preferably, the enzymatic conversion of 3-methylcrotonic acid into isobutene is achieved by making use of a 3-methylcrotonic acid decarboxylase.

The method for the production of isobutene from 3-methylcrotonyl-CoA via 3-methylcrotonic acid or from 3-hydroxyisovalerate (HIV) via 3-methylcrotonic acid may be embedded in a pathway for the production of isobutene starting from acetyl-CoA which is a central component and an important key molecule in metabolism used in many biochemical reactions. The corresponding reactions are schematically shown in FIG. 1.

Therefore, the present invention also relates to pathways starting from acetyl-CoA and leading to 3-methylcrotonic acid (which is then ultimately converted into isobutene) via two alternative pathways which are schematically shown in FIG. 1 and will be explained in more detail further below.

The Routes for the Enzymatic Conversion from Acetyl-CoA into Isobutene Via Acetoacetyl-CoA and 3-Methylcrotonic Acid The Enzymatic Conversion of 3-Methylcrotonic Acid into Isobutene: Step I as Shown in FIG. 1

Figure 2A:
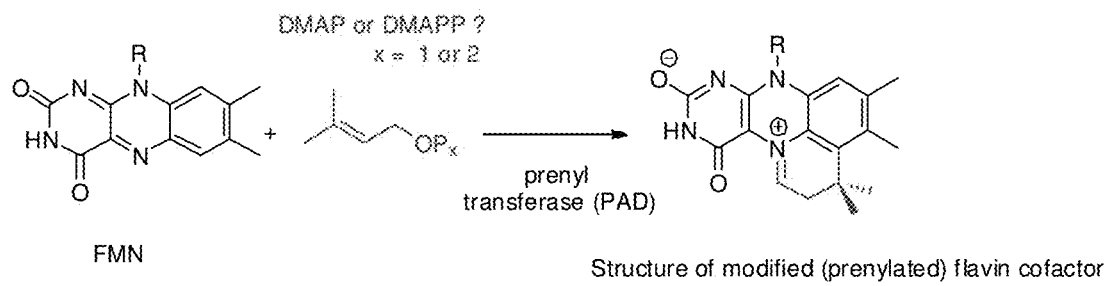
Figure 2B:
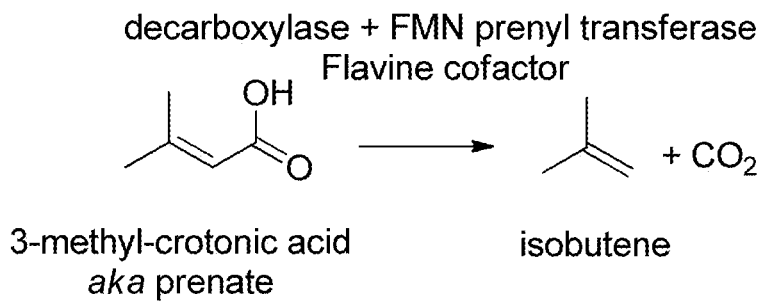

The enzymatic conversion of 3-methylcrotonic acid into isobutene is schematically shown in FIG. 2B.

According to the present invention, the enzymatic conversion of 3-methylcrotonic acid (also termed 3-methyl-2-butenoic acid or 3,3-dimethyl-acrylic acid) into isobutene (also termed isobutylene or 2-methyl-propene) can be achieved by a decarboxylation. "Decarboxylation" is generally a chemical reaction that removes a carboxyl group and releases carbon dioxide ($CO_2$).

The enzymatic conversion of 3-methylcrotonic acid into isobutene can preferably be achieved by making use of a 3-methylcrotonic acid decarboxylase. In accordance with the present invention, a 3-methylcrotonic acid decarboxylase is an enzyme which is capable of converting 3-methylcrotonic acid into isobutene in a decarboxylation reaction.

In preferred embodiments, the 3-methylcrotonic acid decarboxylase is selected from the group consisting of:
(i) an FMN-dependent decarboxylase associated with an FMN prenyl transferase; or
(ii) an aconitate decarboxylase (EC 4.1.1.6); or
(iii) a methylcrotonyl-CoA carboxylase (EC 6.4.1.4); or
(iv) a geranoyl-CoA carboxylase (EC 6.4.1.5).

Thus, according to one aspect, the enzymatic conversion of 3-methylcrotonic acid into isobutene can preferably be achieved by making use of a 3-methylcrotonic acid decarboxylase, wherein said 3-methylcrotonic acid decarboxylase is an FMN-dependent decarboxylase associated with an FMN prenyl transferase.

The enzymatic conversion of 3-methylcrotonic acid into isobutene utilizing an FMN-dependent decarboxylase associated with an FMN prenyl transferase relies on a reaction of two consecutive steps catalyzed by the two enzymes, i.e., the FMN-dependent decarboxylase (catalyzing the actual decarboxylation of 3-methylcrotonic acid into isobutene) with an associated FMN prenyl transferase which provides the modified flavin cofactor. The flavin cofactor may preferably be FMN or FAD. FMN (flavin mononucleotide; also termed riboflavin-5'-phosphate) is a biomolecule produced from riboflavin (vitamin B2) by the enzyme riboflavin kinase and functions as prosthetic group of various reactions. FAD (flavin adenine dinucleotide) is a redox cofactor, more specifically a prosthetic group, involved in several important reactions in metabolism.

Thus, in the conversion of 3-methylcrotonic acid into isobutene, in a first step, a flavin cofactor (FMN or FAD) is modified into a (modified) flavin-derived cofactor. This modification is catalyzed by said FMN prenyl transferase. FMN prenyl transferase prenylates the flavin ring of the flavin cofactor (FMN or FAD) into a (modified) prenylated flavin cofactor. This reaction is schematically illustrated in FIG. 2A.

In a second step, the actual conversion of 3-methylcrotonic acid into isobutene is catalyzed by said FMN-dependent decarboxylase via a 1,3-dipolar cycloaddition based mechanism wherein said FMN-dependent decarboxylase uses the prenylated flavin cofactor (FMN or FAD) provided by the associated FMN prenyl transferase. This reaction is schematically illustrated in FIG. 2B.

In a preferred embodiment, said FMN prenyl transferase which modifies the flavin cofactor (FMN or FAD) into a (modified) flavin-derived cofactor is a phenylacrylic acid decarboxylase (PAD)-type protein, or the closely related prokaryotic enzyme UbiX, an enzyme which is involved in ubiquinone biosynthesis in prokaryotes.

In *Escherichia coli*, the protein UbiX (also termed 3-octaprenyl-4-hydroxybenzoate carboxy-lyase) has been shown to be involved in the third step of ubiquinone biosynthesis.

It catalyses the reaction 3-octaprenyl-4-hydroxybenzoate ⇌ 2-octaprenylphenol+$CO_2$.

Moreover, the knockout of the homologous protein in yeast (Pad1) has been shown to confer sensitivity to phenylacrylic acid, showing that this enzyme functions as a phenylacrylic acid decarboxylase. *E. coli* strains also contain, in addition to UbiX, a second paralogue named Pad1. Its amino acid sequence shows 52% identity to UbiX and slightly higher sequence identity to *Saccharomyces cerevisiae* phenylacrylic acid decarboxylase Pad1. Despite its higher sequence similarity with yeast Pad1, *E. coli* Pad1 does not seem to have phenylacrylic acid decarboxylase activity. Its function is unknown, Pad1 may remove the carboxylate group from derivatives of benzoic acid but not from substituted phenolic acids.

Thus, in a preferred embodiment, the modification of a flavin cofactor (FMN or FAD) into the corresponding (modified) flavin-derived cofactor is catalyzed by the FMN-containing protein phenylacrylic acid decarboxylase (PAD). The enzymes involved in the modification of the flavin cofactor (FMN or FAD) into the corresponding modified flavin-derived cofactor were initially annotated as decarboxylases (EC 4.1.1.-). Some phenylacrylic acid decarboxylases (PAD) are now annotated as flavin prenyl transferases as EC 2.5.1.-.

In a more preferred embodiment, the conversion of 3-methylcrotonic acid into isobutene makes use of a phenylacrylic acid decarboxylase (PAD)-type protein as the FMN prenyl transferase which modifies a flavin cofactor (FMN or FAD) into the corresponding (modified) flavin-derived cofactor wherein said phenylacrylic acid decarboxylase (PAD)-type protein is derived from *Candida albicans* (Uniprot accession number Q5A8L8), *Aspergillus niger* (Uniprot accession number A3F715), *Saccharomyces cerevisiae* (Uniprot accession number P33751) or *Cryptococcus gattii* (Uniprot accession number E6R9Z0).

In a preferred embodiment, the phenylacrylic acid decarboxylase (PAD)-type protein employed in the method of the present invention is a phenylacrylic acid decarboxylase (PAD)-type protein derived from *Candida albicans* (Uniprot accession number Q5A8L8; SEQ ID NO:40), *Aspergillus niger* (Uniprot accession number A3F715; SEQ ID NO:41), *Saccharomyces cerevisiae* (Uniprot accession number P33751; SEQ ID NO:42) or *Cryptococcus gattii* (Uniprot accession number E6R9Z0; SEQ ID NO:43) having the amino acid sequence as shown in SEQ ID NO:40, SEQ ID NO:41, SEQ ID NO:42 and SEQ ID NO:43, respectively.

In a preferred embodiment of the present invention the phenylacrylic acid decarboxylase (PAD)-type protein is an enzyme comprising an amino acid sequence selected from the group consisting of SEQ ID NOs: 40 to 43 or a sequence which is at least n % identical to any of SEQ ID NOs: 40 to 43 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor.

As regards the determination of sequence identity, the following should apply: When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

Amino acid residues located at a position corresponding to a position as indicated herein-below in the amino acid sequence shown in any one of SEQ ID NOs:40 to 43 can be identified by the skilled person by methods known in the art. For example, such amino acid residues can be identified by aligning the sequence in question with the sequence shown in any one of SEQ ID NOs:40 to 43 and by identifying the positions which correspond to the above indicated positions of any one of SEQ ID NOs:40 to 43. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

In another preferred embodiment, the modification of a flavin cofactor (FMN or FAD) into the corresponding (modified) flavin-derived cofactor is catalyzed by the FMN-containing protein 3-octaprenyl-4-hydroxybenzoate carboxy-lyase also termed UbiX (initially annotated EC 4.1.1.-). As mentioned above, the enzymes involved in the modification of the flavin cofactor (FMN or FAD) into the corresponding modified flavin-derived cofactor were initially annotated as decarboxylases. Some phenylacrylic acid decarboxylases (PAD) are now annotated as flavin prenyl transferases as EC 2.5.1.-.

In a more preferred embodiment, the conversion of 3-methylcrotonic acid into isobutene makes use of a 3-octaprenyl-4-hydroxybenzoate carboxy-lyase (also termed UbiX) as the FMN prenyl transferase which modifies the flavin cofactor (FMN or FAD) into the corresponding (modified) flavin-derived cofactor wherein said 3-octaprenyl-4-hydroxybenzoate carboxy-lyase (also termed UbiX) is derived from *Escherichia coli* (Uniprot accession number P0AG03), *Bacillus subtilis* (Uniprot accession, number A0A086WXG4), *Pseudomonas aeruginosa* (Uniprot accession number A0A072ZCW8) or *Enterobacter* sp. DC4 (Uniprot accession number W7P6B1).

In an even more preferred embodiment, the 3-octaprenyl-4-hydroxybenzoate carboxy-lyase (also termed UbiX) employed in the method of the present invention is a 3-octaprenyl-4-hydroxybenzoate carboxy-lyase (also termed UbiX) derived from *Escherichia coli* (Uniprot accession number P0AG03; SEQ ID NO:44), *Bacillus subtilis* (Uniprot accession, number A0A086WXG4; SEQ ID NO:45), *Pseudomonas aeruginosa* (Uniprot accession number A0A072ZCW8; SEQ ID NO:46) or *Enterobacter* sp. DC4 (Uniprot accession number W7P6B1; SEQ ID NO:47) having the amino acid sequence as shown in SEQ ID NO:44, SEQ ID NO:45, SEQ ID NO:46 and SEQ ID NO:47, respectively.

In a preferred embodiment of the present invention the 3-octaprenyl-4-hydroxybenzoate carboxy-lyase is an enzyme comprising an amino acid sequence selected from the group consisting of SEQ ID NOs: 44 to 47 or a sequence which is at least n % identical to any of SEQ ID NOs: 44 to 47 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of modifying a flavin cofactor (FMN or FAD) into the corresponding (modified) flavin-derived cofactor. As regards the determination of the sequence identity, the same applies as has been set forth above.

In another preferred embodiment, the modification of a flavin cofactor (FMN or FAD) into the corresponding (modified) flavin-derived cofactor is catalyzed by a flavin prenyl transferase.

As mentioned above, the actual decarboxylation, i.e., the conversion of 3-methylcrotonic acid into isobutene is catalyzed by an FMN-dependent decarboxylase via a 1,3-dipolar cycloaddition based mechanism wherein said FMN-dependent decarboxylase uses the prenylated flavin cofactor (FMN or FAD) provided by any of the above described associated FMN prenyl transferases.

In a preferred embodiment, said FMN-dependent decarboxylase catalyzing the decarboxylation of 3-methylcrotonic acid into isobutene is catalyzed by a ferulic acid decarboxylase (FDC). Ferulic acid decarboxylases (FDC) belong to the enzyme class EC 4.1.1.-.

In an even more preferred embodiment, the conversion of 3-methylcrotonic acid into isobutene makes use of a ferulic acid decarboxylases (FDC) which is derived from *Saccharomyces cerevisiae* (Uniprot accession number Q03034), *Enterobacter* sp. (Uniprot accession number V3P7U0), *Bacillus pumilus* (Uniprot accession number Q45361), *Aspergillus niger* (Uniprot accession number A2R0P7) or *Candida dubliniensis* (Uniprot accession number B9WJ66).

In a preferred embodiment, the ferulic acid decarboxylases (FDC) employed in the method of the present invention is a ferulic acid decarboxylases (FDC) derived from *Saccharomyces cerevisiae* (Uniprot accession number Q03034; SEQ ID NO:48), *Enterobacter* sp. (Uniprot accession number V3P7U0; SEQ ID NO:49), *Bacillus pumilus* (Uniprot accession number Q45361; SEQ ID NO:50), *Aspergillus niger* (Uniprot accession number A2R0P7; SEQ ID NO:51) or *Candida dubliniensis* (Uniprot accession number B9WJ66; SEQ ID NO:52) having the amino acid sequence as shown in SEQ ID NO:48, SEQ ID NO:49, SEQ ID NO:50, SEQ ID NO:51 and SEQ ID NO:52, respectively.

In another more preferred embodiment, the conversion of 3-methylcrotonic acid into isobutene makes use of a protocatechuate decarboxylase (EC 4.1.1.63).

Thus, in one preferred embodiment, the conversion of 3-methylcrotonic acid into isobutene is catalyzed by a protocatechuate (PCA) decarboxylase (EC 4.1.1.63). PCA decarboxylases (also termed AroY) are known to catalyze the following reaction, i.e., the enzymatic conversion of protocatechuate (PCA) into catechol (Johnson et al., Metabolic Engineering Communications 3 (2016), 111):

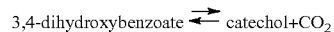

This enzyme occurs in a variety of organisms and has, e.g., been described in *Enterobacter aerogenes, Enterobacter cloacae, Rhodopseudomonas* sp. and *Sedimentibacter hydroxybenzoicus*.

In a preferred embodiment of the present invention, the PCA decarboxylase employed in the method of the present invention is a PCA decarboxylase which is derived from *Klebsiella pneumoniae* (Uniprot accession number B9AM6), *Leptolyngbya* sp. (Uniprot accession number A0A0S3U6D8), or *Phascolarctobacterium* sp. (Uniprot accession number R611V6).

In a preferred embodiment, the PCA decarboxylase employed in the method of the present invention is an enzyme derived from *Klebsiella pneumonia* (SEQ ID NO:78), *Leptolyngbya* sp. (SEQ ID NO:80), or *Phascolarctobacterium* sp. (SEQ ID NO:81). In a preferred embodiment of the present invention the PCA decarboxylase is an enzyme comprising an amino acid sequence selected from the group consisting of SEQ ID NOs: 78, 80 and 81 or a sequence which is at least n % identical to any of SEQ ID NOs: 78, 80 and 81 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

In a preferred embodiment of the present invention the ferulic acid decarboxylase (FDC) is an enzyme comprising an amino acid sequence selected from the group consisting of SEQ ID NOs: 48 to 52 or a sequence which is at least n % identical to any of SEQ ID NOs: 48 to 52 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

In another preferred embodiment, said FMN-dependent decarboxylase catalyzing the decarboxylation of 3-methylcrotonic acid into isobutene is an enzyme which is closely related to the above ferulic acid decarboxylase (FDC), namely a 3-polyprenyl-4-hydroxybenzoate decarboxylase (also termed UbiD). 3-polyprenyl-4-hydroxybenzoate decarboxylase belongs to the UbiD decarboxylase family classified as EC:4.1.1.-.

In a more preferred embodiment, the conversion of 3-methylcrotonic acid into isobutene makes use of a 3-polyprenyl-4-hydroxybenzoate decarboxylase (UbiD) which is derived from *Hypocrea atroviridis* (UniProt Accession number G9NLP8), *Sphaerulina musiva* (UniProt Accession number M3DF95), *Penecillinum requeforti* (UniProt Accession number W6QKP7), *Fusarium oxysporum* f. sp. *lycopersici* (UniProt Accession number W9LTH3), *Saccharomyces kudriavzevii* (UniProt Accession number J8TRN5), *Saccharomyces cerevisiae, Aspergillus parasiticus, Candida albicans, Grosmannia clavigera, Escherichia coli* (Uniprot accession number P0AAB4), *Bacillus megaterium* (Uniprot accession number D5DTL4), *Methanothermobacter* sp. CaT2 (Uniprot accession number T2GKK5), *Mycobacterium chelonae* 1518 (Uniprot accession number X8EX86) or *Enterobacter cloacae* (Uniprot accession number V3DX94).

In an even more preferred embodiment, the 3-polyprenyl-4-hydroxybenzoate decarboxylase (UbiD) employed in the method of the present invention is a 3-polyprenyl-4-hydroxybenzoate decarboxylase (UbiD) derived from *Escherichia coli* (Uniprot accession number P0AAB4; SEQ ID NO:53), *Bacillus megaterium* (Uniprot accession number D5DTL4; SEQ ID NO:54), *Methanothermobacter* sp. CaT2 (Uniprot accession number T2GKK5; SEQ ID NO:55) *Mycobacterium chelonae* 1518 (Uniprot accession number X8EX86; SEQ ID NO:56), *Hypocrea atroviridis* (SEQ ID NO:57), *Sphaerulina musiva* (SEQ ID NO:58), *Penecillinum requeforti* (SEQ ID NO:59), *Fusarium oxysporum* f. sp. *lycopersici* (SEQ ID NO:60), *Saccharomyces kudriavzevii* (SEQ ID NO:61), *Saccharomyces cerevisiae* (SEQ ID NO:62), *Aspergillus parasiticus* (SEQ ID NO:63), *Candida albicans* (SEQ ID NO:64), *Grosmannia clavigera* (SEQ ID NO:65) or *Enterobacter cloacae* (SEQ ID NO:79) having the amino acid sequence as shown in SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, and SEQ ID NO:79, respectively.

In a preferred embodiment of the present invention the 3-polyprenyl-4-hydroxybenzoate decarboxylase (UbiD) is an enzyme comprising an amino acid sequence selected from the group consisting of SEQ ID NOs: 53 to 65 or a sequence which is at least n % identical to any of SEQ ID NOs: 53 to 65 and SEQ ID NO:79 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

As mentioned above, in another aspect, the 3-methylcrotonic acid decarboxylase may preferably be an aconitate decarboxylase (EC 4.1.1.6). This decarboxylase does not require the association with an FMN prenyl transferase as it has been described for the above decarboxylases and, accordingly, does not require the provision of a prenylated cofactor.

Thus, in one preferred embodiment, the conversion of 3-methylcrotonic acid into isobutene is catalyzed by an aconitate decarboxylase (EC 4.1.1.6). Aconitate decarboxylases (EC 4.1.1.6) have been described to catalyze the following reaction:

This enzyme occurs in a variety of organisms, and has, e.g., been described in *Aspergillus itaconicus, Aspergillus terreus, Homo sapiens* and *Mus musculus*. In a preferred embodiment, the aconitate decarboxylase (EC 4.1.1.6) employed in the method of the present invention in the conversion of 3-methylcrotonic acid into isobutene is the aconitase decarboxylase derived from *Aspergillus terreus* (UniProt accession number B31UN8), *Homo sapiens* (UniProt accession number A6NK06) or *Mus musculus* (UniProt accession number P54987).

In a preferred embodiment, the aconitate decarboxylase (EC 4.1.1.6) employed in the method of the present invention in the conversion of 3-methylcrotonic acid into isobutene is a aconitate decarboxylase derived from *Aspergillus terreus* (SEQ ID NO:66).

In a preferred embodiment of the present invention the aconitate decarboxylase is an enzyme comprising the amino acid sequence of SEQ ID NO: 66 or a sequence which is at least n % identical to SEQ ID NO: 66 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

As mentioned above, in another aspect, the 3-methylcrotonic acid decarboxylase may preferably be a methylcrotonyl-CoA carboxylase (EC 6.4.1.4). This decarboxylase does not require the association with an FMN prenyl transferase as it has been described for the above decarboxylases and, accordingly, does not require the provision of a prenylated cofactor.

Thus, in one preferred embodiment, the conversion of 3-methylcrotonic acid into isobutene is catalyzed by a methylcrotonyl-CoA carboxylase (EC 6.4.1.4). Methylcrotonyl-CoA carboxylases have been described to catalyze the following reaction:

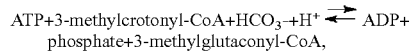

i.e. the carboxylation, but they can also be used to catalyze the reaction of decarboxylation. Methylcrotonyl-CoA carboxylases occur in a variety of organisms, including eukaryotic and prokaryotic organisms, such as plants, animals, fungi and bacteria. The enzyme has, e.g., been described in *Daucus carota, Glycine max, Hordeum vulgare, Pisum sativum, Solanum lycopersicum, Solanum tuberosum, Zea mays, Arabidopsis* sp., *Lens culinaris, Homo sapiens, Bos taurus, Rattus norvegicus, Mus musculus, Pagrus major, Emericella nidulans, Pseudomonas aeruginosa, Pseudomonas citronellolis, Pseudomonas amygdali, Acidaminococcus fermentans, Escherichia coli, Mycobacterium* sp. and *Achromobacter* sp.

In a preferred embodiment, the methylcrotonyl-CoA carboxylase (EC 6.4.1.4) employed in the method of the present invention in the conversion of 3-methylcrotonic acid into isobutene is a methylcrotonyl-CoA carboxylase derived from *Pseudomonas amygdali* (SEQ ID NO:67).

In a preferred embodiment of the present invention the methylcrotonyl-CoA carboxylase is an enzyme comprising the amino acid sequence of SEQ ID NO: 67 or a sequence which is at least n % identical to SEQ ID NO: 67 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

In another preferred embodiment, the methylcrotonyl-CoA carboxylase (EC 6.4.1.4) employed in the method of the present invention in the conversion of 3-methylcrotonic acid into isobutene is a methylcrotonyl-CoA carboxylase derived from *Myxococcus xanthus*. In *Myxococcus xanthus*, the liuB gene codes for an enzyme having the two subunits AibA and AibB (Li et al., Angew. Chem. Int. Ed. 52 (2013), 1304-1308). The methylcrotonyl-CoA carboxylase derived from *Myxococcus xanthus* is a hetero-dimeric enzyme which are annotated as glutaconyl-CoA transferase subunits A and B (SEQ ID NOs: 100 and 101).

In a preferred embodiment of the present invention the methylcrotonyl-CoA carboxylase is an enzyme comprising the amino acid sequence of SEQ ID NO: 100 or 101 a sequence which is at least n % identical to SEQ ID NO: 100 or 101 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid into isobutene. As regards the determination of the sequence identity, the same applies as has been set forth above.

As mentioned above, in another aspect, the 3-methylcrotonic acid decarboxylase may preferably be a geranoyl-CoA carboxylase (EC 6.4.1.5). This decarboxylase does not require the association with an FMN prenyl transferase as it has been described for the above decarboxylases and, accordingly, does not require the provision of a prenylated cofactor.

Thus, in another preferred embodiment, the conversion of 3-methylcrotonic acid via decarboxylasion into isobutene is catalyzed by a geranoyl-CoA carboxylase (EC 6.4.1.5). Geranoyl-CoA carboxylases naturally catalyze the following reaction:

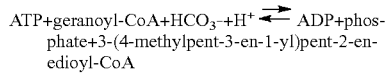

ATP+geranoyl-CoA+HCO$_3^-$+H$^+$ ⇌ ADP+phosphate+3-(4-methylpent-3-en-1-yl)pent-2-enedioyl-CoA The enzyme occurs in eukaryotes and prokaryotes, such as plants and bacteria. The enzyme has, e.g., been described in *Daucus carota, Glycine max, Zea mays, Pseudomonas* sp., *Pseudomonas aeruginosa, Pseudomonas citronellolis* and *Pseudomonas mendocina*.

In another aspect, the 3-methylcrotonic acid decarboxylase may preferably be a 6-methylsalicylate decarboxylase (EC 4.1.1.52).

Thus, in another preferred embodiment, the conversion of 3-methylcrotonic acid via decarboxylasion into isobutene is catalyzed by a 6-methylsalicylate decarboxylase (EC 4.1.1.52). 6-methylsalicylate decarboxylases (EC 4.1.1.52) naturally catalyze the following reaction:

6-methylsalicylate ⇌ 3-methylphenol+CO$_2$

The enzyme occurs in a variety of organisms, in particular in eucaryotes and prokaryotes, such as bacteria and fungi. The enzyme has, e.g., been described in *Aspergillus clavatus* (UniProt Accession number T1PRE6), *Penicillium griseofulvum* and *Valsa friesii*.

In a preferred embodiment, the 6-methylsalicylate decarboxylase (EC 4.1.1.52) employed in the method of the present invention in the conversion 3-methylcrotonic acid via decarboxylasion into isobutene is a 6-methylsalicylate decarboxylase derived from *Aspergillus clavatus* (SEQ ID NO:68).

In a preferred embodiment of the present invention the 6-methylsalicylate decarboxylase is an enzyme comprising the amino acid sequence of SEQ ID NO: 68 or a sequence which is at least n % identical to SEQ ID NO: 68 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid via decarboxylasion into isobutene. As regards the determination of the sequence identity, the same applies as has been set forth above.

In another aspect, the 3-methylcrotonic acid decarboxylase may preferably be a 2-oxo-3-hexenedioate decarboxylase (EC 4.1.1.77).

Thus, in another preferred embodiment, the conversion of 3-methylcrotonic acid via decarboxylasion into isobutene is catalyzed by a 2-oxo-3-hexenedioate decarboxylase (EC 4.1.1.77). 2-oxo-3-hexenedioate decarboxylases (EC 4.1.1.77) naturally catalyze the following reaction:

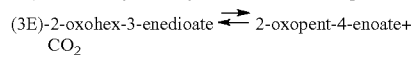

(3E)-2-oxohex-3-enedioate ⇌ 2-oxopent-4-enoate+CO$_2$

The enzyme occurs in a variety of organisms, in particular in prokaryotes, such as bacteria. The enzyme has, e.g., been described in *Bordetella* sp., *Cupriavidus nexator, Geobacillus stearothermophilus* (UniProt Accession number B0VXM8), *Pseudomonas putida* and *Ralstonia pickettii*.

In a preferred embodiment, the 2-oxo-3-hexenedioate decarboxylase (EC 4.1.1.77) employed in the method of the present invention in the conversion 3-methylcrotonic acid via decarboxylasion into isobutene is a 2-oxo-3-hexenedioate decarboxylase derived from *Geobacillus stearothermophilus* (SEQ ID NO:69).

In a preferred embodiment of the present invention the 2-oxo-3-hexenedioate decarboxylase is an enzyme comprising the amino acid sequence of SEQ ID NO: 69 or a sequence which is at least n % identical to SEQ ID NO: 69 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid via decarboxylasion into isobutene. As regards the determination of the sequence identity, the same applies as has been set forth above.

In another possibility, the 3-methylcrotonic acid decarboxylase may preferably be a 5-oxopent-3-ene-1,2,5-tricarboxylate decarboxylase (EC 4.1.1.68).

Thus, in another preferred embodiment, the conversion of 3-methylcrotonic acid via decarboxylasion into isobutene is catalyzed by a 5-oxopent-3-ene-1,2,5-tricarboxylate decarboxylase (EC 4.1.1.68). 5-oxopent-3-ene-1,2,5-tricarboxylate decarboxylases (EC 4.1.1.68) naturally catalyze the following reaction:

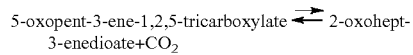

5-oxopent-3-ene-1,2,5-tricarboxylate ⇌ 2-oxohept-3-enedioate+CO$_2$

The enzyme has been described to occur in prokaryotes such as bacteria. The enzyme has, e.g., been described in *E. coli* and *Salmonella dublin*.

In a preferred embodiment, the 5-oxopent-3-ene-1,2,5-tricarboxylate decarboxylase (EC 4.1.1.68) employed in the method of the present invention in the conversion 3-methylcrotonic acid via decarboxylasion into isobutene is a 5-oxopent-3-ene-1,2,5-tricarboxylate decarboxylase derived from *Salmonella dublin* (SEQ ID NO:70).

In a preferred embodiment of the present invention the 5-oxopent-3-ene-1,2,5-tricarboxylate decarboxylase is an enzyme comprising the amino acid sequence of SEQ ID NO: 70 or a sequence which is at least n % identical to SEQ ID NO: 70 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonic acid via decarboxylasion into isobutene. As regards the determination of the sequence identity, the same applies as has been set forth above.

The Enzymatic Conversion of 3-Hydroxyisovalerate (HIV) into 3-Methylcrotonic Acid: Step II as Shown in FIG. 1

The 3-methylcrotonic acid which is converted according to the method of the present invention into isobutene may itself be provided by an enzymatic reaction.

According to the present invention, the 3-methylcrotonic acid can be provided via different routes which are schematically shown in FIG. 1.

Figure 3:
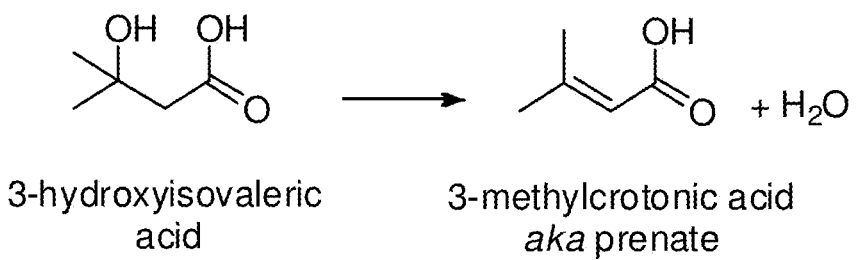

Thus, according to one option, the 3-methylcrotonic acid may itself be provided by the enzymatic conversion of 3-hydroxyisovalerate (HIV) into 3-methylcrotonic acid. The enzymatic conversion of 3-hydroxyisovalerate (HIV) into 3-methylcrotonic acid (step II as shown in FIG. 1) is schematically illustrated in FIG. 3.

According to the present invention, the enzymatic conversion of 3-hydroxyisovalerate (HIV) into said 3-methylcrotonic acid preferably makes use of an enzyme catalyzing the dehydration of a β-hydroxy acid (i.e., e.g., 3-hydroxyisovalerate (HIV)) into an α,β-unsaturated acid (i.e., e.g., 3-methylcrotonic acid). The term "dehydration" generally refers to a reaction involving the removal of $H_2O$. Enzymes catalyzing 3-hydroxyisovalerate (HIV) dehydration are enzymes which catalyze the reaction as shown in FIG. 3. Preferably, such an enzyme belongs to the family of hydro-lyases (EC 4.2.-.-).

Preferred examples of such enzymes which are classified as EC 4.2.-.- (i.e., hydro-lyases) are:
aconitase (EC 4.2.1.3);
fumarase (EC 4.2.1.2); and
enoyl-CoA hydratase/dehydratease (EC 4.2.1.17).

Thus, in one preferred embodiment, the enzymatic conversion of 3-hydroxyisovalerate (HIV) into 3-methylcrotonic acid is achieved by the use of an aconitase (EC 4.2.1.3). Aconitases (EC 4.2.1.3) (also termed aconitase hydratases) are enzymes which catalyze the following reaction:

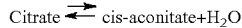
Citrate ⇌ cis-aconitate+$H_2O$

The enzyme is known from a variety of organisms, including eukaryotic and prokaryotic organisms, such as plants, animals, fungi and bacteria. The enzyme has, e.g., been described in *Acer pseudoplatanus, Advenella kashmirensis, Arabidopsis thaliana, Aspergillus niger, Bacillus cereus, Bacillus subtilis, Bacterioides fragilis, Bos taurus, Caenorhabditis elegans, Citrus elementina, Canis lupus familiaris, Corynebacterium glutamicum, Drosophila melanogaster, E. coli, Glycine max, Helobacter pylori, Homo sapiens, Mus musculus, Mycobacterium tuberculosis, Nicotiana benthamiana, Plasmodium falciparum, Pseudomonas aeruginosa, Rattus norvegicus, Rattus rattus, Saccharomyces cerevisiae, Saccharomycopsis lipolytica, Salmonella enterica, Sinapis alba, Sinorhizobium meliloti, Solanum tuberosum, Streptomyces aureus, Streptomyces viridochromogenes, Sulfolobus acidocaldarius, Sulfolobus solfataricus, Sus scorfa, Trametes sanguinea, Trypanosoma brucei, Xanthomonas campestris, Xanthomonas euvesicatoria, Yarrowia lipolytica* and *Zea mays*.

In a preferred embodiment, the aconitase (EC 4.2.1.3) is from *Advenella kashmirensis* (TrEMBL accession number B3TZE0), *Bacteroides fragilis* (SwissProt accession number Q8RP87), *Caenorhabditis elegans* (SwissProt accession number Q23500), *Citrus elementina* (UniProt accession number D3GQL0, D3GQL1, or D3GQL2), *Drosophila melanogaster* (SwissProt accession number Q9NFX3 or Q9NFX2), *E. coli* (SwissProt accession number P36683 or UniProt accession number P25516), *Homo sapiens* (UniProt accession number P21399 or Q99798), *Mus musculus* (UniProt accession number P28271), *Rattus norvegicus* (UniProt accession number Q9ER34 or Q63270), *Sus scorfa* (UniProt accession number P16276) or *Trypanosoma brucei* (SwissProt accession number Q9NJQ8 or Q9NJQ9).

In a preferred embodiment, the aconitase (EC 4.2.1.3) employed in the method of the present invention in the conversion of 3-hydroxyisovalerate (HIV) into 3-methylcrotonic acid is an aconitase derived from *E. coli* (SEQ ID NO:71).

In a preferred embodiment of the present invention the aconitase is an enzyme comprising the amino acid sequence of SEQ ID NO: 71 or a sequence which is at least n % identical to SEQ ID NO: 71 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-hydroxyisovalerate (HIV) into 3-methylcrotonic acid. As regards the determination of the sequence identity, the same applies as has been set forth above.

In another preferred embodiment, the enzymatic conversion of 3-hydroxyisovalerate (HIV) into 3-methylcrotonic acid is achieved by the use of a fumarase (EC 4.2.1.2). Fumarases (EC 4.2.1.2) (also termed fumarase hydratases) are enzymes which catalyze the following reaction:

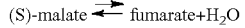
(S)-malate ⇌ fumarate+$H_2O$

The enzyme is known from a variety of organisms, including eukaryotic and prokaryotic organisms, such as plants, animals, fungi and bacteria. The enzyme has, e.g., been described in *Arabidopsis thaliana, Ascaris suum, Azotobacter vinelandii, Brevibacterium flavum, Campylobacter coli, Campylobacter fetus, Campylobacter jejuni, Corynebacterium ammoniagenes, Corynebacterium glutamicum, Erwinia sp., E. coli, Euglena gracilis, Geobacillus stearothermophilus, Gluconacetobacter diazotrophicus, Heliobacter pylori, Homo sapiens, Leishmania major, Mesembryanthemum crystallinum, Mycobacterium tuberculosis, Pelotomaculum thermopropionicum, Pisum sativum, Pseudomonas aeruginosa, Pseudomonas fluorescens, Pycobaculum neutrophilum, Rattus novegicus, Rhizopus oryzae, Rickettsia prowazekii, Saccharomyces bayanus, Saccharomyces cerevisiae, Solanum lycopersicum, Solanum tuberosum, Streptomyces coelicolor, Streptomyces lividans, Streptomyces thermovulgaris, Sulfolobus solfataricus, Sus scrofa, Thermus sp., Thermus thermophilus* and *Zea mays*.

In a preferred embodiment, the fumarase (EC 4.2.1.2) is from *Arabidopsis thaliana* (UniProt accession number P93033 or Q9FI53), *Ascaris suum* (SwissProt accession number Q8NRN8), *Corynebacterium glutamicum* (UniProt accession number P28271), *E. coli* (P05042), *Homo sapiens* (SwissProt accession number P07954), *Mycobacterium tuberculosis* (P9WN93), *Pycobaculum neutrophilum* (UniProt accession number B1Y931 or B1Y932), *Rhizopus oryzae* (UniProt accession number P55250), *Rickettsia prowazekii* (UniProt accession number Q9ZCQ4), *Saccharomyces cerevisiae* (SwissProt accession number P08417), *Streptomyces thermovulgaris* (SwissProt accession number A5Y6J1) or *Sulfolobus solfataricus* (UniProt accession number P39461).

In a preferred embodiment, the fumarase (EC 4.2.1.2) employed in the method of the present invention in the conversion of 3-hydroxyisovalerate (HIV) into 3-methylcrotonic acid is a fumarase derived from *E. coli* (SEQ ID NO:72).

In a preferred embodiment of the present invention the fumarase is an enzyme comprising the amino acid sequence of SEQ ID NO: 72 or a sequence which is at least n % identical to SEQ ID NO: 72 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-hydroxyisovalerate (HIV) into 3-methylcrotonic acid. As regards the determination of the sequence identity, the same applies as has been set forth above.

In another preferred embodiment, the enzymatic conversion of 3-hydroxyisovalerate (HIV) into 3-methylcrotonic acid is achieved by the use of an enoyl-CoA hydratase/dehydratase (EC 4.2.1.17). Enoyl-CoA hydratases/dehydratases (EC 4.2.1.17) catalyze the following reaction:

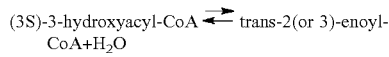

Enoyl-CoA hydratase is an enzyme that normally hydrates the double bond between the second and third carbon atoms on acyl-CoA. However, it can also be employed to catalyze the reaction in the reverse direction.

Enoyl-CoA hydratases/dehydratases (EC 4.2.1.17) are also termed 3-hydroxyacyl-CoA dehydratases and enoyl-CoA hydratases. Both enzymes catalyze the same reaction while the name of one of these enzymes denotes one direction of the corresponding reaction while the other name denotes the reverse reaction. As the reaction is reversible, both enzyme names can be used.

This enzyme, also known as crotonase, is naturally involved in metabolizing fatty acids to produce both acetyl-CoA and energy. Enzymes belonging to this class have been described to occur, e.g. in rat (*Rattus norvegicus*), humans (*Homo sapiens*), mouse (*Mus musculus*), wild boar (*Sus scrofa*), *Bos taurus*, *E. coli, Clostridium acetobutylicum* and *Clostridium aminobutyricum*. Nucleotide and/or amino acid sequences for such enzymes have been determined, e.g. for rat, humans and *Bacillus subtilis* and *Bacillus anthracis*. In principle, any enoyl-CoA hydratase (EC 4.2.1.17) which can catalyze the conversion of 3-hydroxyisovalerate (HIV) into 3-methylcrotonic acid can be used in the context of the present invention. In a preferred embodiment the enoyl-CoA hydratase is an enoyl-CoA hydratase of *Galactomyces reessii* (Dhar et al., J. Ind. Microbiol. Biotechnol. 28 (2002), 81-87), an enoyl-CoA hydratase of *Bacillus subtilis* (Uniprot G4PBC3; SEQ ID NO: 38) or an enoyl-CoA hydratase of *Bacillus anthracis* (Uniprot Q81YG6; SEQ ID NO: 39).

In a preferred embodiment, the enoyl-CoA hydratase employed in the method of the invention has an amino acid sequence as shown in any one of SEQ ID NOs: 38 or 39 or shows an amino acid sequence which is at least x % homologous to any one of SEQ ID NOs: 38 or 39 and has the activity of an enoyl-CoA hydratase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-hydroxyisovalerate (HIV) into 3-methylcrotonic acid as set forth herein above. As regards the determination of the degree of identity, the same applies as has been set forth herein above.

The Enzymatic Condensation of Acetone and Acetyl-CoA into 3-Hydroxyisovalerate (HIV): Step III as Shown in FIG. 1

Figure 4:
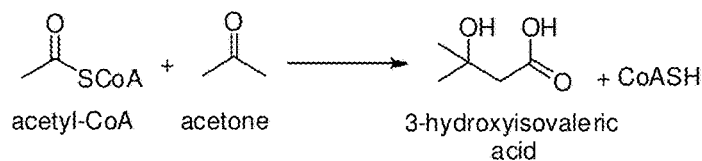

The 3-hydroxyisovalerate (HIV) which is converted according to the method of the present invention into 3-methylcrotonic acid may itself be provided by an enzymatic reaction, namely the enzymatic condensation of acetone and acetyl-CoA into said 3-hydroxyisovalerate (HIV). The condensation of acetone and acetyl-CoA into said 3-hydroxyisovalerate (HIV) (step III as shown in FIG. 1) is schematically illustrated in FIG. 4.

Thus, the present invention also relates to a method for producing isobutene from acetone in which acetone is first condensed with acetyl-CoA into 3-hydroxyisovalerate (HIV) which is then converted into 3-methylcrotonic acid. Further, 3-methylcrotonic acid is then converted into isobutene as described herein above.

According to the present invention, the condensation of acetone and acetyl-CoA into 3-hydroxyisovalerate (HIV) preferably makes use of an enzyme which is capable of catalyzing the formation of a covalent bond between the carbon atom of the oxo (i.e., the C=O) group of acetone and acetyl-CoA, in particular the methyl group of acetyl-CoA. According to this reaction scheme, the oxo group of acetone reacts as an electrophile and the methyl group of acetyl-CoA reacts as a nucleophile. The general reaction of the conversion of acetone and acetyl-CoA is shown in FIG. 4. Enzymes which are capable of enzymatically condensing acetone and acetyl-CoA into 3-hydroxyisovalerate (HIV) are known in the art and have, e.g., been described in WO 2011/032934.

Preferably, the enzyme employed in the enzymatic condensation of acetone and acetyl-CoA into 3-hydroxyisovalerate (HIV) is an enzyme with the activity of a HMG CoA synthase (EC 2.3.3.10) and/or a PksG protein and/or an enzyme with the activity of a C—C bond cleavage/condensation lyase, such as a HMG CoA lyase (EC 4.1.3.4). HMG CoA synthase has been described for various organisms.

Examples of HMG CoA synthases from different organisms are given in SEQ ID NO: 1 to 16. SEQ ID NO: 1 shows the sequence of the cytoplasmic HMG CoA synthase of *Caenorhabditis elegans* (P54871, gene bank F25B4.6), SEQ ID NO: 2 shows the sequence of the cytoplasmic HMG CoA synthase of *Schizosaccharomyces pombe* (fission yeast; P54874), SEQ ID NO: 3 shows the sequence of the cytoplasmic HMG CoA synthase of *Saccharomyces cerevisiae* (baker's yeast; P54839, gene bank CAA65437.1), SEQ ID NO: 4 shows the sequence of the cytoplasmic HMG CoA synthase of *Arabidopsis thaliana* (Mouse-ear cress; P54873), SEQ ID NO: 5 shows the sequence of the cytoplasmic HMG CoA synthase of *Dictyostelium discoideum* (Slime mold; P54872, gene bank L2114), SEQ ID NO: 6 shows the sequence of the cytoplasmic HMG CoA synthase of *Blattella germanica* (German cockroach; P54961, gene bank X73679), SEQ ID NO: 7 shows the sequence of the cytoplasmic HMG CoA synthase of *Gallus gallus* (Chicken; P23228, gene bank CHKHMGCOAS), SEQ ID NO: 8 shows the sequence of the cytoplasmic HMG CoA synthase of *Homo sapiens* (Human; Q01581, gene bank X66435), SEQ ID NO: 9 shows the sequence of the mitochondrial HMG CoA synthase of *Homo sapiens* (Human; P54868, gene bank X83618), SEQ ID NO: 10 shows the sequence of the mitochondrial HMG CoA synthase of *Dictyostelium discoideum* (Slime mold; Q86HL5, gene bank XM_638984), SEQ ID NO: 11 shows the sequence of the HMG CoA synthase of *Staphylococcus epidermidis* (Q9FD76), SEQ ID NO: 12 shows the sequence of the HMG CoA synthase of *Lactobacillus fermentum* (B2GBL1), SEQ ID NO: 13 shows the sequence of the HMG CoA synthase of *Hyperthermus butylicus* (A2BMY8), SEQ ID NO: 14 shows the sequence of the HMG CoA synthase of *Chloroflexus aggregans* (B8G795), SEQ ID NO: 15 shows the sequence of the HMG CoA synthase of *Lactobacillus delbrueckii* (Q1GAH5) and SEQ ID NO: 16 shows the sequence of the HMG CoA synthase of *Staphylococcus haemolyticus* Q4L958 (I98>V difference compared to wild type protein).

In a preferred embodiment of the present invention the HMG CoA synthase is an enzyme comprising an amino acid sequence selected from the group consisting of SEQ ID NOs: 1 to 16 or a sequence which is at least n % identical to any of SEQ ID NOs: 1 to 16 and having the activity of a HMG CoA synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

As regards the determination of sequence identity, the same applies as has been set forth above.

Another example for a protein which can be used in the condensation of acetone and acetyl-CoA into 3-hydroxyisovalerate is a PksG protein. In the context of the present application the term "PksG protein" or "a protein/enzyme having the activity of a PksG protein" refers to any enzyme which is able to catalyze the reaction which is naturally catalyzed by the PksG protein, i.e., the transfer of —$CH_2COO^-$ from acetyl-S-AcpK (Ac-S-AcpK) to a β-ketothioester polyketide intermediate linked to one of the thiolation domains of the PksL protein. This is a reaction which is analogous to that catalyzed by HMG CoA synthase with the difference that the acetyl-thioester of the phosphopantetheyl moiety is attached to a carrier protein rather than to part of Coenzyme A. Although the PksG protein in the reaction which it naturally catalyzes transfers the acetyl group from acetyl-S-AcpK to an acceptor, it has been shown previously that the PksG protein can also effect the reaction which is normally catalyzed by HMG CoA synthase, i.e. the synthesis of HMG CoA starting from acetoacetyl CoA and acetyl CoA.

Examples of PksG proteins are given in SEQ ID NO: 17 and 18. Preferably, the PksG protein is an enzyme comprising an amino acid sequence which is at least n % identical to SEQ ID NO: 17 or 18 and having the activity of a PksG protein with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

SEQ ID NO: 17 shows the amino acid sequence of the PksG protein of *Bacillus subtilis* (P40830) and SEQ ID NO: 18 shows the amino acid sequence of the PksG protein of *Mycobacterium marinum* (B2HGT6).

As regards the determination of the degree of sequence identity the same applies as has been set forth above in connection with HMG CoA synthase.

Examples of "C—C bond cleavage/condensation lyases" in particular include enzymes which are classified as isopropylmalate synthase (EC 2.3.3.13), as homocitrate synthase (EC 2.3.3.14) or as 4-hydroxy-2-ketovalerate aldolase (EC 4.1.3.39). Isopropylmalate synthase catalyzes the following reaction: acetyl-CoA+3-methyl-2-oxobutanoate+ $H_2O \rightleftharpoons$ (2S)-2-isopropylmalate+CoA. Examples for such enzymes are the corresponding enzyme from *Brucella abortus* (strain 2308; Q2YRT1) and the corresponding enzyme from *Hahella chejuensis* (strain KCTC 2396; Q2SFA7).

A homocitrate synthase (EC 2.3.3.14) is an enzyme that catalyzes the chemical reaction acetyl-CoA+$H_2O$+2-oxoglutarate$\rightleftharpoons$(R)-2-hydroxybutane-1,2,4-tricarboxylate+CoA.
The 4-hydroxy-2-ketovalerate aldolase catalyzes the chemical reaction 4-hydroxy-2-oxopentanoate$\rightleftharpoons$acetaldehyde+pyruvate.

Examples for enzymes classified as "HMG CoA lyase" or "a protein/enzyme having the activity of a HMG CoA lyase" in the EC number EC 4.1.3.4, are given in SEQ ID NOs: 19 to 25. SEQ ID NO: 19 shows the sequence of the HMG CoA lyase of *Zea mays* (Accession number B6U7B9, gene bank ACG45252), SEQ ID NO: 20 shows the sequence of the HMG CoA lyase of *Danio rerio* (*Brachydanio rerio*; A8WG57, gene bank BC154587), SEQ ID NO: 21 shows the sequence of the HMG CoA lyase of *Bos taurus* (Uniprot accession number Q29448) and SEQ ID NO: 22 shows the sequence of the HMG CoA lyase of *Homo sapiens* (mitochondrial, Uniprot accession number P35914, gene bank HUMHYMEGLA), SEQ ID NO: 23 shows the sequence of the HMG CoA lyase of *Pseudomonas putida* (Q88H25), SEQ ID NO: 24 shows the sequence of the HMG CoA lyase of *Acinetobacter baumannii* (B7H4C6) and SEQ ID NO: 25 shows the sequence of the HMG CoA lyase of *Thermus thermophilus* (Q72IH0).

In a preferred embodiment of the present invention the HMG CoA lyase is an enzyme comprising an amino acid sequence selected from the group consisting of SEQ ID NOs: 19 to 25 or a sequence which is at least n % identical to any of SEQ ID NOs: 19 to 25 and having the activity of a HMG CoA lyase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

As regards the determination of the degree of sequence identity the same applies as has been set forth above in connection with HMG CoA synthase.

The Enzymatic Conversion of Acetoacetate into Acetone: Step IV as Shown in FIG. 1

Figure 5:
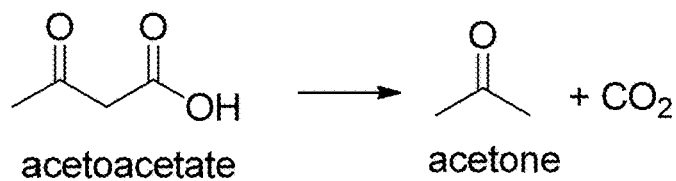

The acetone which is converted according to the method of the present invention into 3-hydroxyisovalerate (HIV) may itself be provided by an enzymatic reaction, namely the enzymatic conversion of acetoacetate into acetone. The conversion of acetoacetate into acetone (step IV as shown in FIG. 1) is schematically illustrated in FIG. 5. This reaction is a decarboxylation reaction and is a natural occurring reaction in organisms capable of producing acetone, i.e., organisms of the genus *Clostridia*.

Thus, the present invention also relates to a method for producing isobutene from acetoacetate in which acetoacetate is first converted into acetone which is then condensed with acetyl-CoA into 3-hydroxyisovalerate (HIV) which is then converted into 3-methylcrotonic acid as described herein above. Further, said 3-methylcrotonic acid is then converted into isobutene as described herein above.

According to the present invention, the conversion of acetoacetate into said acetone preferably makes use of an acetoacetate decarboxylase (EC 4.1.1.4). Nucleotide sequences from several organisms encoding this enzyme are known in the art, e.g. the adc gene from *Clostridium acetobutylicum* (Uniprot accession numbers P23670 and P23673), *Clostridium beijerinckii* (*Clostridium* MP; Q9RPK1), *Clostridium pasteurianum* (Uniprot accession number P81336), *Bradyrhizobium* sp. (strain BTAi1/ATCC BAA-1182; Uniprot accession number A5EBU7), *Burkholderia mallei* (ATCC 10399 A9LBS0), *Burkholderia mallei* (Uniprot accession number A3MAE3), *Burkholderia mallei* FMH A5XJB2, *Burkholderia cenocepacia* (Uniprot accession number A0B471), *Burkholderia ambifaria* (Uniprot accession number Q0b5P1), *Burkholderia phytofirmans* (Uniprot accession number B2T319), *Burkholderia* spec. (Uniprot accession number Q38ZU0), *Clostridium botulinum* (Uniprot accession number B2TLN8), *Ralstonia pickettii* (Uniprot accession number B2UIG7), *Streptomyces nogalater* (Uniprot accession number Q9EYI7), *Streptomyces avermitilis* (Uniprot accession number Q82NF4), *Legionella pneumophila* (Uniprot accession number Q5ZXQ9), *Lactobacillus salivarius* (Uniprot accession number Q1WVG5), *Rhodococcus* spec. (Uniprot accession number Q0S7W4), *Lactobacillus plantarum* (Uniprot accession number Q890G0), *Rhizobium leguminosarum* (Uniprot accession number Q1M911), *Lactobacillus casei* (Uniprot accession number Q031366), *Francisella tularensis* (Uniprot accession number Q0BLC9), *Saccharopolyspora erythreae* (Uniprot accession number A4FKR9), *Korarchaeum cryptofilum* (Uniprot accession number B1L3N6), *Bacillus amyloliquefaciens* (Uniprot accession number A7Z8K8), *Cochliobolus heterostrophus* (Uniprot accession number Q8NJQ3), *Sulfolobus islandicus* (Uniprot accession number C3ML22) and *Francisella tularensis* subsp. *holarctica* (strain OSU18).

In a preferred embodiment, the acetoacetate decarboxylase employed in the method of the present invention in the conversion of acetoacetate into acetone is an acetoacetate decarboxylase (EC 4.1.1.4) derived from *Clostridium acetobutylicum* (Uniprot accession numbers P23670 and P23673).

The Enzymatic Conversion of Acetoacetyl-CoA into Acetoacetate: Step Va and Step Vb as Shown in FIG. 1

Figure 6:
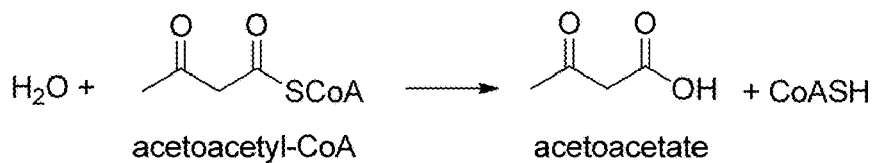
Figure 7:
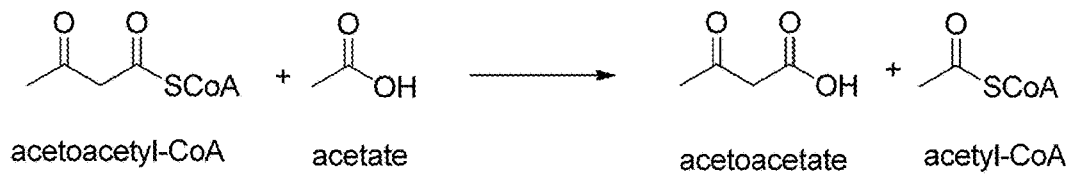

The acetoacetate which is converted according to the method of the present invention into acetone may itself be provided by an enzymatic reaction, namely the enzymatic conversion of acetoacetyl-CoA into acetoacetate. The conversion of acetoacetyl-CoA into acetoacetate can be achieved by two different routes. One possibility is the conversion of acetoacetyl-CoA into acetoacetate by hydrolysing the CoA thioester of acetoacetyl-CoA into acetoacetate. This reaction (step Va as shown in FIG. 1) is schematically illustrated in FIG. 6. In another, more preferred, aspect the CoA group of acetoacetyl-CoA is transferred on acetate, resulting in the formation of acetoacetate and acetyl-CoA. This reaction (step Vb as shown in FIG. 1) is schematically illustrated in FIG. 7.

Thus, the present invention also relates to a method for producing isobutene from acetoacetyl-CoA in which acetoacetyl-CoA is first converted into acetoacetate which is then converted into acetone which is then condensed with acetyl-CoA into 3-hydroxyisovalerate (HIV) which is then converted into 3-methylcrotonic acid as described herein above. Further, said 3-methylcrotonic acid is then converted into isobutene as described herein above.

As mentioned, in one aspect, the CoA thioester of acetoacetyl-CoA is hydrolyzed to result in acetoacetate. According to this aspect of the present invention, the enzymatic conversion of acetoacetyl-CoA into acetoacetate is achieved by preferably making use of an acetoacetyl-CoA hydrolase (EC 3.1.2.11) which naturally catalyzes this reaction.

Acetoacetyl-CoA hydrolases (EC 3.1.2.11) catalyse the following reaction:

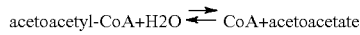

acetoacetyl-CoA+H2O ⇌ CoA+acetoacetate

This enzyme is known from various organisms and has, e.g., been described in eukaryotic organisms. The enzyme has, e.g., been described in *Bos taurus, Columba livia, Gallus gallus, Homo sapiens, Mus musculus, Oncorhynchus mykiss, Oryctolagus cuniculus*, or *Rattus norvegicus*. Thus, in a preferred embodiment, the enzyme is from the genus selected from the group consisting of Bos, *Columba, Gallus, Mus, Oncorhynchus, Oryctolagus*, and *Rattus*. In a more preferred embodiment, the enzyme is from the species selected from the group consisting of *Bos taurus, Columba livia, Gallus gallus, Homo sapiens, Mus musculus, Oncorhynchus mykiss, Oryctolagus cuniculus*, or *Rattus norvegicus*. *Bos taurus, Columba livia, Gallus gallus, Homo sapiens, Mus musculus, Oncorhynchus mykiss, Oryctolagus cuniculus*, and *Rattus norvegicus*.

As mentioned, in another, more preferred, possibility, the CoA group of acetoacetyl-CoA is transferred on acetate, resulting in the formation of acetoacetate and acetyl-CoA.

According to this possibility of the present invention, the enzymatic conversion of acetoacetyl-CoA into acetoacetate is achieved by preferably making use of an enzyme which is capable of transferring the CoA group of acetoacetyl-CoA on acetate.

Preferably, such an enzyme capable of transferring the CoA group of acetoacetyl-CoA on acetate belongs to the family of CoA transferases (EC 2.8.3.-).

Thus, the present invention relates to a method for the enzymatic conversion of acetoacetyl-CoA into acetoacetate by making use of an enzyme capable of transferring the CoA group of acetoacetyl-CoA on acetate, preferably a CoA transferase (EC 2.8.3.-). A preferred example of an enzyme catalysing the conversion of acetoacetyl-CoA into acetoacetate which can be employed in the method of the present invention is an enzyme classified as an acetate CoA transferase (EC 2.8.3.8).

Acetate CoA transferases (EC 2.8.3.8) catalyse the following reaction:

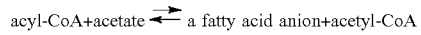

acyl-CoA+acetate ⇌ a fatty acid anion+acetyl-CoA

Acetate CoA transferases (EC 2.8.3.8) are known from various organisms, e.g., from *E. coli* in which it is encoded by the atoD gene atoA genes (UniProt accession numbers P76458 and P76459). An acetate CoA transferase is also known from *Clostrtidium acetobutylicum* in which it is encoded by the ctfAB gene. Thus, in a preferred embodiment, of the invention, an acetate CoA transferase (EC 2.8.3.8) is used for the conversion of acetoacetyl-CoA into acetoacetate which is derived from *E. coli* and which it is encoded by the atoD gene atoA genes (UniProt accession numbers P76458 and P76459) or which is derived from *Clostrtidium acetobutylicum* and which it is encoded by the ctfAB gene.

The Enzymatic Conversion of 3-Methylcrotonyl-CoA into 3-Methylcrotonic Acid: Step VI as Shown in FIG. 1

The 3-methylcrotonic acid can be provided by another possible route which is described in the following.

Figure 8:
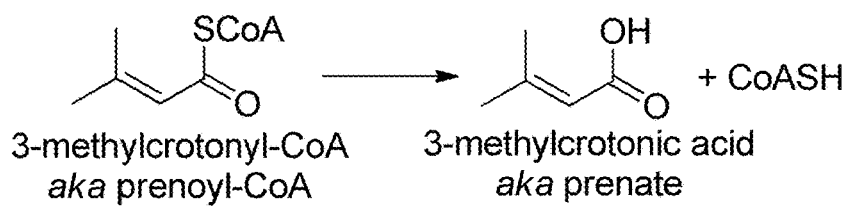

Thus, in another embodiment, the 3-methylcrotonic acid which is converted into isobutene may itself be provided by another enzymatic reaction, namely the enzymatic conversion of 3-methylcrotonyl-CoA into 3-methylcrotonic acid. The conversion of 3-methylcrotonyl-CoA into 3-methylcrotonic acid (step VI as shown in FIG. 1) is schematically illustrated in FIG. 8.

The conversion of 3-methylcrotonyl-CoA into 3-methylcrotonic acid can, e.g., be achieved in different ways, e.g., by three alternative enzymatic routes described in the following and as shown in FIG. 1 (step VIa, step VIb or step VIc as shown in FIG. 1).

Thus, the enzymatic conversion of 3-methylcrotonyl-CoA into 3-methylcrotonic acid may be achieved by (a) a single enzymatic reaction in which 3-methylcrotonyl-CoA is directly converted into 3-methylcrotonic acid, preferably by making use of a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18) (step VIa as shown in FIG. 1);

(b) a single enzymatic reaction in which 3-methylcrotonyl-CoA is directly converted into 3-methylcrotonic acid, preferably by making use of a thioester hydrolase (EC 3.1.2.-), preferably an acetyl-CoA hydrolase (EC 3.1.2.1), an ADP-dependent short-chain-acyl-CoA hydrolase (EC 3.1.2.18) or an acyl-CoA hydrolase (EC 3.1.2.20) (step VIb as shown in FIG. 1); or (c) two enzymatic steps comprising
  (i) first enzymatically converting 3-methylcrotonyl-CoA into 3-methylcrotonyl phosphate; and
  (ii) then enzymatically converting the thus obtained 3-methylcrotonyl phosphate into said 3-methylcrotonic acid (step VIc as shown in FIG. 1).

Thus, one possibility is a two-step conversion from 3-methylcrotonyl-CoA via 3-methylcrotonyl phosphate into 3-methylcrotonic acid. Two other options involve a direct conversion of 3-methylcrotonyl-CoA into 3-methylcrotonic acid. These three options will be discussed in the following.

Figure 11:
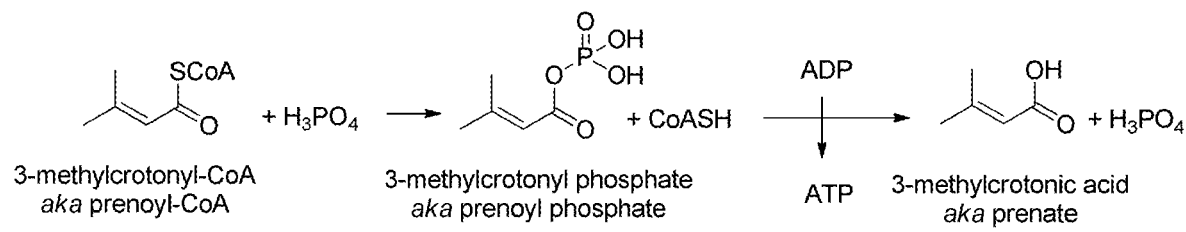

Accordingly, in one embodiment, the enzymatic conversion of 3-methylcrotonyl-CoA into 3-methylcrotonic acid is achieved by two enzymatic steps comprising (i) first enzymatically converting 3-methylcrotonyl-CoA into 3-methylcrotonyl phosphate; and (ii) then enzymatically converting the thus obtained 3-methylcrotonyl phosphate into said 3-methylcrotonic acid (as shown in step VIc of FIG. 1). The corresponding reaction is schematically shown in FIG. 11.

The conversion of 3-methylcrotonyl-CoA into 3-methylcrotonyl phosphate can, e.g., be achieved by the use of a phosphate butyryltransferase (EC 2.3.1.19) or a phosphate acetyltransferase (EC 2.3.1.8).

Phosphate butyryltransferase (EC 2.3.1.19) naturally catalyzes the following reaction

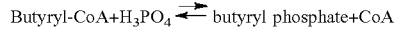

It has been described by Wiesenborn et al. (Appl. Environ. Microbiol. 55 (1989), 317-322) and by Ward et al. (J. Bacteriol. 181 (1999), 5433-5442) that phosphate butyryltransferases (EC 2.3.1.19) can use a number of substrates in addition to butyryl coenzyme A (butyryl-CoA), in particular acetyl-CoA, propionyl-CoA, isobutyryl-CoA, valeryl-CoA and isovaleryl-CoA.

The enzyme has been described to occur in a number of organisms, in particular in bacteria and in protozoae. In one embodiment the enzyme is from the protozoae *Dasytricha ruminantium*. In a preferred embodiment the phosphate butyryltransferase is a phosphate butyryltransferase from a bacterium, preferably from a bacterium of the genus *Bacillus, Butyrivibrio, Enterococcus* or *Clostridium*, more preferably *Enterococcus* or *Clostridium*, and even more preferably from *Bacillus megaterium, Bacillus subtilis, Butyrivibrio fibrisolvens, Clostridium acetobutylicum, Clostridium beijerinckii, Clostridium butyricum, Clostridium kluyveri, Clostridium saccharoacetobutylicum, Clostridium sprorogenes* or *Enterococcus faecalis*. Most preferably, the enzyme is from *Clostridium acetobutylicum*, in particular the enzyme encoded by the ptb gene (Uniprot Accession number F0K6W0; Wiesenborn et al. (Appl. Environ. Microbiol. 55 (1989), 317-322)) or from *Enterococcus faecalis* (Uniprot Accession number K4YRE8; Ward et al. (J. Bacteriol. 181 (1999), 5433-5442)).

In a preferred embodiment, the conversion of 3-methylcrotonyl-CoA into 3-methylcrotonyl phosphate is achieved by making use of a phosphate butyryltransferase from *Clostridium acetobutylicum*, preferably from *Clostridium acetobutylicum* strain ATCC 824. The amino acid sequence of said protein is shown in SEQ ID NO: 26.

It is, of course, not only possible to use an enzyme exactly showing this amino acid of SEQ ID NO:26. It is also possible to use an enzyme which comprises a sequence which is at least 60% identical to the amino acid sequence shown in SEQ ID NO: 26. Preferably, the sequence identity is at least 70%, more preferably at least 80%, 85% or 90%, even more preferably 91%, 92%, 93,%, 94%, 95%, 96%, 97%, 98% and particularly preferred at least 99% to SEQ ID NO:26 and the enzyme has the enzymatic activity of converting 3-methylcrotonyl-CoA into 3-methylcrotonyl phosphate. As regards the determination of the sequence identity, the same applies as has been set forth above.

In another preferred embodiment, the conversion of 3-methylcrotonyl-CoA into 3-methylcrotonyl phosphate is achieved by making use of a phosphate butyryltransferase from *Bacillus subtilis*, preferably from *Bacillus subtilis* having the UniProt Accession number P54530. The amino acid sequence of said protein is shown in SEQ ID NO: 73.

In a preferred embodiment of the present invention the phosphate butyryltransferase is an enzyme comprising the amino acid sequence of SEQ ID NO: 73 or a sequence which is at least n % identical to SEQ ID NO: 73 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonyl-CoA into 3-methylcrotonyl phosphate. As regards the determination of the sequence identity, the same applies as has been set forth above.

In another preferred embodiment, the conversion of 3-methylcrotonyl-CoA into 3-methylcrotonyl phosphate is achieved by making use of a phosphate butyryltransferase from *Enterococcus faecalis*, preferably from *Enterococcus faecalis* having the UniProt Accession number S4BZL5. The amino acid sequence of said protein is shown in SEQ ID NO: 74.

In a preferred embodiment of the present invention the phosphate butyryltransferase is an enzyme comprising the amino acid sequence of SEQ ID NO: 74 or a sequence which is at least n % identical to SEQ ID NO: 74 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonyl-CoA into 3-methylcrotonyl phosphate. As regards the determination of the sequence identity, the same applies as has been set forth above.

Phosphate acetyltransferase (EC 2.3.1.8) naturally catalyzes the following reaction

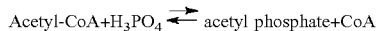

It has been described by Veit et al. (J. Biotechnol. 140 (2009), 75-83) that phosphate acetyltransferase can also use as a substrate butyryl-CoA or propionyl-CoA.

The accession numbers for this enzyme family in InterPro database are IPR012147 and IPR002505, "http://www.ebi.ac.uk/interpro/entry/IPR002505" (http://www.ebi.ac.uk/interpro/entry/IPR012147 http://www.ebi.ac.uk/interpro/entry/IPR002505) See also http://pfam.sanger.ac.uk/family/PF01515

The enzyme has been described in a variety of organisms, in particular bacteria and fungi. Thus, in one preferred embodiment the enzyme is an enzyme from a bacterium, preferably of the genus *Escherichia, Chlorogonium, Clostridium, Veillonella, Methanosarcina, Corynebacterium, Ruegeria, Salmonella, Azotobacter, Bradorhizobium, Lactobacillus, Moorella, Rhodopseudomonas, Sinorhizobium, Streptococcus, Thermotoga* or *Bacillus*, more preferably of the species *Escherichia coli, Chlorogonium elongatum, Clostridium kluyveri, Clostridium acetobutylicum, Clostridium acidurici, Veillonella parvula, Methanosarcina thermophila, Corynebacterium glutamicum, Ruegeria pomeroyi, Salmonella enterica, Azotobacter vinelandii, Bradyrhizobium japonicum, Lactobacillus fermentum, Lactobacillus sanfranciscensis, Moorella thermoacetica, Rhodopseudomonas palustris, Sinorhizobium meliloti, Streptococcus pyogenes, Thermotoga maritima or Bacillus subtilis. In another preferred embodiment the enzyme is an enzyme from a fungus, preferably from the genus Saccharomyces, more preferably of the species Saccharomyces cerevisiae.

In a preferred embodiment, the conversion of 3-methylcrotonyl-CoA into 3-methylcrotonyl phosphate is achieved by making use a phosphate acetyltransferase from Corynebacterium glutamicum, preferably from Corynebacterium glutamicum strain ATCC 13032. The amino acid sequence of said protein is shown in SEQ ID NO: 27.

It is, of course, not only possible to use an enzyme exactly showing this amino acid of SEQ ID NO:27. It is also possible to use an enzyme which comprises a sequence which is at least 60% identical to the amino acid sequence shown in SEQ ID NO: 27. Preferably, the sequence identity is at least 70%, more preferably at least 80%, 85% or 90%, even more preferably 91%, 92%, 93,%, 94%, 95%, 96%, 97%, 98% and particularly preferred at least 99% to SEQ ID NO:27 and the enzyme has the enzymatic activity of converting 3-methylcrotonyl-CoA into 3-methylcrotonyl phosphate. As regards the determination of the sequence identity, the same applies as has been set forth above.

The conversion of 3-methylcrotonyl phosphate into 3-methylcrotonic acid can, e.g., be achieved by making use of an enzyme which is classified as EC 2.7.2.-, i.e., a phosphotransferase. Such enzymes use a carboxy group as acceptor. Thus, the conversion of 3-methylcrotonyl phosphate into 3-methylcrotonic acid can, e.g., be achieved by making use of an enzyme with a carboxy group as acceptor (EC 2.7.2.-). In a preferred embodiment, the conversion of 3-methylcrotonyl phosphate into 3-methylcrotonic acid is achieved by the use of a propionate kinase (EC 2.7.2.15), an acetate kinase (EC 2.7.2.1), a butyrate kinase (EC 2.7.2.7) or a branched-chain-fatty-acid kinase (EC 2.7.2.14).

Butyrate kinases (EC 2.7.2.7) naturally catalyze the following reaction

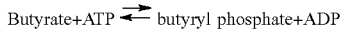
Butyrate+ATP ⇌ butyryl phosphate+ADP

It has been described, e.g. by Hartmanis (J. Biol. Chem. 262 (1987), 617-621) that butyrate kinase can use a number of substrates in addition to butyrate, e.g. valerate, isobutyrate, isovalerate and vinyl acetate. The enzyme has been described in a variety of organisms, in particular bacteria. In one preferred embodiment the enzyme is from a bacterium, preferably from a bacterium of the genus Clostridium, Butyrivibrio, Thermotoga or Enterococcus. Preferred is Clostridium. More preferably the enzyme is from a bacterium of the species Clostridium acetobutylicum, Clostridium proteoclasticum, Clostridium tyrobutyricum, Clostridium butyricum, Clostridium pasteurianum, Clostridium tetanomorphum, Butyrivibrio firbrosolvens, Butyrivibrio hungatei, Thermotoga maritime or Enterococcus durans. Preferred is Clostridium acetobutylicum. For this organism two butyrate kinases have been described: butyrate kinase 1 (Uniprot Accession number: Q45829) and butyrate kinase II (Uniprot Accession number: Q97II9).

In another preferred embodiment, the conversion of 3-methylcrotonyl phosphate into 3-methylcrotonic acid is achieved by making use of a butyrate kinase from Lactobacillus, preferably from Lactobacillus casei (UniProt Accession number K0N529) or a butyrate kinase from Geobacillus, preferably from Geobacillus sp. (UniProt Accession number L8A0E1). The amino acid sequence of these proteins are shown in SEQ ID NO:75 and SEQ ID NO:76, respectively.

In a preferred embodiment of the present invention the butyrate kinase is an enzyme comprising the amino acid sequence of SEQ ID NO: 75 or 76 or a sequence which is at least n % identical to SEQ ID NO: 75 or 76 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylcrotonyl phosphate into 3-methylcrotonic acid. As regards the determination of the sequence identity, the same applies as has been set forth above.

Branched-chain-fatty-acid kinases (EC 2.7.2.14) naturally catalyze the following reaction

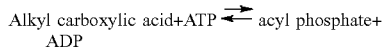
Alkyl carboxylic acid+ATP ⇌ acyl phosphate+ADP wherein "alkyl" may be 2-methylbutanoate, butanoate, isobutanoate, pentanoate or propionate. The latter reaction with propionate has been described for a branched-chain fatty acid kinase from a spirochaete (J. Bacteriol. 152 (1982), 246-54). This enzyme has been described to occur in a number of bacteria. Thus, in one preferred embodiment the enzyme is an enzyme from a bacterium, preferably of the genus Spirochaeta or Thermotoga, more preferably Thermotoga maritime.

Propionate kinases (EC 2.7.2.15) naturally catalyze the following reactions

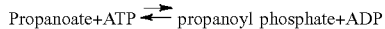
Propanoate+ATP ⇌ propanoyl phosphate+ADP

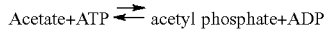
Acetate+ATP ⇌ acetyl phosphate+ADP

This enzyme has been described to occur in a number of bacteria, in particular Enterobacteriaceae. Thus, in one preferred embodiment the enzyme is an enzyme from a bacterium, preferably of the genus Salmonella or Escherichia, more preferably of the species Salmonella enterica, Salmonella typhimurium or Escherichia coli.

In a preferred embodiment, the conversion of 3-methylcrotonyl phosphate into 3-methylcrotonic acid is achieved by making use of a propionate kinase from Salmonella typhimurium, preferably from Salmonella typhimurium strain ATCC 700720. The amino acid sequence of said protein is shown in SEQ ID NO: 28.

It is, of course, not only possible to use an enzyme exactly showing this amino acid of SEQ ID NO:28. It is also possible to use an enzyme which comprises a sequence which is at least 60% identical to the amino acid sequence shown in SEQ ID NO: 28. Preferably, the sequence identity is at least 70%, more preferably at least 80%, 85% or 90%, even more preferably 91%, 92%, 93,%, 94%, 95%, 96%, 97%, 98% and particularly preferred at least 99% to SEQ ID NO:28 and the enzyme has the enzymatic activity of converting 3-methylcrotonyl phosphate into 3-methylcrotonic acid. As regards the determination of the sequence identity, the same applies as has been set forth above.

In another preferred embodiment, the conversion of 3-methylcrotonyl phosphate into 3-methylcrotonic acid is achieved by making use of a propionate kinase from Escherichia coli, preferably from Escherichia coli strain K12. The amino acid sequence of said protein is shown in SEQ ID NO: 29.

It is, of course, not only possible to use an enzyme exactly showing this amino acid of SEQ ID NO:29. It is also possible to use an enzyme which comprises a sequence which is at least 60% identical to the amino acid sequence shown in SEQ ID NO: 29. Preferably, the sequence identity is at least 70%, more preferably at least 80%, 85% or 90%, even more preferably 91%, 92%, 93,%, 94%, 95%, 96%, 97%, 98% and particularly preferred at least 99% to SEQ ID NO:29 and the enzyme has the enzymatic activity of converting 3-methylcrotonyl phosphate into 3-methylcrotonic acid. As regards the determination of the sequence identity, the same applies as has been set forth above.

Acetate kinases (EC 2.7.2.1) naturally catalyze the following reaction

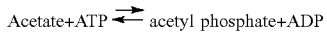

Acetate+ATP ⇌ acetyl phosphate+ADP

This enzyme has been described to occur in a number of organisms, in particular bacteria and eukaryotes. In one preferred embodiment the enzyme is from a bacterium, preferably from a bacterium of the genus *Methanosarcina, Cryptococcus, Ethanoligenens, Propionibacterium, Roseovarius, Streptococcus, Salmonella, Acholeplasma, Acinetobacter, Ajellomyces, Bacillus, Borrelia, Chaetomium, Clostridium, Coccidioides, Coprinopsis, Cryptococcus, Cupriavidus, Desulfovibrio, Enterococcus, Escherichia, Ethanoligenes, Geobacillus, Helicobacter, Lactobacillus, Lactococcus, Listeria, Mesoplasma, Moorella, Mycoplasma, Oceanobacillus, Propionibacterium, Rhodospeudomonas, Roseovarius, Salmonella, Staphylococcus, Thermotoga* or *Veillonella*, more preferably from a bacterium of the species *Methanosarcina thermophila, Cryptococcus neoformans, Ethanoligenens harbinense, Propionibacterium acidipropionici, Streptococcus pneumoniae, Streptococcus enterica, Streptococcus pyogenes, Acholeplasma laidlawii, Acinetobacter calcoaceticus, Ajellomyces capsulatus, Bacillus subtilis, Borrelia burgdorferi, Chaetomium globosum, Clostridium acetobutylicum, Clostridium thermocellum, Coccidioides immitis, Coprinopsis cinerea, Cryptococcus neoformans, Cupriavidus necator, Desulfovibrio vulgaris, Enterococcus faecalis, Escherichia coli, Ethanoligenes harbinense, Geobacillus stearothermophilus, Helicobacter pylori, Lactobacillus delbrueckii, Lactobacillus acidophilus, Lactobacillus sanfranciscensis, Lactococcus lactis, Listeria monocytogenes, Mesoplasma florum, Methanosarcina acetivorans, Methanosarcina mazei, Moorella thermoacetica, Mycoplasma pneumoniae, Oceanobacillus iheyensis, Propionibacterium freudenreichii, Propionibacterium acidipropionici, Rhodospeudomonas palustris, Salmonella enteric, Staphylococcus aureus, Thermotoga maritime* or *Veillonella parvula*.

In another preferred embodiment the enzyme is an enzyme from a fungus, preferably from a fungus of the genus *Aspergillus, Gibberella, Hypocrea, Magnaporthe, Phaeosphaeria, Phanerochaete, Phytophthora, Sclerotinia, Uncinocarpus, Ustilago* or *Neurospora* even more preferably from a fungus of the species *Aspergillus fumigates, Aspergillus nidulans, Gibberella zeae, Hypocrea jecorina, Magnaporthe grisea, Phaeosphaeria nodorum, Phanerochaete chrysosporium, Phytophthora ramorum, Phytophthora sojae, Sclerotinia sclerotiorum, Uncinocarpus reesii, Ustilago maydis* or *Neurospora crassa*.

In a further preferred embodiment the enzyme is an enzyme from a plant or an algae, preferably from the genus *Chlamydomonas*, even more preferably from the species *Chlamydomonas reinhardtii*.

In another embodiment the enzyme is from an organism of the genus *Entamoeba*, more preferably of the species *Entamoeba histolytica*.

The above mentioned enzyme families suitable for the conversion of 3-methylcrotonyl-CoA into 3-methylcrotonyl phosphate have been shown to be evolutionary related and contain common sequence signatures. Theses signatures are referenced and described in Prosite database: http://prosite.expasy.org/cgi-bin/prosite/nicedoc.pl?PS01075

Gao et al. (FEMS Microbiol. Lett. 213 (2002), 59-65) already described genetically modified *E. coli* cells which have been transformed, inter alia, with the ptb gene and the buk gene from *Clostridium acetobutylicum* encoding a phosphate butyryltransferase (EC 2.3.1.19) and a butyrate kinase (EC 2.7.2.7), respectively. These *E. coli* cells have been shown to be able to produce D-(−)-3-hydroxybutyric acid (3HB).

As mentioned above, the conversion of 3-methylcrotonyl-CoA into 3-methylcrotonic acid can also be achieved by two alternative conversions wherein 3-methylcrotonyl-CoA is directly converted into 3-methylcrotonic acid.

Figure 10:
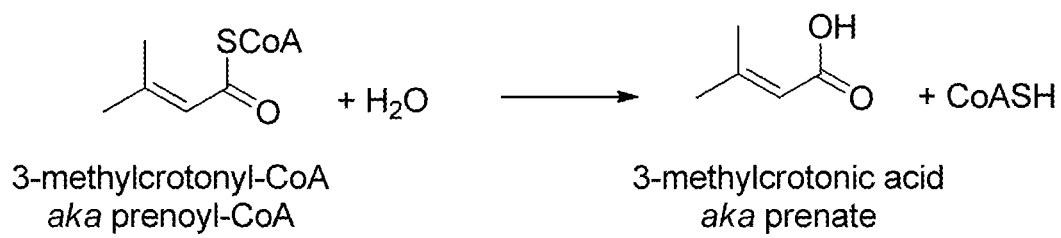

Preferably, in one embodiment, 3-methylcrotonyl-CoA is directly converted into 3-methylcrotonic acid by hydrolyzing the thioester bond of 3-methylcrotonyl-CoA into 3-methylcrotonic acid by making use of an enzyme which belongs to the family of thioester hydrolases (in the following referred to as thioesterases (EC 3.1.2.-)). This reaction is schematically shown in FIG. 10.

Examples for preferred thioester hydrolases (EC 3.1.2.-) are an acetyl-CoA hydrolase (EC 3.1.2.1), an ADP-dependent short-chain-acyl-CoA hydrolase (EC 3.1.2.18) and an acyl-CoA hydrolase (EC 3.1.2.20) (step VIb as shown in FIG. 1).

Figure 9:
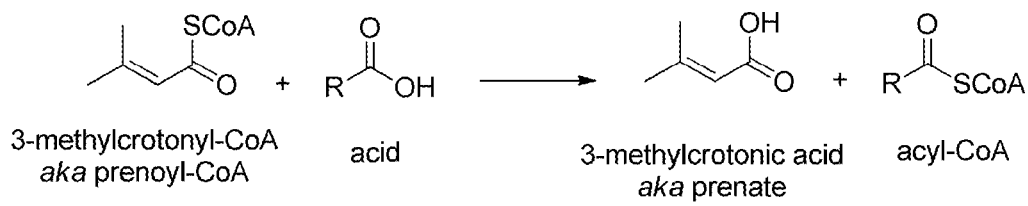

In an alternative embodiment, 3-methylcrotonyl-CoA is directly converted into 3-methylcrotonic acid, preferably by making use of an enzyme which belongs to the family of CoA-transferases (EC 2.8.3.-). This reaction is schematically shown in FIG. 9.

Examples for preferred CoA transferases (EC 2.8.3.-) are a propionate:acetate-CoA transferase (EC 2.8.3.1), an acetate CoA-transferase (EC 2.8.3.8) and a succinyl-CoA:acetate CoA-transferase (EC 2.8.3.18) (step VIa as shown in FIG. 1).

Thioesterases (TEs; also referred to as thioester hydrolases) are enzymes which are classified as EC 3.1.2. Presently thioesterases are classified as EC 3.1.2.1 through EC 3.1.2.30 while TEs which are not yet classified/unclassified are grouped as enzymes belonging to EC 3.1.2.-. Cantu et al. (Protein Science 19 (2010), 1281-1295) describe that there are 23 families of thioesterases which are unrelated to each other as regards the primary structure. However, it is assumed that all members of the same family have essentially the same tertiary structure. Thioesterases hydrolyze the thioester bond between a carbonyl group and a sulfur atom.

In a preferred embodiment, a thioesterase employed in a method according to the present invention for converting 3-methylcrotonyl-CoA into 3-methylcrotonic acid is selected from the group consisting of:

acetyl-CoA hydrolase (EC 3.1.2.1);
palmitoyl-CoA hydrolase (EC 3.1.2.2);
3-hydroxyisobutyryl-CoA hydrolase (EC 3.1.2.4);
oleoyl-[acyl-carrier-protein] hydrolase (EC 3.1.2.14);
ADP-dependent short-chain-acyl-CoA hydrolase (EC 3.1.2.18);
ADP-dependent medium-chain-acyl-CoA hydrolase (EC 3.1.2.19); and
acyl-CoA hydrolase (EC 3.1.2.20).

Thus, in one preferred embodiment the direct conversion of 3-methylcrotonyl-CoA into 3-methylcrotonic acid is achieved by making use of an acetyl-CoA hydrolase (EC 3.1.2.1). Acetyl-CoA hydrolases are enzymes which catalyze the following reaction:

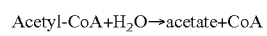

Acetyl-CoA+H$_2$O→acetate+CoA

This enzyme occurs in a variety of organism, including eukaryotic and prokaryotic organisms, such as plants, animals, fungi and bacteria. The enzyme has, e.g., been described in *Rattus norvegicus* (Uniprot Accession number: Q99NB7), *Mus musculus*, *Sus scrofa*, *Bos taurus*, *Gallus gallus*, *Platyrrhini*, *Ovis aries*, *Mesocricetus auratus*, *Ascaris suum*, *Homo sapiens* (Uniprot Accession number: Q8WYK0), *Pisum sativum*, *Cucumis sativus*, *Panicus* sp., *Ricinus communis*, *Solanum tuberosum*, *Spinacia oleracea*, *Zea mays*, *Glycine max*, *Saccharomyces cerevisiae*, *Neurospora crassa*, *Candida albicans*, *Trypanosoma brucei brucei*, *Trypanosoma cruzi*, *Trypanosoma dionisii*, *Trypanosoma vespertilionis*, *Crithidia fasciculate*, *Clostridium aminovalericum*, *Acidaminococcus fermaentans*, *Bradyrhizobium japonicum* and *Methanosarcina barkeri*.

In another preferred embodiment the direct conversion of 3-methylcrotonyl-CoA into 3-methylcrotonic acid is achieved by making use of a palmitoyl-CoA hydrolase (EC 3.1.2.2). Palmitoyl-CoA hydrolases are enzymes which catalyze the following reaction:

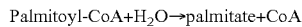

Palmitoyl-CoA+H₂O→palmitate+CoA

This enzyme occurs in a variety of organism, including eukaryotic and prokaryotic organisms, such as plants, animals, fungi and bacteria. The enzyme has, e.g., been described in *Arabidopsis thaliana* (Uniprot Accession number: Q8GYW7), *Pisum sativum*, *Spinacia oleracea*, *Bumilleriopsis filiformis*, *Eremosphaera viridis*, *Mougeotia scalaris*, *Euglena gracilis*, *Rhodotorula aurantiaca*, *Saccharaomyces cerevisiae*, *Candida rugosa*, *Caenorhabditis elegans*, *Mus musculus* (Uniprot Accession number: P58137), *Homo sapiens*, *Platyrrhini*, *Bos taurus*, *Canis lupus familiaris*, *Sus scrofa*, *Cavia procellus*, *Columba* sp., *Cricetulus griseus*, *Mesocricetus auratus*, *Drosophila melanogaster*, *Rattus norvegicus*, *Oryctolagus cuniculus*, *Gallus gallus*, *Anas platyrhynchos*, *Mycobacterium tuberculosis*, *Mycobacterium phlei*, *Mycobacterium smegmatis*, *Acinetobacter colcaceticus*, *Haemophilus influenza*, *Helicobacter pylori*, *Bacillus subtilis*, *Pseudomonas aeruginosa*, *Rhodobacter shpaeroides*, *Streptomyces coelicolor*, *Streptomyces venezuelae* and *E. coli*.

In a further preferred embodiment the direct conversion of 3-methylcrotonyl-CoA into 3-methylcrotonic acid is achieved by making use of a 3-hydroxyisobutyryl-CoA hydrolase (EC 3.1.2.4). 3-hydroxyisobutyryl-CoA hydrolases are enzymes which catalyze the following reaction:

3-hydroxyisobutyryl-CoA+H₂O→3-hydroxyisobutyrate+CoA

This enzyme occurs in a variety of organism, including eukaryotic and prokaryotic organisms, such as plants, animals, fungi and bacteria. The enzyme has, e.g., been described in *Arabidopsis thaliana*, *Homo sapiens*, *Canus lupus familiaris*, *Rattus norvegicus*, *Bacillus cereus*, *Pseudomonas fluorescens* and *Pseudomonas aeruginosa*.

In yet another preferred embodiment the direct conversion of 3-methylcrotonyl-CoA into 3-methylcrotonic acid is achieved by making use of an oleoyl-[acyl-carrier-protein] hydrolase (EC 3.1.2.14). Oleoyl-[acyl-carrier-protein] hydrolases are enzymes which catalyze the following reaction:

oleoyl-[acyl-carrier-protein]+H₂O→oleate+[acyl-carrier-protein]

This enzyme occurs in a variety of plants and bacteria. The enzyme has, e.g., been described in *Arabidopsis thaliana*, *Allium ampeloprasum*, *Curcurbita moschata*, *Cuphea calophylla*, *Cuphea hookeriana*, *Cuphea lanceolata*, *Cuphea wrightii*, *Umbellularia californica*, *Coriandrum sativum*, *Spinacia oleracea*, *Elaeis* sp., *Elaeis guineensis*, *Glycine max*, *Persea americana*, *Pisum sativum*, *Sinapis alba*, *Ulmus americana*, *Zea mays*, *Brassica juncea*, *Brassica napus*, *Brassica rapa* subsp. *campestris*, *Jatropha curcas*, *Ricinus communis*, *Cinnamomum camphorum*, *Macadamia tetraphylla*, *Magnifera indica*, *Madhuca longifolia*, *Populus tomentosa*, *Chimonanthus praecox*, *Gossypium hirsutum*, *Diploknema butyracea*, *Helianthus annuus* and *Streptococcus pyogenes*.

In yet another preferred embodiment the direct conversion of 3-methylcrotonyl-CoA into 3-methylcrotonic acid is achieved by making use of an ADP-dependent short-chain-acyl-CoA hydrolase (EC 3.1.2.18). ADP-dependent short-chain-acyl-CoA hydrolases are enzymes which catalyze the following reaction:

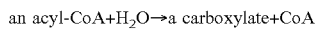

an acyl-CoA+H₂O→a carboxylate+CoA

This enzyme occurs in a variety of animals and has, e.g., been described in *Mus musculus*, *Rattus norvegicus* and *Mesocricetus auratus*.

In yet another preferred embodiment the direct conversion of 3-methylcrotonyl-CoA into 3-methylcrotonic acid is achieved by making use of an ADP-dependent medium-chain-acyl-CoA hydrolase (EC 3.1.2.19). ADP-dependent medium-chain-acyl-CoA hydrolases are enzymes which catalyze the following reaction:

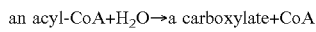

an acyl-CoA+H₂O→a carboxylate+CoA

This enzyme occurs in a variety of animals and has, e.g., been described in *Rattus norvegicus* and *Mesocricetus auratus*.

In a further preferred embodiment the direct conversion of 3-methylcrotonyl-CoA into 3-methylcrotonic acid is achieved by making use of an acyl-CoA hydrolase (EC 3.1.2.20). Acyl-CoA hydrolases are enzymes which catalyze the following reaction:

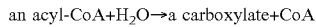

an acyl-CoA+H₂O→a carboxylate+CoA

This enzyme occurs in a variety of organism, including eukaryotic and prokaryotic organisms, such as plants, animals, fungi and bacteria. The enzyme has, e.g., been described in *Arabidopsis thaliana*, *Rhodotorula aurantiaca*, *Bumilleriopsis filiformis*, *Eremosphaera viridis*, *Euglena gracilis*, *Mus musculus*, *Rattus norvegicus*, *Homo sapiens*, *Sus, scrofa*, *Bos taurus*, *Cais lupus familiaris*, *Cavia porcellus*, *Cricetus griseus*, *Drosophila melanogaster*, *Anas platyrhynchos*, *Gallus gallus*, *Caenorhabditis elegans*, *Saccharomyces cerevisiae*, *Candida rugosa*, *Escherichia coli*, *Haemophilus influenzae*, *Xanthomonas campestris*, *Streptomyces* sp., *Streptomyces coelicolor*, *Alcaligenes faecalis*, *Pseudomonas aeruginosa*, *Pseudomonas putida*, *Amycolatopsis mediterranei*, *Acinetobacter calcoaceticus*, *Helicobacter pylori*, *Rhodobacter spaeroides* and *Mycobacterium phlei*. In a preferred embodiment the acyl-CoA hydrolase is an enzyme from *Escherichia coli*, from *Pseudomonas putida* or from *Haemophilus influenza*, more preferably the YciA enzyme from *E. coli* or its closely related homolog H10827 from *Haemophilus influenza* (Zhuang et al., Biochemistry 47 (2008), 2789-2796). The YciA enzyme from *Haemophilus influenza* is described to catalyze the hydrolysis of propionyl-CoA into propionic acid (Zhuang et al., Biochemistry 47 (2008), 2789-2796). In another preferred embodiment the acetyl-CoA hydrolase is an enzyme from *Homo sapiens* (UniProt: Q9NPJ3) which is described to hydrolyze propionyl-CoA (Cao et al., Biochemistry 48 (2009), 1293-1304).

Particularly preferred enzymes are the above-described acyl-CoA hydrolase YciA enzyme from *Haemophilus influenza* strain R2866 (SEQ ID NO: 30) and the acetyl-CoA hydrolase enzyme from *Homo sapiens* (UniProt: Q9NPJ3; SEQ ID NO:31). Particularly preferred are also the enzymes acyl-CoA thioester hydrolase from *E. coli* (Uniprot P0A8Z0; SEQ ID NO: 32), acyl-CoA thioesterase 2 from *E. coli* (Uniprot P0AGG2; SEQ ID NO: 33) and acyl-CoA thioesterase II from *Pseudomonas putida* (Uniprot Q88DR1; SEQ ID NO: 34). Particularly preferred is the thioesterase TesB from *E. coli* K12 (uniprot: P0AGG2), as this enzyme is already described to efficiently catalyze this reaction in *E. coli* for the biosynthesis of propionic acid (Tseng and Prather, P.N.A.S. 2012, 109(44), p 17925-17930).

In another preferred embodiment, the acyl-CoA hydrolase is an enzyme derived from the family of 1,4-dihydroxy-2-naphthoyl-CoA hydrolases. Enzymes of this family of 1,4-dihydroxy-2-naphthoyl-CoA hydrolases are known to catalyze the following reaction:

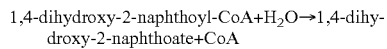

1,4-dihydroxy-2-naphthoyl-CoA+H$_2$O→1,4-dihydroxy-2-naphthoate+CoA

These enzymes are also often referred to as YdiI thioesterases. Enzymes of this family occur in a variety of organisms and have, e.g., been described in *Escherichia coli* and *Salmonella enterica*.

Thus, particularly preferred acyl-CoA hydrolases for the enzymatic conversion of 3-methylcrotonyl-CoA into 3-methylcrotonic acid of the present invention are enzymes which belong to the family of 1,4-dihydroxy-2-naphthoyl-CoA hydrolases, more preferably the 1,4-dihydroxy-2-naphthoyl-CoA hydrolase derived from *Escherichia coli* (SEQ ID NO:82) or the 1,4-dihydroxy-2-naphthoyl-CoA hydrolase derived from *Salmonella enterica* (SEQ ID NO:83).

In a particularly preferred embodiment, the acyl-CoA hydrolase employed in the method of the invention has an amino acid sequence as shown in any one of SEQ ID NOs: 30 to 34 and SEQ ID NOs:82 and 83 or shows an amino acid sequence which is at least x % homologous to any one of SEQ ID NOs: 30 to 34 and SEQ ID NOs:82 and 83 and has the activity of an acyl-CoA hydrolase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of catalyzing the conversion of 3-methylcrotonyl-CoA into 3-methylcrotonic acid. As regards the determination of the sequence identity, the same applies as has been set forth above.

As described above, the direct conversion of 3-methylcrotonyl-CoA into 3-methylcrotonic acid can also be achieved by making use of an enzyme which is classified as a CoA-transferase (EC 2.8.3.-) capable of transferring the CoA group of 3-methylcrotonyl-CoA to a carboxylic acid.

CoA-transferases are found in organisms from all lines of descent. Most of the CoA-transferases belong to two well-known enzyme families (referred to in the following as families I and II) and there exists a third family which had been identified in anaerobic metabolic pathways of bacteria. A review describing the different families can be found in Heider (FEBS Letters 509 (2001), 345-349).

Family I contains, e.g., the following CoA-transferases:
For 3-oxo acids: enzymes classified in EC 2.8.3.5 or EC 2.8.3.6;
For short chain fatty acids: enzymes classified in EC 2.8.3.8 or EC 2.8.3.9;
For succinate: succinyl-CoA:acetate CoA-transferases, i.e. enzymes classified in EC 2.8.3.18 (see also Mullins et al., Biochemistry 51(2012), 8422-34; Mullins et al., J. Bacteriol. 190 (2006), 4933-4940).

Most enzymes of family I naturally use succinyl-CoA or acetyl-CoA as CoA donors. These enzymes contain two dissimilar subunits in different aggregation states. Two conserved amino acid sequence motives have been identified:

Prosites entry PS01273 (http://prosite.expasy.org/cgi-bin/prosite/prosite-search-ac?PDOC00980)
COA_TRANSF_1, PS01273; Coenzyme A transferases signature 1 (PATTERN) Consensus pattern:
[DN]-[GN]-x(2)-[LIVMFA](3)-G-G-F-x(3)-G-x-P
and
Prosites entries PS01273 (http://prosite.expasy.org/cgi-bin/prosite/prosite-search-ac?PDOC00980)
COA_TRANSF_2, PS01274; Coenzyme A transferases signature 2 (PATTERN) Consensus pattern:
[LF]-[HQ]-S-E-N-G-[LIVF](2)-[GA]
E (glutamic acid) is an active site residue.

The family II of CoA-transferases consists of the homodimeric α-subunits of citrate lyase (EC 2.8.3.10) and citramalate lyase (EC 2.8.3.11). These enzymes catalyse the transfer of acyl carrier protein (ACP) which contains a covalently bound CoA-derivative. It was shown that such enzymes also accept free CoA-thioester in vitro, such as acetyl-CoA, propionyl-CoA, butyryl-CoA in the case of citrate lyase (Dimroth et al., Eur. J. Biochem. 80 (1977), 479-488) and acetyl-CoA and succinyl-CoA in the case of citramalate lyase (Dimroth et al., Eur. J. Biochem. 80 (1977), 469-477).

According to Heider (loc. cit.) family III of CoA-transferases consists of formyl-CoA: oxalate CoA-transferase, succinyl-CoA:(R)-benzylsuccinate CoA-transferase, (E)-cinnamoyl-CoA:(R)-phenyl lactate CoA-transferase and butyrobetainyl-CoA:(R)-carnitine CoA-transferase. A further member of family III is succinyl-CoA:L-malate CoA-transferase whose function in autrophic CO$_2$ fixation of *Chloroflexus aurantiacus* is to activate L-malate to its CoA thioester with succinyl-CoA as the CoA donor (Friedman S. et al. J. Bacteriol. 188 (2006), 2646-2655). The amino acid sequences of the CoA-tranferase of this family show only a low degree of sequence identity to those of families I and II. These CoA-transferases occur in prokaryotes and eukaryotes.

In a preferred embodiment the CoA-transferase employed in a method according to the present invention is a CoA-transferase which belongs to family I or II as described herein-above.

Preferably, the CoA-transferase employed in a method according to the present invention for the direct conversion of 3-methylcrotonyl-CoA into 3-methylcrotonic acid is selected from the group consisting of:
propionate:acetate-CoA transferase (EC 2.8.3.1);
acetate CoA-transferase (EC 2.8.3.8); and
butyrate-acetoacetate CoA-transferase (EC 2.8.3.9).

Thus, in one preferred embodiment the direct conversion of 3-methylcrotonyl-CoA into 3-methylcrotonic acid is achieved by making use of an acetate CoA-transferase (EC 2.8.3.8). Acetate CoA-transferases are enzymes which catalyze the following reaction:

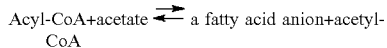

Acyl-CoA+acetate ⇌ a fatty acid anion+acetyl-CoA

This enzyme occurs in a variety of bacteria and has, e.g., been described in *Anaerostipes caccae*, *Eubacterium hallii*, *Faecalibacterium prausnitzii*, *Roseburia hominis*, *Roseburia intestinalis*, *Coprococcus* sp. and *Escherichia coli*.

In another preferred embodiment the direct conversion of 3-methylcrotonyl-CoA into 3-methylcrotonic acid is achieved by making use of a butyrate-acetoacetate CoA-transferase (EC 2.8.3.9). Butyrate-acetoacetate CoA-transferase are enzymes which catalyze the following reaction:

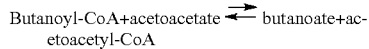
Butanoyl-CoA+acetoacetate ⇌ butanoate+acetoacetyl-CoA

This enzyme occurs in a variety of organism, including eukaryotic and prokaryotic organisms, such as animals and bacteria. The enzyme has, e.g., been described in *Bos taurus*, *Clostridium* sp. and *Escherichia coli*.

In another preferred embodiment the direct conversion of 3-methylcrotonyl-CoA into 3-methylcrotonic acid is achieved by making use of a propionate:acetate-CoA transferase (EC 2.8.3.1). Propionate:acetate-CoA transferases are enzymes which catalyze the following reaction:

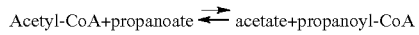
Acetyl-CoA+propanoate ⇌ acetate+propanoyl-CoA

This enzyme occurs in a variety of organism including prokaryotic organisms and the enzyme has, e.g., been described in *Clostridium kluyveri*, *Clostridium propionicum*, *Clostridium propionicum* JCM1430, *Cupriavidus necator* and *Emericella nidulans*.

In another preferred embodiment the direct conversion of 3-methylcrotonyl-CoA into 3-methylcrotonic acid is achieved by making use of a succinyl-CoA:acetate-CoA transferase (EC 2.8.3.18). Succinyl-CoA:acetate CoA-transferases are enzymes which catalyze the following reaction:

Succinyl-CoA+acetate ⇌ acetyl-CoA+succinate

This enzyme occurs in a variety of organism, including prokaryotic organisms, and the enzyme has, e.g., been described in *Acetobacter aceti*, *Trichomonas vaginalis*, *Tritrichomonas foetus*, *Tritrichomonas foetus* ATCC 30924 and *Trypanosoma brucei*.

In another preferred embodiment, the direct conversion of 3-methylcrotonyl-CoA into 3-methylcrotonic acid is achieved by making use of a CoA-transferase derived from *Megasphaera* sp. (Uniprot accession number S7HFR5), an enzyme which belongs to the of CoA-transferases (EC 2.8.3.-) as defined herein-above.

In a preferred embodiment, the CoA-transferase employed in the method of the present invention is a CoA-transferase derived from *Megasphaera* sp. (Uniprot accession number S7HFR5; SEQ ID NO:84).

In a preferred embodiment of the present invention the CoA-transferase is an enzyme comprising the amino acid sequence of SEQ ID NO: 84 or a sequence which is at least n % identical to SEQ ID NO: 84 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of directly converting 3-methylcrotonyl-CoA into 3-methylcrotonic acid. As regards the determination of the sequence identity, the same applies as has been set forth above.

Figure 32:
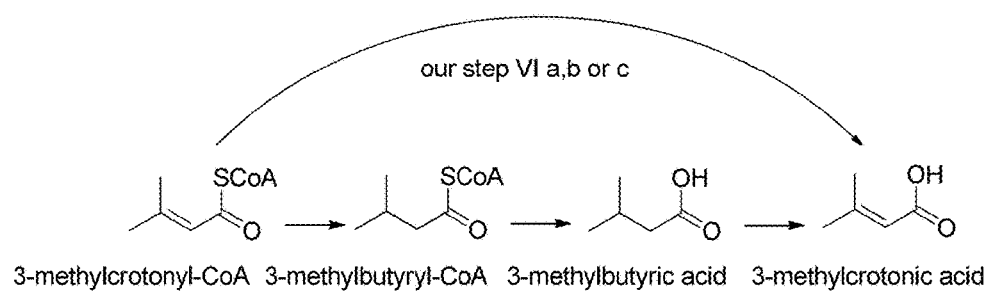

The Enzymatic Conversion of 3-Methylcrotonyl-CoA into 3-Methylcrotonic Acid: An Alternative Route to the Above-Described Step VI In another preferred embodiment, the conversion of 3-methylcrotonyl-CoA into 3-methylcrotonic acid is achieved by an alternative route wherein 3-methylcrotonyl-CoA is first enzymatically converted into 3-methylbutyryl-CoA which is then enzymatically converted into 3-methylbutyric acid which is then ultimately converted into 3-methylcrotonic acid. This alternative conversion of 3-methylcrotonyl-CoA into 3-methylcrotonic acid via 3-methylbutyryl-CoA and 3-methylbutyric acid is schematically illustrated in FIG. 32.

Accordingly, the present invention relates to a method for producing isobutene from 3-methylcrotonyl-CoA in which 3-methylcrotonyl-CoA is first enzymatically converted into 3-methylbutyryl-CoA which is then enzymatically converted into 3-methylbutyric acid which is then converted into 3-methylcrotonic acid which is then further converted into isobutene as described herein above.

The first enzymatic conversion, i.e., the conversion of 3-methylcrotonyl-CoA into 3-methylbutyryl-CoA, is a desaturation reaction, i.e., reduction of the double bond C═C of 3-methylcrotonyl-CoA into 3-methylbutyryl-CoA. The enzymatic conversion of 3-methylcrotonyl-CoA into 3-methylbutyryl-CoA, i.e. the reduction of the double bond in 3-methylcrotonyl-CoA, can, for example, be achieved by employing an enzyme classified as EC 1.3._._. Enzymes classified as EC 1.3._._ are oxidoreductases acting on the CH—CH group of a donor molecule. This subclass contains enzymes that reversibly catalyze the conversion of a carbon-carbon single bond to a carbon-carbon double bond between two carbon atoms. Sub-classes of EC 1.3 are classified depending on the acceptor. In one preferred embodiment the enzyme is an enzyme which is classified as EC 1.3._._ and which uses NADH or NADPH as co-factor. In one particularly preferred embodiment the enzyme is an enzyme which uses NADPH as a co-factor. In a preferred embodiment the enzyme is selected from the group consisting of:

acyl-CoA dehydrogenase (NADP+) (EC 1.3.1.8);
enoyl-[acyl-carrier-protein] reductase (NADPH, Si-specific) (EC 1.3.1.10);
cis-2-enoyl-CoA reductase (NADPH) (EC 1.3.1.37);
trans-2-enoyl-CoA reductase (NADPH) (EC 1.3.1.38);
enoyl-[acyl-carrier-protein] reductase (NADPH, Re-specific) (EC 1.3.1.39); and
crotonyl-CoA reductase (EC 1.3.1.86).

Thus, in one preferred embodiment the conversion of 3-methylcrotonyl-CoA into 3-methylbutyryl-CoA is achieved by making use of an acyl-CoA dehydrogenase (NADP+) (EC 1.3.1.8). Acyl-CoA dehydrogenases are enzymes which catalyze the following reaction:

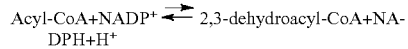
Acyl-CoA+NADP+ ⇌ 2,3-dehydroacyl-CoA+NADPH+H+

This enzyme occurs in a variety of organism, including eukaryotic and prokaryotic organisms, such as plants, animals, fungi and bacteria. The enzyme has, e.g., been described in *Bos, taurus, Rattus novegicus, Mus musculus, Columba* sp., *Arabidopsis thaliana, Nicotiana benthamiana, Allium ampeloprasum, Euglena gracilis, Candida albicans, Streptococcus collinus, Rhodobacter sphaeroides* and *Mycobacterium smegmatis*.

In a further preferred embodiment the conversion of 3-methylcrotonyl-CoA into 3-methylbutyryl-CoA is achieved by making use of an enoyl-[acyl-carrier-protein] reductase (NADPH, Si-specific) (EC 1.3.1.10). Enoyl-[acyl-carrier-protein] reductases (NADPH, Si-specific) are enzymes which catalyze the following reaction:

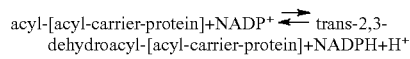
acyl-[acyl-carrier-protein]+NADP+ ⇌ trans-2,3-dehydroacyl-[acyl-carrier-protein]+NADPH+H+

This enzyme occurs in a variety of organism, including eukaryotic and prokaryotic organisms, such as plants, fungi and bacteria. The enzyme has, e.g., been described in *Carthamus tinctorius, Candida tropicalis, Saccharomyces cerevisiae, Streptococcus collinus, Streptococcus pneumo-* niae, *Staphylococcus aureus, Bacillus subtilis, Bacillus cereus, Porphyromonas gingivalis, Escherichia coli* and *Salmonella enterica.*

In a further preferred embodiment the conversion of 3-methylcrotonyl-CoA into 3-methylbutyryl-CoA is achieved by making use of a cis-2-enoyl-CoA reductase (NADPH) (EC 1.3.1.37). Cis-2-enoyl-CoA reductases (NADPH) are enzymes which catalyze the following reaction:

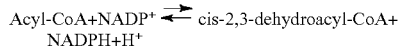
Acyl-CoA+NADP$^+$ ⇌ cis-2,3-dehydroacyl-CoA+ NADPH+H$^+$

This enzyme has been described to occur in *Escherichia coli.*

In a further preferred embodiment the conversion of 3-methylcrotonyl-CoA into 3-methylbutyryl-CoA is achieved by making use of a trans-2-enoyl-CoA reductase (NADPH) (EC 1.3.1.38). Trans-2-enoyl-CoA reductases (NADPH) are enzymes which catalyze the following reaction:

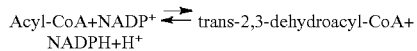
Acyl-CoA+NADP$^+$ ⇌ trans-2,3-dehydroacyl-CoA+ NADPH+H$^+$

This enzyme occurs in a variety of organism, including eukaryotic and prokaryotic organisms, such as plants, animals and bacteria. The enzyme has, e.g., been described in *Homo sapien, Rattus norvegicus, Mus musculus, Cavia porcellus, Caenorhabditis elegans, Phalaenopsis amabilis, Gossypium hirsutum, Mycobacterium tuberculosis, Streptococcus collinu* and *Escherichia coli.*

In a further preferred embodiment the conversion of 3-methylcrotonyl-CoA into 3-methylbutyryl-CoA is achieved by making use of an enoyl-[acyl-carrier-protein] reductase (NADPH, Re-specific) (EC 1.3.1.39). Enoyl-[acyl-carrier-protein] reductases (NADPH, Re-specific) are enzymes which catalyze the following reaction:

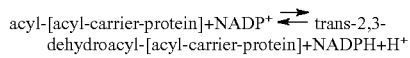
acyl-[acyl-carrier-protein]+NADP$^+$ ⇌ trans-2,3-dehydroacyl-[acyl-carrier-protein]+NADPH+H$^+$ This enzyme occurs in a variety of organism, including eukaryotic and prokaryotic organisms, such as animals and bacteria. The enzyme has, e.g., been described in *Gallus gallus, Pigeon, Rattus norvegicus, Cavia porcellus, Staphylococcus aureus, Bacillus subtilis* and *Porphyromonas gingivalis.*

In a further preferred embodiment the conversion of 3-methylcrotonyl-CoA into 3-methylbutyryl-CoA is achieved by making use of a crotonyl-CoA reductase (EC 1.3.1.86). Crotonyl-CoA reductases are enzymes which catalyze the following reaction:

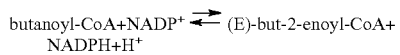
butanoyl-CoA+NADP$^+$ ⇌ (E)-but-2-enoyl-CoA+ NADPH+H$^+$

This enzyme occurs in a variety of organism, including eukaryotic and prokaryotic organisms, such as animals, fungi and bacteria. The enzyme has, e.g., been described in *Bos taurus, Salinospora tropica, Clostridium difficile, Streptomyces collinus, Streptomyces cinnamonensis* and *Streptomyces hygroscopicus.*

The second enzymatic conversion, i.e., the conversion of 3-methylbutyryl-CoA into 3-methylbutyric acid, can be achieved by different enzymatic conversions. One possibility is the direct conversion via a hydrolysis reaction. Another possibility is the direct conversion via a reaction catalyzed by a CoA-transferase and a third possibility is a two-step conversion via 3-methylbutyryl phosphate.

Thus, according to the present invention, the enzymatic conversion of 3-methylbutyryl-CoA into 3-methylbutyric acid is achieved by (a) a single enzymatic reaction in which 3-methylbutyryl-CoA is directly converted into 3-methylbutyric acid, preferably by making use of a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18);

(b) a single enzymatic reaction in which 3-methylbutyryl-CoA is directly converted into 3-methylbutyric acid, preferably by making use of a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20); or (c) two enzymatic steps comprising
  (i) first enzymatically converting 3-methylbutyryl-CoA into 3-methylbutyryl phosphate; and
  (ii) then enzymatically converting the thus obtained 3-methylbutyryl phosphate into said 3-methylbutyric acid.

As regards the preferred embodiments for the CoA transferase (EC 2.8.3.-), the propionate:acetate-CoA transferase (EC 2.8.3.1), the acetate CoA-transferase (EC 2.8.3.8) or a succinyl-CoA:acetate CoA-transferase (EC 2.8.3.18), the thioester hydrolase (EC 3.1.2.-), the acetyl-CoA hydrolase (EC 3.1.2.1), the ADP-dependent short-chain-acyl-CoA hydrolase (EC 3.1.2.18), the acyl-CoA hydrolase (EC 3.1.2.20), the enzyme capable of converting 3-methylbutyryl-CoA into 3-methylbutyryl phosphate and the enzyme capable of converting 3-methylbutyryl phosphate into said 3-methylbutyric acid, the same applies as has been set forth above in connection with the enzymatic conversion of step VIa, step VIb and step VIc according to the invention.

The third enzymatic conversion, i.e., the conversion of 3-methylbutyric acid into 3-methylcrotonic acid can, e.g., be achieved by a 2-enoate reductase (EC 1.3.1.31). 2-enoate reductases are enzymes which naturally catalyze the following reaction:

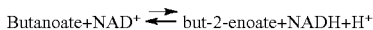
Butanoate+NAD$^+$ ⇌ but-2-enoate+NADH+H$^+$

This enzyme occurs in a variety of organism, including eukaryotic and prokaryotic organisms, such as animals, fungi and bacteria. The enzyme has, e.g., been described in *Cichorium intybus, Marchantia polymorpha, Solanum lycopersicum, Absidia glauca, Kluyveromyces lactis, Penicillium citrinum; Rhodosporidium, Saccharomyces cerevisiae, Clostridium kluyveri, Clostridium bifermentans, Clostridium botulinum, Clostridium difficile, Clostridium ghonii, Clostridium mangenotii, Clostridium oceanicum, Clostridium sordellii, Clostridium sporogenes, Clostridium sticklandii, Clostridium tyrobutyricum, Achromobacter* sp., *Burkholderia* sp., *Gluconobacter oxydans, Lactobacillus casei, Pseudomonas putida, Shewanella* sp., *Yersinia bercovieri, Bacillus subtilis, Moorella thermoacetica* and *Peptostreptococcus anaerobius.* The enoate reductase of Clostridiae has been described, e.g., in Tischler et al. (Eur. J. Bioche. 97 (1979), 103-112).

The Enzymatic Conversion of 3-Methylglutaconyl-CoA into 3-Methylcrotonyl-CoA: Step VII as Shown in FIG. 1

Figure 12:
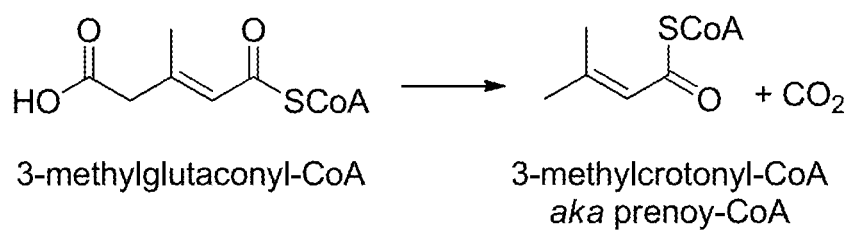

The 3-methylcrotonyl-CoA which is converted according to the method of the present invention into 3-methylcrotonic acid according to any of the above described methods (and further converted according to the method of the present invention into isobutene according to any of the above described methods) may itself be provided by an enzymatic reaction, namely the enzymatic conversion of 3-methylglutaconyl-CoA into 3-methylcrotonyl-CoA. The conversion of 3-methylglutaconyl-CoA into 3-methylcrotonyl-CoA is schematically illustrated in FIG. 12.

Accordingly, the present invention relates to a method for producing isobutene from 3-methylglutaconyl-CoA in which 3-methylglutaconyl-CoA is first converted into 3-methylcrotonyl-CoA which is then further converted into 3-methylcrotonic acid which is then further converted into isobutene as described herein above.

The conversion of 3-methylglutaconyl-CoA into 3-methylcrotonyl-CoA may be catalyzed by different enzymes. According to the present invention, the conversion of 3-methylglutaconyl-CoA into said 3-methylcrotonyl-CoA preferably makes use of (i) a methylcrotonyl-CoA carboxylase (EC 6.4.1.4); or (ii) a geranoyl-CoA carboxylase (EC 6.4.1.5) (as shown in step VII of FIG. 1).

Methylcrotonyl-CoA carboxylases (EC 6.4.1.4) and geranoyl-CoA carboxylases (EC 6.4.1.5) as well as preferred enzymes of these enzyme classes have already been described above. Accordingly, as regards these enzymes, the same applies to the conversion of 3-methylglutaconyl-CoA into 3-methylcrotonyl-CoA as has been set forth above.

In another preferred embodiment the conversion of 3-methylglutaconyl-CoA via decarboxylation into 3-methylcrotonyl-CoA is catalyzed by a 3-methylglutaconyl-CoA decarboxylase, e.g. a 3-methylglutaconyl-CoA decarboxylase of *Myxococcus xanthus* encoded by the liuB gene. This gene codes for an enzyme having the two subunits AibA and AibB (Li et al., Angew. Chem. Int. Ed. 52 (2013), 1304-1308). This enzyme has already described above as a methylcrotonyl-CoA carboxylase derived from *Myxococcus xanthus* in the context of conversion of 3-methylcrotonic acid into isobutene.

The same enzyme derived from *Myxococcus xanthus* encoded by the liuB gene having the two subunits AibA and AibB (Li et al., Angew. Chem. Int. Ed. 52 (2013), 1304-1308) has been described above with reference to SEQ ID NOs: 100 and 101 and can also be used for the conversion of 3-methylglutaconyl-CoA via decarboxylation into 3-methylcrotonyl-CoA.

In a preferred embodiment of the present invention the 3-methylglutaconyl-CoA decarboxylase is an enzyme comprising the amino acid sequence of SEQ ID NO: 100 or a sequence which is at least n % identical to SEQ ID NO: 100 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylglutaconyl-CoA into 3-methylcrotonyl-CoA. As regards the determination of the sequence identity, the same applies as has been set forth above. In another preferred embodiment of the present invention the 3-methylglutaconyl-CoA decarboxylase is an enzyme comprising the amino acid sequence of SEQ ID NO: 101 or a sequence which is at least n % identical to SEQ ID NO: 101 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylglutaconyl-CoA into 3-methylcrotonyl-CoA. As regards the determination of the sequence identity, the same applies as has been set forth above.

In another preferred embodiment of the present invention the 3-methylglutaconyl-CoA decarboxylase is a heterodimeric enzyme comprising a combination of the amino acid sequence of SEQ ID NO: 100 and 101 or a sequence which is at least n % identical to SEQ ID NO: 100 and 101 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylglutaconyl-CoA into 3-methylcrotonyl-CoA. As regards the determination of the sequence identity, the same applies as has been set forth above.

The Enzymatic Conversion of 3-Hydroxy-3-Methylglutaryl-CoA into 3-Methylglutaconyl-CoA: Step VIII as Shown in FIG. 1

Figure 13:
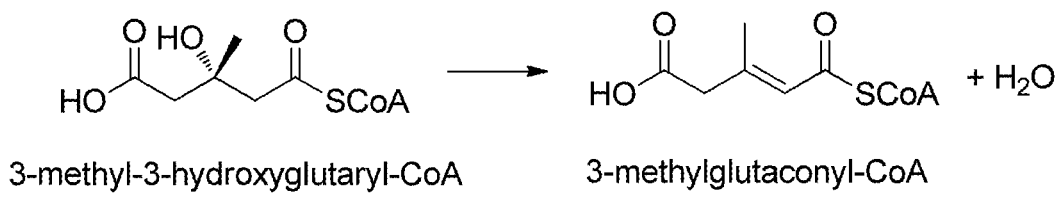

The 3-methylglutaconyl-CoA which is converted into 3-methylcrotonyl-CoA may itself be provided by an enzymatic reaction, namely the enzymatic conversion of 3-hydroxy-3-methylglutaryl-CoA into 3-methylglutaconyl-CoA; see FIG. 13.

Accordingly, the present invention also relates to a method for producing isobutene from 3-hydroxy-3-methylglutaryl-CoA in which 3-hydroxy-3-methylglutaryl-CoA is first converted into 3-methylglutaconyl-CoA which is then converted into 3-methylcrotonyl-CoA which is then further converted into 3-methylcrotonic acid which is then further converted into isobutene as described herein above.

According to the present invention, the enzymatic conversion of 3-hydroxy-3-methylglutaryl-CoA into 3-methylglutaconyl-CoA is an enzymatic dehydration reaction which occurs naturally, and which is catalyzed, e.g., by enzymes classified as 3-methylglutaconyl-coenzyme A hydratase (EC 4.2.1.18). Accordingly, the enzymatic conversion of 3-hydroxy-3-methylglutaryl-CoA into 3-methylglutaconyl-CoA preferably makes use of a 3-methylglutaconyl-coenzyme A hydratase (EC 4.2.1.18) (as shown in step VIII of FIG. 1).

3-methylglutaconyl-coenzyme A hydratases are enzymes which catalyze the following reaction:

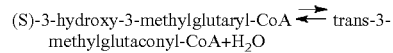

(S)-3-hydroxy-3-methylglutaryl-CoA ⇌ trans-3-methylglutaconyl-CoA+H₂O

This enzyme occurs in a variety of organisms, including eukaryotic and prokaryotic organisms, such as plants, animals and bacteria. The enzyme has, e.g., been described in *Catharantus roseus, Homo sapiens, Bos taurus, Ovis aries, Acinetobacter* sp., *Myxococcus* sp. and *Pseudomonas putida*. In a preferred embodiment the 3-methylglutaconyl-coenzyme A hydratase is an enzyme from *Myxococcus* sp., and even more preferably an enzyme which has an amino acid sequence as shown in SEQ ID NO: 35 or shows an amino acid sequence which is at least x % homologous to SEQ ID NO: 35 and has the activity of a 3-methylglutaconyl-coenzyme A hydratase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting 3-hydroxy-3-methylglutaryl-CoA into 3-methylglutaconyl-CoA as set forth herein above. As regards the determination of the degree of identity, the same applies as has been set forth herein above.

The conversion of 3-hydroxy-3-methylglutaryl-CoA into 3-methylglutaconyl-CoA can also be achieved by making use of a 3-hydroxy-3-methylglutaryl-coenzyme A dehydratase activity which has been identified, e.g., in *Myxococcus xanthus* and which is encoded by the liuC gene (Li et al., Angew. Chem. Int. Ed. 52 (2013), 1304-1308). The 3-hydroxy-3-methylglutaryl-coenzyme A dehydratase derived from *Myxococcus xanthus* has the Uniprot Accession number Q1D5Y4.

Thus, in a preferred embodiment, the 3-hydroxy-3-methylglutaryl-coenzyme A dehydratase employed in the method of the present invention is an enzyme derived from *Myxococcus xanthus* (Uniprot Accession number Q1D5Y4; SEQ ID NO:98). In a preferred embodiment of the present invention the 3-hydroxy-3-methylglutaryl-coenzyme A dehydratase is an enzyme comprising an amino acid sequence of SEQ ID NO:98 or a sequence which is at least n % identical to SEQ ID NO:98 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-hydroxy-3-methylglutaryl-CoA into 3-methylglutaconyl-CoA. As regards the determination of the sequence identity, the same applies as has been set forth above.

The enzymatic conversion of 3-hydroxy-3-methylglutaryl-CoA into 3-methylglutaconyl-CoA can also be achieved by making use of a 3-hydroxyacyl-CoA dehydratase or an enoyl-CoA hydratase. 3-hydroxyacyl-CoA dehydratases and enoyl-CoA hydratases catalyze the same reaction while the name of one of these enzymes denotes one direction of the corresponding reaction while the other name denotes the reverse reaction. As the reaction is reversible, both enzyme names can be used.

3-hydroxyacyl-CoA dehydratases and enoyl-CoA hydratases belong to enzymes classified as EC 4.2.1.-.

3-hydroxyacyl-CoA dehydratases and enoyl-CoA hydratases have, e.g., been identified in *Pseudomonas* sp., *Acinetobacter baumanii* (Uniprot accession number A0A0D5YDD4), *Pseudomonas aeruginosa* (Uniprot accession number Q9HZV7), *Marinobacter santoriniensis* (Uniprot accession number M7CV63), *Pseudomonas knackmussii*, *Pseudomonas pseudoalcaligenes* (Uniprot accession number L8MQT6), *Pseudomonas flexibilis* and *Alcanivorax dieselolei* as well as in *Ustilago maydis* (Uniprot accession number Q4PEN0), *Bacillus* sp. GeD10 (Uniprot accession number N1LWG2) and in *Labilithrix luteola* (Uniprot accession number A0A0K1PN19).

In a preferred embodiment, the 3-hydroxyacyl-CoA dehydratase/enoyl-CoA hydratase employed in the method of the present invention for the conversion of 3-hydroxy-3-methylglutaryl-CoA into 3-methylglutaconyl-CoA is an enzyme derived from *Pseudomonas* sp. (SEQ ID NO:85), *Acinetobacter baumanii* (Uniprot accession number A0A0D5YDD4; SEQ ID NO:86), *Pseudomonas aeruginosa* (Uniprot accession number Q9HZV7; SEQ ID NO:87), *Marinobacter santoriniensis* (Uniprot accession number Q9HZV7; SEQ ID NO:88), *Pseudomonas knackmussii* (SEQ ID NO:89), *Pseudomonas pseudoalcaligenes* (Uniprot accession number L8MQT6; SEQ ID NO:90), *Pseudomonas flexibilis* (SEQ ID NO:91), *Alcanivorax dieselolei* (SEQ ID NO:92), *Ustilago maydis* (Uniprot accession number Q4PEN0; SEQ ID NO:95), *Bacillus* sp. GeD10 (Uniprot accession number N1LWG2; SEQ ID NO:96) or *Labilithrix luteola* (Uniprot accession number A0A0K1PN19; SEQ ID NO:97).

In a preferred embodiment of the present invention the 3-hydroxyacyl-CoA dehydratase/enoyl-CoA hydratase is an enzyme comprising an amino acid sequence selected from the group consisting of SEQ ID NOs: 85 to 92 and SEQ ID NOs: 95 to 97 or a sequence which is at least n % identical to any of SEQ ID NOs: 85 to 92 and SEQ ID NOs: 95 to 97 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-hydroxy-3-methylglutaryl-CoA into 3-methylglutaconyl-CoA. As regards the determination of the sequence identity, the same applies as has been set forth above.

The Enzymatic Conversion of Acetoacetyl-CoA into 3-Hydroxy-3-Methylglutaryl-CoA: Step IX as Shown in FIG. 1

Figure 14:
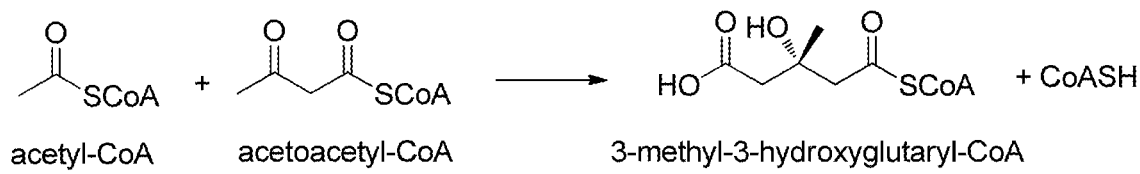

The 3-hydroxy-3-methylglutaryl-CoA which is converted into 3-methylglutaconyl-CoA may itself be provided by an enzymatic reaction, namely the enzymatic condensation of acetoacetyl-CoA and acetyl-CoA into 3-hydroxy-3-methylglutaryl-CoA; see FIG. 14.

Accordingly, the present invention also relates to a method for producing isobutene from acetoacetyl-CoA and acetyl-CoA in which acetoacetyl-CoA and acetyl-CoA are first condensed into 3-hydroxy-3-methylglutaryl-CoA which is then converted into 3-methylglutaconyl-CoA which is then converted into 3-methylcrotonyl-CoA which is then further converted into 3-methylcrotonic acid which is then further converted into isobutene as described herein above.

According to the present invention, the enzymatic condensation of acetoacetyl-CoA and acetyl-CoA into 3-hydroxy-3-methylglutaryl-CoA makes preferably use of a 3-hydroxy-3-methylglutaryl-CoA synthase (see step IX of FIG. 1).

The condensation of acetyl-CoA and acetoacetyl-CoA is a reaction which is naturally catalyzed by the enzyme 3-hydroxy-3-methylglutaryl-CoA synthase (also referred to as HMG-CoA synthase). Thus, preferably, the condensation of acetyl-CoA and acetoacetyl-CoA into 3-hydroxy-3-methylglutaryl-CoA makes use of a 3-hydroxy-3-methylglutaryl-CoA synthase (also referred to as HMG-CoA synthase). HMG-CoA synthases are classified in EC 2.3.3.10 (formerly, HMG-CoA synthase has been classified as EC 4.1.3.5 but has been transferred to EC 2.3.3.10). The term "HMG-CoA synthase" refers to any enzyme which is able to catalyze the reaction where acetyl-CoA condenses with acetoacetyl-CoA to form 3-hydroxy-3-methylglutaryl-CoA (HMG-CoA) (see FIG. 14). HMG-CoA synthase is part of the mevalonate pathway. Two pathways have been identified for the synthesis of isopentenyl pyrophosphate (IPP), i.e. the mevalonate pathway and the glyceraldehyde 3-phosphate-pyruvate pathway. HMG-CoA synthase catalyzes the biological Claisen condensation of acetyl-CoA with acetoacetyl-CoA and is a member of a superfamily of acyl-condensing enzymes that includes beta-ketothiolases, fatty acid synthases (beta-ketoacyl carrier protein synthase) and polyketide synthases.

HMG-CoA synthase has been described for various organisms. Also amino acid and nucleic acid sequences encoding HMG-CoA synthases from numerous sources are available. Generally, the sequences only share a low degree of overall sequence identity. For example, the enzymes from *Staphylococcus* or *Streptococcus* show only about 20% identity to those of human and avian HMG-CoA synthase. In some sources it is reported that the bacterial HMG-CoA synthases and their animal counterparts exhibit only about 10% overall sequence identity (Sutherlin et al., J. Bacteriol. 184 (2002), 4065-4070). However, the amino acid residues involved in the acetylation and condensation reactions are conserved among bacterial and eukaryotic HMG-CoA synthases (Campobasso et al., J. Biol. Chem. 279 (2004), 44883-44888). The three-dimensional structure of three HMG-CoA synthase enzymes has been determined and the amino acids crucial for the enzymatic reaction are in principle well characterized (Campobasso et al., loc. cit.; Chun et al., J. Biol. Chem. 275 (2000), 17946-17953; Nagegowda et al., Biochem. J. 383 (2004), 517-527; Hegardt, Biochem. J. 338 (1999), 569-582). In eukaryotes, there exist two forms of the HMG-CoA synthase, i.e. a cytosolic and a mitochondrial form. The cytosolic form plays a key role in the production of cholesterol and other isoprenoids and the mitochondrial form is involved in the production of ketone bodies.

In principle any HMG-CoA synthase enzyme can be used in the context of the present invention, in particular from prokaryotic or eukaryotic organisms.

Prokaryotic HMG-CoA synthases are described, e.g., from *Staphylococcus aureus* (Campobasso et al., loc. cit.; Uniprot accession number Q9FD87), *Staphylococcus epidermidis* (Uniprot accession number Q9FD76), *Staphylococcus haemolyticus* (Uniprot accession number Q9FD82), *Enterococcus faecalis* (Sutherlin et al., loc. cit.; Uniprot accession number Q9FD71; SEQ ID NO:99), *Enterococcus faecium* (Uniprot accession number Q9FD66), *Streptococcus pneumonia* (Uniprot accession number Q9FD56), *Streptococcus pyogenes* (Uniprot accession number Q9FD61) and *Methanobacterium thermoautotrophicum* (accession number AE000857), *Borrelia burgdorferi* (NCBI accession number BB0683). Further HMG-CoA synthases are, e.g., described in WO 2011/032934. A preferred HMG-CoA synthase is the enzyme from *Schizosaccharomyces pombe* (Uniprot P54874). In a particularly preferred embodiment, the HMG-CoA synthase employed in the method of the invention has an amino acid sequence as shown in SEQ ID NO: 36 or SEQ ID NO:99 or shows an amino acid sequence which is at least x % homologous to SEQ ID NO: 36 or SEQ ID NO:99 and has the activity of a HMG-CoA synthase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of catalyzing the condensation of acetyl-CoA and acetoacetyl-CoA into 3-hydroxy-3-methylglutaryl-CoA. As regards the determination of the degree of identity, the same applies as has been set forth herein above.

The Enzymatic Conversion of Acetyl-CoA into Acetoacetyl-CoA: Steps XIII, XIV and XV as Shown in FIG. 1

The acetoacetyl-CoA which is either converted into 3-hydroxy-3-methylglutaryl-CoA or which is converted into acetoacetate may itself be provided by an enzymatic reaction, namely the enzymatic conversion of acetyl-CoA into acetoacetyl-CoA.

Figure 15:
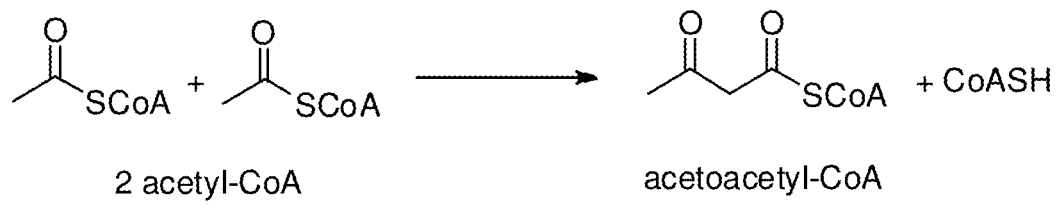

According to the present invention, the conversion of acetyl-CoA into said acetoacetyl-CoA can be achieved by different routes. One possibility is to first convert acetyl-CoA into malonyl-CoA (step XIV as shown in FIG. 1) and then to further condense said malonyl-CoA and acetyl-CoA into acetoacetyl-CoA (step XV as shown in FIG. 1). Another possibility is to directly condense in a single enzymatic reaction two molecules of acetyl-CoA into acetoacetyl-CoA (step XIII as shown in FIG. 1). These reactions are schematically shown in FIG. 15 (step XIII), FIG. 16 (step XIV) and FIG. 17 (step XV), respectively.

Thus, the present invention also relates to a method for producing isobutene from acetyl-CoA in which acetyl-CoA is first converted into acetoacetyl-CoA by any of the above-mentioned routes which is then condensed with acetyl-CoA into 3-hydroxy-3-methylglutaryl-CoA which is then converted into 3-methylglutaconyl-CoA which is then converted into 3-methylcrotonyl-CoA which is then further converted into 3-methylcrotonic acid which is then further converted into isobutene as described herein above.

Moreover, the present invention also relates to a method for producing isobutene from acetyl-CoA in which acetyl-CoA is first converted into acetoacetyl-CoA by any of the above-mentioned routes by any of the above-mentioned routes which is then converted into acetoacetate which is then converted into acetone which is then condensed with acetyl-CoA into 3-hydroxyisovalerate (HIV) which is then converted into 3-methylcrotonic acid as described herein above. Further, said 3-methylcrotonic acid is then further converted into isobutene as described herein above.

According to the present invention, the enzymatic conversion of acetyl-CoA into malonyl-CoA preferably makes use of an acetyl-CoA carboxylase (EC 6.4.1.2) (step XIV as shown in FIG. 1). This naturally occurring reaction fixes $CO_2$ on acetyl-CoA utilizing ATP resulting in malonyl-CoA. Enzymes classified as an acetyl-CoA carboxylases (EC 6.4.1.2) catalyze the following reaction:

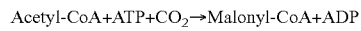

Acetyl-CoA+ATP+$CO_2$→Malonyl-CoA+ADP

Moreover, according to the present invention, the enzymatic condensation of malonyl-CoA and acetyl-CoA into said acetoacetyl-CoA preferably makes use of an acetoacetyl-CoA synthase (EC 2.3.1.194) (step XV as shown in FIG. 1). This is a natural occurring reaction and condenses malonyl-CoA and acetyl-CoA in a decarboxylation reaction. Enzymes classified as acetoacetyl-CoA synthases (EC 2.3.1.194) catalyze the enzymatic conversion of acetyl-CoA and malonyl-CoA into acetoacetyl-CoA according to the following reaction.

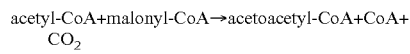

acetyl-CoA+malonyl-CoA→acetoacetyl-CoA+CoA+$CO_2$

This reaction is catalyzed by an enzyme called acetoacetyl-CoA synthase (EC 2.3.1.194). The gene encoding this enzyme was identified in the mevalonate pathway gene cluster for terpenoid production in a soil-isolated Gram-positive *Streptomyces* sp. Strain CL190 (Okamura et al., PNAS USA 107 (2010), 11265-11270, 2010). Moreover a biosynthetic pathway using this enzyme for acetoacetyl-CoA production was recently developed in *E. coli* (Matsumoto K et al., Biosci. Biotechnol. Biochem, 75 (2011), 364-366).

Alternatively, the enzymatic conversion of acetyl-CoA into said acetoacetyl-CoA consists of a single enzymatic reaction in which acetyl-CoA is directly converted into acetoacetyl-CoA by the enzymatic condensation of two molecules of acetyl-CoA into acetoacetyl-CoA. Preferably, the enzymatic conversion of acetyl-CoA into acetoacetyl-CoA is achieved by making use of an acetyl-CoA acetyltransferase (EC 2.3.1.9).

Thus, acetoacetyl-CoA can be produced from acetyl-CoA as, e.g., described in WO 2013/057194. Therefore, according to the present invention, acetyl-CoA can, for example, be converted into acetoacetyl-CoA by the following reaction:

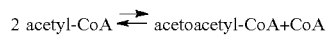

2 acetyl-CoA ⇌ acetoacetyl-CoA+CoA

This reaction is a naturally occurring reaction and is catalyzed by enzymes called acetyl-CoA C-acetyltransferases which are classified as EC 2.3.1.9. Enzymes belonging to this class and catalyzing the above shown conversion of two molecules of acetyl-CoA into acetoacetyl-CoA and CoA occur in organisms of all kingdoms, i.e. plants, animals, fungi, bacteria etc. and have extensively been described in the literature. Nucleotide and/or amino acid sequences for such enzymes have been determined for a variety of organisms, like *Homo sapiens, Arabidopsis thaliana, E. coli, Bacillus subtilis, Clostridium acetobutylicum* and *Candida*, to name just some examples. In principle, any acetyl-CoA C-acetyltransferase (EC 2.3.1.9) can be used in the context of the present invention. In one preferred embodiment the enzyme is an acetyl-CoA acetyltransferase from *Clostridium acetobutylicum* (Uniprot P45359). In a particularly preferred embodiment, the acetyl-CoA acetyltransferase employed in the method of the invention has an amino acid sequence as shown in SEQ ID NO: 37 or shows an amino acid sequence which is at least x % homologous to SEQ ID NO: 37 and has the activity of an acetyl-CoA acetyltransferase with x being an integer between 30 and 100, preferably 35, 40, 45, 50, 55, 60, 65, 70, 75, 80, 85, 90, 91, 92, 93, 94, 95, 96, 97, 98 or 99 wherein such an enzyme is capable of converting acetyl-CoA into acetoacetyl-CoA as set forth herein above.

As regards the determination of the degree of identity, the same applies as has been set forth herein above.

The Enzymatic Recycling of Metabolites Occurring in the Pathway of the Present Invention: Steps Xa, Xb, XI and XII as Shown in FIG. 1

Figure 18:
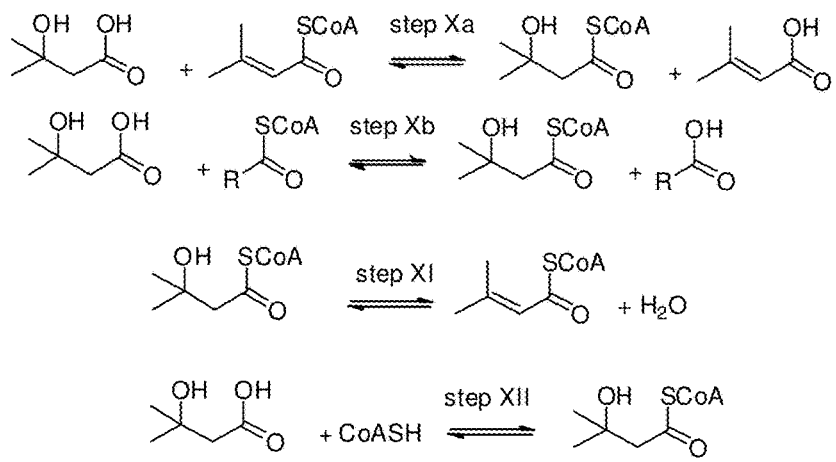

The above-described method of the present invention for producing isobutene from acetyl-CoA may be supplemented by one or more of the following reactions as shown in step Xa, step Xb, step XI and step XII of FIG. 18.

These steps relate to alternative bioconversions which may occur concomitantly to any of the above-described methods for producing isobutene.

Figure 19:
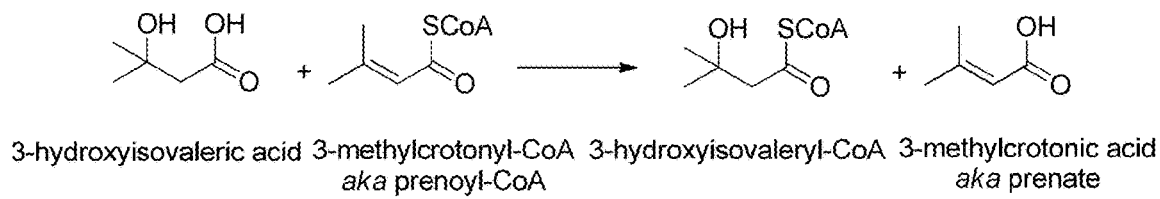
Figure 20:
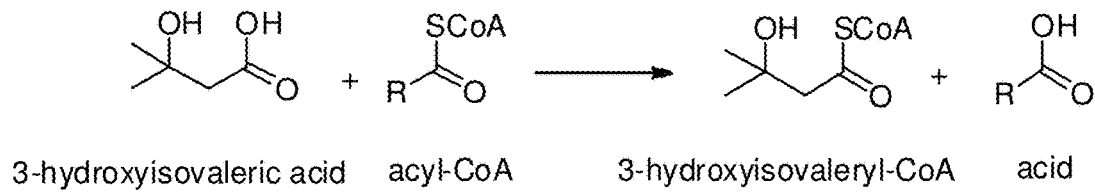
Figure 21:
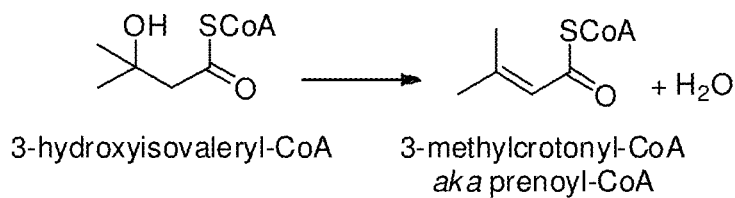
Figure 22:
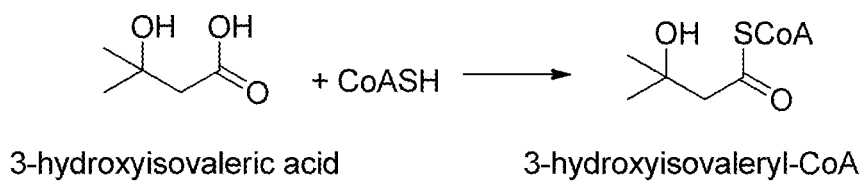

Thus, the present invention relates to any of the above-described methods for producing isobutene from 3-methylcrotonic acid (or from any of the above-described intermediates in the described pathways from acetyl-CoA into isobutene) wherein additionally a) 3-hydroxyisovalerate (HIV) is enzymatically converted into 3-methylcrotonic acid with a concomitant transfer of CoA from 3-methylcrotonyl-CoA on 3-hydroxyisovalerate (HIV) to result in 3-hydroxyisovaleryl-CoA (step Xa as schematically shown in FIG. 19); and/or b) 3-hydroxyisovalerate (HIV) is enzymatically converted into 3-hydroxyisovaleryl-CoA (step Xb as schematically shown in FIG. 20); and/or c) 3-hydroxyisovaleryl-CoA is enzymatically converted into 3-methylcrotonyl-CoA (step XI as schematically shown in FIG. 21); and/or d) 3-hydroxyisovalerate (HIV) is enzymatically converted into 3-hydroxyisovaleryl-CoA (step XII as schematically shown in FIG. 22).

These reactions which will be described in more detail in the following, may occur concomitantly to any of the above-described methods for producing isobutene are beneficial for several reasons. First, it is known that the hydration of an enoyl-CoA (such as, e.g., 3-methylcrotonyl-CoA) is a favoured reaction in vivo in an aqueous medium. Accordingly, the above reactions represent possibilities which allow to drive the metabolic flux toward the precursor of isobutene, i.e., 3-methylcrotonic acid, even in case the pathway "leaks" into the direction of 3-hydroxyisovalerate (HIV) and/or 3-hydroxyisovaleryl-CoA. Second, the above conversions beneficially involve the conservation of energy into a thioester CoA bond via a transfer of a thioester group.

The Enzymatic Conversion of 3-Hydroxyisovalerate (HIV) into 3-Methylcrotonic Acid with a Concomitant Transfer of CoA from 3-Methylcrotonyl-CoA on 3-Hydroxyisovalerate (HIV) to Result in 3-Hydroxyisovaleryl-CoA as Shown in Step Xa of FIG. 18

Thus, in a first aspect, the 3-methylcrotonic acid which is converted into isobutene may be provided by an enzymatic reaction wherein 3-hydroxyisovalerate (HIV) is enzymatically converted into 3-methylcrotonic acid with a concomitant transfer of CoA from 3-methylcrotonyl-CoA to 3-hydroxyisovalerate (HIV) to result in 3-hydroxyisovaleryl-CoA (step Xa as shown in FIG. 18). This reaction is schematically illustrated in FIG. 19.

Thus, the present invention also relates to a method for producing isobutene from 3-hydroxyisovalerate (HIV) wherein 3-hydroxyisovalerate (HIV) is enzymatically converted into 3-methylcrotonic acid with a concomitant transfer of CoA from 3-methylcrotonyl-CoA on 3-hydroxyisovalerate (HIV) to result in 3-hydroxyisovaleryl-CoA. Further, the thus produced 3-methylcrotonic acid is then enzymatically converted into isobutene as described herein above.

Moreover, the present invention also relates to a method for producing 3-methylcrotonic acid and 3-hydroxyisovaleryl-CoA from 3-hydroxyisovalerate (HIV) and from 3-methylcrotonyl-CoA wherein 3-hydroxyisovalerate (HIV) is enzymatically converted into 3-methylcrotonic acid with a concomitant transfer of CoA from 3-methylcrotonyl-CoA on 3-hydroxyisovalerate (HIV) to result in 3-hydroxyisovaleryl-CoA.

According to the present invention, the conversion of 3-hydroxyisovalerate (HIV) and 3-methylcrotonyl-CoA into 3-methylcrotonic acid and 3-hydroxyisovaleryl-CoA wherein 3-hydroxyisovalerate (HIV) is enzymatically converted into 3-methylcrotonic acid with a concomitant transfer of CoA from 3-methylcrotonyl-CoA on 3-hydroxyisovalerate (HIV) to result in 3-hydroxyisovaleryl-CoA preferably makes use of an enzyme which is classified as a CoA-transferase (EC 2.8.3.-) capable of transferring the CoA group of 3-methylcrotonyl-CoA to a carboxylic acid, i.e., 3-hydroxyisovalerate (HIV).

CoA-transferases (EC 2.8.3.-) as well as preferred enzymes of this enzyme class have already been described above. Accordingly, as regards these enzymes, the same applies to the conversion of 3-hydroxyisovalerate (HIV) and 3-methylcrotonyl-CoA into 3-methylcrotonic acid and 3-hydroxyisovaleryl-CoA as has been set forth above.

Preferably, the CoA-transferase employed in a method according to the present invention in the enzymatic conversion of 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA is a CoA-transferase selected from the group consisting of:

propionate:acetate-CoA transferase (EC 2.8.3.1);
acetate CoA-transferase (EC 2.8.3.8); and
butyrate-acetoacetate CoA-transferase (EC 2.8.3.9).

Propionate:acetate-CoA transferases (EC 2.8.3.1), acetate CoA-transferases (EC 2.8.3.8) and butyrate-acetoacetate CoA-transferases (EC 2.8.3.9) as well as preferred enzymes of these enzyme classes have already been described above. Accordingly, as regards these enzymes, the same applies to the conversion of 3-hydroxyisovalerate (HIV) and 3-methylcrotonyl-CoA into 3-methylcrotonic acid and 3-hydroxyisovaleryl-CoA as has been set forth above.

The Enzymatic Conversion of 3-Hydroxyisovalerate (HIV) into 3-Hydroxyisovaleryl-CoA as Shown in Step Xb of FIG. 18

In addition or in the alternative to the above-described methods (step Xa), the 3-hydroxyisovaleryl-CoA may also be provided by an enzymatic conversion of 3-hydroxyisovalerate into said 3-hydroxyisovaleryl-CoA (step Xb as shown in FIG. 18). In this reaction, 3-hydroxyisovalerate reacts with an acyl-CoA to result in 3-hydroxyisovaleryl-CoA and an acid. This reaction is schematically illustrated in FIG. 19.

Preferably, said acyl-CoA is acetyl-CoA.

Thus, the present invention also relates to a method for producing 3-hydroxyisovaleryl-CoA from 3-hydroxyisovalerate (HIV) wherein 3-hydroxyisovalerate reacts with an acyl-CoA, preferably with acetyl-CoA, to result in 3-hydroxyisovaleryl-CoA and a respective acid.

Preferably, this conversion is achieved by making use of an enzyme which is classified as a CoA-transferase (EC 2.8.3.-). As regards the preferred embodiments of said CoA-transferase (EC 2.8.3.-) in the context of step Xb, the same applies, mutatis mutandis, as has been set forth above with respect to the CoA-transferases (EC 2.8.3.-) in the enzymatic conversion of 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA (step Xa as shown in FIG. 18).

The Enzymatic Conversion of 3-Hydroxyisovaleryl-CoA into 3-Methylcrotonyl-CoA as Shown in Step XI of FIG. 18

In addition or in the alternative to the above-described methods (step VII), the 3-methylcrotonyl-CoA may be provided by an enzymatic reaction wherein 3-hydroxyisovaleryl-CoA is enzymatically converted into 3-methylcrotonyl-CoA (step XI as shown in FIG. 18). This reversible reaction is a dehydration reaction wherein 3-hydroxyisovaleryl-CoA is dehydrated into 3-methylcrotonyl-CoA and is schematically illustrated in FIG. 21.

Thus, the present invention also relates to a method for producing isobutene from 3-hydroxyisovaleryl-CoA wherein 3-hydroxyisovaleryl-CoA is first enzymatically converted into 3-methylcrotonyl-CoA wherein 3-methylcrotonyl-CoA is further enzymatically converted into 3-methylcrotonic acid according to any of the above-described methods. Further, the thus produced 3-methylcrotonic acid is then enzymatically converted into isobutene as described herein above.

According to the present invention, the enzymatic conversion of 3-hydroxyisovaleryl-CoA into 3-methylcrotonyl-CoA preferably makes use of
(i) an enoyl-CoA hydratase (EC 4.2.1.17);
(ii) a long-chain-enoyl-CoA hydratase (EC 4.2.1.74);
(iii) a 3-hydroxypropionyl-CoA dehydratase (EC 4.2.1.116);
(iv) a 3-hydroxybutyryl-CoA dehydratase (EC 4.2.1.55);
(v) a 3-hydroxyoctanoyl-[acyl-carrier-protein] dehydratase (EC 4.2.1.59);
(vi) a crotonyl-[acyl-carrier-protein] hydratase (EC 4.2.1.58);
(vii) a 3-hydroxydecanoyl-[acyl-carrier-protein] dehydratase (EC 4.2.1.60);
(viii) a 3-hydroxypalmityl-[acyl-carrier-protein] dehydratase (EC 4.2.1.61); or
(ix) a 3-methylglutaconyl-CoA hydratase (EC 4.2.1.18).

In a preferred embodiment of the method according to the invention the conversion of 3-hydroxyisovaleryl-CoA into 3-methylcrotonyl-CoA is achieved by the use of an enoyl-CoA hydratase (EC 4.2.1.17). Enoyl-CoA hydratases (EC 4.2.1.17) as well as preferred enzymes of this enzyme class have already been described above. Accordingly, as regards these enzymes, the same applies to the conversion of 3-hydroxyisovaleryl-CoA into 3-methylcrotonyl-CoA as has been set forth above.

In another preferred embodiment of the method according to the invention the conversion of 3-hydroxyisovaleryl-CoA into 3-methylcrotonyl-CoA is achieved by the use of a long-chain-enoyl-CoA hydratase (EC 4.2.1.74). Long-chain-enoyl-CoA hydratases (EC 4.2.1.74) catalyze the following reaction:

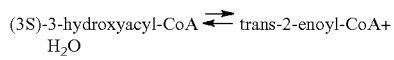

(3S)-3-hydroxyacyl-CoA ⇌ trans-2-enoyl-CoA+ H₂O

This enzyme belongs to the family of lyases, specifically the hydro-lyases, which cleave carbon-oxygen bonds. The systematic name of this enzyme class is long-chain-(3S)-3-hydroxyacyl-CoA hydro-lyase. This enzyme is also called long-chain enoyl coenzyme A hydratase and it participates in fatty acid elongation in mitochondria and fatty acid metabolism. This enzyme occurs in a number of organisms, e.g., in *Rattus norvegicus* (Wu et al., Org. Lett. 10 (2008), 2235-2238), *Sus scrofa* and *Cavia porcellus* (Fong and Schulz, J. Biol. Chem. 252 (1977), 542-547; Schulz, Biol. Chem. 249 (1974), 2704-2709) and in principle any long-chain-enoyl-CoA hydratase which can catalyze the conversion of 3-hydroxyisovaleryl-CoA into 3-methylcrotonyl-CoA can be employed in the method of the invention.

The Enzymatic Conversion of 3-Hydroxyisovalerate (HIV) into 3-Hydroxyisovaleryl-CoA as Shown in Step XII of FIG. 18

In addition or in the alternative to the above-described methods (step Xa or step Xb), the 3-hydroxyisovaleryl-CoA may also be provided by an enzymatic conversion of 3-hydroxyisovalerate (HIV) into said 3-hydroxyisovaleryl-CoA (step XII as shown in FIG. 18). This general reaction wherein coenzyme A (CoASH) is fixed is schematically illustrated in FIG. 22.

Thus, the present invention also relates to a method for producing isobutene from 3-hydroxyisovalerate (HIV) in which 3-hydroxyisovalerate (HIV) is first converted into 3-hydroxyisovaleryl-CoA wherein 3-hydroxyisovaleryl-CoA is then enzymatically converted into 3-methylcrotonyl-CoA wherein 3-methylcrotonyl-CoA is further enzymatically converted into 3-methylcrotonic acid according to any of the above-described methods. Further, the thus produced 3-methylcrotonic acid is then enzymatically converted into isobutene as described herein above.

Moreover, the present invention also relates to a method for producing 3-hydroxyisovaleryl-CoA from 3-hydroxyisovalerate (HIV).

According to the present invention, the enzymatic conversion of 3-hydroxyisovalerate (HIV) into 3-hydroxyisovaleryl-CoA preferably makes use of an enzyme belonging to the family of ligases forming a carbon-sulfur bond (EC 6.2.1.-). The general reaction of the enzymatic conversion of 3-hydroxyisovalerate (HIV) into 3-hydroxyisovaleryl-CoA wherein coenzyme A (CoASH) is fixed can be catalyzed by an enzyme belonging to the family of ligases forming a carbon-sulfur bond (EC 6.2.1.-) via two alternative mechanisms. In a first alternative reaction, an acyl-AMP is generated as an intermediate before coenzyme A is fixed as schematically illustrated in FIG. 23.

Figure 24:
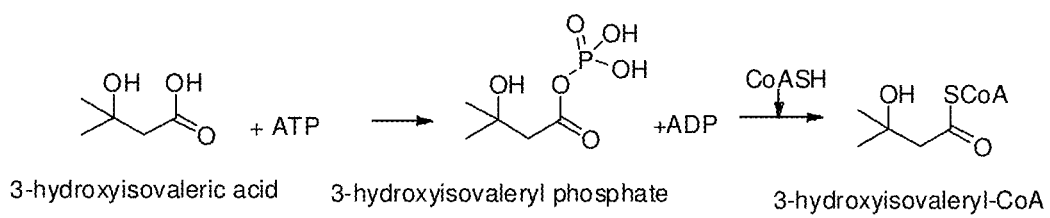

In a second alternative reaction, an acyl phosphate is generated as an intermediate before coenzyme A is fixed as schematically illustrated in FIG. 24.

Enzymes which belong to the family of ligases forming a carbon-sulfur bond (EC 6.2.1.-) which are capable of enzymatically converting 3-hydroxyisovalerate (HIV) into 3-hydroxyisovaleryl-CoA wherein an acyl-AMP intermediate (i.e., the acyl adenylate intermediate 3-hydroxyisovaleryl-adenosine monophosphate) is generated before coenzyme A is fixed coenzyme A (CoASH) share common structural motifs which are referenced in the InterPro (InterPro44.0; Release Sep. 25, 2013) as InterPro IPR020845, AMP-binding, conserved site (http://www.ebi.ac.uk/interpro/entry/IPR020845) and IPR000873 (http://www.ebi.ac.uk/interpro/entry/IPR000873). The accession number for these enzymes in the Pfam database is PF00501.

Figure 23:
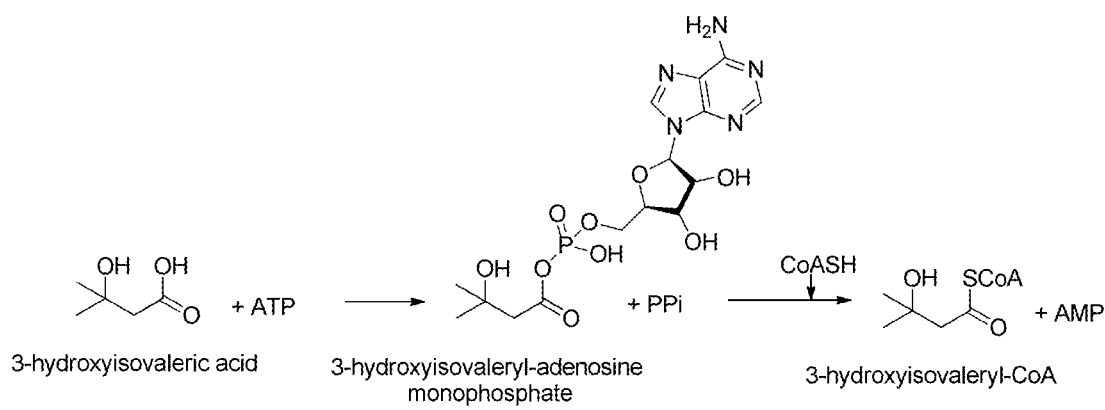

As regards the first alternative reaction (wherein an acyl-AMP is generated as an intermediate before coenzyme A is fixed as schematically illustrated in FIG. 23), examples of enzymes which belong to the above family of ligases forming a carbon-sulfur bond (EC 6.2.1.-) which are capable of enzymatically converting 3-hydroxyisovalerate (HIV)

into 3-hydroxyisovaleryl-CoA wherein an acyl-AMP intermediate (i.e., the acyl adenylate intermediate 3-hydroxyisovaleryl-adenosine monophosphate) is generated before coenzyme A is fixed coenzyme A (CoASH) and which may be used in the method for producing 3-hydroxyisovaleryl-CoA from 3-hydroxyisovalerate (HIV) are summarized in the following Table A:

TABLE A

CoA ligases (EC 6.2.1.—) capable of enzymatically converting 3-hydroxyisovalerate (HIV) into 3-hydroxyisovaleryl-CoA involving an acyl-adenylate as an intermediate

| Enzyme name | EC number |
|---|---|
| Acetate-CoA ligase | 6.2.1.1 |
| Butyrate-CoA ligase | 6.2.1.2 |
| Long chain fatty-acid-CoA ligase | 6.2.1.3 |
| 4-coumarate-CoA ligase | 6.2.1.12 |
| Arachidonate-CoA ligase | 6.2.1.15 |
| Propionate-CoA ligase | 6.2.1.17 |
| Phytanate-CoA ligase | 6.2.1.24 |
| o-succinylbenzoate-CoA ligase | 6.2.1.26 |
| 3-alpha,7-alpha-dihydroxy-5-beta-cholestanate-CoA ligase | 6.2.1.28 |
| 2-furoate-CoA ligase | 6.2.1.31 |
| 4-chlorobenzoate-CoA ligase | 6.2.1.33 |
| 3-hydroxybenzoate-CoA ligase | 6.2.1.37 |
| 4-hydroxybutyrate-CoA ligase | 6.2.1.40 |
| 3-oxocholest-4-en-26-oate--CoA ligase | 6.2.1.42 |
| 3-(methylthio)propionyl-CoA ligase | 6.2.1.44 |
| Cholate-CoA ligase | 6.2.1.7 |
| Oxalate-CoA ligase | 6.2.1.8 |
| Biotin-CoA ligase | 6.2.1.11 |
| 6-carboxyhexanoate-CoA ligase | 6.2.1.14 |
| Acetoacetate--CoA ligase | 6.2.1.16 |
| Dicarboxylate-CoA ligase | 6.2.1.23 |
| Benzoate-CoA ligase | 6.2.1.25 |
| 4-hydroxybenzoate-CoA ligase | 6.2.1.27 |
| Phenylacetate-CoA ligase | 6.2.1.30 |
| Anthranilate-CoA ligase | 6.2.1.32 |
| 3-hydroxypropionyl-CoA synthase | 6.2.1.36 |
| (2,2,3-trimethyl-5-oxocyclopent-3-enyl)acetyl-CoA synthase | 6.2.1.38 |
| 3-((3aS,4S,7aS)-7a-methyl-1,5-dioxo-octahydro-1H-inden-4-yl)propanoate-CoA ligase | 6.2.1.41 |
| 2-hydroxy-7-methoxy-5-methyl-1-naphthoate--CoA ligase | 6.2.1.43 |
| Malonate-CoA ligase | 6.2.1.n3 |

In a preferred embodiment, the enzymatic conversion of 3-hydroxyisovalerate (HIV) into 3-hydroxyisovaleryl-CoA via an acyl adenylate intermediate can, e.g., be achieved by the use of a butanoate:CoA ligase (AMP forming) (EC 6.2.1.2). Butanoate:CoA ligases are enzymes which catalyze the following reaction:

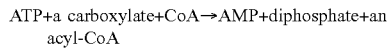

ATP+a carboxylate+CoA→AMP+diphosphate+an acyl-CoA

These enzymes participate in butanoate metabolism. The occurrence of these enzymes has been described for a large number of organisms, including prokaryotes and eukaryotes, in particular, bacteria, algae, fungi, plants and animals, e.g. for *Methanobacterium formicum, Streptomyces coelicolor, Mycobacterium avium, Penicillium chrysogenum, Paecilomyces variotii, Pseudomonas aeruginosa, Dictyostelium discoideum, Cavia porcellus, Ovis aries, Sus scrofa, Bos taurus, Mus musculus, Rattus norvegicus*, and *Homo sapiens*.

In a preferred embodiment, the enzymatic conversion of 3-hydroxyisovalerate (HIV) into 3-hydroxyisovaleryl-CoA via an acyl adenylate intermediate is achieved by making use of a butanoate:CoA ligase (AMP forming) (EC 6.2.1.2) derived from *Methanobacterium formicum*. The amino acid sequence of said protein is shown in SEQ ID NO: 77.

In a preferred embodiment of the present invention the butanoate:CoA ligase (AMP forming) is an enzyme comprising the amino acid sequence of SEQ ID NO: 77 or a sequence which is at least n % identical to SEQ ID NO: 77 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-hydroxyisovalerate (HIV) into 3-hydroxyisovaleryl-CoA. As regards the determination of the sequence identity, the same applies as has been set forth above.

As regards the second alternative reaction (wherein an acyl phosphate is generated as an intermediate before coenzyme A is fixed as schematically illustrated in FIG. 24), examples of enzymes which belong to the above family of ligases forming a carbon-sulfur bond (EC 6.2.1.-) which are capable of enzymatically converting 3-hydroxyisovalerate (HIV) into 3-hydroxyisovaleryl-CoA wherein an acyl phosphate intermediate (i.e., the acyl phosphate intermediate 3-hydroxyisovaleryl phosphate) is generated before coenzyme A is fixed coenzyme A (CoASH) and which may be used in the method for producing 3-hydroxyisovaleryl-CoA from 3-hydroxyisovalerate (HIV) are summarized in the following Table B.

TABLE B

CoA ligases (EC 6.2.1.—) capable of enzymatically converting 3-hydroxyisovalerate (HIV) into 3-hydroxyisovaleryl-CoA involving an acyl phosphate as an intermediate

| Enzyme name | EC number |
|---|---|
| Succinate-CoA ligase (GDP-forming) | 6.2.1.4 |
| Glutarate-CoA ligase | 6.2.1.6 |
| Acid-CoA ligase (GDP-forming) | 6.2.1.10 |
| Citrate-CoA ligase | 6.2.1.18 |
| Succinate-CoA ligase (ADP-forming) | 6.2.1.5 |
| Malate-CoA ligase | 6.2.1.9 |
| Acetate-CoA ligase (ADP-forming) | 6.2.1.13 |

The Alternative Route for the Enzymatic Conversion from Acetyl-CoA into Isobutene Via 3-Methyl-3-Butenoyl-CoA and 3-Methyl-3-Butenoic Acid In an alternative to the above, the present invention also relates to a method for the production of isobutene via an alternative route as also shown in FIG. 1 wherein isobutene is produced by the enzymatic conversion of 3-methyl-3-butenoic acid into isobutene. Thus, the present invention provides a method for the production of isobutene comprising the enzymatic conversion of 3-methyl-3-butenoic acid into isobutene. Preferably, the enzymatic conversion of 3-methyl-3-butenoic acid into isobutene is achieved by making use of an 3-methyl-3-butenoic acid decarboxylase.

In accordance with this alternative route, the present invention not only relates to a method for the production of isobutene from 3-methyl-3-butenoic acid. Rather, as will be outlined in more detail further below, this conversion is preferably embedded in a pathway for the production of isobutene starting from acetyl-CoA which is a central component and an important key molecule in metabolism used in many biochemical reactions.

Therefore, the present invention also relates to a pathway starting from acetyl-CoA wherein two acetyl-CoA molecules are enzymatically condensed into acetoacetyl-CoA. Alternatively, acetyl-CoA is enzymatically converted into malonyl-CoA which may then be converted into said acetoacetyl-CoA by the enzymatic condensation of malonyl-CoA and acetyl-CoA into said acetoacetyl-CoA.

Further, the thus produced acetoacetyl-CoA can enzymatically be converted into 3-methyl-3-butenoic acid (which is then ultimately converted into isobutene) via the following briefly summarized pathway.

In this pathway, the thus produced acetoacetyl-CoA can further enzymatically be converted into 3-hydroxy-3-methylglutaryl-CoA. Moreover, the thus produced 3-hydroxy-3-methylglutaryl-CoA can further enzymatically be converted into 3-methylglutaconyl-CoA. Further, the thus produced 3-methylglutaconyl-CoA can enzymatically be converted into 3-methyl-3-butenoyl-CoA. Further, the thus produced 3-methyl-3-butenoyl-CoA can further be converted in a subsequent enzymatic reaction into 3-methyl-3-butenoic acid (which can then ultimately be converted into isobutene as described above and further below).

The Enzymatic Conversion of 3-Methyl-3-Butenoic Acid into Isobutene: Step XVI as Shown in FIG. 1

According to the present invention, the enzymatic conversion of 3-methyl-3-butenoic acid into isobutene can be achieved by a decarboxylation. "Decarboxylation" is generally a chemical reaction that removes a carboxyl group and releases carbon dioxide ($CO_2$); see FIG. 25.

The enzymatic conversion of 3-methyl-3-butenoic acid into isobutene can preferably be achieved by making use of an 3-methyl-3-butenoic acid decarboxylase. In accordance with the present invention, an 3-methyl-3-butenoic acid decarboxylase is an enzyme which is capable of converting 3-methyl-3-butenoic acid into isobutene. In preferred embodiments, the 3-methyl-3-butenoic acid decarboxylase is selected from the group consisting of:
(i) an FMN-dependent decarboxylase associated with an FMN prenyl transferase; or
(ii) an aconitate decarboxylase (EC 4.1.1.6); or
(iii) a methylcrotonyl-CoA carboxylase (EC 6.4.1.4); or
(iv) a geranoyl-CoA carboxylase (EC 6.4.1.5); or
(v) a protocatechuate (PCA) decarboxylase (EC 4.1.1.63).

In other preferred embodiments, the 3-methyl-3-butenoic acid decarboxylase is selected from the group consisting of: 6-methylsalicylate decarboxylase (EC 4.1.1.52), 2-oxo-3-hexenedioate decarboxylase (EC 4.1.1.77) and 5-oxopent-3-ene-1,2,5-tricarboxylate decarboxylase (EC 4.1.1.68).

As regards the afore-mentioned embodiment, for the FMN-dependent decarboxylase associated with an FMN prenyl transferase, the aconitate decarboxylase (EC 4.1.1.6), the methylcrotonyl-CoA carboxylase (EC 6.4.1.4), the geranoyl-CoA carboxylase (EC 6.4.1.5), the protocatechuate (PCA) decarboxylase (EC 4.1.1.63), the 6-methylsalicylate decarboxylase (EC 4.1.1.52), the 2-oxo-3-hexenedioate decarboxylase (EC 4.1.1.77) and the 5-oxopent-3-ene-1,2,5-tricarboxylate decarboxylase (EC 4.1.1.68), the same applies as has been set forth above in connection with other methods of the present invention.

The Enzymatic Conversion of 3-Methyl-3-Butenoyl-CoA into 3-Methyl-3-Butenoic Acid: Steps XVIIa, XVIIb or XVIIc as Shown in FIG. 1

Figure 26:
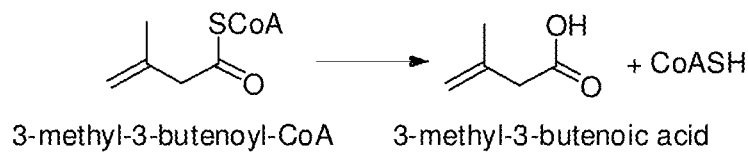

The 3-methyl-3-butenoic acid may itself be provided by an enzymatic reaction, namely the enzymatic conversion of 3-methyl-3-butenoyl-CoA into 3-methyl-3-butenoic acid; see FIG. 26.

Accordingly, the present invention relates to a method for producing isobutene from 3-methyl-3-butenoyl-CoA in which 3-methyl-3-butenoyl-CoA is first converted into 3-methyl-3-butenoic acid which is then further converted into isobutene as described herein above.

According to the present invention, the conversion of 3-methyl-3-butenoyl-CoA into 3-methyl-3-butenoic acid can, e.g., be achieved by three different alternative enzymatic routes, i.e., by:
(a) a single enzymatic reaction (see FIG. 27) in which 3-methyl-3-butenoyl-CoA is directly converted into 3-methyl-3-butenoic acid, preferably by making use of a CoA transferase (EC 2.8.3.-), preferably a propionate: acetate-CoA transferase (EC 2.8.3.1), an acetate CoA-transferase (EC 2.8.3.8) or a succinyl-CoA:acetate CoA-transferase (EC 2.8.3.18);
(b) a single enzymatic reaction (see FIG. 28) in which 3-methyl-3-butenoyl-CoA is directly converted into 3-methyl-3-butenoic acid, preferably by making use of a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20); or
(c) two enzymatic steps (see FIG. 29) comprising
   (i) first enzymatically converting 3-methyl-3-butenoyl-CoA into 3-methyl-3-butenoyl phosphate, preferably by making use of a phosphate butyryltransferase (EC 2.3.1.19) or a phosphate acetyltransferase (EC 2.3.1.8); and
   (ii) then enzymatically converting the thus obtained 3-methyl-3-butenoyl phosphate into said 3-methyl-3-butenoic acid, preferably by making use of a phosphotransferase with a carboxy group as acceptor (EC 2.7.2.-), preferably a propionate kinase (EC 2.7.2.15), an acetate kinase (EC 2.7.2.1), a butyrate kinase (EC 2.7.2.7) or a branched-chain-fatty-acid kinase (EC 2.7.2.14).

As regards the aforementioned embodiments, for the CoA transferase (EC 2.8.3.-), the propionate:acetate-CoA transferase (EC 2.8.3.1), the acetate CoA-transferase (EC 2.8.3.8), the succinyl-CoA:acetate CoA-transferase (EC 2.8.3.18), the thioester hydrolase (EC 3.1.2.-), the acetyl-CoA hydrolase (EC 3.1.2.1), the ADP-dependent short-chain-acyl-CoA hydrolase (EC 3.1.2.18), the an acyl-CoA hydrolase (EC 3.1.2.20) the phosphate butyryltransferase (EC 2.3.1.19), the phosphate acetyltransferase (EC 2.3.1.8), the phosphotransferase with a carboxy group as acceptor (EC 2.7.2.-), the propionate kinase (EC 2.7.2.15), the acetate kinase (EC 2.7.2.1), the butyrate kinase (EC 2.7.2.7) and the branched-chain-fatty-acid kinase (EC 2.7.2.14), the same applies as has been set forth above in connection with the other methods of the present invention.

The Enzymatic Conversion of 3-Methylglutaconyl-CoA into 3-Methyl-3-Butenoyl-CoA: Step XVIII as Shown in FIG. 1

Figure 30:
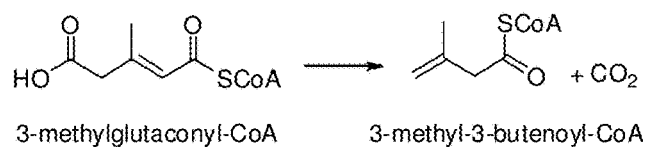

The 3-methyl-3-butenoyl-CoA may itself be provided by an enzymatic reaction, namely the enzymatic conversion of 3-methylglutaconyl-CoA into 3-methyl-3-butenoyl-CoA; see FIG. 30.

Accordingly, the present invention relates to a method for producing isobutene from 3-methyl-3-butenoyl-CoA in which 3-methylglutaconyl-CoA is first converted into 3-methyl-3-butenoyl-CoA which is then further converted into 3-methyl-3-butenoic acid which is then further converted into isobutene as described herein above.

Moreover, the present invention relates to a method for producing 3-methyl-3-butenoyl-CoA by converting 3-methylglutaconyl-CoA into 3-methyl-3-butenoyl-CoA. According to the present invention, the conversion of 3-methylglutaconyl-CoA into 3-methyl-3-butenoyl-CoA can preferably be achieved by making use of (a) (i) a methylcrotonyl-CoA carboxylase (EC 6.4.1.4); or
(ii) a geranoyl-CoA carboxylase (EC 6.4.1.5),
(b) an N-terminal domain of CurF from *Lynbya majuscula* multifunctional protein or a 3-methylglutaconyl-CoA decarboxylase, preferably a 3-methylglutaconyl-CoA decarboxylase of *Myxococcus xanthus* encoded by the liuB gene; or
(c) an enzyme of the 4-oxalocrotonate decarboxylase family.

As regards the aforementioned embodiments, for the methylcrotonyl-CoA carboxylase (EC 6.4.1.4), the geranoyl-CoA carboxylase (EC 6.4.1.5) and the 3-methylglutaconyl-CoA decarboxylase, preferably the 3-methylglutaconyl-CoA decarboxylase of *Myxococcus xanthus* encoded by the liuB gene, the same applies as has been set forth above in connection with the other methods of the present invention.

Figure 31:
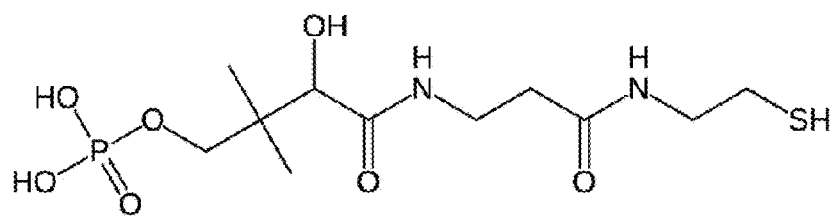

In a preferred embodiment the conversion of 3-methylglutaconyl-CoA via decarboxylation into 3-methyl-3-butenoyl-CoA is catalyzed by an N-terminal domain of CurF from *Lynbya majuscula* multifunctional protein. The N-terminal domain of CurF from *Lynbya majuscula* multifunctional protein is a domain of a polyketide synthase (PKS)/non ribosomale peptide synthase (NRPS) of the CurF multifunctional protein from *Lynbya majuscula*. This N-terminal domain of CurF has been classified as a protein belonging to the crotonase superfamily by studying the crystal structure and it naturally catalyzes the decarboxylation of 3-methylglutaconyl-ACP (Acyl Carrier Protein) into 3-methyl-crotonyl-ACP. ACP is similar to CoA as both molecules have a phosphopantetheine moiety in common (as shown in FIG. 31). Moreover, both ACP and CoA can form a thioester with a biological acid (J. Biol. Chem. 289: 35957-35963 (2007) and Chemistry & Biology 11:817-833 (2004)).

In another preferred embodiment the conversion of 3-methylglutaconyl-CoA via decarboxylation into 3-methyl-3-butenoyl-CoA is catalyzed by an enzyme of the 4-oxalocrotonate decarboxylase family (EC 4.1.1.77).

4-oxalocrotonate decarboxylases (EC 4.1.1.77) catalyse the following reaction:

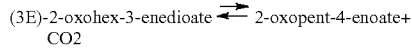

(3E)-2-oxohex-3-enedioate ⇌ 2-oxopent-4-enoate+ CO2

This enzyme is known from various organisms and has, e.g., been described in *Bortetella* sp., *Cupriavidus nector, Geobacillus stearothermophilus, Pseudomonas putida* and *Ralstonia pickettii*. Thus, in a preferred embodiment, the 4-oxalocrotonate decarboxylase used for the conversion of 3-methylglutaconyl-CoA via decarboxylation into 3-methyl-3-butenoyl-CoA is a 4-oxalocrotonate decarboxylase derived from genus *Bortetella, Cupriavidus, Geobacillus, Pseudomonas* pr *Ralstonia*, more preferably from the species *Bortetella* sp., *Cupriavidus nector, Geobacillus stearothermophilus, Pseudomonas putida* or *Ralstonia pickettii*. In an even more preferred embodiment, the 4-oxalocrotonate decarboxylase used for the conversion of 3-methylglutaconyl-CoA via decarboxylation into 3-methyl-3-butenoyl-CoA is the 4-oxalocrotonate decarboxylase of *Geobacillus stearothermophilus* (UniProt Accession number B0VXM8).

In a preferred embodiment, the 4-oxalocrotonate decarboxylase employed in the method of the present invention in the conversion of 3-methylglutaconyl-CoA via decarboxylation into 3-methyl-3-butenoyl-CoA is derived from *Geobacillus stearothermophilus* and has an amino acid sequence as shown SEQ ID NO:69.

In a preferred embodiment of the present invention the 4-oxalocrotonate decarboxylase is an enzyme comprising the amino acid sequence of SEQ ID NO: 69 or a sequence which is at least n % identical to SEQ ID NO: 69 with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99 and wherein the enzyme has the enzymatic activity of converting 3-methylglutaconyl-CoA via decarboxylation into 3-methyl-3-butenoyl-CoA. As regards the determination of the sequence identity, the same applies as has been set forth above.

The Enzymatic Conversion of 3-Hydroxy-3-Methylglutaryl-CoA into 3-Methylglutaconyl-CoA: Step VIII as Shown in FIG. 1

The 3-methylglutaconyl-CoA which can be converted into 3-methyl-3-butenoyl-CoA according to any of the above described methods may itself be provided by an enzymatic reaction, namely the enzymatic conversion of 3-hydroxy-3-methylglutaryl-CoA into 3-methylglutaconyl-CoA.

Accordingly, the present invention also relates to a method for producing isobutene from 3-hydroxy-3-methylglutaryl-CoA in which 3-hydroxy-3-methylglutaryl-CoA is first converted into 3-methylglutaconyl-CoA which is then converted into 3-methyl-3-butenoyl-CoA which is then further converted into 3-methyl-3-butenoic acid which is then further converted into isobutene as described herein above.

According to the present invention, the enzymatic conversion of 3-hydroxy-3-methylglutaryl-CoA into 3-methylglutaconyl-CoA is an enzymatic dehydration reaction which occurs naturally, and which is catalyzed, e.g., by enzymes classified as 3-methylglutaconyl-coenzyme A hydratase (EC 4.2.1.18). Accordingly, the enzymatic conversion of 3-hydroxy-3-methylglutaryl-CoA into 3-methylglutaconyl-CoA preferably makes use of a 3-methylglutaconyl-coenzyme A hydratase (EC 4.2.1.18).

As regards the afore-mentioned embodiment, for the enzymes classified as 3-methylglutaconyl-coenzyme A hydratase (EC 4.2.1.18), the same applies as has been set forth above in connection with the other methods of the present invention.

The Enzymatic Conversion of Acetoacetyl-CoA into 3-Hydroxy-3-Methylglutaryl-CoA: Step IX as Shown in FIG. 1

The 3-hydroxy-3-methylglutaryl-CoA may itself be provided by an enzymatic reaction, namely the enzymatic condensation of acetoacetyl-CoA and acetyl-CoA into 3-hydroxy-3-methylglutaryl-CoA which has already been described in detail above.

Accordingly, the present invention also relates to a method for producing isobutene from acetoacetyl-CoA and acetyl-CoA in which acetoacetyl-CoA and acetyl-CoA are first condensed into 3-hydroxy-3-methylglutaryl-CoA which is then converted into 3-methylglutaconyl-CoA which is then converted into 3-methyl-3-butenoyl-CoA which is then further converted into 3-methyl-3-butenoic acid which is then further converted into isobutene as described herein above.

The Enzymatic Conversion of Acetyl-CoA into Acetoacetyl-CoA: Step XIII, Step XIV and Step XV as Shown in FIG. 1

The acetoacetyl-CoA may itself be provided by an enzymatic reaction, namely the enzymatic conversion of acetyl-CoA into acetoacetyl-CoA via several different routes which have already been described in detail above.

Thus, the present invention also relates to a method for producing isobutene from acetyl-CoA in which acetyl-CoA is first converted into acetoacetyl-CoA by any of the above-mentioned routes which is then condensed with acetyl-CoA into 3-hydroxy-3-methylglutaryl-CoA which is then converted into 3-methylglutaconyl-CoA which is then converted into 3-methyl-3-butenoyl-CoA which is then further converted into 3-methyl-3-butenoic acid which is then further converted into isobutene as described herein above.

Summarizing the alternative route for the enzymatic conversion from acetyl-CoA into isobutene via 3-methyl-3-butenoyl-CoA and 3-methyl-3-butenoic acid as outlined above, the present invention also relates to the following embodiments as characterized by the following items 1 to 26:

1. A method for the production of isobutene comprising the enzymatic conversion of 3-methyl-3-butenoic acid into isobutene.
2. The method of item 1, wherein the enzymatic conversion of 3-methyl-3-butenoic acid into isobutene is achieved by making use of an 3-methyl-3-butenoic acid decarboxylase.
3. The method of item 2, wherein the 3-methyl-3-butenoic acid decarboxylase is:
   (i) an FMN-dependent decarboxylase associated with an FMN prenyl transferase; or
   (ii) an aconitate decarboxylase (EC 4.1.1.6); or
   (iii) a methylcrotonyl-CoA carboxylase (EC 6.4.1.4); or
   (iv) a geranoyl-CoA carboxylase (EC 6.4.1.5); or
   (v) a protocatechuate (PCA) decarboxylase (EC 4.1.1.63).
4. The method of item 1 or 2, further comprising providing the 3-methyl-3-butenoic acid by the enzymatic conversion of 3-methyl-3-butenoyl-CoA into 3-methyl-3-butenoic acid.
5. The method of item 4, wherein the enzymatic conversion of 3-methyl-3-butenoyl-CoA into 3-methyl-3-butenoic acid is achieved by
   (a) a single enzymatic reaction in which 3-methyl-3-butenoyl-CoA is directly converted into 3-methyl-3-butenoic acid by making use of a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18);
   (b) a single enzymatic reaction in which 3-methyl-3-butenoyl-CoA is directly converted into 3-methyl-3-butenoic acid by making use of a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20);
   (c) two enzymatic steps comprising
      (i) first enzymatically converting 3-methyl-3-butenoyl-CoA into 3-methyl-3-butenoyl phosphate; and
      (ii) then enzymatically converting the thus obtained 3-methyl-3-butenoyl phosphate into said 3-methyl-3-butenoic acid.
6. The method of item 5(c), wherein the enzymatic conversion of said 3-methyl-3-butenoyl-CoA into 3-methyl-3-butenoyl phosphate is achieved by making use of a phosphate butyryltransferase (EC 2.3.1.19) or a phosphate acetyltransferase (EC 2.3.1.8) and the enzymatic conversion of said 3-methyl-3-butenoyl phosphate into said 3-methyl-3-butenoic acid is achieved by making use of a phosphotransferase with a carboxy group as acceptor (EC 2.7.2.-), preferably a propionate kinase (EC 2.7.2.15), an acetate kinase (EC 2.7.2.1), a butyrate kinase (EC 2.7.2.7) or a branched-chain-fatty-acid kinase (EC 2.7.2.14).
7. The method of any one of items 1 to 4, further comprising providing the 3-methyl-3-butenoyl-CoA by the enzymatic conversion of 3-methylglutaconyl-CoA into 3-methyl-3-butenoyl-CoA.
8. The method of item 7, wherein the enzymatic conversion of 3-methylglutaconyl-CoA into 3-methyl-3-butenoyl-CoA is achieved by making use of
   (a) (i) a methylcrotonyl-CoA carboxylase (EC 6.4.1.4); or
      (ii) a geranoyl-CoA carboxylase (EC 6.4.1.5),
   (b) an N-terminal domain of CurF from Lynbya majuscula multifunctional protein or a 3-methylglutaconyl-CoA decarboxylase, preferably a 3-methylglutaconyl-CoA decarboxylase of Myxococcus xanthus encoded by the liuB gene; or
   (c) an enzyme of the 4-oxalocrotonate decarboxylase family.
9. The method of any one of items 1 to 8, further comprising providing the 3-methylglutaconyl-CoA by the enzymatic conversion of 3-hydroxy-3-methylglutaryl-CoA into 3-methylglutaconyl-CoA.
10. The method of item 9, wherein the enzymatic conversion of 3-hydroxy-3-methylglutaryl-CoA into 3-methylglutaconyl-CoA is achieved by making use of a 3-methylglutaconyl-coenzyme A hydratase (EC 4.2.1.18), a 3-hydroxyacyl-CoA dehydratase (EC 4.2.1.-) or an enoyl-CoA hydratase (EC 4.2.1.-).
11. The method of any one of items 1 to 10, further comprising providing the 3-hydroxy-3-methylglutaryl-CoA by the enzymatic condensation of acetoacetyl-CoA and acetyl-CoA into 3-hydroxy-3-methylglutaryl-CoA.
12. The method of item 11, wherein the enzymatic condensation of acetoacetyl-CoA and acetyl-CoA into 3-hydroxy-3-methylglutaryl-CoA is achieved by making use of a 3-hydroxy-3-methylglutaryl-CoA synthase.
13. The method of any one of items 1 to 12, further comprising providing the acetoacetyl-CoA by the enzymatic conversion of acetyl-CoA into acetoacetyl-CoA comprising:
   (a) two enzymatic steps comprising
      (i) first the enzymatic conversion of acetyl-CoA into malonyl-CoA; and
      (ii) then enzymatically condensing the thus obtained malonyl-CoA and acetyl-CoA into said acetoacetyl-CoA; or
   (b) a single enzymatic reaction in which two molecules of acetyl-CoA are directly condensed into acetoacetyl-CoA.
14. The method of item 13(a)(i), wherein the enzymatic conversion of acetyl-CoA into malonyl-CoA is achieved by making use of an acetyl-CoA carboxylase (EC 6.4.1.2).
15. The method of item 13(a)(ii), wherein the enzymatic condensation of malonyl-CoA and acetyl-CoA into said acetoacetyl-CoA is achieved by making use of an acetoacetyl-CoA synthase (EC 2.3.1.194).
16. The method of item 13(b), wherein the direct enzymatic condensation of two molecules of acetyl-CoA into acetoacetyl-CoA is achieved by making use of an acetyl-CoA C-acetyltransferase (EC 2.3.1.9).
17. A recombinant organism or microorganism which expresses
   (i) an enzyme as defined in any one of items 1 to 3; and
   (ii) an enzyme as defined in any one of items 4 to 6.
18. The recombinant organism or microorganism of item 17, further expressing an enzyme as defined in item 7 or 8.
19. The recombinant organism or microorganism of item 18, further expressing an enzyme as defined in item 9 or 10.
20. The recombinant organism or microorganism of item 19, further expressing an enzyme as defined in item 11 or 12.
21. The recombinant organism or microorganism of item 20, further expressing an enzyme as defined in claim 13.

22. The recombinant organism or microorganism of item 21, further expressing an enzyme as defined in any one of claims 14 to 16.
23. Use of a recombinant organism or microorganism as defined in any one of items 17 to 22 for the production of isobutene.
24. The use of a recombinant organism or microorganism of item 23, wherein said recombinant organism or microorganism expresses an enzyme catalyzing the enzymatic conversion of 3-methyl-3-butenoic acid into isobutene.
25. Use of an enzyme catalyzing the enzymatic conversion of 3-methyl-3-butenoic acid into isobutene for the production of isobutene from 3-methyl-3-butenoic acid.
26. A composition comprising 3-methyl-3-butenoic acid and a recombinant organism or microorganism as defined in any one of items 17 to 22; or 3-methyl-3-butenoic acid and an enzyme as defined in any one of items 1 to 16.

A method according to the present invention may be carried out in vitro or in vivo. An in vitro reaction is understood to be a reaction in which no cells are employed, i.e. an acellular reaction. Thus, in vitro preferably means in a cell-free system. The term "in vitro" in one embodiment means in the presence of isolated enzymes (or enzyme systems optionally comprising possibly required cofactors). In one embodiment, the enzymes employed in the method are used in purified form.

For carrying out the method in vitro the substrates for the reaction and the enzymes are incubated under conditions (buffer, temperature, cosubstrates, cofactors etc.) allowing the enzymes to be active and the enzymatic conversion to occur. The reaction is allowed to proceed for a time sufficient to produce the respective product. The production of the respective products can be measured by methods known in the art, such as gas chromatography possibly linked to mass spectrometry detection.

The enzymes may be in any suitable form allowing the enzymatic reaction to take place. They may be purified or partially purified or in the form of crude cellular extracts or partially purified extracts. It is also possible that the enzymes are immobilized on a suitable carrier.

In another embodiment the method according to the invention is carried out in culture, in the presence of an organism, preferably a microorganism, producing the enzymes described above for the conversions of the methods according to the present invention as described herein above. A method which employs a microorganism for carrying out a method according to the invention is referred to as an "in vivo" method. It is possible to use a microorganism which naturally produces the enzymes described above for the conversions of the methods according to the present invention or a microorganism which had been genetically modified so that it expresses (including overexpresses) one or more of such enzymes. Thus, the microorganism can be an engineered microorganism which expresses enzymes described above for the conversions of the methods according to the present invention, i.e. which has in its genome a nucleotide sequence encoding such enzymes and which has been modified to overexpress them. The expression may occur constitutively or in an induced or regulated manner.

In another embodiment the microorganism can be a microorganism which has been genetically modified by the introduction of one or more nucleic acid molecules containing nucleotide sequences encoding one or more enzymes described above for the conversions of the methods according to the present invention. The nucleic acid molecule can be stably integrated into the genome of the microorganism or may be present in an extrachromosomal manner, e.g. on a plasmid.

Such a genetically modified microorganism can, e.g., be a microorganism that does not naturally express enzymes described above for the conversions of the methods according to the present invention and which has been genetically modified to express such enzymes or a microorganism which naturally expresses such enzymes and which has been genetically modified, e.g. transformed with a nucleic acid, e.g. a vector, encoding the respective enzyme(s), and/or insertion of a promoter in front of the endogenous nucleotide sequence encoding the enzyme in order to increase the respective activity in said microorganism.

However, the invention preferably excludes naturally occurring microorganisms as found in nature expressing an enzyme as described above at levels as they exist in nature. Instead, the microorganism of the present invention and employed in a method of the present invention is preferably a non-naturally occurring microorganism, whether it has been genetically modified to express (including overexpression) an exogenous enzyme of the invention not normally existing in its genome or whether it has been engineered to overexpress an exogenous enzyme.

Thus, the enzymes and (micro)organisms employed in connection with the present invention are preferably non-naturally occurring enzymes or (micro)organisms, i.e. they are enzymes or (micro)organisms which differ significantly from naturally occurring enzymes or microorganism and which do not occur in nature. As regards the enzymes, they are preferably variants of naturally occurring enzymes which do not as such occur in nature. Such variants include, for example, mutants, in particular prepared by molecular biological methods, which show improved properties, such as a higher enzyme activity, higher substrate specificity, higher temperature resistance and the like. As regards the (micro)organisms, they are preferably genetically modified organisms as described herein above which differ from naturally occurring organisms due to a genetic modification. Genetically modified organisms are organisms which do not naturally occur, i.e., which cannot be found in nature, and which differ substantially from naturally occurring organisms due to the introduction of a foreign nucleic acid molecule.

By overexpressing an exogenous or endogenous enzyme as described herein above, the concentration of the enzyme is substantially higher than what is found in nature, which can then unexpectedly force the reaction of the present invention which uses a non-natural for the respective enzyme. Preferably, the concentration of the overexpressed enzyme is at least 5%, 10%, 20%, 30% or 40% of the total host cell protein.

A "non-natural" substrate is understood to be a molecule that is not acted upon by the respective enzyme in nature, even though it may actually coexist in the microorganism along with the endogenous enzyme. This "non-natural" substrate is not converted by the microorganism in nature as other substrates are preferred (e.g. the "natural substrate"). Thus, the present invention contemplates utilizing a non-natural substrate with the enzymes described above in an environment not found in nature.

Thus, it is also possible in the context of the present invention that the microorganism is a microorganism which naturally does not have the respective enzyme activity but which is genetically modified so as to comprise a nucleotide sequence allowing the expression of a corresponding enzyme. Similarly, the microorganism may also be a microorganism which naturally has the respective enzyme activity but which is genetically modified so as to enhance such an activity, e.g. by the introduction of an exogenous nucleotide sequence encoding a corresponding enzyme or by the introduction of a promoter for the endogenous gene encoding the enzyme to increase endogenous production to overexpressed (non-natural) levels.

If a microorganism is used which naturally expresses a corresponding enzyme, it is possible to modify such a microorganism so that the respective activity is overexpressed in the microorganism. This can, e.g., be achieved by effecting mutations in the promoter region of the corresponding gene or introduction of a high expressing promoter so as to lead to a promoter which ensures a higher expression of the gene. Alternatively, it is also possible to mutate the gene as such so as to lead to an enzyme showing a higher activity.

By using microorganisms which express enzymes described above for the conversions of the methods according to the present invention, it is possible to carry out the methods according to the invention directly in the culture medium, without the need to separate or purify the enzymes.

In one embodiment the organism employed in a method according to the invention is a microorganism which has been genetically modified to contain a foreign nucleic acid molecule encoding at least one enzyme described above for the conversions of the methods according to the present invention. The term "foreign" or "exogenous" in this context means that the nucleic acid molecule does not naturally occur in said microorganism. This means that it does not occur in the same structure or at the same location in the microorganism. In one preferred embodiment, the foreign nucleic acid molecule is a recombinant molecule comprising a promoter and a coding sequence encoding the respective enzyme in which the promoter driving expression of the coding sequence is heterologous with respect to the coding sequence. "Heterologous" in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the microorganism, i.e. a promoter which does naturally not occur in the respective microorganism. Even more preferably, the promoter is an inducible promoter. Promoters for driving expression in different types of organisms, in particular in microorganisms, are well known to the person skilled in the art.

In a further embodiment the nucleic acid molecule is foreign to the microorganism in that the encoded enzyme is not endogenous to the microorganism, i.e. is naturally not expressed by the microorganism when it is not genetically modified. In other words, the encoded enzyme is heterologous with respect to the microorganism. The foreign nucleic acid molecule may be present in the microorganism in extrachromosomal form, e.g. as a plasmid, or stably integrated in the chromosome. A stable integration is preferred. Thus, the genetic modification can consist, e.g. in integrating the corresponding gene(s) encoding the enzyme(s) into the chromosome, or in expressing the enzyme(s) from a plasmid containing a promoter upstream of the enzyme-coding sequence, the promoter and coding sequence preferably originating from different organisms, or any other method known to one of skill in the art.

The term "microorganism" in the context of the present invention refers to bacteria, as well as to fungi, such as yeasts, and also to algae and archaea. In one preferred embodiment, the microorganism is a bacterium. In principle any bacterium can be used. Preferred bacteria to be employed in the process according to the invention are bacteria of the genus *Bacillus, Clostridium, Corynebacterium, Pseudomonas, Zymomonas* or *Escherichia*. In a particularly preferred embodiment the bacterium belongs to the genus *Escherichia* and even more preferred to the species *Escherichia coli*. In another preferred embodiment the bacterium belongs to the species *Pseudomonas putida* or to the species *Zymomonas mobilis* or to the species *Corynebacterium glutamicum* or to the species *Bacillus subtilis*.

It is also possible to employ an extremophilic bacterium such as *Thermus thermophilus*, or anaerobic bacteria from the family Clostridiae.

In another preferred embodiment the microorganism is a fungus, more preferably a fungus of the genus *Saccharomyces, Schizosaccharomyces, Aspergillus, Trichoderma, Kluyveromyces* or *Pichia* and even more preferably of the species *Saccharomyces cerevisiae, Schizosaccharomyces pombe, Aspergillus niger, Trichoderma reesei, Kluyveromyces marxianus, Kluyveromyces lactis, Pichia pastoris, Pichia torula* or *Pichia utilis*.

In another embodiment, the method according to the invention makes use of a photosynthetic microorganism expressing at least one enzyme for the conversion according to the invention as described above. Preferably, the microorganism is a photosynthetic bacterium, or a microalgae. In a further embodiment the microorganism is an algae, more preferably an algae belonging to the diatomeae.

It is also conceivable to use in the method according to the invention a combination of microorganisms wherein different microorganisms express different enzymes as described above. The genetic modification of microorganisms to express an enzyme of interest will also be further described in detail below.

In a preferred embodiment, the method of the present invention makes use of an organism, preferably a microorganism, which is genetically modified in order to avoid the leakage of acetyl-CoA, thereby increasing the intracellular concentration of acetyl-CoA. Genetic modifications leading to an increase in the intracellular concentration of acetyl-CoA are known in the art. Without being bound to theory, such an organism, preferably a microorganism, may preferably be genetically modified by deleting or inactivating the following genes:

ΔackA (acetate kinase), Δldh (lactate dehydrogenase), ΔadhE (alcohol dehydrogenase), ΔfrdB and/or ΔfrdC (fumarate reductase and fumarate dehydrogenase).

Alternatively, or in addition to any of the above deletions, the organism or microorganism may genetically be modified by overexpressing the gene panK/coaA encoding Pantothenate kinase, thereby increasing the CoA/acetyl-CoA intracellular pool.

These modifications which avoid the leakage of acetyl-CoA are known in the art and corresponding modified organisms have been used in methods for the bioconversion of exogenous isoamyl alcohol into isoamyl acetate by an *E. coli* strain expressing ATF2 (Metab. Eng. 6 (2004), 294-309).

In another embodiment, the method of the invention comprises the step of providing the organism, preferably the microorganism carrying the respective enzyme activity or activities in the form of a (cell) culture, preferably in the form of a liquid cell culture, a subsequent step of cultivating the organism, preferably the microorganism in a fermenter (often also referred to a bioreactor) under suitable conditions allowing the expression of the respective enzyme and further comprising the step of effecting an enzymatic conversion of a method of the invention as described herein above. Suitable fermenter or bioreactor devices and fermentation conditions are known to the person skilled in the art. A bioreactor or a fermenter refers to any manufactured or engineered device or system known in the art that supports a biologically active environment. Thus, a bioreactor or a fermenter may be a vessel in which a chemical/biochemical like the method of the present invention is carried out which involves organisms, preferably microorganisms and/or biochemically active substances, i.e., the enzyme(s) described above derived from such organisms or organisms harbouring the above described enzyme(s). In a bioreactor or a fermenter, this process can either be aerobic or anaerobic. These bioreactors are commonly cylindrical, and may range in size from litres to cubic metres, and are often made of stainless steel. In this respect, without being bound by theory, the fermenter or bioreactor may be designed in a way that it is suitable to cultivate the organisms, preferably microorganisms, in, e.g., a batch-culture, feed-batch-culture, perfusion culture or chemostate-culture, all of which are generally known in the art.

The culture medium can be any culture medium suitable for cultivating the respective organism or microorganism.

In a preferred embodiment the method according to the present invention also comprises the step of recovering the isobutene produced by the method. For example, if the method according to the present invention is carried out in vivo by fermenting a corresponding microorganism expressing the necessary enzymes, the isobutene can be recovered from the fermentation off-gas by methods known to the person skilled in the art.

In a preferred embodiment, the present invention relates to a method as described herein above in which a microorganism as described herein above is employed, wherein the microorganism is capable of enzymatically converting 3-methylcrotonic acid into isobutene, wherein said method comprises culturing the microorganism in a culture medium.

The enzymes used in the method according to the invention can be naturally occurring enzymes or enzymes which are derived from a naturally occurring enzymes, e.g. by the introduction of mutations or other alterations which, e.g., alter or improve the enzymatic activity, the stability, etc.

Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic modification in prokaryotic cells, a nucleic acid molecule encoding a corresponding enzyme can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be ligated by using adapters and linkers complementary to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting enzyme variants are then tested for the desired activity, e.g., enzymatic activity, with an assay as described above and in particular for their increased enzyme activity.

As described above, the microorganism employed in a method of the invention or contained in the composition of the invention may be a microorganism which has been genetically modified by the introduction of a nucleic acid molecule encoding a corresponding enzyme. Thus, in a preferred embodiment, the microorganism is a recombinant microorganism which has been genetically modified to have an increased activity of at least one enzyme described above for the conversions of the method according to the present invention. This can be achieved e.g. by transforming the microorganism with a nucleic acid encoding a corresponding enzyme. A detailed description of genetic modification of microorganisms will be given further below. Preferably, the nucleic acid molecule introduced into the microorganism is a nucleic acid molecule which is heterologous with respect to the microorganism, i.e. it does not naturally occur in said microorganism.

In the context of the present invention, an "increased activity" means that the expression and/or the activity of an enzyme in the genetically modified microorganism is at least 10%, preferably at least 20%, more preferably at least 30% or 50%, even more preferably at least 70% or 80% and particularly preferred at least 90% or 100% higher than in the corresponding non-modified microorganism. In even more preferred embodiments the increase in expression and/or activity may be at least 150%, at least 200% or at least 500%. In particularly preferred embodiments the expression is at least 10-fold, more preferably at least 100-fold and even more preferred at least 1000-fold higher than in the corresponding non-modified microorganism.

The term "increased" expression/activity also covers the situation in which the corresponding non-modified microorganism does not express a corresponding enzyme so that the corresponding expression/activity in the non-modified microorganism is zero. Preferably, the concentration of the overexpressed enzyme is at least 5%, 10%, 20%, 30%, or 40% of the total host cell protein.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

In the context of the present invention the term "recombinant" means that the microorganism is genetically modified so as to contain a nucleic acid molecule encoding an enzyme as defined above as compared to a wild-type or non-modified microorganism. A nucleic acid molecule encoding an enzyme as defined above can be used alone or as part of a vector.

The nucleic acid molecules can further comprise expression control sequences operably linked to the polynucleotide comprised in the nucleic acid molecule. The term "operatively linked" or "operably linked", as used throughout the present description, refers to a linkage between one or more expression control sequences and the coding region in the polynucleotide to be expressed in such a way that expression is achieved under conditions compatible with the expression control sequence.

Expression comprises transcription of the heterologous DNA sequence, preferably into a translatable mRNA. Regulatory elements ensuring expression in fungi as well as in bacteria, are well known to those skilled in the art. They encompass promoters, enhancers, termination signals, targeting signals and the like. Examples are given further below in connection with explanations concerning vectors.

Promoters for use in connection with the nucleic acid molecule may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

The vectors can further comprise expression control sequences operably linked to said polynucleotides contained in the vectors. These expression control sequences may be suited to ensure transcription and synthesis of a translatable RNA in bacteria or fungi.

In addition, it is possible to insert different mutations into the polynucleotides by methods usual in molecular biology (see for instance Sambrook and Russell (2001), Molecular Cloning: A Laboratory Manual, CSH Press, Cold Spring Harbor, N.Y., USA), leading to the synthesis of polypeptides possibly having modified biological properties. The introduction of point mutations is conceivable at positions at which a modification of the amino acid sequence for instance influences the biological activity or the regulation of the polypeptide.

Moreover, mutants possessing a modified substrate or product specificity can be prepared. Preferably, such mutants show an increased activity. Alternatively, mutants can be prepared the catalytic activity of which is abolished without losing substrate binding activity.

Furthermore, the introduction of mutations into the polynucleotides encoding an enzyme as defined above allows the gene expression rate and/or the activity of the enzymes encoded by said polynucleotides to be reduced or increased.

For genetically modifying bacteria or fungi, the polynucleotides encoding an enzyme as defined above or parts of these molecules can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods.

Thus, in accordance with the present invention a recombinant microorganism can be produced by genetically modifying fungi or bacteria comprising introducing the above-described polynucleotides, nucleic acid molecules or vectors into a fungus or bacterium.

The polynucleotide encoding the respective enzyme is expressed so as to lead to the production of a polypeptide having any of the activities described above. An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, New York, (1982), 462-481; DeBoer et al., Proc. Natl. Acad. Sci. USA (1983), 21-25), Ip1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

The transformation of the host cell with a polynucleotide or vector as described above can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

Recombinant Organisms or Microorganisms Expressing Enzymes of Step I and Step II, and Optionally Further Expressing Enzymes of Step III, Step IV and Step V as Well as Optionally Further Expressing Enzymes of Steps XIII, XIV and XV The present invention also relates to a recombinant organism or microorganism which expresses (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1).

In a preferred embodiment, the enzyme capable of converting 3-methylcrotonic acid into isobutene is a 3-methylcrotonic acid decarboxylase as defined herein above.

More preferably, the 3-methylcrotonic acid decarboxylase is
(i) an FMN-dependent decarboxylase associated with an FMN prenyl transferase; or
(ii) an aconitate decarboxylase (EC 4.1.1.6); or
(iii) a methylcrotonyl-CoA carboxylase (EC 6.4.1.4); or
(iv) a geranoyl-CoA carboxylase (EC 6.4.1.5); or
(v) a protocatechuate (PCA) decarboxylase (EC 4.1.1.63)
as defined herein above.

In another preferred embodiment, this recombinant organism or microorganism is a recombinant organism or microorganism, wherein the 3-methylcrotonic acid decarboxylase is selected from the group consisting of: 6-methylsalicylate decarboxylase (EC 4.1.1.52), 2-oxo-3-hexenedioate decarboxylase (EC 4.1.1.77) and 5-oxopent-3-ene-1,2,5-tricarboxylate decarboxylase (EC 4.1.1.68).

As regards the 3-methylcrotonic acid decarboxylase, the FMN-dependent decarboxylase, the associated FMN prenyl transferase, the aconitate decarboxylase (EC 4.1.1.6), the methylcrotonyl-CoA carboxylase (EC 6.4.1.4), and the geranoyl-CoA carboxylase (EC 6.4.1.5) as well as preferred embodiments of said 3-methylcrotonic acid decarboxylase, said protocatechuate (PCA) decarboxylase (EC 4.1.1.63), said FMN-dependent decarboxylase, said associated FMN prenyl transferase, said aconitate decarboxylase (EC 4.1.1.6), said methylcrotonyl-CoA carboxylase (EC 6.4.1.4) and said geranoyl-CoA carboxylase (EC 6.4.1.5), as well as said 6-methylsalicylate decarboxylase (EC 4.1.1.52), 2-oxo-3-hexenedioate decarboxylase (EC 4.1.1.77) and 5-oxopent-3-ene-1,2,5-tricarboxylate decarboxylase (EC 4.1.1.68), the same applies to the recombinant organism or microorganism as has been set forth above for the methods according to the present invention.

In a preferred embodiment, the recombinant organism or microorganism which expresses (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1) is a recombinant organism or microorganism, wherein the enzyme capable of enzymatically converting 3-hydroxyisovalerate (HIV) into 3-methylcrotonic acid is a hydro-lyase (EC 4.2.-.-) as defined herein above, preferably an aconitase (EC 4.2.1.3), a fumarase (EC 4.2.1.2) or an enoyl-CoA hydratase/dehydratease (EC 4.2.1.17) as defined herein above.

As regards the hydro-lyase (EC 4.2.-.-), the aconitase (EC 4.2.1.3), the fumarase (EC 4.2.1.2) and the enoyl-CoA hydratase/dehydratease (EC 4.2.1.17) as well as the preferred embodiments of said hydro-lyase (EC 4.2.-.-), said aconitase (EC 4.2.1.3), said fumarase (EC 4.2.1.2) and said enoyl-CoA hydratase/dehydratease (EC 4.2.1.17) the same applies to the recombinant organism or microorganism as has been set forth above for the methods according to the present invention.

In a further aspect, the above recombinant organism or microorganism is an organism or microorganism which further expresses an enzyme capable of enzymatically condensing acetone and acetyl-CoA into 3-hydroxyisovalerate (HIV) (step III as shown in FIG. 1). In a preferred embodiment, the enzyme capable of enzymatically condensing acetone and acetyl-CoA into 3-hydroxyisovalerate (HIV) is a HMG CoA synthase (EC 2.3.3.10) or a PksG protein or an enzyme with the activity of a C—C bond cleavage/condensation lyase, such as a HMG CoA lyase (EC 4.1.3.4) as defined herein above.

As regards the HMG CoA synthase (EC 2.3.3.10), the PksG protein, the enzyme with the activity of a C—C bond cleavage/condensation lyase and the HMG CoA lyase (EC 4.1.3.4) as well as the preferred embodiments of said enzymes the same applies to the recombinant organism or microorganism as has been set forth above for the methods according to the present invention.

In a further aspect, the above recombinant organism or microorganism is an organism or microorganism which further expresses an enzyme capable of enzymatically converting acetoacetate into acetone (step IV as shown in FIG. 1), preferably an acetoacetate decarboxylase (EC 4.1.1.4) as described herein above.

As regards said enzyme capable of enzymatically converting acetoacetate into acetone and said acetoacetate decarboxylase (EC 4.1.1.4) as well as preferred embodiments of said enzymes, the same applies to the recombinant organism or microorganism as has been set forth above for the methods according to the present invention.

In a further aspect, the above recombinant organism or microorganism is an organism or microorganism which further expresses an enzyme capable of converting acetoacetyl-CoA into acetoacetate (step Va or Vb as shown in FIG. 1), preferably
(i) an acetoacetyl-CoA hydrolase (EC 3.1.2.11); or
(ii) an enzyme which is capable of transferring the CoA group of acetoacetyl-CoA on acetate
as described herein above.

In a preferred embodiment, the enzyme capable of transferring the CoA group of acetoacetyl-CoA on acetate is a CoA transferase (EC 2.8.3.-), preferably an acetate CoA transferase (EC 2.8.3.8) as described herein above.

As regards said enzyme which is capable of converting acetoacetyl-CoA into acetoacetate, said acetoacetyl-CoA hydrolase (EC 3.1.2.11), said enzyme which is capable of transferring the CoA group of acetoacetyl-CoA, the CoA transferase (EC 2.8.3.-) and said acetate CoA transferase (EC 2.8.3.8) as well as the preferred embodiments of said enzymes, the same applies to the recombinant organism or microorganism as has been set forth above for the methods according to the present invention.

In a further aspect, the above recombinant organism or microorganism is an organism or microorganism which further expresses an enzyme capable of enzymatically converting acetyl-CoA into acetoacetyl-CoA comprising
(a) (i) an enzyme capable of converting acetyl-CoA into malonyl-CoA (step XIV as shown in FIG. 1); and
(ii) an enzyme capable of condensing malonyl-CoA and acetyl-CoA into acetoacetyl-CoA (step XV as shown in FIG. 1); or
(b) an enzyme capable of directly condensing two molecules of acetyl-CoA into acetoacetyl-CoA (step XIII as shown in FIG. 1).

In a preferred embodiment, the enzyme capable of converting acetyl-CoA into malonyl-CoA is an acetyl-CoA carboxylase (EC 6.4.1.2) as described herein above.

In another preferred embodiment, the enzyme capable of condensing malonyl-CoA and acetyl-CoA into acetoacetyl-CoA is an acetoacetyl-CoA synthetase (EC 2.3.1.194) as described herein above.

In a preferred embodiment, the enzyme capable of directly condensing two molecules of acetyl-CoA into acetoacetyl-CoA is an acetyl-CoA C-acetyltransferase (EC 2.3.1.9) as described herein above.

As regards the enzyme which is capable of converting acetyl-CoA into malonyl-CoA, the enzyme capable of condensing malonyl-CoA and acetyl-CoA into acetoacetyl-CoA, the acetyl-CoA carboxylase (EC 6.4.1.2), the acetoacetyl-CoA synthetase (EC 2.3.1.194), the enzyme capable of directly condensing two molecules of acetyl-CoA into acetoacetyl-CoA and the acetyl-CoA C-acetyltransferase (EC 2.3.1.9) as well as the preferred embodiments of said enzymes, the same applies to the recombinant organism or microorganism as has been set forth above for the methods according to the present invention.

Recombinant Organisms or Microorganisms Expressing Enzymes of Step I and Step VI, and Optionally Further Expressing Enzymes of Step VII, Step VIII and Step IX as Well as Optionally Further Expressing Enzymes of Steps XIII, XIV and XV The present invention also relates to a recombinant organism or microorganism which expresses (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1).

In a preferred embodiment, the enzyme capable of converting 3-methylcrotonic acid into isobutene is a 3-methylcrotonic acid decarboxylase, preferably
(i) an FMN-dependent decarboxylase associated with an FMN prenyl transferase; or
(ii) an aconitate decarboxylase (EC 4.1.1.6); or
(iii) a methylcrotonyl-CoA carboxylase (EC 6.4.1.4); or
(iv) a geranoyl-CoA carboxylase (EC 6.4.1.5); or
(v) a protocatechuate (PCA) decarboxylase (EC 4.1.1.63)
as defined herein above.

As regards the 3-methylcrotonic acid decarboxylase, the FMN-dependent decarboxylase, the associated FMN prenyl transferase, the aconitate decarboxylase (EC 4.1.1.6), the methylcrotonyl-CoA carboxylase (EC 6.4.1.4), the (v) protocatechuate (PCA) decarboxylase (EC 4.1.1.63) and the geranoyl-CoA carboxylase (EC 6.4.1.5) as well as preferred embodiments of said enzymes, the same applies to the recombinant organism or microorganism as has been set forth above for the methods according to the present invention.

In a preferred embodiment, the enzyme capable of enzymatically converting 3-methylcrotonyl-CoA into 3-methylcrotonic acid is
(a) an enzyme capable of directly converting 3-methylcrotonyl-CoA into 3-methylcrotonic acid wherein said enzyme capable of directly converting 3-methylcrotonyl-CoA into 3-methylcrotonic acid is a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18) (step VIa as shown in FIG. 1) as described herein above; or (b) an enzyme capable of directly converting 3-methylcrotonyl-CoA into 3-methylcrotonic acid wherein said enzyme capable of directly converting 3-methylcrotonyl-CoA into 3-methylcrotonic acid is a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20) (step VIb as shown in FIG. 1) as described herein above.

In another preferred embodiment, the recombinant organism or microorganism is a recombinant organism or microorganism which expresses the following two enzymes, namely
(c) (i) an enzyme capable of enzymatically converting 3-methylcrotonyl-CoA into 3-methylcrotonyl phosphate as described herein above; and
(ii) an enzyme capable of converting 3-methylcrotonyl phosphate into 3-methylcrotonic acid (step VIc as shown in FIG. 1) as described herein above.

In a preferred embodiment, the enzyme capable of converting 3-methylcrotonyl-CoA into 3-methylcrotonyl phosphate is a phosphate butyryltransferase (EC 2.3.1.19) or a phosphate acetyltransferase (EC 2.3.1.8) and the enzyme capable of converting 3-methylcrotonyl phosphate into 3-methylcrotonic acid is a phosphotransferase with a carboxy group as acceptor (EC 2.7.2.-), preferably a propionate kinase (EC 2.7.2.15), an acetate kinase (EC 2.7.2.1), a butyrate kinase (EC 2.7.2.7) or a branched-chain-fatty-acid kinase (EC 2.7.2.14) as described herein above.

As regards the above-mentioned enzymes, the same applies to the recombinant organism or microorganism as has been set forth above for the methods according to the present invention.

In a further aspect, the above recombinant organism or microorganism is an organism or microorganism which further expresses an enzyme capable of enzymatically converting 3-methylglutaconyl-CoA into 3-methylcrotonyl-CoA (step VII as shown in FIG. 1), preferably (i) a methylcrotonyl-CoA carboxylase (EC 6.4.1.4); or (ii) a geranoyl-CoA carboxylase (EC 6.4.1.5) as described herein above.

As regards said enzymes as well as preferred embodiments of said enzymes, the same applies to the recombinant organism or microorganism as has been set forth above for the methods according to the present invention.

In a further aspect, the above recombinant organism or microorganism is an organism or microorganism which further expresses an enzyme capable of enzymatically converting 3-hydroxy-3-methylglutaryl-CoA into 3-methylglutaconyl-CoA (step VIII as shown in FIG. 1), preferably a 3-methylglutaconyl-coenzyme A hydratase (EC 4.2.1.18), a 3-hydroxyacyl-CoA dehydratase (EC 4.2.1.-) or an enoyl-CoA hydratase (EC 4.2.1.-).

As regards said enzyme as well as preferred embodiments of said enzymes, the same applies to the recombinant organism or microorganism as has been set forth above for the methods according to the present invention.

In a further aspect, the above recombinant organism or microorganism is an organism or microorganism which further expresses an enzyme capable of enzymatically condensing acetoacetyl-CoA and acetyl-CoA into 3-hydroxy-3-methylglutaryl-CoA (step IX as shown in FIG. 1), preferably a 3-hydroxy-3-methylglutaryl-CoA synthase.

As regards said enzyme as well as preferred embodiments of said enzyme, the same applies to the recombinant organism or microorganism as has been set forth above for the methods according to the present invention.

In a further aspect, the above recombinant organism or microorganism which expresses (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1) (and optionally further expressing an enzyme capable of enzymatically converting 3-methylglutaconyl-CoA into 3-methylcrotonyl-CoA and optionally further expressing an enzyme capable of enzymatically converting 3-hydroxy3-methylglutaryl-CoA into 3-methylgutaconyl-CoA and optionally further expressing an enzyme capable of enzymatically condensing acetoacetyl-CoA and acetyl-CoA into 3-hydroxy-3-methylglutaryl-CoA) is preferably an organism or microorganism which further expresses an enzyme capable of enzymatically converting acetyl-CoA into acetoacetyl-CoA comprising an enzyme capable of directly condensing two molecules of acetyl-CoA into acetoacetyl-CoA (step XIII as shown in FIG. 1).

In another preferred embodiment, the recombinant organism or microorganism is a recombinant organism or microorganism which expresses the following two enzymes, namely (i) an enzyme capable of converting acetyl-CoA into malonyl-CoA (step XIV as shown in FIG. 1); and
(ii) an enzyme capable of condensing malonyl-CoA and acetyl-CoA into acetoacetyl-CoA (step XV as shown in FIG. 1).

In a preferred embodiment, the enzyme capable of converting acetyl-CoA into malonyl-CoA is an acetyl-CoA carboxylase (EC 6.4.1.2) as described herein above.

In another preferred embodiment, the enzyme capable of condensing malonyl-CoA and acetyl-CoA into acetoacetyl-CoA is an acetoacetyl-CoA synthetase (EC 2.3.1.194) as described herein above.

In a preferred embodiment, the enzyme capable of directly condensing two molecules of acetyl-CoA into acetoacetyl-CoA is an acetyl-CoA C-acetyltransferase (EC 2.3.1.9) as described herein above.

As regards the above-mentioned enzymes as well as the preferred embodiments of said enzymes, the same applies to the recombinant organism or microorganism as has been set forth above for the methods according to the present invention.

Recombinant Organisms or Microorganisms of the Alternative Route for the Enzymatic Conversion from Acetyl-CoA into Isobutene Via 3-Methyl-3-Butenoyl-CoA and 3-Methyl-3-Butenoic Acid: Recombinant Organisms or Microorganisms Expressing Enzymes of Step XVI and Step XVII, and Optionally Further Expressing Enzymes of Step XVIII, Step VIII and Step IX as Well as Optionally Further Expressing Enzymes of Steps XIII, XIV and XV As mentioned above, in an alternative to the above first route for the production of isobutene via 3-methylcrotonic acid, the present invention also relates to a method for the production of isobutene via an alternative route wherein isobutene is produced by the enzymatic conversion of 3-methyl-3-butenoic acid into isobutene. In the following, the recombinant organisms or microorganisms of this alternative route for the enzymatic conversion from acetyl-CoA into isobutene via 3-methyl-3-butenoyl-CoA and 3-methyl-3-butenoic acid are described.

The present invention also relates to a recombinant organism or microorganism which expresses (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1).

In a preferred embodiment, the enzyme capable of enzymatically converting 3-methyl-3-butenoic acid into isobutene is an 3-methyl-3-butenoic acid decarboxylase as described herein above, more preferably (i) an FMN-dependent decarboxylase associated with an FMN prenyl transferase; or
(ii) an aconitate decarboxylase (EC 4.1.1.6); or
(iii) a methylcrotonyl-CoA carboxylase (EC 6.4.1.4); or
(iv) a geranoyl-CoA carboxylase (EC 6.4.1.5); or
(v) a protocatechuate (PCA) decarboxylase (EC 4.1.1.63)
as described herein above.

In another preferred embodiment, the 3-methyl-3-butenoic acid decarboxylase is selected from the group consisting of 6-methylsalicylate decarboxylase (EC 4.1.1.52), 2-oxo-3-hexenedioate decarboxylase (EC 4.1.1.77) and 5-oxopent-3-ene-1,2,5-tricarboxylate decarboxylase (EC 4.1.1.68) as described herein above.

As regards the above-mentioned enzymes as well as preferred embodiments of said enzymes, the same applies to the recombinant organism or microorganism as has been set forth above for the methods according to the present invention.

In a preferred embodiment, the enzyme capable of enzymatically converting 3-methyl-3-butenoyl-CoA into 3-methyl-3-butenoic acid is (a) an enzyme capable of directly converting 3-methyl-3-butenoyl-CoA into 3-methyl-3-butenoic acid, wherein said enzyme capable of directly converting 3-methyl-3-butenoyl-CoA into 3-methyl-3-butenoic acid is a CoA transferase (EC 2.8.3.-), preferably a propionate:acetate-CoA transferase (EC 2.8.3.1), an acetate CoA-transferase (EC 2.8.3.8) or a succinyl-CoA:acetate CoA-transferase (EC 2.8.3.18) (step XVIIa as shown in FIG. 1) as described herein above.

In another preferred embodiment, the recombinant organism or microorganism is a recombinant organism or microorganism which expresses the following two enzymes, namely (b) an enzyme capable of directly converting 3-methyl-3-butenoyl-CoA into 3-methyl-3-butenoic acid, wherein said enzyme capable of directly converting 3-methyl-3-butenoyl-CoA into 3-methyl-3-butenoic acid is a thioester hydrolase (EC 3.1.2.-), preferably acetyl-CoA hydrolase (EC 3.1.2.1), an ADP-dependent short-chain-acyl-CoA hydrolase (EC 3.1.2.18) or an acyl-CoA hydrolase (EC 3.1.2.20) (step XVIIb as shown in FIG. 1) as described herein above; or (c) (i) an enzyme capable of enzymatically converting 3-methyl-3-butenoyl-CoA into 3-methyl-3-butenoyl phosphate; and
(ii) an enzyme capable of enzymatically converting 3-methyl-3-butenoyl phosphate into said 3-methyl-3-butenoic acid (step XVIII as shown in FIG. 1) as described herein above.

In a preferred embodiment, the enzyme capable of enzymatically converting said 3-methyl-3-butenoyl-CoA into 3-methyl-3-butenoyl phosphate is a phosphate butyryltransferase (EC 2.3.1.19) or a phosphate acetyltransferase (EC 2.3.1.8) and the enzyme capable of enzymatically converting 3-methyl-3-butenoyl phosphate into 3-methyl-3-butenoic acid is a phosphotransferase with a carboxy group as acceptor (EC 2.7.2.-), preferably a propionate kinase (EC 2.7.2.15), an acetate kinase (EC 2.7.2.1), a butyrate kinase (EC 2.7.2.7) or a branched-chain-fatty-acid kinase (EC 2.7.2.14) as described herein above.

As regards the above-mentioned enzymes as well as preferred embodiments of said enzymes, the same applies to the recombinant organism or microorganism as has been set forth above for the methods according to the present invention.

In a further aspect, the above recombinant organism or microorganism is an organism or microorganism which further expresses an enzyme capable of enzymatically converting 3-methylglutaconyl-CoA into 3-methyl-3-butenoyl-CoA (step XVIII as shown in FIG. 1), preferably
(a) (i) a methylcrotonyl-CoA carboxylase (EC 6.4.1.4); or
    (ii) a geranoyl-CoA carboxylase (EC 6.4.1.5), or
(b) an N-terminal domain of CurF from *Lynbya majuscula* multifunctional protein or a 3-methylglutaconyl-CoA decarboxylase, preferably a 3-methylglutaconyl-CoA decarboxylase of *Myxococcus xanthus* encoded by the liuB gene; or
(c) an enzyme of the 4-oxalocrotonate decarboxylase family, as described herein above.

As regards the above-mentioned enzymes as well as preferred embodiments of said enzymes, the same applies to the recombinant organism or microorganism as has been set forth above for the methods according to the present invention.

In a further aspect, the above recombinant organism or microorganism is an organism or microorganism which further expresses an enzyme capable of enzymatically converting 3-hydroxy-3-methylglutaryl-CoA into 3-methylglutaconyl-CoA (step VIII as shown in FIG. 1),preferably a 3-methylglutaconyl-coenzyme A hydratase (EC 4.2.1.18), a 3-hydroxyacyl-CoA dehydratase (EC 4.2.1.-) or an enoyl-CoA hydratase (EC 4.2.1.-).

As regards the above-mentioned enzyme as well as preferred embodiments of said enzyme, the same applies to the recombinant organism or microorganism as has been set forth above for the methods according to the present invention.

In a further aspect, the above recombinant organism or microorganism is an organism or microorganism which further expresses an enzyme capable of enzymatically condensing acetoacetyl-CoA and acetyl-CoA into 3-hydroxy-3-methylglutaryl-CoA (step IX as shown in FIG. 1).

In a preferred embodiment, the enzyme capable of enzymatically condensing acetoacetyl-CoA and acetyl-CoA into 3-hydroxy-3-methylglutaryl-CoA is a 3-hydroxy-3-methylglutaryl-CoA synthase.

As regards the afore-mentioned enzyme as well as preferred embodiments of said enzyme, the same applies to the recombinant organism or microorganism as has been set forth above for the methods according to the present invention.

In a further aspect, the above recombinant organism or microorganism is an organism or microorganism which further expresses an enzyme or several enzymes capable of enzymatically converting acetyl-CoA into acetoacetyl-CoA.

In one preferred embodiment, the recombinant organism or microorganism expresses a combination of enzymes, namely
(i) an enzyme capable of converting acetyl-CoA into malonyl-CoA (step XIV as shown in FIG. 1); and
(ii) an enzyme capable of condensing malonyl-CoA and acetyl-CoA into acetoacetyl-CoA (step XV as shown in FIG. 1).

In an alternative embodiment, the recombinant organism or microorganism expresses an enzyme capable of directly condensing two molecules of acetyl-CoA into acetoacetyl-CoA (step XIII as shown in FIG. 1).

As regards the first above-mentioned embodiment, the enzyme capable of converting acetyl-CoA into malonyl-CoA is preferably an acetyl-CoA carboxylase (EC 6.4.1.2) as described herein above.

Moreover, the enzyme capable of condensing malonyl-CoA and acetyl-CoA into acetoacetyl-CoA is an acetoacetyl-CoA synthetase (EC 2.3.1.194) as described herein above.

As regards the second above-mentioned embodiment, the enzyme capable of directly condensing two molecules of acetyl-CoA into acetoacetyl-CoA is preferably an acetyl-CoA C-acetyltransferase (EC 2.3.1.9) as described herein above.

As regards the above-mentioned enzymes as well as the preferred embodiments of said enzymes, the same applies to the recombinant organism or microorganism as has been set forth above for the methods according to the present invention.

Recombinant Organisms or Microorganisms Expressing Enzymes of the Additional/Supplemental Pathways of Steps Xa, Xb, XI and XII As mentioned above, the above-described methods of the present invention for producing isobutene from acetyl-CoA may be supplemented by one or more of the reactions as shown in step Xa, step Xb, step XI and step XII of FIG. 18 and as described in detail herein above.

Thus, in a further aspect, the present invention relates to any of the above-described recombinant organism or microorganism wherein the organism or microorganism which additionally further expresses
a) an enzyme capable of enzymatically converting 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA (step Xa as schematically shown in FIG. 19); and/or
b) an enzyme capable of enzymatically converting 3-hydroxyisovalerate (HIV) into 3-hydroxyisovaleryl-CoA (step Xb as schematically shown in FIG. 20); and/or
c) an enzyme capable of enzymatically converting 3-hydroxyisovaleryl-CoA into 3-methylcrotonyl-CoA (step XI as schematically shown in FIG. 21); and/or
d) an enzyme capable of enzymatically converting 3-hydroxyisovalerate (HIV) into 3-hydroxyisovaleryl-CoA (step XII as schematically shown in FIG. 22)
as described herein above.

As regards the above-mentioned enzymes as well as preferred embodiments of said enzymes, the same applies to the recombinant organism or microorganism as has been set forth above for the methods according to the present invention.

The above microorganism is preferably a bacterium, a yeast or a fungus. In another preferred embodiment, the organism is a plant or a non-human animal. As regards other preferred embodiments of the bacterium, recombinant organism or microorganism, the same applies as has been set forth above in connection with the methods according to the present invention.

The present invention also relates to the use of any of the above-described recombinant organisms or microorganisms for the production of isobutene. Thus, the present invention furthermore relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii)

an enzyme capable of enzymatically converting 3-hydroxyisovalerate (HIV) into 3-methylcrotonic acid (step II as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1) which further expresses an enzyme capable of enzymatically condensing acetone and acetyl-CoA into 3-hydroxyisovalerate (HIV) (step III as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1), which further expresses an enzyme capable of enzymatically condensing acetone and acetyl-CoA into 3-hydroxyisovalerate (HIV) (step III as shown in FIG. 1) and which further expresses an enzyme capable of enzymatically converting acetoacetate into acetone (step IV as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1), which further expresses an enzyme capable of enzymatically condensing acetone and acetyl-CoA into 3-hydroxyisovalerate (HIV) (step III as shown in FIG. 1), which further expresses an enzyme capable of enzymatically converting acetoacetate into acetone (step IV as shown in FIG. 1) and which further expresses an enzyme capable of converting acetoacetyl-CoA into acetoacetate (step Va or Vb as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1), which further expresses an enzyme capable of enzymatically condensing acetone and acetyl-CoA into 3-hydroxyisovalerate (HIV) (step III as shown in FIG. 1), which further expresses an enzyme capable of enzymatically converting acetoacetate into acetone (step IV as shown in FIG. 1), which further expresses an enzyme capable of converting acetoacetyl-CoA into acetoacetate (step Va or Vb as shown in FIG. 1) and which further expresses an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

In a more preferred embodiment, the present invention relates to any of the above uses of a recombinant organisms or microorganisms for the production of isobutene wherein said recombinant organism or microorganism expresses an enzyme catalyzing the enzymatic conversion of 3-methylcrotonic acid into isobutene.

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

The present invention furthermore relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1) and which further expresses an enzyme capable of enzymatically converting 3-methylglutaconyl-CoA into 3-methylcrotonyl-CoA (step VII as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1), which further expresses an enzyme capable of enzymatically converting 3-methylglutaconyl-CoA into 3-methylcrotonyl-CoA (step VII as shown in FIG. 1) and which further expresses an enzyme capable of enzymatically converting 3-hydroxy-3-methylglutaryl-CoA into 3-methylglutaconyl-CoA (step VIII as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1), which further expresses an enzyme capable of enzymatically converting 3-methylglutaconyl-CoA into 3-methylcrotonyl-CoA (step VII as shown in FIG. 1), which further expresses an enzyme capable of enzymatically converting 3-hydroxy-3-methylglutaryl-CoA into 3-methylglutaconyl-CoA (step VIII as shown in FIG. 1) and which further expresses an enzyme capable of enzymatically condensing acetoacetyl-CoA and acetyl-CoA into 3-hydroxy-3-methylglutaryl-CoA (step IX as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1), which further expresses an enzyme capable of enzymatically converting 3-methylglutaconyl-CoA into 3-methylcrotonyl-CoA (step VII as shown in FIG. 1), which further expresses an enzyme capable of enzymatically converting 3-hydroxy-3-methylglutaryl-CoA into 3-methylglutaconyl-CoA (step VIII as shown in FIG. 1), which further expresses an enzyme capable of enzymatically condensing acetoacetyl-CoA and acetyl-CoA into 3-hydroxy-3-methylglutaryl-CoA (step IX as shown in FIG. 1) and which further expresses an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

In a more preferred embodiment, the present invention relates to any of the above uses of a recombinant organisms or microorganisms for the production of isobutene wherein said recombinant organism or microorganism expresses an enzyme catalyzing the enzymatic conversion of 3-methylcrotonic acid into isobutene.

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

The present invention furthermore relates to the use of a recombinant organism or microorganism for the production of isobutene, wherein said recombinant organism or microorganism expresses (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1) and which further expresses an enzyme capable of enzymatically converting 3-methylglutaconyl-CoA into 3-methyl-3-butenoyl-CoA (step XVIII as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1), which further expresses an enzyme capable of enzymatically converting 3-methylglutaconyl-CoA into 3-methyl-3-butenoyl-CoA (step XVIII as shown in FIG. 1) and which further expresses an enzyme capable of enzymatically converting 3-hydroxy-3-methylglutaryl-CoA into 3-methylglutaconyl-CoA (step VIII as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1), which further expresses an enzyme capable of enzymatically converting 3-methylglutaconyl-CoA into 3-methyl-3-butenoyl-CoA (step XVIII as shown in FIG. 1), which further expresses an enzyme capable of enzymatically converting 3-hydroxy-3-methylglutaryl-CoA into 3-methylglutaconyl-CoA (step VIII as shown in FIG. 1) and which further expresses an enzyme capable of enzymatically condensing acetoacetyl-CoA and acetyl-CoA into 3-hydroxy-3-methylglutaryl-CoA (step IX as shown in FIG. 1).

In another preferred embodiment, the present invention relates to the use of a recombinant organism or microorganism for the production of isobutene, wherein said recombinant organism or microorganism expresses (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1), which further expresses an enzyme capable of enzymatically converting 3-methylglutaconyl-CoA into 3-methyl-3-butenoyl-CoA (step XVIII as shown in FIG. 1), which further expresses an enzyme capable of enzymatically converting 3-hydroxy-3-methylglutaryl-CoA into 3-methylglutaconyl-CoA (step VIII as shown in FIG. 1), which further expresses an enzyme capable of enzymatically condensing acetoacetyl-CoA and acetyl-CoA into 3-hydroxy-3-methylglutaryl-CoA (step IX as shown in FIG. 1) and which further expresses an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

In a more preferred embodiment, the present invention relates to any of the above uses of a recombinant organisms or microorganisms for the production of isobutene wherein said recombinant organism or microorganism expresses an enzyme catalyzing the enzymatic conversion of 3-methyl-3-butenoic acid into isobutene.

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

In a further aspect, the present invention relates to the use of any of the above-described recombinant organism or microorganism for the production of isobutene, wherein the organism or microorganism is an organism or microorganism which additionally further expresses a) an enzyme capable of enzymatically converting 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA (step Xa as schematically shown in FIG. 19); and/or b) an enzyme capable of enzymatically converting 3-hydroxyisovalerate (HIV) into 3-hydroxyisovaleryl-CoA (step Xb as schematically shown in FIG. 20); and/or c) an enzyme capable of enzymatically converting 3-hydroxyisovaleryl-CoA into 3-methylcrotonyl-CoA (step XI as schematically shown in FIG. 21); and/or d) an enzyme capable of enzymatically converting 3-hydroxyisovalerate (HIV) into 3-hydroxyisovaleryl-CoA (step XII as schematically shown in FIG. 22)

as described herein above.

As regards the above-mentioned enzymes as well as preferred embodiments of said enzymes, the same applies to the recombinant organism or microorganism as has been set forth above for the methods according to the present invention.

The present invention furthermore relates to the use of an enzyme catalyzing the enzymatic conversion of 3-methylcrotonic acid into isobutene for the production of isobutene from 3-methylcrotonic acid.

The present invention furthermore relates to the use of (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1) for the production of isobutene.

In another preferred embodiment, the present invention relates to the use (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1) and an enzyme capable of enzymatically condensing acetone and acetyl-CoA into 3-hydroxyisovalerate (HIV) (step III as shown in FIG. 1) for the production of isobutene.

In another preferred embodiment, the present invention relates to the use of (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1), an enzyme capable of enzymatically condensing acetone and acetyl-CoA into 3-hydroxyisovalerate (HIV) (step III as shown in FIG. 1) and an enzyme capable of enzymatically converting acetoacetate into acetone (step IV as shown in FIG. 1) for the production of isobutene.

In another preferred embodiment, the present invention relates to the use of (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1); an enzyme capable of enzymatically condensing acetone and acetyl-CoA into 3-hydroxyisovalerate (HIV) (step III as shown in FIG. 1), an enzyme capable of enzymatically converting acetoacetate into acetone (step IV as shown in FIG. 1) and an enzyme capable of converting acetoacetyl-CoA into acetoacetate (step Va or Vb as shown in FIG. 1) for the production of isobutene.

In another preferred embodiment, the present invention relates to the use of (i) an enzyme capable of enzymatically converting 3-methylcrotonic acid into isobutene (step I as shown in FIG. 1); and (ii) an enzyme capable of enzymatically converting 3-hydroxyisovalerate (HIV) into 3-methylcrotonic acid (step II as shown in FIG. 1); an enzyme capable of enzymatically condensing acetone and acetyl-CoA into 3-hydroxyisovalerate (HIV) (step III as shown in FIG. 1), an enzyme capable of enzymatically converting acetoacetate into acetone (step IV as shown in FIG. 1), an enzyme capable of converting acetoacetyl-CoA into acetoacetate (step Va or Vb as shown in FIG. 1) and an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1) for the production of isobutene.

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

The present invention furthermore relates to the use of (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1) for the production of isobutene.

In another preferred embodiment, the present invention relates to the use of (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1) and an enzyme capable of enzymatically converting 3-methylglutaconyl-CoA into 3-methylcrotonyl-CoA (step VII as shown in FIG. 1) for the production of isobutene.

In another preferred embodiment, the present invention relates to the use of (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1); an enzyme capable of enzymatically converting 3-methylglutaconyl-CoA into 3-methylcrotonyl-CoA (step VII as shown in FIG. 1) and an enzyme capable of enzymatically converting 3-hydroxy-3-methylglutaryl-CoA into 3-methylglutaconyl-CoA (step VIII as shown in FIG. 1) for the production of isobutene.

In another preferred embodiment, the present invention relates to the use of (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1); an enzyme capable of enzymatically converting 3-methylglutaconyl-CoA into 3-methylcrotonyl-CoA (step VII as shown in FIG. 1); an enzyme capable of enzymatically converting 3-hydroxy-3-methylglutaryl-CoA into 3-methylglutaconyl-CoA (step VIII as shown in FIG. 1) and an enzyme capable of enzymatically condensing acetoacetyl-CoA and acetyl-CoA into 3-hydroxy-3-methylglutaryl-CoA (step IX as shown in FIG. 1) for the production of isobutene.

In another preferred embodiment, the present invention relates to the use of (i) an enzyme capable of enzymatically converting 3-methylcrotonic acid into isobutene (step I as shown in FIG. 1); and (ii) an enzyme capable of enzymatically converting 3-methylcrotonyl-CoA into 3-methylcrotonic acid (step VIa, VIb or VIc as shown in FIG. 1); an enzyme capable of enzymatically converting 3-methylglutaconyl-CoA into 3-methylcrotonyl-CoA (step VII as shown in FIG. 1); an enzyme capable of enzymatically converting 3-hydroxy-3-methylglutaryl-CoA into 3-methylglutaconyl-CoA (step VIII as shown in FIG. 1); an enzyme capable of enzymatically condensing acetoacetyl-CoA and acetyl-CoA into 3-hydroxy-3-methylglutaryl-CoA (step IX as shown in FIG. 1) and an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1) for the production of isobutene.

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

The present invention furthermore relates to the use of an enzyme catalyzing the enzymatic conversion of 3-methyl-3-butenoic acid into isobutene for the production of isobutene from 3-methyl-3-butenoic acid.

The present invention furthermore relates to the use of (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1) for the production of isobutene.

In another preferred embodiment, the present invention relates to the use of (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1) an enzyme capable of enzymatically converting 3-methylglutaconyl-CoA into 3-methyl-3-butenoyl-CoA (step XVIII as shown in FIG. 1) for the production of isobutene.

In another preferred embodiment, the present invention relates to the use of (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1), an enzyme capable of enzymatically converting 3-methylglutaconyl-CoA into 3-methyl-3-butenoyl-CoA (step XVIII as shown in FIG. 1) and an enzyme capable of enzymatically converting 3-hydroxy-3-methylglutaryl-CoA into 3-methylglutaconyl-CoA (step VIII as shown in FIG. 1) for the production of isobutene.

In another preferred embodiment, the present invention relates to the use of (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1); an enzyme capable of enzymatically converting 3-methylglutaconyl-CoA into 3-methyl-3-butenoyl-CoA (step XVIII as shown in FIG. 1); an enzyme capable of enzymatically converting 3-hydroxy-3-methylglutaryl-CoA into 3-methylglutaconyl-CoA (step VIII as shown in FIG. 1) and an enzyme capable of enzymatically condensing acetoacetyl-CoA and acetyl-CoA into 3-hydroxy-3-methylglutaryl-CoA (step IX as shown in FIG. 1) for the production of isobutene.

In another preferred embodiment, the present invention relates to the use of (i) an enzyme capable of enzymatically converting 3-methyl-3-butenoic acid into isobutene (step XVI as shown in FIG. 1) and (ii) an enzyme capable of enzymatically converting 3-methyl-3-butenoyl-CoA into 3-methyl-3-butenoic acid (step XVII as shown in FIG. 1); an enzyme capable of enzymatically converting 3-methylglutaconyl-CoA into 3-methyl-3-butenoyl-CoA (step XVIII as shown in FIG. 1); an enzyme capable of enzymatically converting 3-hydroxy-3-methylglutaryl-CoA into 3-methylglutaconyl-CoA (step VIII as shown in FIG. 1); an enzyme capable of enzymatically condensing acetoacetyl-CoA and acetyl-CoA into 3-hydroxy-3-methylglutaryl-CoA (step IX as shown in FIG. 1) and an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1) for the production of isobutene.

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

In a further aspect, the present invention relates to any of the above uses of enzymes for the production of isobutene, wherein additionally a) an enzyme capable of enzymatically converting 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA (step Xa as schematically shown in FIG. 19); and/or b) an enzyme capable of enzymatically converting 3-hydroxyisovalerate (HIV) into 3-hydroxyisovaleryl-CoA (step Xb as schematically shown in FIG. 20); and/or c) an enzyme capable of enzymatically converting 3-hydroxyisovaleryl-CoA into 3-methylcrotonyl-CoA (step XI as schematically shown in FIG. 21); and/or d) an enzyme capable of enzymatically converting 3-hydroxyisovalerate (HIV) into 3-hydroxyisovaleryl-CoA (step XII as schematically shown in FIG. 22)

as described herein above is used.

As regards the above-mentioned enzymes as well as preferred embodiments of said enzymes, the same applies to the recombinant organism or microorganism as has been set forth above for the methods according to the present invention.

Furthermore, the present invention relates to a composition comprising 3-methylcrotonic acid and a recombinant organism or microorganism, wherein said recombinant organism or microorganism expresses (i) an enzyme capable of enzymatically converting 3-methylcrotonic acid into isobutene (step I as shown in FIG. 1); and/or (ii) an enzyme capable of enzymatically converting 3-hydroxyisovalerate (HIV) into 3-methylcrotonic acid (step II as shown in FIG. 1), and/or which further expresses an enzyme capable of enzymatically condensing acetone and acetyl-CoA into 3-hydroxyisovalerate (HIV) (step III as shown in FIG. 1), and/or which further expresses an enzyme capable of enzymatically converting acetoacetate into acetone (step IV as shown in FIG. 1), and/or which further expresses an enzyme capable of converting acetoacetyl-CoA into acetoacetate (step Va or Vb as shown in FIG. 1) and/or which further expresses an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

Furthermore, the present invention relates to a composition comprising 3-methylcrotonic acid (i) an enzyme capable of enzymatically converting 3-methylcrotonic acid into isobutene (step I as shown in FIG. 1); and/or (ii) an enzyme capable of enzymatically converting 3-hydroxisovalerate (HIV) into 3-methylcrotonic acid (step II as shown in FIG. 1); and/or an enzyme capable of enzymatically condensing acetone and acetyl-CoA into 3-hydroxyisovalerate (HIV) (step III as shown in FIG. 1), and/or an enzyme capable of enzymatically converting acetoacetate into acetone (step IV as shown in FIG. 1), and/or an enzyme capable of converting acetoacetyl-CoA into acetoacetate (step Va or Vb as shown in FIG. 1) and/or an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

Furthermore, the present invention relates to a composition comprising 3-methylcrotonic acid and a recombinant organism or microorganism, wherein said recombinant organism or microorganism expresses (i) an enzyme capable of enzymatically converting 3-methylcrotonic acid into isobutene (step I as shown in FIG. 1); and/or (ii) an enzyme capable of enzymatically converting 3-methylcrotonyl-CoA into 3-methylcrotonic acid (step VIa, VIb or VIc as shown in FIG. 1), and/or which further expresses an enzyme capable of enzymatically converting 3-methylglutaconyl-CoA into 3-methylcrotonyl-CoA (step VII as shown in FIG. 1), and/or which further expresses an enzyme capable of enzymatically converting 3-hydroxy-3-methylglutaryl-CoA into 3-methylglutaconyl-CoA (step VIII as shown in FIG. 1), and/or which further expresses an enzyme capable of enzymatically condensing acetoacetyl-CoA and acetyl-CoA into 3-hydroxy-3-methylglutaryl-CoA (step IX as shown in FIG. 1) and/or which further expresses an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

Furthermore, the present invention relates to a composition comprising 3-methylcrotonic acid and (i) an enzyme capable of enzymatically converting 3-methylcrotonic acid into isobutene (step I as shown in FIG. 1); and/or (ii) an enzyme capable of enzymatically converting 3-methylcrotonyl-CoA into 3-methylcrotonic acid (step VIa, VIb or VIc as shown in FIG. 1); and/or an enzyme capable of enzymatically converting 3-methylglutaconyl-CoA into 3-methylcrotonyl-CoA (step VII as shown in FIG. 1); and/or an enzyme capable of enzymatically converting 3-hydroxy-3-methylglutaryl-CoA into 3-methylglutaconyl-CoA (step VIII as shown in FIG. 1); and/or an enzyme capable of enzymatically condensing acetoacetyl-CoA and acetyl-CoA into 3-hydroxy-3-methylglutaryl-CoA (step IX as shown in FIG. 1) and/or an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

Furthermore, the present invention relates to a composition comprising 3-methyl-3-butenoic acid and a recombinant organism or microorganism, wherein said recombinant organism or microorganism expresses (i) an enzyme capable of enzymatically converting 3-methyl-3-butenoic acid into isobutene (step XVI as shown in FIG. 1) and/or (ii) an enzyme capable of enzymatically converting 3-methyl-3-butenoyl-CoA into 3-methyl-3-butenoic acid (step XVII as shown in FIG. 1), and/or which further expresses an enzyme capable of enzymatically converting 3-methylglutaconyl-CoA into 3-methyl-3-butenoyl-CoA (step XVIII as shown in FIG. 1), and/or which further expresses an enzyme capable of enzymatically converting 3-hydroxy-3-methylglutaryl-CoA into 3-methylglutaconyl-CoA (step VIII as shown in FIG. 1), and/or which further expresses an enzyme capable of enzymatically condensing acetoacetyl-CoA and acetyl-CoA into 3-hydroxy-3-methylglutaryl-CoA (step IX as shown in FIG. 1) and/or which further expresses an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1).

Furthermore, the present invention relates to a composition comprising 3-methyl-3-butenoic acid and (i) an enzyme capable of enzymatically converting 3-methyl-3-butenoic acid into isobutene (step XVI as shown in FIG. 1) and/or (ii) an enzyme capable of enzymatically converting 3-methyl-3-butenoyl-CoA into 3-methyl-3-butenoic acid (step XVII as shown in FIG. 1); and/or an enzyme capable of enzymatically converting 3-methylglutaconyl-CoA into 3-methyl-3-butenoyl-CoA (step XVIII as shown in FIG. 1); and/or an enzyme capable of enzymatically converting 3-hydroxy-3-methylglutaryl-CoA into 3-methylglutaconyl-CoA (step VIII as shown in FIG. 1); and/or an enzyme capable of enzymatically condensing acetoacetyl-CoA and acetyl-CoA into 3-hydroxy-3-methylglutaryl-CoA (step IX as shown in FIG. 1) and/or an enzyme capable of enzymatically converting acetyl-CoA into acetoacetyl-CoA comprising (a) (i) an enzyme capable of converting acetyl-CoA into malonyl-CoA (step XIV as shown in FIG. 1); and (ii) an enzyme capable of condensing malonyl-CoA and acetyl-CoA into acetoacetyl-CoA (step XV as shown in FIG. 1); or (b) an enzyme capable of directly condensing two molecules of acetyl-CoA into acetoacetyl-CoA (step XIII as shown in FIG. 1) for the production of isobutene.

As regards the above-mentioned enzymes as well as preferred embodiments of said enzymes, the same applies to the use of the recombinant organism or microorganism for the production of isobutene as has been set forth above for the methods and recombinant organisms or microorganisms according to the present invention.

In a further aspect, the present invention relates to any of the above-described compositions, wherein the organism or microorganism is an organism or microorganism which additionally further expresses a) an enzyme capable of enzymatically converting 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA (step Xa as schematically shown in FIG. 19); and/or
b) an enzyme capable of enzymatically converting 3-hydroxyisovalerate (HIV) into 3-hydroxyisovaleryl-CoA (step Xb as schematically shown in FIG. 20); and/or
c) an enzyme capable of enzymatically converting 3-hydroxyisovaleryl-CoA into 3-methylcrotonyl-CoA (step XI as schematically shown in FIG. 21); and/or
d) an enzyme capable of enzymatically converting 3-hydroxyisovalerate (HIV) into 3-hydroxyisovaleryl-CoA (step XII as schematically shown in FIG. 22)
as described herein above.

In a further aspect, the present invention relates to any of the above-described compositions which further additionally comprises a) an enzyme capable of enzymatically converting 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA (step Xa as schematically shown in FIG. 19); and/or
b) and enzyme capable of enzymatically converting 3-hydroxyisovalerate (HIV) into 3-hydroxyisovaleryl-CoA (step Xb as schematically shown in FIG. 20); and/or
c) an enzyme capable of enzymatically converting 3-hydroxyisovaleryl-CoA into 3-methylcrotonyl-CoA (step XI as schematically shown in FIG. 21); and/or
d) an enzyme capable of enzymatically converting 3-hydroxyisovalerate (HIV) into 3-hydroxyisovaleryl-CoA (step XII as schematically shown in FIG. 22)
as described herein above.

As regards the above-mentioned enzymes as well as preferred embodiments of said enzymes, the same applies to the recombinant organism or microorganism as has been set forth above for the methods according to the present invention.

FIG. 1: shows an artificial pathway for isobutene production from acetyl-CoA via 3-methylcrotonic acid. Moreover, enzymatic recycling of metabolites which may occur during the pathway are shown in steps Xa, Xb, XI and XII.

FIG. 2A: Schematic reaction of the enzymatic prenylation of a flavin mononucleotide (FMN) into the corresponding modified (prenylated) flavin cofactor.

FIG. 2B: Schematic reaction of the enzymatic conversion of 3-methylcrotonic acid into isobutene.

FIG. 3: Schematic reaction of the enzymatic conversion of 3-hydroxyisovalerate (HIV) into 3-methylcrotonic acid.

FIG. 4: Schematic reaction of the enzymatic condensation of acetyl-CoA and acetone into 3-hydroxyisovalerate.

FIG. 5: Schematic reaction of the enzymatic conversion of acetoacetate into acetone.

FIG. 6: Schematic reaction of the enzymatic conversion of acetoacetyl-CoA into acetoacetate by hydrolysing the CoA thioester of acetoacetyl-CoA resulting in acetoacetate.

FIG. 7: Schematic reaction of the enzymatic conversion of acetoacetyl-CoA into acetoacetate by transferring the CoA group of acetoacetyl-CoA on acetate, resulting in the formation of acetoacetate and acetyl-CoA.

FIG. 8: Schematic reaction of the enzymatic conversion of 3-methylcrotonyl-CoA into 3-methylcrotonic acid.

FIG. 9: Schematic reaction of the enzymatic conversion of 3-methylcrotonyl-CoA into 3-methylcrotonic acid via step VIa as shown in FIG. 1.

FIG. 10: Schematic reaction of the enzymatic conversion of 3-methylcrotonyl-CoA into 3-methylcrotonic acid via step VIb as shown in FIG. 1.

FIG. 11: Schematic reaction of the enzymatic conversion of 3-methylcrotonyl-CoA into 3-methylcrotonic acid via step VIc as shown in FIG. 1.

FIG. 12: Schematic reaction of the enzymatic conversion of 3-methylglutaconyl-CoA into 3-methylcrotonyl-CoA.

FIG. 13: Schematic reaction of the enzymatic conversion of 3-hydroxy-3-methylglutaryl-CoA into 3-methylglutaconyl-CoA.

FIG. 14: Schematic reaction of the enzymatic condensation of acetylCoA and acetoacetyl-CoA into 3-hydroxy-3-methylglutaryl-CoA.

FIG. 15: Schematic reaction of the enzymatic condensation of two molecules of acetyl-CoA into acetoacetyl-CoA.

Figure 16:
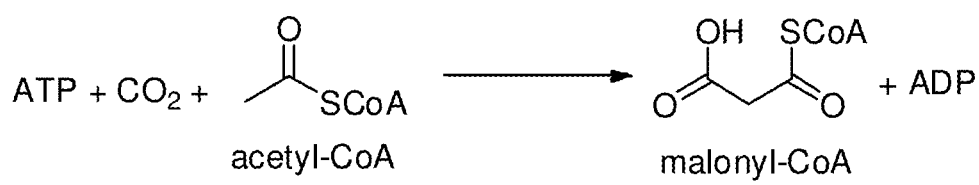

FIG. 16: Schematic reaction of the enzymatic conversion of acetyl-CoA into malonyl-CoA.

Figure 17:
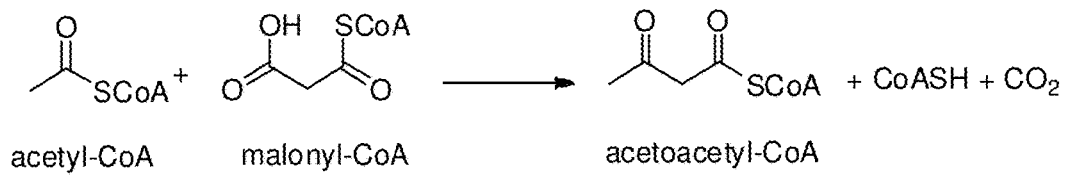

FIG. 17: Schematic reaction of the enzymatic condensation of malonyl-CoA and acetyl-CoA into acetoacetyl-CoA.

FIG. 18: shows enzymatic recycling steps of metabolites (steps Xa, Xb, XI and XII as also shown in FIG. 1) which may occur during the pathway of isobutene production from acetyl-CoA via 3-methylcrotonic acid.

FIG. 19: Schematic reaction of the enzymatic conversion of 3-hydroxyisovalerate (HIV) into 3-methylcrotonic acid with a concomitant transfer of CoA from 3-methylcrotonyl-CoA on 3-hydroxyisovalerate (HIV) to result in 3-hydroxyisovaleryl-CoA.

FIG. 20: Schematic reaction of the enzymatic conversion of 3-hydroxyisovalerate (HIV) into 3-hydroxyisovaleryl-CoA.

FIG. 21: Schematic reaction of the enzymatic conversion of 3-hydroxyisovaleryl-CoA into 3-methylcrotonyl-CoA.

FIG. 22: Schematic reaction of the general enzymatic conversion of 3-hydroxyisovalerate (HIV) into 3-hydroxyisovaleryl-CoA.

FIG. 23: Schematic reaction of the enzymatic conversion of 3-hydroxyisovalerate (HIV) into 3-hydroxyisovaleryl-CoA via 3-hydroxyisovaleryl-adenosine monophosphate.

FIG. 24: Schematic reaction of the enzymatic conversion of 3-hydroxyisovalerate (HIV) into 3-hydroxyisovaleryl-CoA via 3-hydroxyisovaleryl phosphate.

Figure 25:
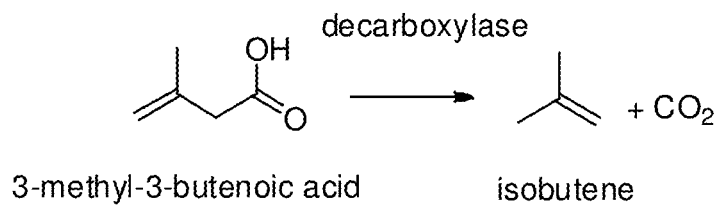

FIG. 25: Schematic reaction of the enzymatic conversion of 3-methyl-3-butenoic acid into isobutene.

FIG. 26: Schematic reaction of the enzymatic conversion of 3-methyl-3-butenoyl-CoA into 3-methyl-3-butenoic acid.

Figure 27:
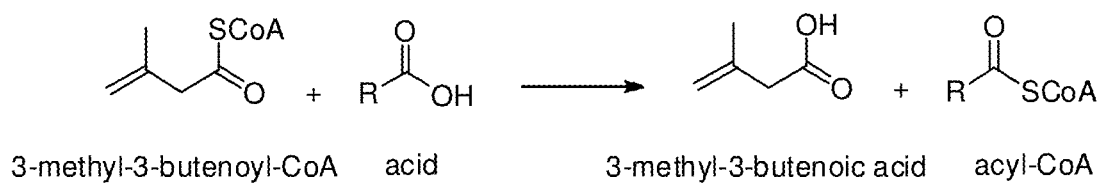

FIG. 27: Schematic reaction of the enzymatic conversion of 3-methyl-3-butenoyl-CoA into 3-methyl-3-butenoic acid by making use of a CoA-transferase.

Figure 28:
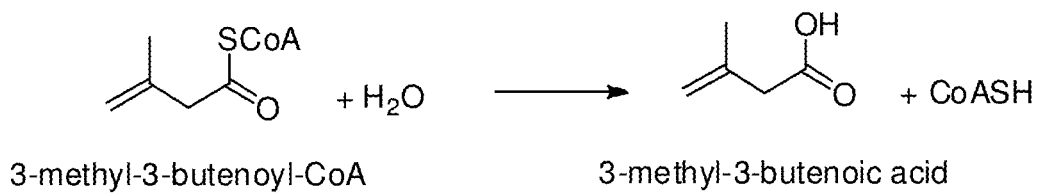

FIG. 28: Schematic reaction of the enzymatic conversion of 3-methyl-3-butenoyl-CoA into 3-methyl-3-butenoic acid by making use of a thioester hydrolase.

Figure 29:
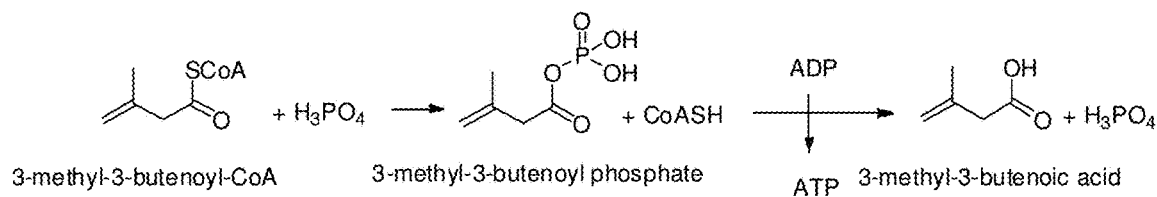

FIG. 29: Schematic reaction of the enzymatic conversion of 3-methyl-3-butenoyl-CoA into 3-methyl-3-butenoic acid in a two-step reaction via 3-methyl-3-butenoyl phosphate.

FIG. 30: Schematic reaction of the enzymatic conversion of 3-methylglutaconyl-CoA into 3-methyl-3-butenoyl-CoA.

FIG. 31: Structure of a phosphopantetheine moiety.

FIG. 32: Schematic illustration for the conversion of 3-methylcrotonyl-CoA into 3-methylcrotonic acid via 3-methylbutyryl-CoA and 3-methylbutyric acid.

Figure 33:
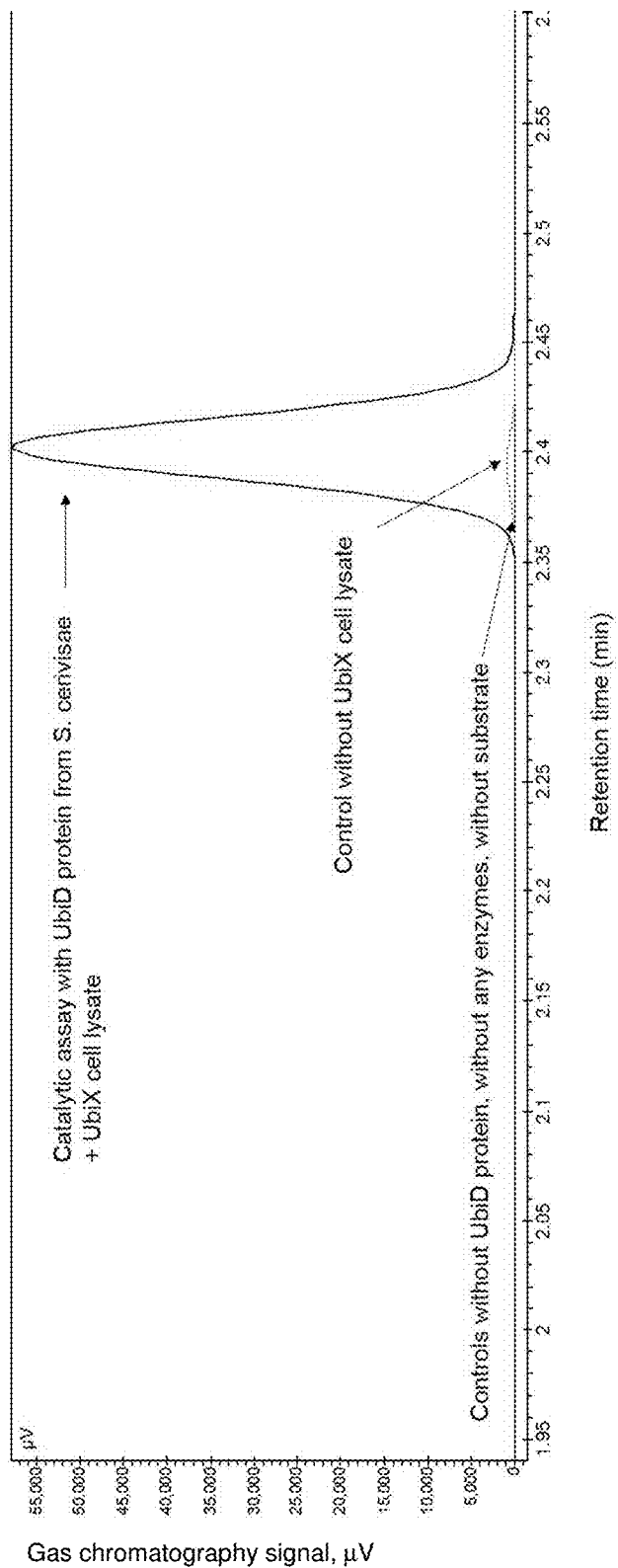

FIG. 33: shows an overlay of typical GC-chromatograms obtained for the catalytic assay of UbiD protein from *Saccharomyces cerevisiae* with the corresponding controls as outlined in Example 2.

Figure 34A:
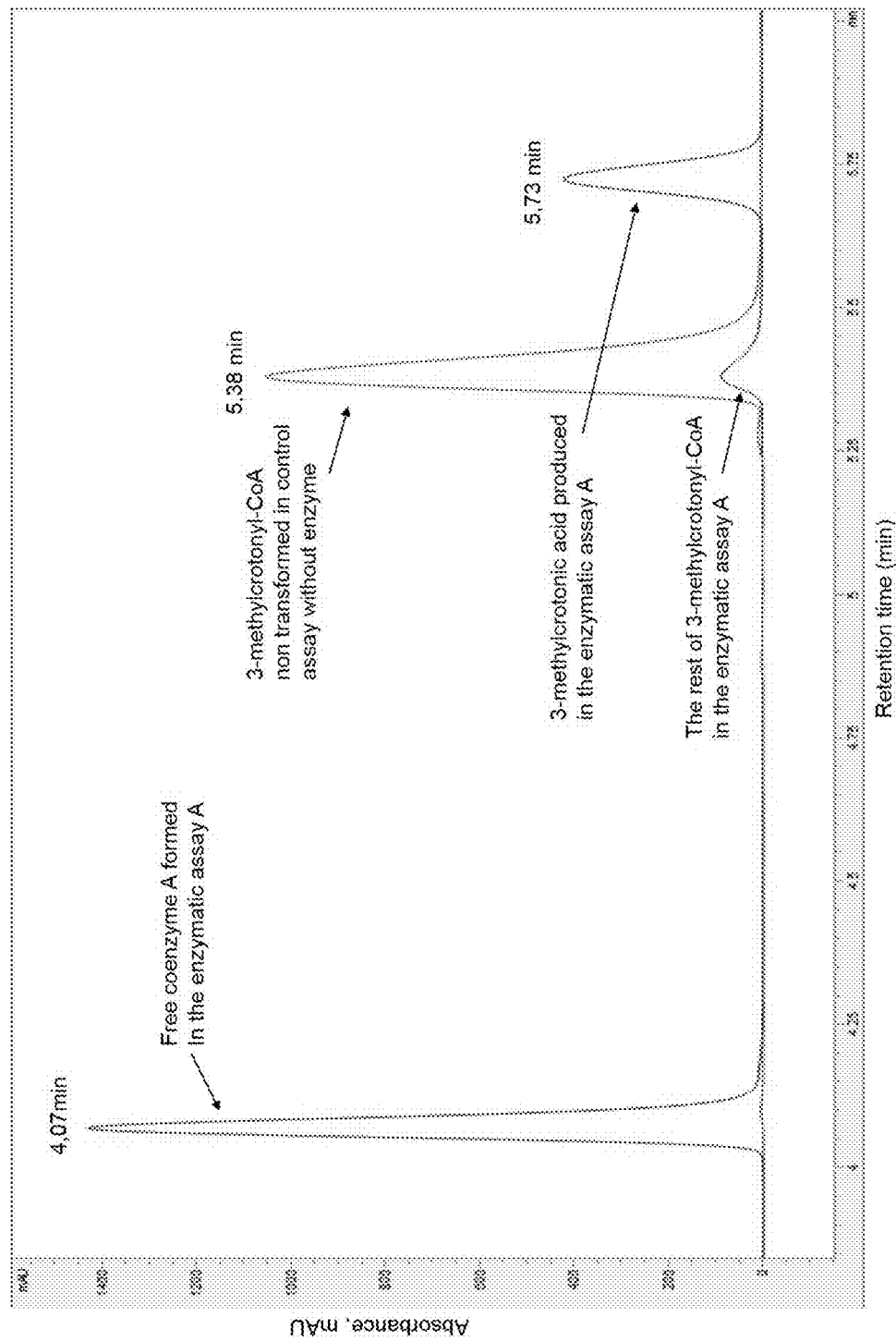

FIG. 34*a*: shows an overlay of typical HPLC-chromatograms (analysis of 3-methylcrotonyl-CoA, 3-methylcrotonic acid and CoA-SH) obtained for the "Enzymatic assay" (assay A, Example 3) and the "Enzyme-free assay" (assay H, Example 3). The consumption of 3-methylcrotonyl-CoA with simultaneous production of CoA-SH and 3-methylcrotonic acid was observed in the enzymatic assay combining phosphate butyryltransferase with butyrate kinase.

Figure 34B:
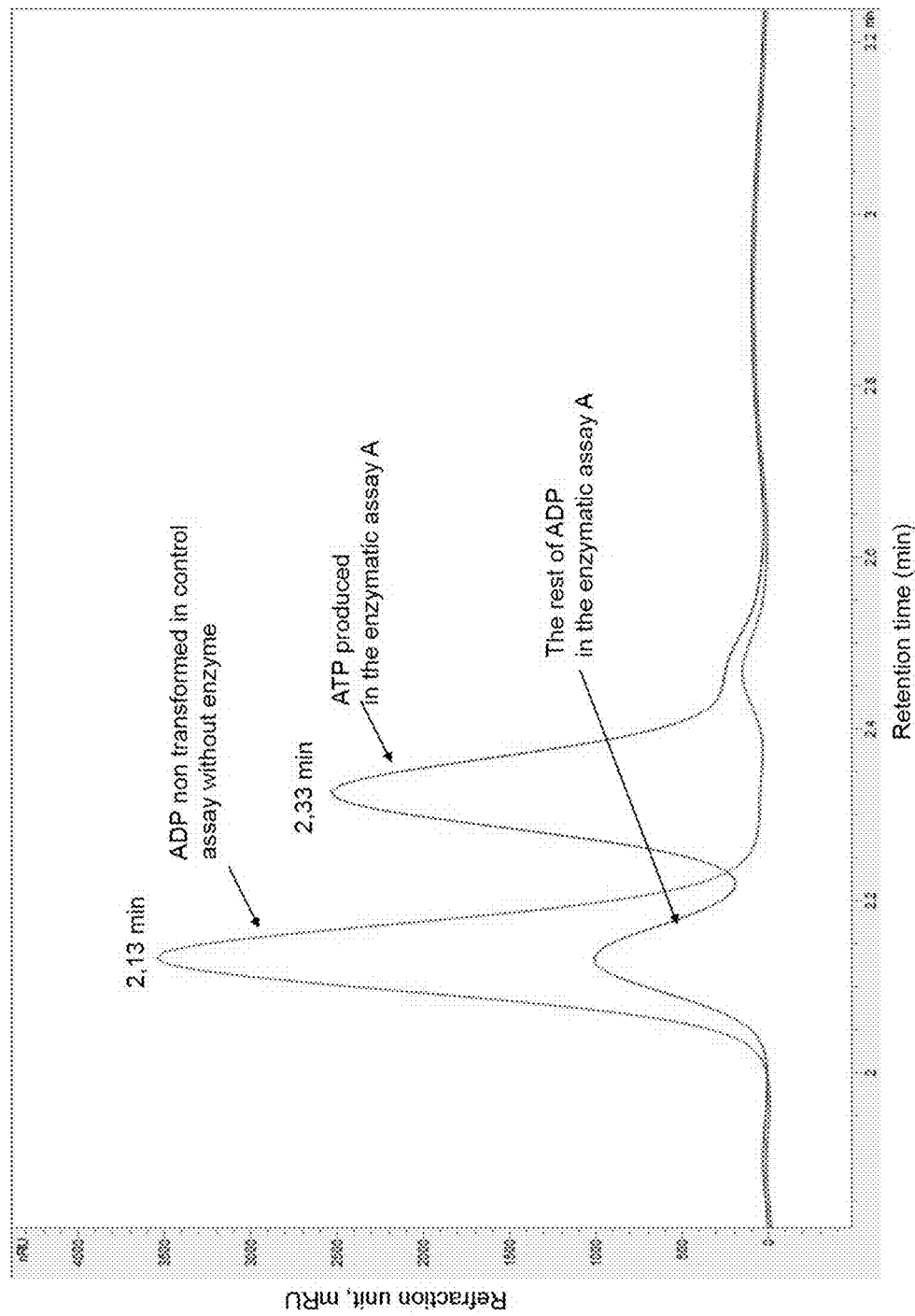

FIG. 34*b*: shows an overlay of typical HPLC-chromatograms (analysis of ADP and ATP) obtained for the "Enzymatic assay" (assay A, Example 3) and the "Enzyme-free assay" (assay H, Example 3). The consumption of ADP with simultaneous production of ATP was observed in the enzymatic assay combining phosphate butyryltransferase with butyrate kinase.

Figure 35:
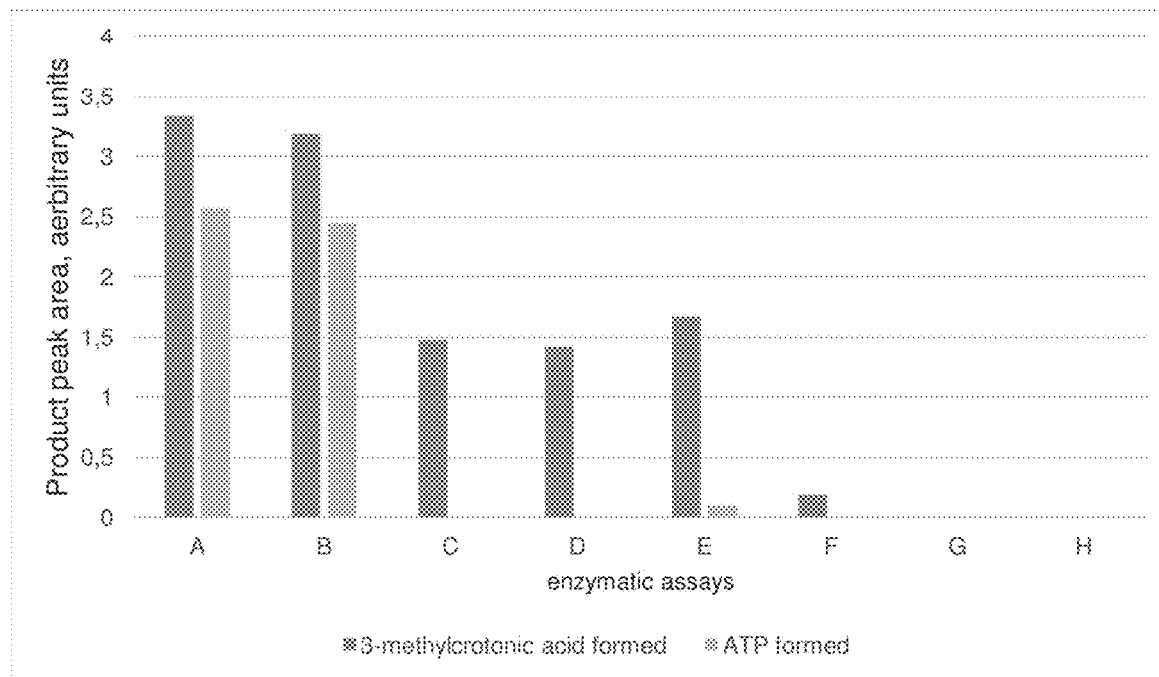

FIG. 35: shows the results of the production of 3-methylcrotonic acid and ATP in the enzymatic assays, comprising phosphate butyryltransferase from *Bacillus subtilis* combined with different butyrate kinases. Moreover, the production of 3-methylcrotonic acid and ATP in control assays is shown.

Figure 36:
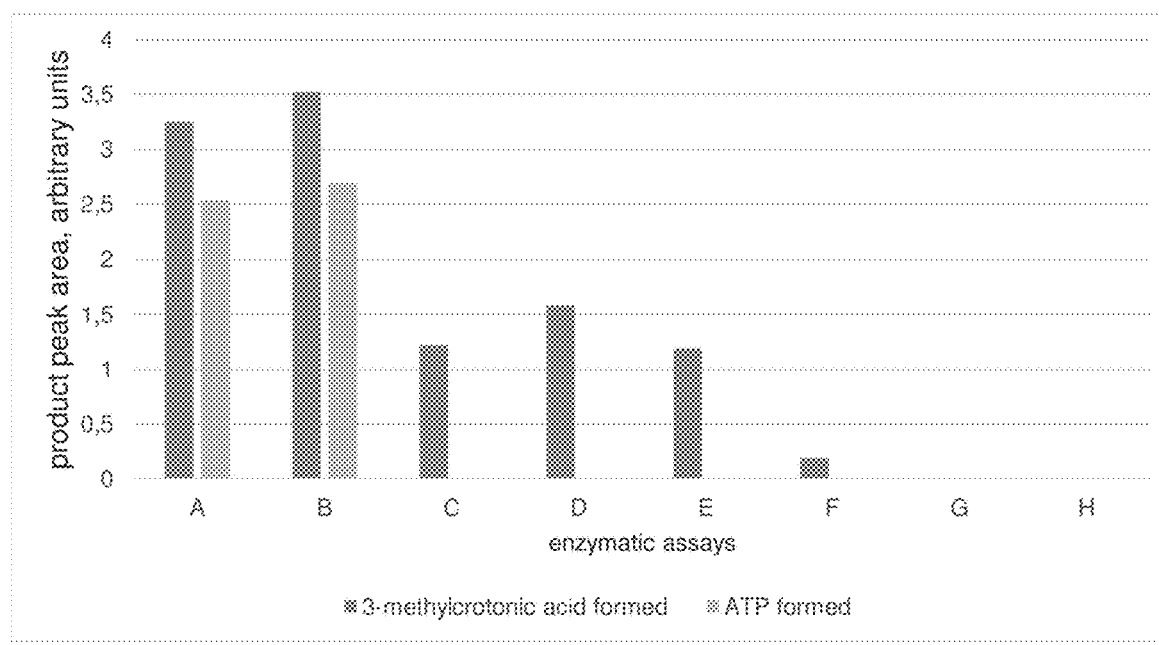

FIG. 36: shows the results of the production of 3-methylcrotonic acid and ATP in the enzymatic assays, comprising phosphate butyryltransferase from from *Enterococcus faecalis* combined with different butyrate kinases. Moreover, the production of 3-methylcrotonic acid and ATP in different control assays is shown.

Figure 37:
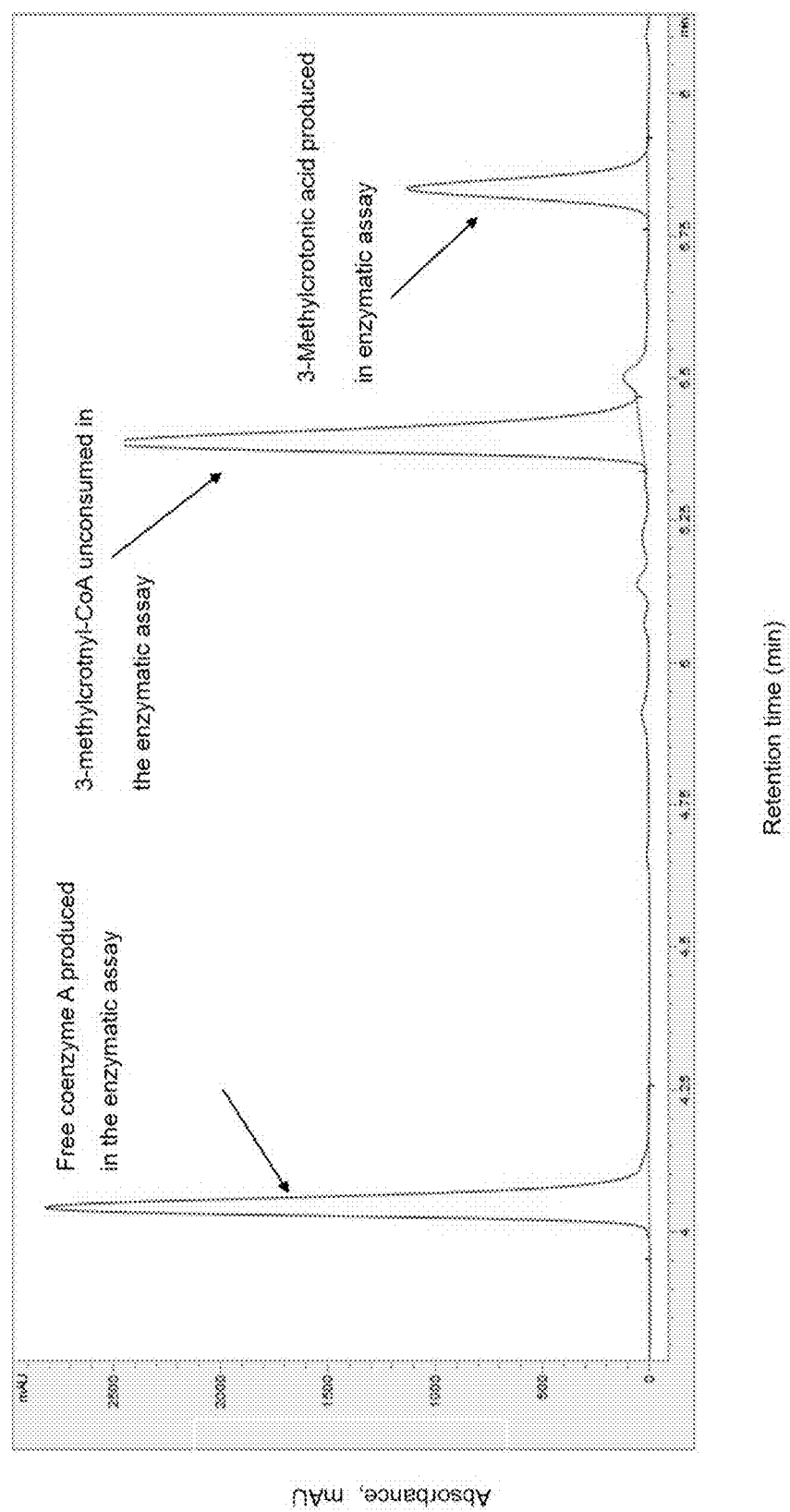

FIG. 37: shows an example of typical HPLC-chromatogram obtained for the enzymatic assay with acyl-CoA thioesterase II from *Pseudomonas putida* as outlined in Example 5.

Figure 38:
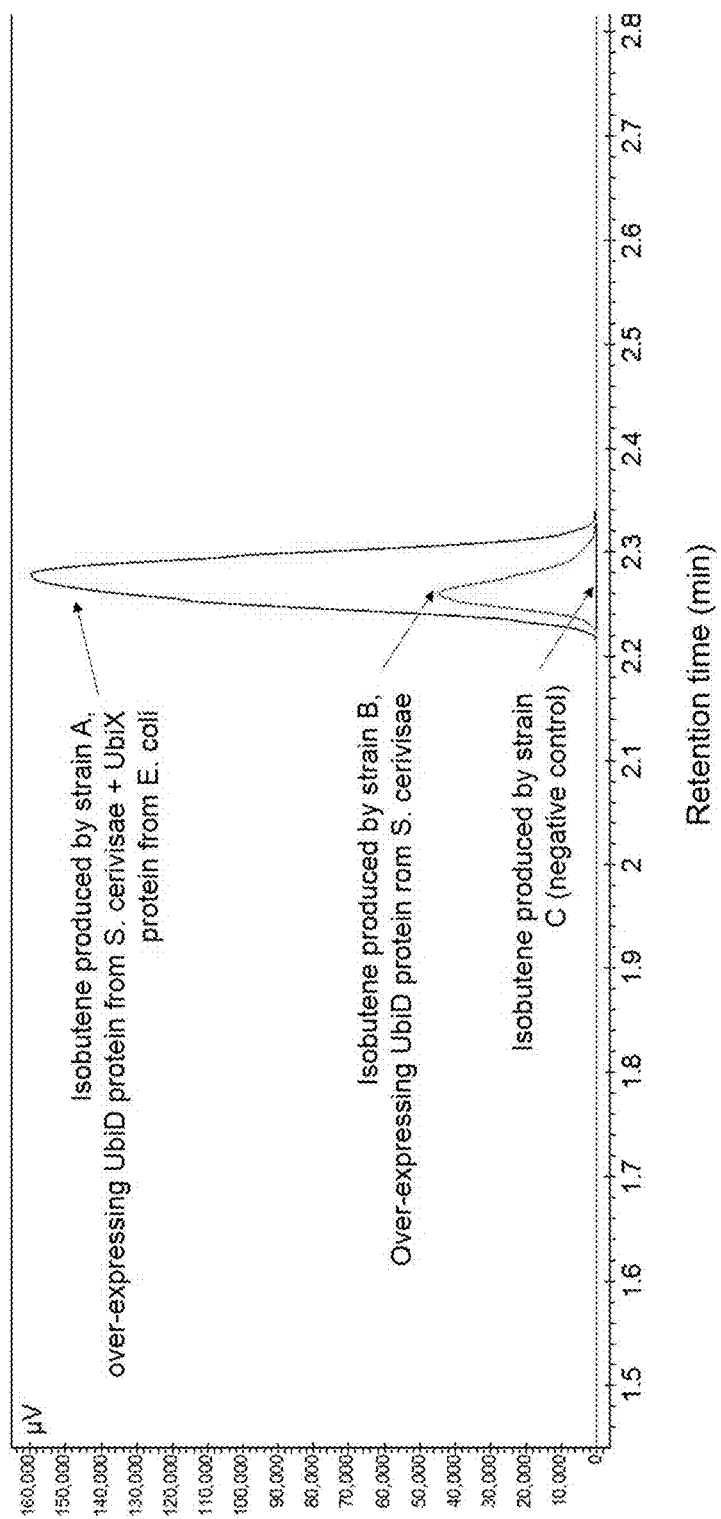

FIG. 38: shows an overlay of typical chromatograms obtained for the production of isobutene from 3-methylcrotonic in a recombinant *E. coli* strain overexpressing UbiD protein from *Saccharomyces cerevisiae* and UbiX protein from *Escherichia coli* (strain A) or overexpressing UbiD protein from *Saccharomyces cerevisiae* alone (strain B) or carrying an empty vector (negative control, strain C).

Figure 39:
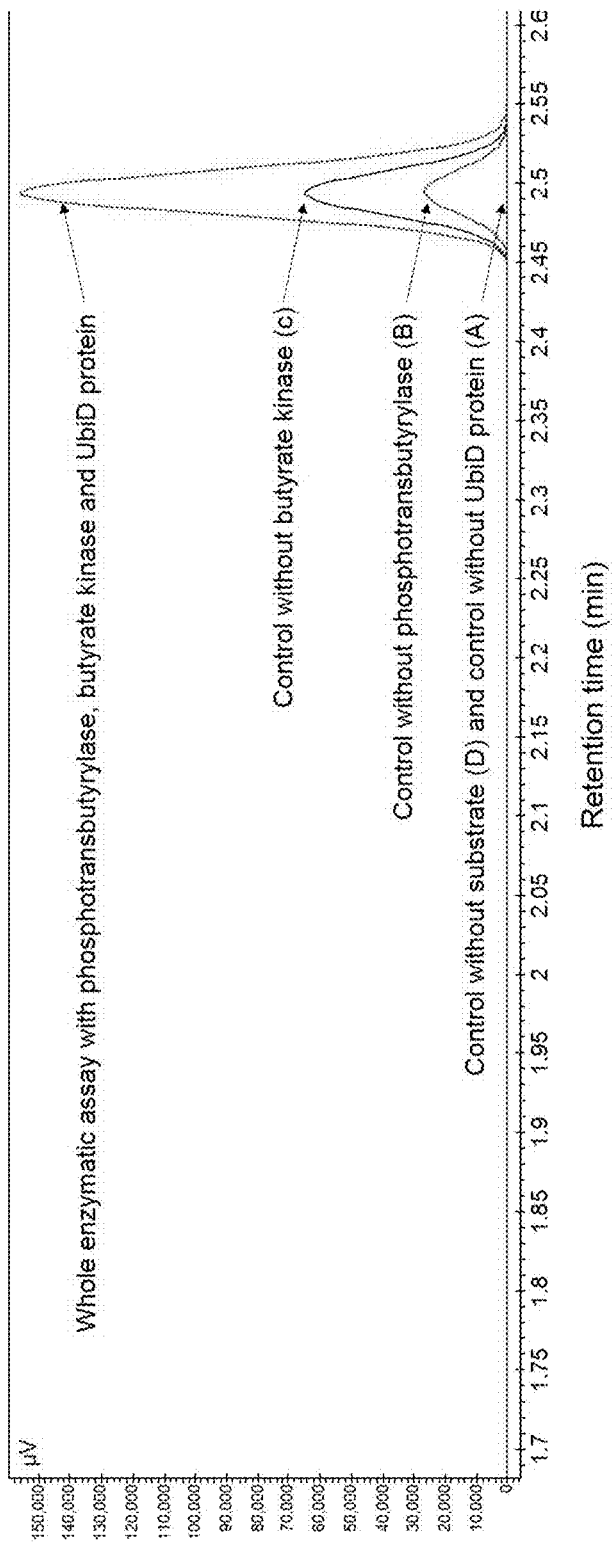

FIG. 39: shows an overlay of typical chromatograms obtained for the production of isobutene from 3-methylcrotonyl-CoA in the one pot enzymatic assay as outlined in Example 7, and the corresponding controls.

Figure 40A:
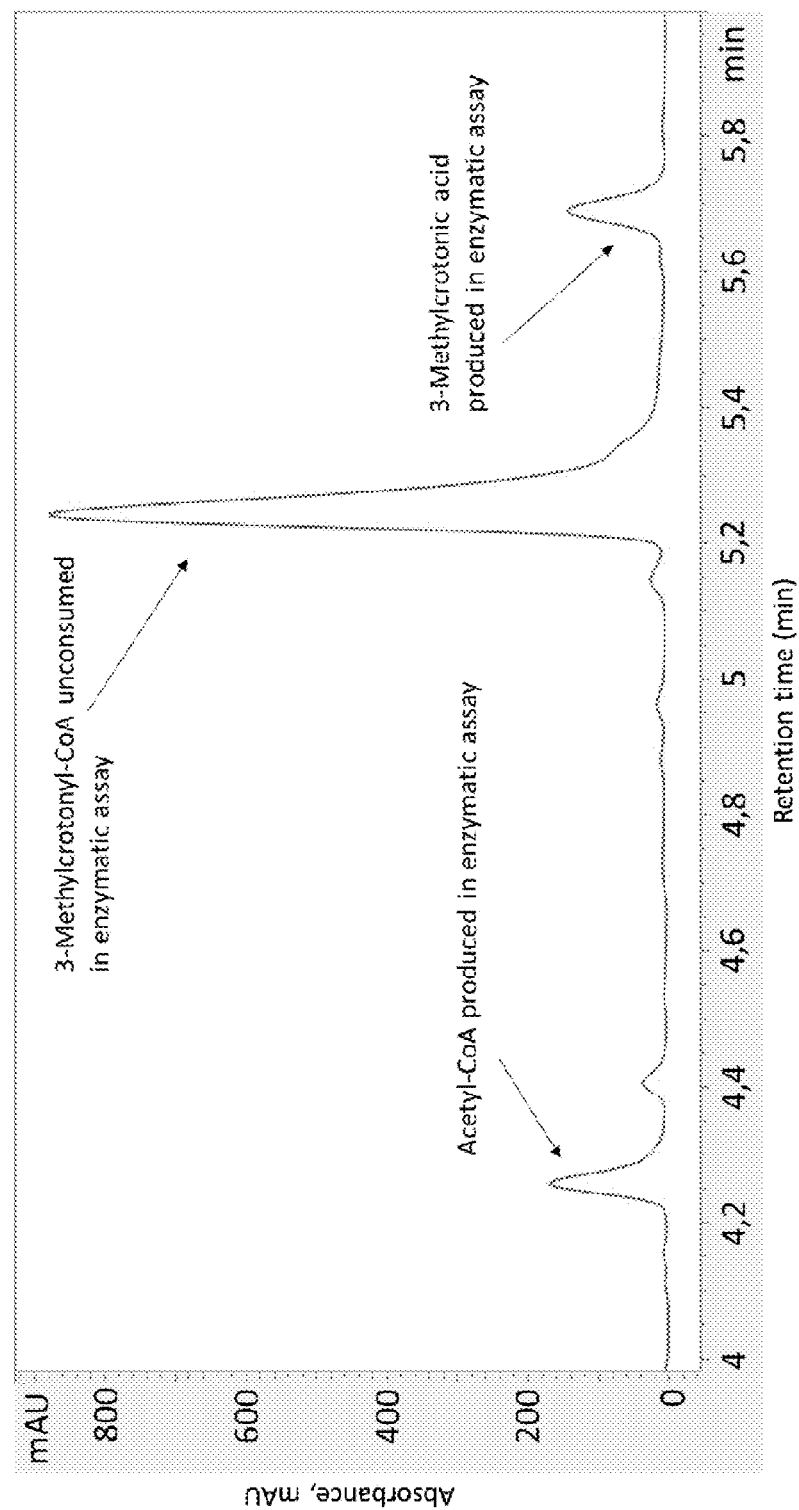
Figure 40B:
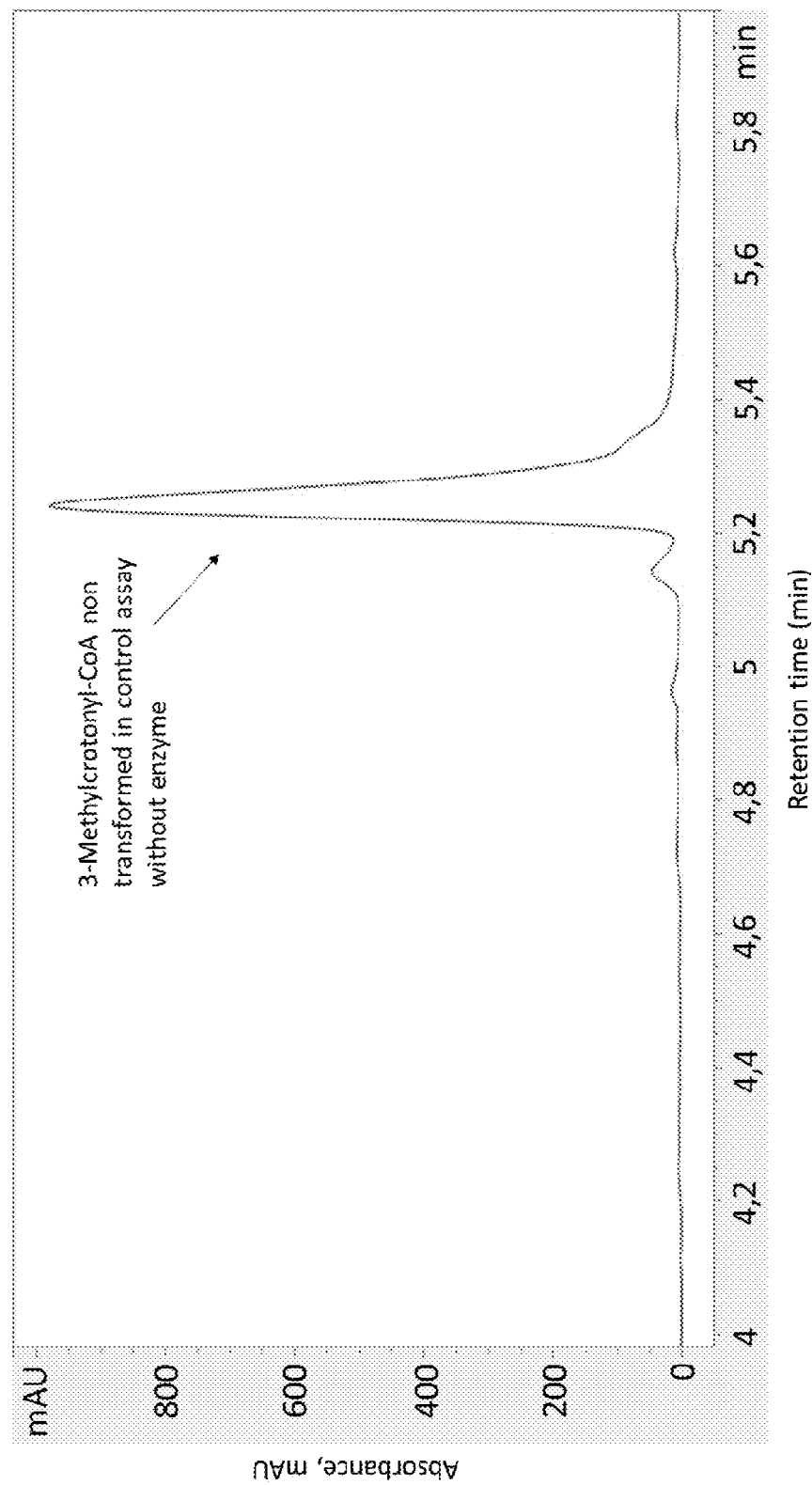

FIG. 40: shows chromatograms for enzymatic assays (a) and control assays (b). A significant quantity of acetyl-CoA and 3-methylcrotonic acid was produced from acetate and 3-methylcrotonyl-CoA in the presence of Co-A transferase (a) while no product was observed in the control assay without enzyme (b).

Figure 41:
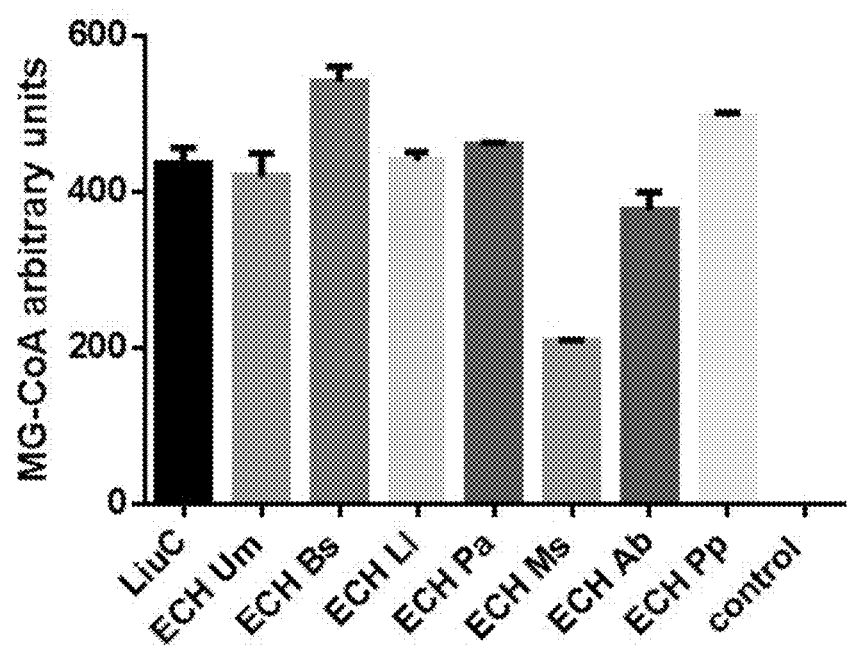

FIG. 41: shows 3-methylglutaconyl-CoA (MG-CoA) peak areas obtained from HPLC-based analysis.

Figure 42:
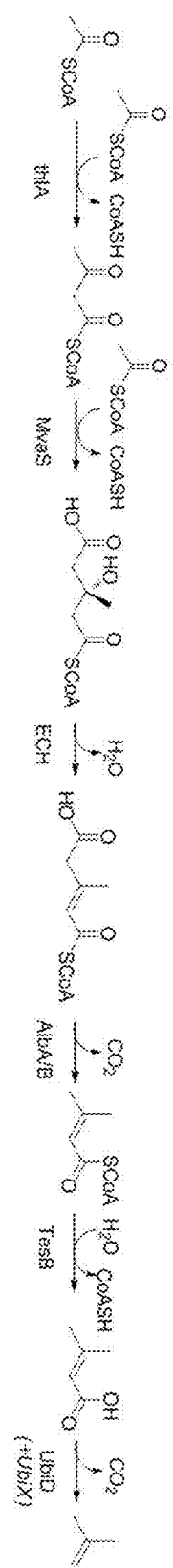

FIG. 42: Metabolic pathway for the biosynthesis of isobutene from acetyl-CoA via 3-methylcrotonic acid, implemented in *Escherichia coli*.

In this specification, a number of documents including patent applications are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention will now be described by reference to the following examples which are merely illustrative and are not to be construed as a limitation of the scope of the present invention.

EXAMPLES

General Methods and Materials

All reagents and materials used in the experiences were obtained from Sigma-Aldrich Company (St. Louis, Mo.) unless otherwise specified. Materials and methods suitable for growth of bacterial cultures and protein expression are well known in the art.

Example 1: Gene Synthesis, Cloning and Expression of Recombinant Proteins

The sequences of the studied enzymes were generated by oligonucleotide concatenation to fit the codon usage of *E. coli* (genes were commercially synthesized by GeneArt®). A stretch of 6 histidine codons was inserted after the methionine initiation codon to provide an affinity tag for purification. The gene thus synthesized was cloned in a pET-25b (+) expression vector (vectors were constructed by GeneArt®). Vector pCAN contained gene coding for UbiX protein (3-octaprenyl-4-hydroxybenzoate carboxy-lyase partner protein) from *Escherichia coli* (Uniprot Accession Number: P0AG03) was purchased from NAIST (Nara Institute of Science and Technology, Japan, ASKA collection). Provided vector contained a stretch of 6 histidine codons after the methionine initiation codon.

Competent *E. coli* BL21 (DE3) cells (Novagen) were transformed with these vectors according to standard heat shock procedure. The transformed cells were grown with shaking (160 rpm) using ZYM-5052 auto-induction medium (Studier F W, Prot. Exp. Pur. 41, (2005), 207-234) for 6 h at 30° C. and protein expression was continued at 18° C. overnight (approximately 16 h). For the recombinant strain over-expressing UbiX from *E. coli*, 500 µM of Flavin Mononucleotide (FMN) were added to the growth medium. The cells were collected by centrifugation at 4° C., 10,000 rpm for 20 min and the pellets were stored at −80° C.

Protein Purification and Concentration

The pellets from 200 ml of cultured cells were thawed on ice and resuspended in 6 ml of 50 mM Tris-HCl buffer pH 7.5 containing 100 mM NaCl in the case of the recombinant strain overexpressing UbiX protein and in 6 ml of 50 mM Tris-HCl buffer pH 7.5, 10 mM MgCl$_2$, 10 mM imidazole and 5 mM DTT in the case of the recombinant strain overexpressing UbiD protein. Twenty microliters of lysonase (Novagen) were added. Cells were then incubated 10 min at room temperature, returned to ice for 20 min and the lysis was completed by sonication 3×15 seconds. The cellular lysate contained UbiX protein was reserved on ice. The bacterial extracts contained UbiD proteins were then clarified by centrifugation at 4° C., 4000 rpm for 40 min. The clarified bacterial lysates were loaded onto a PROTINO-2000 Ni-TED column (Macherey-Nagel) allowing adsorption of 6-His tagged proteins. Columns were washed and the enzymes of interest were eluted with 6 ml of 100 mM Tris-HCl buffer pH 7.5 containing 100 mM NaCl and 250 mM imidazole. Eluates were then concentrated, desalted on Amicon Ultra-4 10 kDa filter unit (Millipore) and enzymes were resuspended in 50 mM Tris-HCl buffer pH 7.5, containing 50 mM NaCl and 5 mM DTT.

The purity of proteins thus purified varied from 80% to 90% as estimated by SDS-PAGE analysis. Protein concentration was determined by direct UV 280 nm measurement on the NanoDrop 1000 spectrophotometer (Thermo Scientific) and by Bradford assay (BioRad).

Example 2: In Vitro Decarboxylation of 3-Methylcrotonic Acid into Isobutene Catalyzed by an Association of Lysate, Containing UbiX Protein, with Purified UbiD Protein 0.5 M stock solution of 3-methylcrotonic acid was prepared in water and adjusted to pH 7.0 with 10 M solution of NaOH.

Two UbiD proteins (Table C) were purified according to the procedure described in Example 1.

Enzymatic assays were carried out in 2 ml glass vials (Interchim) under the following conditions:

50 mM Tris-HCl buffer pH 7.5

20 mM NaCl 10 mM $MgCl_2$ 5 mM DTT 50 mM 3-methylcrotonic acid 1 mg/ml purified UbiD protein 50 µl lysate contained UbiX protein Total volume of the assays were 300 µl.

A series of control assays were performed in parallel (Table C).

The vials were sealed and incubated for 120 min at 30° C. The assays were stopped by incubating for 2 min at 80° C. and the isobutene formed in the reaction headspace was analysed by Gas Chromatography (GC) equipped with Flame Ionization Detector (FID).

For the GC analysis, one ml of the headspace gas was separated in a Bruker GC-450 system equipped with a GS-alumina column (30 m×0.53 mm) (Agilent) using isothermal mode at 130° C. Nitrogen was used as carrier gas with a flow rate of 6 ml/min.

The enzymatic reaction product was identified by comparison with an isobutene standard. Under these GC conditions, the retention time of isobutene was 2.42 min. A significant production of isobutene from 3-methylcrotonic acid was observed in the combined assays (UbiD protein+ UbiX protein). Incubation of lysate containing UbiX protein alone did not result in isobutene production. These data indicate that the two enzymes present in the assays cooperated to perform the decarboxylation of 3-methylcrotonic acid into isobutene. A typical chromatogram obtained in the assay with UbiD protein from *Saccharomyces cerevisiae* is shown on FIG. 33.

TABLE C

| Assay composition | Isobutene production, arbitrary units |
|---|---|
| UbiD protein from *C. dubliniensis* (Uniprot Acession Number: B9WJ66) + lysate contained UbiX protein from *E. coli* + substrate | 470 |
| UbiD protein from *C. dubliniensis* (Uniprot Acession Number: B9WJ66) + substrate | 9.2 |
| UbiD protein from *S. cervisiae* (Uniprot Acession Number: Q03034) + lysate contained UbiX protein from *E. coli* + substrate | 1923 |
| UbiD protein from *S. cerivisae* (Uniprot Acession Number: Q03034) + substrate | 31 |
| Lysate contained UbiX protein from *E. coli* + substrate | 0 |
| "No substrate control": UbiD protein from *C. dubliniensis* (Uniprot Acession Number: B9WJ66) + lysate contained UbiX protein from *E. coli*, without substrate | 0 |
| "No substrate control": UbiD protein from *S. cervisiae* (Uniprot Acession Number: Q03034) + lysate contained UbiX protein from *E. coli*, without substrate | 0 |

Example 3: Conversion of 3-Methylcrotonyl-CoA and ADP into 3-Methylcrotonic Acid and ATP Catalysed by the Combined Action of Phosphate Butyryltransferase from *Bacillus subtilis* and Butyrate Kinase from *Lactobacillus casei* or *Geobacillus* sp The corresponding enzymes were obtained and purified according to the procedure described in Example 1.

The enzymatic assays were conducted in a total reaction volume of 0.2 ml

The standard reaction mixture contained:

50 mM potassium phosphate buffer pH 7.5

4 mM 3-methylcrotonyl-CoA 4 mM ADP 10 mM $MgCl_2$ 10 mM NaCl 0.2 mg/ml purified phosphate butyryltransferase from *Bacillus subtilis* (Uniprot Accession Number: P54530)

0.2 mg/ml purified butyrate kinase from *Lactobacillus casei* (Uniprot Accession Number: K0N529) or *Geobacillus* sp. (Uniprot accession number: L8A0E1). A series of controls were performed in parallel (Assays C—H Table D).

TABLE D

| | Assay composition | | | | | | | |
|---|---|---|---|---|---|---|---|---|
| | A | B | C | D | E | F | G | H |
| 3-methylcrotonyl-CoA | + | + | + | + | + | + | + | + |
| ADP | + | + | | | + | + | + | + |
| phosphate butyryltransferase from *Bacillus subtilis* | + | + | + | + | + | | | |
| butyrate kinase from *Lactobacillus casei* | + | | + | | | + | | |
| butyrate kinase from *Geobacillus* sp | | + | | + | | | + | |

Assays were incubated for 20 min with shaking at 30° C.

After an incubation period, the reactions were stopped by heating the reaction medium 4 min at 90° C. The samples were centrifuged, filtered through a 0.22 µm filter and the clarified supernatants were transferred into a clean vial for the further analysis. The consumption of ADP and 3-methylcrotonyl-CoA, and the formation of ATP, 3-methylcrotonic acid and free coenzyme A (CoA-SH) were followed by using HPLC-based methods.

HPLC-Based Analysis of ADP and ATP

HPLC analysis was performed using 1260 Inifinity LC System (Agilent), equipped with column heating module and RI detector. 2 µl of samples were separated on Polaris C18-A column (150×4.6 mm, 5 µm particle size, column temp. 30° C.) with a mobile phase flow rate of 1.5 ml/min. The separation was performed using 8.4 mM sulfuric acid in $H_2O$/MeOH mixed solution (99/1) (V/V). In these conditions, the retention time of ADP and ATP were 2.13 min and 2.33 min, respectively.

HPLC Based Analysis of 3-Methylcrotonyl-CoA, 3-Methylcrotonic Acid and Free Coenzyme A (CoA-SH)

HPLC analysis was performed using 1260 Inifinity LC System (Agilent), equipped with column heating module and UV detector (260 nm). 1 µl of samples were separated on Zorbax SB-Aq column (250×4.6 mm, 5 µm particle size, column temp. 30° C.), with a mobile phase flow rate of 1.5 ml/min. The separation was performed using mixed A ($H_2O$ containing 8.4 mM sulfuric acid) and B (acetonitrile) solutions in a linear gradient (0% B at initial time 0 min→70% B at 8 min). In these conditions, the retention time of 3-methylcrotonyl-CoA, 3-methylcrotonic acid and free coenzyme A (CoA-SH) were 5.38 min, 5.73 min and 4.07 min, respectively.

Typical chromatograms obtained for the enzymatic assay A and enzyme-free assay H are shown on FIGS. 34a and 34b.

The results of HPLC analysis are summarized in FIG. 35.

The obtained data indicate that 3-methylcrotonyl-CoA was converted into 3-methylcrotonic acid with the concomitant generation of ATP from ADP in a two-step reaction, catalyzed respectively by two enzymes (assays A and B). Thus, the conversion occurred through the formation of the intermediate 3-methylcrotonyl phosphate followed by the transfer of phosphate group from this intermediate on ADP thereby releasing ATP.

A certain quantity of 3-methylcrotonic acid was produced without simultaneous generation of ATP, when phosphate butyryltransferase was used alone (assay E). This production is due to a spontaneous hydrolysis of 3-methylcrotonyl phosphate generated by the action of phosphate butyryltransferase.

The production of 3-methylcrotonic acid was observed in the same manner for the control assays without ADP (assays C and D). This production was also due to a hydrolysis of the 3-methylcrotonyl phosphate generated by the action of phosphate butyryltransferase.

Example 4: Conversion of 3-Methylcrotonyl-CoA and ADP into 3-Methylcrotonic Acid and ATP Catalysed by the Combined Action of the Phosphate Butyryltransferase from *Enterococcus faecalis* and Butyrate Kinase from *Lactobacillus casei* or *Geobacillus* sp The corresponding enzymes were obtained and purified according to the procedure described in Example 1.

The enzymatic assays were conducted in a total reaction volume of 0.2 ml

The standard reaction mixture contained:
50 mM potassium phosphate buffer pH 7.5
4 mM 3-methylcrotonyl-CoA
4 mM ADP
10 mM $MgCl_2$
10 mM NaCl
0.2 mg/ml purified phosphate butyryltransferase from *Enterococcus faecalis* (Uniprot Accession Number: S4BZL5)
0.2 mg/ml purified butyrate kinase from *Lactobacillus casei* (Uniprot Accession Number: K0N529) or *Geobacillus* sp. (Uniprot Accession Number: L8A0E1) A series of controls were performed in parallel (Assays C—H Table E).

TABLE E

| | Assay composition | | | | | | | |
|---|---|---|---|---|---|---|---|---|
| | A | B | C | D | E | F | G | H |
| 3-methylcrotonyl-CoA | + | + | + | + | + | + | + | + |
| ADP | + | + | | | + | + | + | + |
| phosphate butyryltransferase from *Enterococcus faecalis* | + | + | + | + | + | | | |
| butyrate kinase from *Lactobacillus casei* | + | | + | | | + | | |
| butyrate kinase from *Geobacillus* sp | | + | | + | | | + | |

Assays were incubated for 20 min with shaking at 30° C.

After an incubation period, the reactions were stopped by heating the reaction medium 4 min at 90° C. The samples were centrifuged, filtered through a 0.22 µm filter and the clarified supernatants were transferred into a clean vial for further analysis. The consumption of ADP and 3-methylcrotonyl-CoA, and the formation of ATP and 3-methylcrotonic acid and free coenzyme A (CoA-SH) were followed by HPLC analysis according to the methods described in Example 3.

The results of HPLC analysis are summarized in FIG. 36.

The obtained data indicate that 3-methylcrotonyl-CoA was converted into 3-methylcrotonic acid with the concomitant generation of ATP from ADP in a two-step reaction, catalyzed respectively by two enzymes (assays A and B). Thus, the conversion occurred through the formation of the intermediate 3-methylcrotonyl phosphate followed by transfer of phosphate group from this intermediate on ADP thereby releasing ATP.

A significant production of 3-methylcrotonic acid, without simultaneous generation of ATP, was observed when phosphate butyryltransferase was used alone (assay E). This production was due to a hydrolysis of 3-methylcrotonyl phosphate generated by the action of phosphate butyryltransferase.

The production of 3-methylcrotonic acid was observed in the same manner for the control assays without ADP (assays C and D). This production was also due to a hydrolysis of the 3-methylcrotonyl phosphate generated by the action of phosphate butyryltransferase.

Example 5: Enzyme-Catalyzed Hydrolysis of 3-Methylcrotonyl-CoA into 3-Methylcrotonic Acid and Free Coenzyme A The gene coding for acyl-CoA thioesterase II from *Pseudomonas putida* was synthesized according to the procedure described in Example 1.

Vector pCAN contained gene encoding acyl-CoA thioesterase 2 (TesB) from *Escherichia coli* were purchased from NAIST (Nara Institute of Science and Technology, Japan, ASKA collection). Provided vector contained a stretch of 6 histidine codons after the methionine initiation codon. The corresponding enzymes were produced according to the procedure described in Example 1.

The enzymatic assays were conducted in a total reaction volume of 0.2 ml.

The standard reaction mixture contained:
50 mM HEPES pH 7.0
10 mM 3-methylcrotonyl-CoA
20 mM MgCl2
20 mM NaCl
1 mg/ml purified recombinant thioesterase.

Control assays were performed in which either no enzyme was added, or no substrate was added.

The assays were incubated for 30 min with shaking at 30° C., the reactions were stopped by the addition of 0.1 ml acetonitrile and the samples were then analysed by HPLC-based procedure.

HPLC Based Analysis of the Consumption of 3-Methylcrotonyl-CoA and the Formation of 3-Methylcrotonic Acid and Free Coenzyme A (CoA-SH)

HPLC analysis was performed using 1260 Inifinity LC System (Agilent), equipped with column heating module and UV detector (210 nm). 5 µl of samples were separated on Zorbax SB-Aq column (250×4.6 mm, 5 µm particle size, column temp. 30° C.), with a mobile phase flow rate of 1.5 ml/min. The separation was performed using mixed A ($H_2O$ containing 8.4 mM sulfuric acid) and B (acetonitrile) solutions in a linear gradient (0% B at initial time 0 min→70% B at 8 min). Commercial 3-methylcrotonyl-CoA, 3-methylcrotonic acid (Sigma-Aldrich) and CoA-SH (Sigma-Aldrich) were used as references. In these conditions, the retention time of free coenzyme A (CoA-SH), 3-methylcrotonyl-CoA and 3-methylcrotonic acid were 4.05, 5.38 and 5.83 min, respectively.

No 3-methylcrotonic acid signal was observed in control assays.

The both studied thioesterases catalyzed the hydrolysis of 3-methylcrotonyl-CoA with the formation of 3-methylcrotonic acid. An example of chromatogram obtained with acyl-CoA thioesterase II from *Pseudomonas putida* is shown on FIG. 37.

The production of 3-methylcrotonic acid observed in the enzymatic assays are shown in Table F.

TABLE F

| Gene name | Organism | Uniprot Accession Number | 3-methylcrotonic acid produced, mM |
|---|---|---|---|
| tesB | Escherichia coli | P0AGG2 | 0.6 |
| tesB | Pseudomonas putida | Q88DR1 | 3.1 |

Example 6: In Vivo Decarboxylation of 3-Methylcrotonic Acid into Isobutene Catalyzed by an Association of UbiX Protein from *Escherichia coli* and UbiD Protein from *Saccharomyces cerevisiae*

The gene coding for UbiD protein from *S. cerevisiae* (Uniprot Accession Number: Q03034) was codon optimized for expression in *E. coli* and synthesized by GeneArt® (Life Technologies). This studied gene was then PCR amplified from the pMK-RQ vector (master plasmid provided by GeneArt) using forward primer with NcoI restriction site and a reverse primer, containing BamHI restriction site. The gene coding for UbiX protein from *E. coli* (Uniprot Accession Number: P0AG03) was amplified by PCR with a forward primer, containing NdeI restriction site and a reverse primer containing KpnI restriction site. The previously described pCAN vector (Example 1) served as template for this PCR step. These two obtained PCR products (UbiD protein and UbiX protein) were cloned into pET-Duet™-1 co-expression vector (Novagen). The constructed recombinant plasmid was verified by sequencing. Competent *E. coli* BL21(DE3) cells (Novagen) were transformed with this vector according to standard heat shock procedure and plated out onto LB agar plates supplemented with ampicillin (0.1 mg/ml) (termed "strain A").

BL21(DE3) strain transformed with pET-25b(+) vector, carrying only the gene of UbiD protein from *S. cerevisae* was also used in this study (termed "strain B"). BL21(DE3) strain transformed with an empty pET-25b(+) vector was used as a negative control in the subsequent assays (termed "strain C").

Single transformants were used to inoculate LB medium, supplemented with ampicillin, followed by incubation at 30° C. overnight. 1 ml of this overnight culture was used to inoculate 300 ml of ZYM-5052 auto-inducing media (Studier F W (2005), local citation). The cultures were grown for 20 hours at 30° C. and 160 rpm shaking.

A volume of cultures corresponding to OD600 of 30 was removed and centrifuged. The pellet was resuspended in 30 ml of MS medium (Richaud C., Mengin-Leucreulx D., Pochet S., Johnson E J., Cohen G N. and MarHere P, The Journal of Biological Chemistry, 268, (1993), 26827-26835), containing glucose (45 g/L) and MgSO4 (1 mM) and supplemented with 10 mM 3-methylcrotonic acid. These cultures were then incubated in 160 ml bottles, sealed with a screw cap, at 30° C. with shaking for 22 h. The pH value of the cultures was adjusted to 8.5 after 8 hours of incubation by using 30% NH4OH.

After an incubation period, the isobutene produced in the headspace was analysed by Gas Chromatography (GC) equipped Flame Ionization Detector (FID). One ml of the headspace gas phase was separated and analysed according to the method described in Example 2.

No isobutene was formed with the control strain C carrying an empty vector. The highest production of isobutene was observed for the strain A over-expressing the both genes, UbiD protein from *S. cerevisiae* and UbiX protein from *E. coli*. A significant production of isobutene was observed for the strain B over-expressing UbiD protein alone. Thus, endogenous UbiX of *E. coli* can probably contribute to activate UbiD protein from *S. cerevisiae* (FIG. 38).

Example 7: One Pot Enzymatic Synthesis of Isobutene from 3-Methylcrotonyl-CoA Catalyzed by an Association of Phosphotransbutyrylase from *Bacillus subtilis*, Butyrate Kinase from *Geobacillus* sp. and UbiD Protein from *Saccharomyces cerevisiae*

A pETDuet™-1 co-expression vector, carrying the UbiD gene from *Saccharomyces cerevisiae* (Uniprot Accession Number Q03034) and the UbiX gene from *Escherichia coli* (Uniprot Accession Number P0AG03) (Example 6), was used to produce and purify UbiD protein according to the protocol described in Example 1. The phosphotransbutyrylase from *Bacillus subtilis* and the butyrate kinase from *Geobacillus* sp. were purified as described in Example 4.

The enzymatic assays were conducted in a total reaction volume of 0.3 ml.

The standard reaction mixture contained:
50 mM Tris-HCl pH 7.5
10 mM 3-methylcrotonyl-CoA 10 mM MgCl$_2$
10 mM NaCl
10 mM potassium phosphate buffer pH 7.5.
10 mM ADP
0.02 mg/ml purified phosphotransbutyrylase from *B. subtilis*
0.02 mg/ml purified butyrate kinase from *Geobacillus* sp.
1 mg/ml purified UbiD from *S. cerevisiae*
Catalysis was conducted at 30° C. during 18 h.

A series of control assays were performed in parallel in which either no UbiD protein (control A) or phosphotransbutyrylase (control B) or butyrate kinase (control C) were added or no substrate was added (control D). After the incubation period, the isobutene produced in the headspace was analysed by Gas Chromatography (GC) equipped Flame Ionization Detector (FID). One ml of the headspace gas phase was separated and analysed according to the method described in Example 2. An overlay of typical chromatogram obtained for the whole enzymatic assay, and the corresponding controls is shown on FIG. 39.

The highest production of isobutene was observed in the assay comprised phosphotransbutyrylase, butyrate kinase and UbiD protein. The control assay without phosphotransbutyrylase (control B) and control assay without butyrate kinase (control C) also showed a significant production of isobutene. These results could be explained by spontaneous hydrolysis of 3-methylcrotonyl-CoA into 3-methylcrotonic acid. Enzymatic production of isobutene from 3-methylcrotonyl-CoA can thus be achieved by three consecutive steps, through the formation of 3-methylcrotonyl phosphate and 3-methylcrotonic acid as intermediates.

Example 8: In Vitro Screening of the UbiD Proteins for the Decarboxylation of 3-Methylcrotonic Acid into Isobutene Several genes coding for UbiD protein were codon optimized for the expression in *E. coli* and synthesized by GeneArt® (Thermofisher). The corresponding enzymes were purified according to the procedure described in Example 1. The list of the studied enzymes is shown in Table G.

Enzymatic assays were carried out in 2 ml glass vials (Interchim) under the following conditions:
50 mM Tris-HCl buffer pH 7.5
20 mM NaCl
10 mM MgCl2
1 mM DTT
50 mM 3-methylcrotonic acid
1 mg/ml purified UbiD protein
100 µl lysate contained UbiX protein from *E. coli*
Total volume of the assays were 300 µl.

A series of control assays were performed in parallel, in which either no UbiD protein was added, or no enzymes were added (Table G).

The vials were sealed and incubated for 60 min at 30° C. The assays were stopped by incubating for 2 min at 80° C. and the isobutene formed in the reaction headspace was analysed by Gas Chromatography (GC) equipped with Flame Ionization Detector (FID), according to the procedure described in Example 2.

The results of the GC analysis are shown in Table G. No isobutene production was observed in control reactions. These results show that all the UbiD proteins, studied under the conditions of this screening assay, were able to perform the decarboxylation of 3-methylcrotonic acid into isobutene in presence of *E. coli* cell lysate contained UbiX protein.

TABLE G

| Candidate UbiD protein | Assay composition | Isobutene produced, arbitrary units |
|---|---|---|
| *Saccharomyces cerevisae* (Uniprot Accession Number: Q03034) | UbiD protein alone | 9 |
| | UbiD protein + Cell lysate contained UbiX protein | 945 |
| *Sphaerulina musiva* (Uniprot Accession Number: M3DF95) | UbiD protein alone | 70 |
| | UbiD protein + Cell lysate contained UbiX protein | 3430 |
| *Penicillium roqueforti* (Uniprot Accession Number: W6QKP7) | UbiD protein alone | 34 |
| | UbiD protein + Cell lysate contained UbiX protein | 1890 |
| *Hypocrea atroviridis* (Uniprot Accession Number: G9NLP8) | UbiD protein alone | 60 |
| | UbiD protein + Cell lysate contained UbiX protein | 5200 |
| *Fusarium oxysporum* sp. *lycopersici* (Uniprot Accession Number: W9LTH3) | UbiD protein alone | 13 |
| | UbiD protein + Cell lysate contained UbiX protein | 1390 |
| *Saccharomyces kudriavzevii* (Uniprot Accession Number: J8TRN5) | UbiD protein alone | 10 |
| | UbiD protein + Cell lysate contained UbiX protein | 920 |
| «No UbiD control»: Cell lysate contained UbiX protein alone | | 0 |
| Control without any enzymes | | 0 |

Example 9: Conversion of 3-Methylcrotonyl-CoA and Acetate into 3-Methylcrotonic Acid and Acetyl-CoA Catalysed by Coenzyme A Transferase from *Megasphaera* sp The enzyme was produced and purified according to the procedure described in Example 1.

The enzymatic assays were conducted in a total reaction volume of 0.2 ml

The standard reaction mixture contained:
50 mM Tris-HCl buffer pH 7.5
5 mM 3-methylcrotonyl-CoA
10 mM sodium acetate
10 mM MgCl$_2$
10 mM NaCl
3 mg/ml purified CoA-transferase from *Megasphaera* sp. (Uniprot Accession Number: S7HFR5).

Control assays were performed in which either no enzyme was added, or no 3-methylcrotonyl-CoA was added. The assays were incubated for 6 h at 30° C. The assays were stopped by adding 100 µl MeCN in the medium. The samples were centrifuged, filtered through a 0.22 µm filter and the clarified supernatants were transferred into a clean vial for the HPLC-based analysis.

HPLC analysis was performed using 1260 Inifinity LC System (Agilent), equipped with a column heating module and UV detector (260 nm). 5 µl of samples were separated on Zorbax SB-Aq column (250×4.6 mm, 5 µm particle size, column temp. 30° C.), with a mobile phase flow rate of 1.5 ml/min. The separation was performed using mixed A (H$_2$O containing 8.4 mM sulfuric acid) and B (acetonitrile) solutions in a linear gradient (0% B at initial time 0 min→70% B at 8 min). In these conditions, the retention time of 3-methylcrotonyl-CoA, 3-methylcrotonic acid and acetyl-CoA were 5.22 min, 5.70 min and 4.25 min, respectively.

Significant amounts of acetyl-CoA and 3-methylcrotonic acid were observed in the enzyme assay while none of the two compounds was not observed in control Significant amounts of acetyl-CoA and 3-methylcrotonic acid were observed in the enzyme assay while none of these two compounds was formed in control assays.

Typical chromatograms for enzymatic and control assays are shown on FIG. 40.

Example 10: Enzymatic Decarboxylation of 3-Methylcrotonic Acid into Isobutene Catalyzed in the Presence of a Lysate Containing UbiX Protein and with Purified Decarboxylase 0.5 M stock solution of 3-methylcrotonic acid was prepared in water and adjusted to pH 7.0 with 10 M solution of NaOH.

Proteins encoded by the aroY gene and one protein annotated as UbiD protein were produced according to the procedure described in Example 1.

Enzymatic assays were carried out in 2 ml glass vials (Interchim) under the following conditions:
50 mM potassium phosphate buffer pH 7.5
20 mM NaCl
10 mM $MgCl_2$
5 mM DTT
50 mM 3-methylcrotonic acid
1 mg/ml purified AroY or UbiD protein
50 μl lysate contained UbiX protein
Total volume of the assays were 300 μl.

A series of control assays were performed in parallel (Table H).

The vials were sealed and incubated for 120 min at 30° C. The assays were stopped by incubating for 2 min at 80° C. and the isobutene formed in the reaction headspace was analysed by Gas Chromatography (GC) equipped with Flame Ionization Detector (FID).

For the GC analysis, one ml of the headspace gas was separated in a Bruker GC-450 system equipped with a GS-alumina column (30 m×0.53 mm) (Agilent) using isothermal mode at 130° C. Nitrogen was used as carrier gas with a flow rate of 6 ml/min.

The enzymatic reaction product was identified by comparison with an isobutene standard. Under these GC conditions, the retention time of isobutene was 2.42 min. A significant production of isobutene from 3-methylcrotonic acid was observed in the combined assays (AroY or UbiD protein+UbiX protein). Incubation of lysate containing UbiX protein alone did not result in isobutene production. These data indicate that the proteins encoded by aroY gene in association with UbiX protein can catalyze the decarboxylation of 3-methylcrotonic acid into isobutene.

TABLE H

| Assay composition | Isobutene production, arbitrary units |
|---|---|
| AroY protein from *K. pneumoniae* (Uniprot Acession Number: B9A9M6) + lysate contained UbiX protein from *E. coli* + substrate | 10.5 |
| AroY protein from *K. pneumoniae* (Uniprot Acession Number: B9A9M6) + substrate | 0 |
| UbiD protein from *E. cloacae* (Uniprot Acession Number: V3DX94) + lysate, contained UbiX protein from *E. coli* + substrate | 8 |
| UbiD protein from *E. cloacae* (Uniprot Acession Number: V3DX94) + substrate | 0 |
| AroY protein from *Leptolyngbya* sp. (Uniprot Acession Number: A0A0S3U6D8) + lysate, contained UbiX protein from *E. coli* + substrate | 5.5 |
| AroY protein from *Leptolyngbya* sp. (Uniprot Acession Number: A0A0S3U6D8) + substrate | 0 |
| AroY protein from *Phascolarctobacterium* sp. (Uniprot Acession Number: R6IIV6) + lysate, contained UbiX protein from *E. coli* + substrate | 5.5 |
| AroY protein from *Phascolarctobacterium* sp. (Uniprot Acession Number: R6IIV6) + substrate | 0 |
| Lysate contained UbiX protein from *E. coli* + substrate | 0 |

Example 11: Enzyme-Catalyzed Dehydration of 3-Hydroxy-3-Methylglutaryl-CoA into 3-Methylglutaconyl-CoA The genes coding for 3-hydroxyacyl-CoA dehydratases (also termed enoyl-CoA hydratases, abbreviated in the following by ECH) (Table I) were synthesized and the corresponding enzymes were further produced according to the procedure described in Example 1. Stock solution of 20 mM 3-hydroxy-3-methylglutaryl-CoA (HMG-CoA) was prepared in water. The enzymatic assays were conducted in total volume of 0.2 ml in the following conditions:
50 mM Tris-HCl buffer pH 7.5
100 mM NaCl
2 mM of 3-hydroxy-3-methylglutaryl-CoA (HMG-CoA)
0.1 mg/ml purified 3-hydroxyacyl-CoA dehydratase.

Enzymatic assays were started by adding the 20 μl of 20 mM substrate, were run for 10 min at 30° C. run for and stopped by adding 100 μL of acetonitrile in the reaction medium. All the enzymatic assays were performed in duplicate. The samples were then centrifuged, filtered through a 0.22 μm filter and the clarified supernatants were transferred into a clean vial for HPLC based analysis.

The analysis was performed using 1260 Inifinity LC System (Agilent), equipped with column heating module and UV detector (260 nm). 5 μl of samples were separated on Zorbax SB-Aq column (250×4.6 mm, 5 μm particle size, column temp. 30° C.), with a mobile phase flow rate of 1.5 ml/min. The separation was performed using mixed A ($H_2O$ containing 8.4 mM sulfuric acid) and B (acetonitrile) solutions in a linear gradient (0% B at initial time 0 min→70% B at 8 min). In these conditions, the retention time of HMG-CoA, 3-methylglutaconyl-CoA (MG-CoA) and free coenzyme A were respectively 4.26 min, 4.76 min and 3.96 min. FIG. 41 shows 3-methylglutaconyl-CoA (MG-CoA) peak areas obtained from the HPLC-based analysis.

TABLE I

| Enzyme's abbreviation | Source and Uniprot Accession Numbers |
|---|---|
| LiuC | 3-hydroxybutyryl-CoA dehydratase from *Myxococcus xanthus* (Q1D5Y4) |
| ECH Um | Putative enoyl-CoA hydratase from *Ustilago maydis* (Q4PEN0) |
| ECH Bs | Methylglutaconyl-CoA hydratase from *Bacillus* sp. GeD10 (N1LWG2) |

TABLE I-continued

| Enzyme's abbreviation | Source and Uniprot Accession Numbers |
|---|---|
| ECH Ll | Methylglutaconyl-CoA hydratase from *Labilithrix luteola* (A0A0K1PN19) |
| ECH Pa | Putative isohexenylglutaconyl-CoA hydratase from *Pseudomonas aeruginosa* (Q9HZV7) |
| ECH Ms | Enoyl-CoA hydratase from *Marinobacter santoriniensis* (M7CV63) |
| ECH Ab | Enoyl-CoA hydratase from *Acinetobacter baumannii* (A0A0D5YDD4) |
| ECH Pp | Isohexenylglutaconyl-CoA hydratase from *Pseudomonas pseudoalcaligenes* (L8MQT6) |

Example 12: Microorganism for the Production of Isobutene from Acetyl-CoA Via 3-Methylcrotonic Acid This example shows the direct production of isobutene by a recombinant *E. coli* strain which expresses exogenous genes, thereby constituting the isobutene pathway.

Like most organisms, *E. coli* converts glucose to acetyl-CoA. The enzymes used in this study to convert acetyl-CoA into isobutene via 3-methylcrotonic acid (FIG. 42) are summarized in Table J.

TABLE J

| Step | Enzyme | Gene abbreviation | NCBI reference | Uniprot Accession number |
|---|---|---|---|---|
| XIII | Acetyl-CoA transferase from *Clostridium acetobulyticum* (ThlA) | thlA | WP_010966157.1 | P45359 |
| IX | Hydroxymethylglutaryl-CoA synthase from *Enterococcus faecalis* (MvaS) | mvaS | WP_002357756.1 | Q9FD71 |
| VIII | Isohexenylglutaconyl-CoA hydratase from *Pseudomonas pseudoalcaligenes* KF707 (ECH) | ppKF707_3831 | WP_004422368.1 | L8MQT6 |
| VII | Glutaconate CoA-transferase from *Myxococcus xanthus* (AibA/B) | MXAN_4264 MXAN_4265 | WP_011554268.1 WP_011554267.1 | Q1D4I3 Q1D4I4 |
| VI | Acyl-CoA thioesterase 2 from *Escherichia coli* (TesB) | tesB | WP_000075876.1 | P0AGG2 |
| I | Ferulic acid decarboxylase from *Hypocrea atroviridis* (UbiD) | FDC1 | XP_013946967.1 | G9NLP8 |
|  | Flavin prenyl transferase from *Escherichia coli* (UbiX) | ubiX | WP_000825700.1 | P0AG03 |

Expression of Isobutene Biosynthetic Pathway in *E. coli*

All the corresponding genes were codon optimized for the expression in *E. coli* and synthesized by GeneArt® (Life Technologies), except the gene encoding for UbiX protein which was directly amplified from the genomic DNA of *E. coli* MG1655. The modified version of pUC18 (New England Biolabs), containing a modified Multiple Cloning Site (pUC18 MCS) (WO 2013/007786), was used for the overexpression of the ubiX gene. This plasmid conferred ampicillin resistance to the recombinant strain. The constructed vector was named pGB 5796 and the corresponding nucleotidic sequence is indicated in Table K.

TABLE K

| Plasmid name | Nucleotidic sequence |
|---|---|
| pGB 5796 | tcgcgcgtttcggtgatgacggtgaaaacctctgacacatgc agctcccggagacggtcacagcttgtctgtaagcggatgccg ggagcagacaagcccgtcagggcgcgtcagcgggtgttggcg ggtgtcggggctggcttaactatgcggcatcagagcagattg tactgagagtgcaccatatgcggtgtgaaataccgcacagat gcgtaaggagaaaataccgcatcaggcgccattcgccattca ggctgcgcaactgttgggaagggcgatcggtgcgggctctt cgctattacgccagctggcgaaaggggggatgtgctgcaaggc gattaagttgggtaacgccagggttttcccagtcacgacgtt gtaaaacgacggccagtgccAAGCTTGCGGCCGCGGGGTTAA TTAATTTCTCCTCTTTAATAAAGCAAATAAATTTTTTATGAT TTGTTTAAACCTAGGCATGCCtctagaTTAttaTGCGCCCTG CCAGCGGGCAAAGAGATCTTCAGGAAGGGTTATCGCAAACTG GTCAAGAACACGATTAACCGTCTGATTTATCACATCATCAAG GGATTGCGGGCGATGATAAAACGCCGGAACGGGAGGCATAAT CACCGCACCGATTTCTGCCGCCTGAGTCATTAAACGCAGATG GCCTAAGTGCAATGGTGTTTCACGCACGCAGAGCACCAACGG GCGACGCTCTTTCAGCACCACATCTGCCGCACGGGTCAGTAA GCCATCAGTATAGCTATGGACAATGCCGGAAAGGGTTTTGAT TGAACAGGGTAAAATCACCATCCCCAGCGTCTGGAAAGAACC GGAAGAGATGCTGGCGGCAATATCGCGCCATCGTGCGTGAC ATCGGCTAATGCCTGCACTTCGCGCAGAGAAAAATCCGTTTC GAGGGATAAGGTCTGGCGCGCTGCCTGGCTCATCACCAGATG cCGTTTCGATATCTGTGACATCGCGCAGAACCTGTAATAAGC GCACGCCATAAATCGCGCCGCTGGCACCGCTGATGCCTACAA TGAGTCGTTTcatAAAAAAAATGTATATCTCCTTCggtaccG AGCTCGAACCTGCAGGAATTCgtaatcatggtcatagctgtt tcctgtgtgaaattgttatccgctcacaattccacaaacata cgagccggaagcataaagtgtaaagcctggggtgcctaatga |

TABLE K-continued

| Plasmid name | Nucleotidic sequence |
|---|---|
|  | gtgagctaactcacattaattgcgttgcgctcactgcccgct ttccagtcgggaaacctgtcgtgccagctgcattaatgaatc ggccaacgcgcggggagaggcggtttgcgtattgggcgctct tccgcttcctcgctcactgactcgctgcgctcggtcgttcgg ctgcggcgagcggtatcagctcactcaaaggcggtaatacgg ttatccacagaatcagggggataacgcaggaaagaacatgtga gcaaaaggccagcaaaaggccaggaaccgtaaaaaggccgcg ttgctggcgtttttccataggctccgcccccctgacgagcat cacaaaaatcgacgctcaagtcagaggtggcgaaacccgaca |

TABLE K-continued

| Plasmid name | Nucleotidic sequence |
|---|---|
| | ggactataaagataccaggcgtttcccctggaagctccctc |
| | gtgcgctctcctgttccgaccctgccgcttaccggatacctg |
| | tccgcctttctcccttcgggaagcgtggcgctttctcatagc |
| | tcacgctgtaggtatctcagttcggtgtaggtcgttcgctcc |
| | aagctgggctgtgtgcacgaaccccccgttcagcccgaccgc |
| | tgcgccttatccggtaactatcgtcttgagtccaaccggta |
| | agacacgacttatcgccactggcagcagccactggtaacagg |
| | attagcagagcgaggtatgtaggcggtgctacagagttcttg |
| | aagtggtggcctaactacggctacactagaaggacagtattt |
| | ggtatctgcgctctgctgaagccagttaccttcggaaaaaga |
| | gttggtagctcttgatccggcaaacaaaccaccgctggtagc |
| | ggtggtttttttgtttgcaagcagcagattacgcgcagaaaa |
| | aaaggatctcaagaagatcctttgatcttttctacggggtct |
| | gacgctcagtggaacgaaaactcacgttaagggattttggtc |
| | atgagattatcaaaaaggatcttcacctagatcctttaaat |
| | taaaaatgaagttttaaatcaatctaaagtatatatgagtaa |
| | acttggtctgacagttaccaatgcttaatcagtgaggcacct |
| | atctcagcgatctgtctatttcgttcatccatagttgcctga |
| | ctccccgtcgtgtagataactacgatacgggagggcttacca |
| | tctggccccagtgctgcaatgataccgcgagacccacgctca |
| | ccggctccagatttatcagcaatasaaccagccagccggaagg |
| | gccgagcgcagaagtggtcctgcaactttatccgcctccatc |
| | cagtctattaattgttgccgggaagctagagtaagtagttcg |
| | ccagttaatagtttgcgcaacgttgttgccattgctacaggc |
| | atcgtggtgtcacgctcgtcgtttggtatggcttcattcagc |
| | tccggttcccaacgatcaaggcgagttacatgatcccccatg |

| Plasmid name | Nucleotidic sequence |
|---|---|
| | ttgtgcaaaaaagcggttagctccttcggtcctccgatcgtt |
| | gtcagaagtaagttggccgcagtgttatcactcatggttatg |
| | gcagcactgcataattctcttactgtcatgccatccgtaaga |
| | tgcttttctgtgactggtgagtactcaaccaagtcattctga |
| | gaatagtgtatgcggcgaccgagttgctcttgcccggcgtca |
| | atacgggataataccgcgccacatagcagaactttaaaagtg |
| | ctcatcattggaaaacgttcttcggggcgaaaactctcaagg |
| | atcttaccgctgttgagatccagttcgatgtaacccactcgt |
| | gcacccaactgatcttcagcatcttttactttcaccagcgtt |
| | tctgggtgagcaaaaacaggaaggcaaaatgccgcaaaaaag |
| | ggaataagggcgacacggaaatgttgaatactcatactcttc |
| | cttttcaatattattgaagcatttatcagggttattgtctc |
| | atgagcggatacatatttgaatgtatttagaaaaataaacaa |
| | ataggggttccgcgcacatttccccgaaaagtgccacctgac |
| | gtctaagaaaccattattatcatgacattaacctataaaaat |
| | aggcgtatcacgaggccctttcgtc (SEQ ID NO: 93) |

An expression vector containing the origin of replication pSC was used for the expression of the genes: thIA, MvaS, ppKF707_3831, MXAN_4264/MXAN_4265, FDC1. This plasmid conferred spectinomycin resistance to the recombinant strain. The constructing vector was named pGB 5771 and the corresponding nucleotidic sequence is indicated in Table L.

TABLE L

| Plasmid name | Nucleotidic sequence |
|---|---|
| pGB 5771 | ctcactactttagtcagttccgcagtattacaaaaggatgtcgcaaacgctgtttgctcctctacaaaac |
| | agacctttaaaacctaaaggcttaagtagcaccctcgcaagctcgggcaaatcgctgaatattccttt |
| | gtctccgaccatcaggcacctgagtcgctgtctttttcgtgacattcagttcgctgcgctcacggctctgg |
| | cagtgaatgggggtaaatggcactacaggcgccttttatggattcatgcaaggaaactacccataat |
| | acaagaaaagcccgtcacgcttctcagggcgttttatggcgggtctgctatgtggtgctatctgacttttt |
| | gctgttcagcagttcctgccctctgattttccagtctgaccctagtcaaggccttaagtgagtcgtattacg |
| | gactggccgtcgttttacaacgtcgtgactgggaaaaccctggcgttacccaacttaatcgccttgcag |
| | cacatccccctttcgccagctggcgtaatagcgaagaggcccgcaccgatcgcccttcccaacagtt |
| | gcgcagcctgaatggcgaatggcgcctgatgcggtattttctccttacgcatctgtgcggtatttcacac |
| | cgCCCGGGGAACTATAGtttaaacTTTTCAATGAATTCATTTaaGCGGCCG |
| | CatcaatTCTAGAattttaaatagtcaaaagcctccgaccggaggcttttgactgACCTATTG |
| | ACAATTAAAGGCTAAAATGCTATAATTCCACtaatagaaataattttgttttaacttta |
| | ggtctctatcgtaaGAAGGAGATATatgaaagaagtggtgattgccagcgcagttcgtaccgc |
| | aattggtagctatggtaaaagcctgaaagatgttccggcagttgatctgggtgcaaccgcaattaaag |
| | aagcagttaaaaaagccggtattaaaccggaagatgtgaacgaagttattctgggtaatgttctgcaa |
| | gcaggtctgggtcagaatccggcacgtcaggcctcgtttaaagcaggtctgccggttgaaattccgg |
| | caatgaccattaacaaagtttgtggtagcggtctgcgtaccgttagcctggcagcacagattatcaaa |
| | gccggtgatgcagatgttattattgccggtggtatggaaaatatgagccgtgcaccgtatctggcaaat |
| | aatgcacgttgggtttatcgtatgggtaatgccaaatttgtggatgagatgattaccgatggtctgtggg |
| | atgcctttaatgattatcacatgggtattaccgcagagaatattgcagaacgtggaatattagccgtga |
| | agaacaggatgaatttgcactggcaagccagaaaaaagcagaagaagcaattaaaagcggtca |
| | gttcaaagatgaaattgtgccggttgttatcaaaggtcgtaaaggtgaaaccgttgttgataccgatga |
| | acatccgcgttttggtagcaccattgaaggtctgcaaaactgaaaccggcattcaaaaaagatggc |
| | accgttaccgcaggtaatgcaagcggtctgaatgattgtgcagcagttctggttattatgagcgcaga |
| | aaaagcaaaagaactgggtgttaaaccgctggcaaaaattgtgagctatggtagtgccggtgttgat |
| | ccggcaattatgggttatggtccgttttatgcaaccaaagcagcaattgaaaaagcaggttggaccgt |
| | tgatgaactggatctgattgaaagcaatgaagcatttgcagcacagagcctggcagttgcaaaaga |
| | cctgaaattcgatatgaataaagtgaatgtgaatggcggtgcaattgccctgggtcatccgattggtgc |
| | aagcggtgcacgtattctggttaccctggttcatgcaatgcagaaacgtgatgcaaaaaaaggtctg |
| | gccaccctgtgtattggtggtggtcagggcaccgcaattctgctggaaaaatgctaataagcttGAA |
| | GGAGATATAATGACCATTGGTATTGATAAAATCAGCTTTTTCGTGCCT |
| | CCGTACTATATTGATATGACCGCACTGGCCGAAGCACGTAATGTTGA |
| | TCCGGGTAAATTTCATATTGGTATTGGTCAGGATCAGATGGCCGTTA |
| | ATCCGATTAGCCAGGATATTGTTACCTTTGCAGCAAATGCAGCAGAA |
| | GCAATTCTGACCAAAGAAGATAAAGAGGCCATTGATATGGTTATTGT |
| | TGGCACCGAAAGCAGCATTGATGAAAGCAAAGCAGCAGCAGTTGTT |
| | CTGCATCGTCTGATGGGTATTCAGCCGTTTGCACGTAGCTTTGAAAT |
| | TAAAGAAGCATGTTACGGAGCAACCGCAGGTCTGCAACTGGCAAAA |
| | AATCATGTTGCACTGCATCCGGATAAAAAGTTCTGGTTGTTGCAGC |
| | AGATATTGCCAAATATGGTCTGAATAGCGGTGGTGAACCGACCCAG |
| | GGTGCCGGTGCAGTTGCAATGCTGGTTGCAAGCGAACCGCGTATTC |
| | TGGCACTGAAAGAAGATAATGTTATGCTGACCCAGGATATTTATGAT |

TABLE L-continued

| Plasmid name | Nucleotidic sequence |
|---|---|
| | TTTTGGCGTCCGACCGGTCATCCGTATCCGATGGTTGATGGTCCGC<br>TGAGCAATGAAACCTATATTCAGAGCTTTGCACAGGTGTGGGATGAA<br>CATAAAAAACGTACCGGTCTGGATTTCGCAGATTATGATGCACTGGC<br>ATTTCATATCCCGTATACCAAAATGGGTAAAAAAGCACTGCTGGCCA<br>AAATTAGCGATCAGACCGAAGCCGAACAAGAACGCATTCTGGCACG<br>TTATGAAGAAAGCATTGTTTATAGCCGTCGTGTGGGTAATCTGTATA<br>CCGGTAGCCTGTATCTGGGTCTGATTAGCCTGCTGGAAAATGCAAC<br>CACCCTGACCGCAGGTAATCAGATTGGTCTGTTTAGCTATGGTAGC<br>GGTGCCGTTGCAGAATTTTTCACAGGTGAACTGGTTGCAGGTTATCA<br>GAATCATCTGCAAAAAGAAACCCATCTGGCACTGCTGGATAATCGTA<br>CCGAACTGAGCATTGCAGAATATGAAGCAATGTTTGCAGAAACCCTG<br>GATACCGATATTGATCAGACCCTGGAAGATGAACTGAAATATAGCAT<br>TAGCGCCATTAATAACACCGTGCGTAGCTATCGTAACTAATAAggtaG<br>AAGGAGATATACATatgagtcaggcgctaaaaaatttactgacattgttaaatctggaaaaa<br>attgaggaaggactctttcgcggccagagtgaagatttaggtttacgccaggtgtttggcggccaggt<br>cgtgggtcaggccttgtatgctgcaaaagagacGgtccctgaagaAcggctggtacattcgtttcac<br>agctactttcttcgccctggcgatagtaagaagccgattatttatgatgtcgaaacgctgcgtgacggta<br>acagcttcagcgcccgccgggttgctgctattcaaaacggcaaaccgattttttatatgactgcctcttc<br>caggcaccagaagcgggtttcgaacatcaaaaaacaatgccgtccgcgccagcgcctgatggcct<br>cccttcggaaacgcaaatcgcccaatcgctggcgcacctgctgccgccagtgctgaaagataaatt<br>catctgcgatcgtccgctggaagtccgtccggtggagtttcataacccactgaaaggtcacgtcgcag<br>aaccacatcgtcaggtgtggatTcgcgcaaatggtagcgtgccggatgacctgcgcgttcatcagta<br>tctgctcggttacgcttctgatcttaacttcctgccggtagctctacagccgcacggcatcggttttctcga<br>accgggggattcagattgccaccattgaccattccatgtggttccatcgcccgtttaatttgaatgaatgg<br>ctgctgtatagcgtggagagcacctcggcgtccagcgcacgtggctttgtgcgcggtgagttttatacc<br>caagacggcgtactggttgcctcgaccgttcaggaaggggtgatgcgtaatcacaattaataagaac<br>GAAGGAGATATAAtgAAAACCGCACGTTGGTGTAGCCTGGAAGAAGC<br>AGTTGCAAGCATTCCGGATGGTGCAAGCCTGGCAACCGGTGGTTTT<br>ATGCTGGGTCGTGCACCGATGGCACTGGTTATGGAACTGATTGCAC<br>AGGGTAAACGTGATCTGGGTCTGATTAGCCTGCCGAATCCGCTGCC<br>AGCAGAATTTCTGGTTGCCGGTGGTTGTCTGGCTCGTCTGGAAATT<br>GCATTTGGTGCACTGAGTCTGCAAGGTCGTGTTCGTCCGATGCCGT<br>GTCTGAAACGTGCAATGGAACAGGGCACCCTGGCATGGCGTGAACA<br>TGATGGTTATCGTGTTGTTCAGCGTCTGCGTGCAGCAAGCATGGGT<br>CTGCCGTTTATTCCGGCACCGGATGCAGATGTTAGCGGTCTGGCAC<br>GTACCGAACCGCCTCCGACCGTTGAAGATCCGTTTACCGGTCTGCG<br>TGTTGCAGTTGAACCGGCATTTTATCCGGATGTTGCACTGCTGCACG<br>CACGTGCAGCCGATGAACGTGGTAATCTGTATATGGAAGATCCGAC<br>CACCGATCTGCTGGTTGCGGGTGCAGCAAAACGTGTTATTGCAACC<br>GTTGAAGAACGTGTTGCAAAACTGCCTCGTGCAACCCTGCCTGGTTT<br>TCAGGTTGATCGTATTGTTCTGGCACCGGGTGGTGCACTGCCGACC<br>GGTTGTGCAGGTCTGTATCCGCATGATGATGAAATGCTGGCACGTT<br>ATCTGAGCCTGGCAGAAACCGGTCGTGAAGCCGAATTTCTGGAAAC<br>CCTGCTGACCCGTCGTGCAGCATAATGAggatccGAAGGAGATATACA<br>TAtgAGCGCAACCCTGGATATTACACCGGCAGAAACCGTTGTTAGCC<br>TGCTGGCACGTCAGATTGATGATGGTGGTGTTGTTGCAACCGGTGT<br>TGCAAGTCCGCTGGCAATTCTGGCCATTGCAGTTGCACGTGCCACC<br>CATGCACCGGATCTGACCTATCTGGCATGTGTTGGTAGCCTGGACC<br>CGGAAATTCCGACCCTGCTGCCGAGCAGCGAAGACCTGGGTTATCT<br>GGATGGTCGTAGCGCAGAAATTACCATTCCGGACCTGTTTGATCATG<br>CACGTCGTGGTCGTGTTGATACCGTTTTTTTTGGTGCAGCCGAAGTT<br>GATGCCGAAGGTCGTACCAATATGACCGCAAGCGGTAGTCTGGATA<br>AACCGCGTACCAAATTTCCGGGTGTTGCCGGTGCAGCCACCCTGCG<br>TCAGTGGGTTCGTCGTCCGGTTCTGCTGGTTCCGCGTCAGAGCCGT<br>CGTAATCTGGTTCCGGAAGTTCAGGTTGCAACCACCCGTGATCCGC<br>GTCGTCCGGTGACCCTGATTAGCGATCTGGGTGTTTTTGAACTGGG<br>TGCAAGCGGTGCACGTCTGCTGGCACGCCATCCGTGGGCAAGCGA<br>AGAACATATTGCAGAACGTACCGGTTTTGCATTTCAGGTTAGCGAAG<br>CACTGAGCGTTACCAGCCTGCCGGATGCACGTACCGTTGCAGCAAT<br>TCGTGCAATTGATCCGCATGGCTATCGTGATGCACTGGTTGGTGCAT<br>AATTAgtcagaaggagatataCATATGAGCCTGCCGCATTGTGAAACCCTG<br>CTGCTGGAACCGATTGAAGGTGTTCTGCGTATTACCCTGAATCGTCC<br>GCAGAGCCGTAATGCAATGAGCCTGGCAATGGTTGGTGAACTGCGT<br>GCAGTTCTGGCAGCAGTTCGTGATGATCGTAGCGTTCGTGCACTGG<br>TTCTGCGTGGTGCAGATGGTCATTTTTGTGCCGGTGGTGATATTAAA<br>GATATGGCAGGCGCACGTGCAGCCGGTGCAGAAGCATATCGTACAC<br>TGAATCGTGCATTTGGTAGCCTGCTGGAAGAAGCACAGGCAGCACC<br>GCAGCTGCTGGTTGCACTGGTTGAAGGTGCCGTTCTGGGTGGTGGT<br>TTTGGTCTGGCATGTGTTAGTGATGTTGCAATTGCAGCAGCAGATGC<br>ACAGTTTGGTCTGCCGGAAACCAGCCTGGGTATTCTGCCTGCACAG<br>ATTGCACCGTTTGTTGTTCGTCGTATTGGTCTGACCCAGGCACGTCG<br>TCTGGCACTGACCGCAGCACGTTTTGATGGTCGTAAGCACTGCGT<br>CTGGGTCTGGTTCATTTTTGTGAAGCAGATGCAGATGCACTGGAACA<br>GCGTCTGGAAGAAACCCTGGAACAGCTGCGTCGTTGTGCACCGAAT<br>GCAAATGCAGCAACCAAAGCACTGCTGCTGGCAAGCGAAAGCGGTG<br>AACTGGGTGCACTGCTGGATGATGCAGCACGTCAGTTTGCCGAAGC<br>AGTTGGTGGTGCAGAAGGTAGCGAAGGCACCCTGGCATTTGTTCAG |

TABLE L-continued

| Plasmid name | Nucleotidic sequence |
|---|---|
| | AAACGTAAACCGGTTTGGGCACAGTAATAAtgaaagagaccagcctgatacag
attaaatcagaacgcagaagcggtctgataaaacagaatttgcctggcggcagtagcgcggtggtc
ccacctgacccatgccgaactcagaagtgaaacgccgtagcgccgatggtagtgtggggtcacc
ccatgcgagagtagggaactgccaggcatcaaataaaacgaaaggctcagtcgaaagactgggc
ctttcgttttatctgttgtttgtcggtgaactACTAGAatttaaatagtcaaaagcctccgaccggaggc
ttttgactgACCTATTGACAATTAAAGGCTAAAATGCTATAATTCCACtaatag
aaataattttgtttaacttttaggtctctatcgaccataaTTAATTAActttaagaaggagatatacaT
atgAGCAGCACCACCTATAAAAGCGAAGCATTTGATCCGGAACCGCC
TCATCTGAGCTTTCGTAGCTTTGTTGAAGCACTGCGTCAGGATAATG
ATCTGGTGGATATTAATGAACCGGTTGATCCGGATCTGGAAGCAGC
AGCAATTACCCGTCTGGTTTGTGAAACCGATGATAAAGCACCGCTGT
TTAATAACGTGATTGGTGCAAAAGATGGTCTGTGGCGTATTCTGGGT
GCACCGGCAAGCCTGCGTAGCAGCCCGAAAGAACGTTTTGGTCGTC
TGGCACGTCATCTGGCACTGCCTCCGACCGCAAGCGCAAAAGATAT
TCTGGATAAAATGCTGAGCGCCAATAGCATTCCGCCTATTGAACCGG
TTATTGTTCCGACCGGTCCGGTTAAAGAAAATAGCATTGAAGGCGAA
AACATTGATCTGGAAGCCCTGCCTGCACCGATGGTTCATCAGAGTG
ATGGTGGCAAGTATATCCAGACCTATGGTATGCATGTTATCCAGAGT
CCGGATGGTTGTTGGACCAATTGGAGCATTGCCCGTGCAATGGTTA
GCGGTAAACGTACCCTGGCAGGTCTGGTTATTAGTCCGCAGCATAT
TCGTAAAATTCAGGATCAGTGGCGTGCAATTGGTCAAGAAGAAATTC
CTTGGGCACTGGCATTTGGTGTTCCGCCTACCGCAATTATGGCAAG
CAGTATGCCGATTCCGGATGGTGTTAGCGAAGCAGGTTATGTTGGT
GCAATTGCCGGTGAACCGATTAAACTGGTTAAATGCGATACCAACAA
TCTGTATGTTCCGGCAAATAGCGAAATTGTTCTGGAAGGCACCCTGA
GCACCACCAAAATGGCACCGGAAGGTCCGTTTGGTGAAATGCATGG
TTATGTTTATCCGGGTGAAAGCCATCCGGGTCCGGTTTATACCGTTA
ACAAAATTACCTATCGCAACAATGCAATTCTGCCGATGAGCGCATGT
GGTCGTCTGACCGATGAAACCCAGACCATGATTGGCACCCTGGCAG
CAGCAGAAATTCGTCAGCTGTGTCAGGATGCAGGTCTGCCGATTAC
CGATGCATTTGCACCGTTTGTTGGTCAGGCAACCTGGGTTGCACTG
AAAGTTGATACCAAACGTCTGCGTGCAATGAAAACCAATGGTAAAGC
ATTTGCAAAACGTGTTGGTGATGTTGTGTTTACCCAGAAACCGGGTT
TTACCATTCATCGTCTGATTCTGGTTGGTGATGATATTGATGTGTATG
ACGATAAAGATGTGATGTGGGCATTTACCACCCGTTGTCGTCCGGG
TACAGATGAAGTTTTTTTTGATGATGTTGTGGGCTTTCAGCTGATCCC
GTATATGAGTCATGGTAATGCCGAAGCAATTAAAGGTGGTAAAGTTG
TTAGTGATGCACTGCTGACCGCAGAATATACCACCGGTAAAGATTGG
GAAAGCGCAGATTTCAAAAACAGCTATCCGAAAAGCATCCAGGATAA
AGTTCTGAATAGCTGGGAACGCCTGGGTTTCAAAAAACTGGATTAAT
AACCATGGttataagagagaccagcctGACTCCTGTTGATAGATCCAGTAAT
GACCTCAGAACTCCATCTGGATTTGTTCAGAACGCTCGGTTGCCGC
CGGGCGTTTTTTATTGGTGAGAATaactACTAGTtggcggGCGGCCGCTta
gctCTGCAGatgagaaattcttgaagacgaaagggcctcgtgatacgcctattttttataggttaatg
tcatgataataatggtttAAGCTTcttagaataGCTCTTCTATGaggtggcacttttcgggga
aaGATATCcgcatatatggtgcactctcagtacaatctgctctgatgccgcatagttaagccagtat
acactccgctatcgctacgtgactgggtcatggctgcgccccgacaccgccaacacccgctgacg
cgccctgacgggcttgtctgctcccggcatccgcttacagacaagctgtgaccgtctccgggagctgc
atgtgtcagaggttttcaccgtcatcaccgaaacgcgcgaggcagctgcggtaaagctcatcagcgt
ggtcgtgaagcgattcacagatgtctgcctgttcatcGGTACCtttcatgatatatctcccaatttgtgt
agggcttattatgcacgcttaaaaataataaaaagcagactttgacctgatagtttggctgtgagcaattat
gtgcttagtgcatctaacgcttgagttaagccgcgccgcgaagcggcgtcggcttgaacgaattgtta
gacattatttgccgactaccttggtgatctcgcctttcacgtagtggacaaattcttccaactgatctgcgc
gcgaggccaagcgatcttcttcttgtccaagataagcctgtctagcttcaagtatgacgggctgatact
gggccggcaggcgctccattgcccagtcggcagcgacatccttcggcgcgattttgccggttactgc
gctgtaccaaatgcgggacaacgtaagcactacatttcgctcatcgccagcccagtcgggcggcga
gttccatagcgttaaggtttcatttagcgcctcaaatagatcctgttcaggaaccggatcaaagagttcc
tccgccgctggacctaccaaggcaacgctatgttctcttgcttttgtcagcaagatagcagatcaatgt
cgatcgtggctggctcgaagatacctgcaagaatgtcattgcgctgccattctccaaattgcagttcgc
gcttagctggataacgcacggaatgatgtcgtcgtgcacaacaatggtgacttctacagcgcggag
aatctcgctctctccaggggaagccgaagtttccaaaaggtcgttgatcaaagctcgccgcgttgtttc
atcaagccttacggtcaccgtaaccagcaaatcaatatcactgtgtggcttcaggccgccatccactg
cggagccgtacaaatgtacggccagcaacgtcggttcgagatggcgctcgatgacgccaactacct
ctgatagttgagtcgatacttcggcgatcaccgcttccctcatgatgtttaacttttgttttagggcgactgc
cctgctgcgtaacatcgttgctgctccataacatcaaacatcgacccacggcgtaacgcgcttgctgct
tggatgcccgaggcatagactgtaccccaaaaaaacagtcataacaagccatgaaaaccgccac
GAGCTCctgtcagaccaagtttacgagctcgcttggactcctgttgatagatccagtaatgacctca
gaactccatctggatttgttcagaacgctcggttgccgccgggcgtttttattggtgagaatccaagca
ctagggacagtaagacgggtaagcctgttgatgataccgctgccttactgggtgcattagccagtctg
aatgacctgtcacgggataatccgaagtggtcagactggaaaatcagagggcaggaactgctgaa
cagcaaaaagtcagatagcaccacatagcagacccgccataaaacgcccctgagaagcccgtga
cgggcttttcttgtattatgggtagtttccttgcatgaatccataaaaagcgcctgtagtgccatttaccc
cattcactgccagagccgtgagcgcagcgaactgaatgtcacgaaaaagacagcgactcaggtg
cctgatggtcggagacaaaaggaatattcagcgatttgcccgagcttgcgagggtgctacttaagcct
ttagggttttaaggtctgtttttgtagaggagcaaacagcgtttgcgacatccttttgtaatactgcggaact
gactaaagtagtgagttatacacagggctgggatctattcttttttatcttttttttatt ctttcttt attctataaatt
ataaccacttgaatataaacaaaaaaaacacacaaaggtctagcggaatttacagagggtctagc |

TABLE L-continued

| Plasmid name | Nucleotidic sequence |
|---|---|
| | agaatttacaagttttccagcaaaggtctagcagaatttacagatacccacaactcaaaggaaaag<br>gacatgtaattatcattgactagcccatctcaattggtatagtgattaaaatcacctagaccaattgaga<br>tgtatgtctgaattagttgttttcaaagcaaatgaactagcgattagtcgctatgacttaacggagcatga<br>aaccaagctaattttatgctgtgtggcactactcaacccacgattgaaaacctacaaggaaagaa<br>cggacggtatcgttcacttataaccaatacgctcagatgatgaacatcagtagggaaaatgcttatgg<br>tgtattagctaaagcaaccagagagctgatgacgagaactgtggaaatcaggaatcctttggttaaa<br>ggctttgagattttccagtggacaaactatgccaagttctcaagcgaaaaattagaattagttttttagtga<br>agagatattgccttatcttttccagttaaaaaaattcataaaatataatctggaacatgttaagtctttgaa<br>aacaaatactctatgaggatttatgagtggttattaaaagaactaacacaaaagaaaactcacaagg<br>caaatatagagattagccttgatgaatttaagttcatgttaatgcttgaaaataactaccatgagtttaaa<br>aggcttaaccaatgggttttgaaaccaataagtaaagatttaaacacttacagcaatatgaaattggtg<br>gttgataagcgaggccgcccgactgatacgttgattttccaagttgaactagatagacaaatggatctc<br>gtaaccgaacttgagaacaaccagataaaaatgaatggtgacaaaataccaacaaccattacatc<br>agattcctacctacgtaacggactaagaaaaacactacacgatgctttaactgcaaaaattcagctc<br>accagttttgaggcaaaattttgagtgacatgcaaagtaagcatgatctcaatggttcgttctcatggct<br>cacgcaaaaacaacgaaccacactagagaacatactggctaaatacggaaggatctgaggttctt<br>atggctcttgtatctatcagtgaagcatcaagactaacaaacaaaagtagaacaactgttcaccgtta<br>gatatcaaagggaaaactgtccataagcacagatgaaacggtgtaaaaaagatagatacatcag<br>agcttttacgagttttggtgcatttaaagctgttcaccatgaacagatcgacaatgtaacGCATGCa<br>ccgagcgcagcgagtcagtgagcgaggaagcggaacagcgcctg (SEQ ID NO: 94) |

These recombinant pGBE 5771 and pGBE5796 plasmids were verified by sequencing.

MG1655 *E. coli* strain was made electrocompetent and was transformed with pGBE5771 and pGBE5796 or with the corresponding empty vectors (pUC18 MCS and pGB2021) in order to create negative controls. The strains thus produced are summarized in Table M.

TABLE M

| Strain number | Vectors |
|---|---|
| Strain 1 (metabolic pathway-free control), containing the empty vectors. | pUC18_MCS + pGB 2021 |
| Strain 2, expressing only UbiX protein | pGB 5796 + pGB 2021 |
| Strain 3, expressing the whole metabolic pathway, without overexpression of UbiX protein on plasmid. | pUC18_MCS + PGB 5771 |
| Strain 4, expressing the whole metabolic pathway, comprising overexpression of UbiX protein on plasmid. | pGB 5796 + pGB 5771 |

The transformed cells were then plated on LB plates, supplied with ampicillin (100 µg/ml) and spectinomycin (100 µg/ml). Plates were incubated overnight at 30° C. Isolated colonies were used to inoculate 1.4 ml of ZYM-5052 auto-inducing media (Studier F W, Prot. Exp. Pur. 41, (2005), 207-234) supplemented with ampicillin, spectinomycin and 0.5 mM flavin mononucleotide. These cultures were grown for 16 h at 30° C. and 700 rpm shaking in 96 deep-well microplates. Then the cultures were centrifuged and the pellets were resuspended in 0.4 ml of MS medium (Richaud C., Mengin-Leucreulx D., Pochet S., Johnson E J., Cohen G N. and MarHere P, The Journal of Biological Chemistry, 268, (1993), 26827-26835) containing glucose (45 g/L), and MgSO4 (1 mM). The cultures were further incubated in 96 deep-well sealed microplates at 30° C., 700 rpm shaking for 24 hours. The production of isobutene was stopped by incubating the microplates for 5 min at 80° C. and the isobutene formed in the reaction headspace was analysed by Gas Chromatography (GC) equipped with Flame Ionization Detector (FID). 100 µL of headspace gases from each enzymatic reaction are injected in a Brucker GC-450 system equipped with a Flame Ionization Detector (FID). Compounds present in samples were separated by chromatography using a GS-alumina column (30 m×0.53 mm) (Agilent) using isothermal mode at 130° C. Nitrogen was used as carrier gas with a flow rate of 6 ml/min. Upon injection, peak areas of isobutene were calculated; Table N.

TABLE N

| Strain number | Vectors | IBN production, arbitrary units |
|---|---|---|
| Strain 1 (metabolic pathway-free control), containing the empty vectors | pUC18_MCS + pGB 2021 | 950 |
| Strain 2, expressing only UbiX proteine | pGB 5796 + pGB 2021 | 710 |
| Strain 3, expressing the whole metabolic pathway, without overexpression of UbiX protein on plasmid | pUC18_MCS + PGB 5771 | 625 |
| Strain 4, expressing the whole metabolic pathway, comprising overexpression of UbiX protein on plasmid | pGB 5796 + pGB 5771 | 15192 |

The invention claimed is:

1. A method for the production of isobutene comprising
   (a) enzymatically converting 3-methylcrotonyl-CoA into 3-methylcrotonic acid,
   wherein the conversion of 3-methylcrotonyl-CoA into 3-methylcrotonic acid is carried out by:
   i. a single enzymatic reaction in which 3-methylcrotonyl-CoA is directly converted into 3-methylcrotonic acid by a CoA transferase (EC 2.8.3.-);
   ii. a single enzymatic reaction in which 3-methylcrotonyl-CoA is directly converted into 3-methylcrotonic acid by a thioester hydrolase (EC 3.1.2.-); or
   iii. two enzymatic steps comprising
      a. first enzymatically converting 3-methylcrotonyl-CoA into 3-methylcrotonyl phosphate by a phosphate butyryltransferase (EC 2.3.1.19) or a phosphate acetyltransferase (EC 2.3.1.8); and
      b. then enzymatically converting the thus obtained 3-methylcrotonyl phosphate into said 3-methylcrotonic acid by a phosphotransferase with a carboxy group as acceptor (EC 2.7.2.-), and
   (b) enzymatically converting the 3-methylcrotonic acid produced in (a) into isobutene, wherein the conversion of 3-methylcrotonic acid into isobutene is carried out by a 3-methylcrotonic acid decarboxylase selected from:
      i. an FMN-dependent decarboxylase associated with an FMN prenyl transferase (EC 2.5.1.-); or
      ii. an aconitate decarboxylase (EC 4.1.1.6); or
      iii. a methylcrotonyl-CoA carboxylase (EC 6.4.1.4); or
      iv. a geranoyl-CoA carboxylase (EC 6.4.1.5); or
      v. a protocatechuate (PCA) decarboxylase (EC 4.1.1.63).

2. The method of claim 1, wherein the CoA transferase (EC 2.8.3.-) is selected from a propionate:acetate-CoA transferase (EC 2.8.3.1), an acetate CoA-transferase (EC 2.8.3.8) or a succinyl-CoA:acetate CoA-transferase (EC 2.8.3.18).

3. The method of claim 1, wherein the thioester hydrolase (EC 3.1.2.-) is selected from an acetyl-CoA hydrolase (EC 3.1.2.1), an ADP-dependent short-chain-acyl-CoA hydrolase (EC 3.1.2.18) or an acyl-CoA hydrolase (EC 3.1.2.20).

4. The method of claim 1, wherein the phosphotransferase with a carboxy group as acceptor (EC 2.7.2.-) is selected from a propionate kinase (EC 2.7.2.15), an acetate kinase (EC 2.7.2.1), a butyrate kinase (EC 2.7.2.7) or a branched-chain-fatty-acid kinase (EC 2.7.2.14).

5. The method of claim 1, wherein the method further comprises enzymatically converting 3-methylglutaconyl-CoA into 3-methylcrotonyl-CoA by a methylcrotonyl-CoA carboxylase (EC 6.4.1.4) or a geranoyl-CoA carboxylase (EC 6.4.1.5).

6. The method of claim 5, wherein the method further comprises enzymatically converting 3-hydroxy-3-methyl-glutaryl-CoA into 3-methylglutaconyl-CoA by a 3-methylglutaconyl-coenzyme A hydratase (EC 4.2.1.18), a 3-hydroxyacyl-CoA dehydratase (EC 4.2.1.-) or an enoyl-CoA hydratase (EC 4.2.1.-).

7. The method of claim 6, wherein the method further comprises enzymatically condensing acetoacetyl-CoA and acetyl-CoA into 3-hydroxy-3-methylglutaryl-CoA by a 3-hydroxy-3-methylglutaryl-CoA synthase.

8. The method of claim 2, wherein the 3-methylcrotonic acid decarboxylase is a FMN-dependent decarboxylase associated with an FMN prenyl transferase (EC 2.5.1.-).

9. The method of claim 3, wherein the 3-methylcrotonic acid decarboxylase is a FMN-dependent decarboxylase associated with an FMN prenyl transferase (EC 2.5.1.-).

10. The method of claim 4, wherein the 3-methylcrotonic acid decarboxylase is a FMN-dependent decarboxylase associated with an FMN prenyl transferase (EC 2.5.1.-).

11. The method of claim 5, wherein the thioester hydrolase (EC 3.1.2.-) is selected from an acetyl-CoA hydrolase (EC 3.1.2.1), an ADP-dependent short-chain-acyl-CoA hydrolase (EC 3.1.2.18) or an acyl-CoA hydrolase (EC 3.1.2.20).

12. The method of claim 11, wherein the 3-methylcrotonic acid decarboxylase is a FMN-dependent decarboxylase associated with an FMN prenyl transferase (EC 2.5.1.-).

13. The method of claim 6, wherein the thioester hydrolase (EC 3.1.2.-) is selected from an acetyl-CoA hydrolase (EC 3.1.2.1), an ADP-dependent short-chain-acyl-CoA hydrolase (EC 3.1.2.18) or an acyl-CoA hydrolase (EC 3.1.2.20).

14. The method of claim 13, wherein the 3-methylcrotonic acid decarboxylase is a FMN-dependent decarboxylase associated with an FMN prenyl transferase (EC 2.5.1.-).

15. The method of claim 7, wherein the thioester hydrolase (EC 3.1.2.-) is selected from an acetyl-CoA hydrolase (EC 3.1.2.1), an ADP-dependent short-chain-acyl-CoA hydrolase (EC 3.1.2.18) or an acyl-CoA hydrolase (EC 3.1.2.20).

16. The method of claim 15, wherein the 3-methylcrotonic acid decarboxylase is a FMN-dependent decarboxylase associated with an FMN prenyl transferase (EC 2.5.1.-).

* * * * *